United States Patent [19]

Bodor

[11] Patent Number: 5,389,623
[45] Date of Patent: Feb. 14, 1995

[54] REDOX CARRIERS FOR BRAIN-SPECIFIC DRUG DELIVERY

[75] Inventor: Nicholas S. Bodor, Gainesville, Fla.

[73] Assignee: University of Florida, Gainesville, Fla.

[21] Appl. No.: 766,528

[22] Filed: Sep. 27, 1991

Related U.S. Application Data

[60] Division of Ser. No. 295,663, Jan. 11, 1989, Pat. No. 5,087,618, which is a division of Ser. No. 666,210, Oct. 29, 1984, Pat. No. 4,829,070, which is a continuation-in-part of Ser. No. 379,316, May 18, 1982, Pat. No. 4,479,932, and Ser. No. 461,543, Jan. 27, 1983, abandoned, and Ser. No. 475,493, Mar. 15, 1983, Pat. No. 4,622,218, and a continuation-in-part of Ser. No. 516,382, Jul. 22, 1983, Pat. No. 4,540,564.

[30] Foreign Application Priority Data

May 12, 1983 [WO] WIPO ............... PCT/US83/00725
May 16, 1983 [CA] Canada ........................... 428192

[51] Int. Cl.$^6$ ............... A61K 31/56; A61K 31/455
[52] U.S. Cl. ................. 514/169; 514/170; 514/356; 540/109; 540/110
[58] Field of Search ............. 540/109, 110; 514/169, 514/170, 356

[56] References Cited

U.S. PATENT DOCUMENTS

| | | | |
|---|---|---|---|
| 3,987,175 | 10/1976 | Cousse | 546/316 |
| 4,065,566 | 12/1977 | Bodor | 560/40 |
| 4,083,996 | 4/1978 | Tanaka et al. | 546/316 |
| 4,143,146 | 5/1979 | Saari | 546/316 |
| 4,152,521 | 5/1979 | Cousse et al. | 546/316 |
| 4,157,396 | 6/1979 | Tanaka et al. | 546/316 |
| 4,195,984 | 12/1980 | Stein et al. | 546/323 |
| 4,479,932 | 10/1984 | Bodor | 424/9 |
| 4,532,251 | 7/1985 | Spatz | 514/354 |
| 4,540,564 | 9/1985 | Bodor | 424/9 |
| 4,555,520 | 11/1985 | Misra et al. | 514/546 |
| 4,558,150 | 12/1985 | Gordon et al. | 546/316 |
| 4,727,079 | 2/1988 | Bodor | 514/307 |
| 5,087,618 | 2/1992 | Bodor | 514/45 |

OTHER PUBLICATIONS

Wu et al., *CA* 77: 19978m (1972).
Endo et al, *CA* 92: 21076y (1979).
Endo et al, *CA* 87: 53561m (1977).
Bodor et al, *Science* 190, 155–156 (1975).
Shek et al, *J. Med. Chem.* 19, 113–117 (1976).
Bodor et al, in *Design of Biopharmaceutical Properties through Prodrugs and Analogs*, ed. Edward B. Roche, American Pharmaceutical Association, Washington, D.C., 98–135 (1977).
Bodor et al, *J. Pharm. Sci.* 67, 685–687 (1978).
Bodor et al, *Science* 214, 1370–1372 (1981).
*The Friday Evening Post*, Health Center Communications, University of Florida, Gainesville, Fla., Aug. 14, 1981.
*Chemical and Engineering News*, pp. 24–25, Dec. 21, 1981.
*Science News*, vol. 121, #1, p. 7, Jan. 2, 1982.
Brewster III, Dis. Abst. Int. B., vol. 43, #9, p. 2910B (1983).
Bodor et al, *J. Med. Chem.* 26, 313–318 (1983).
Bodor et al, *J. Med. Chem.* 26, 528–534 (1983).
Bodor et al, *Pharmac. Ther.* 19, 337–386 (1983).
Bodor et al, *J. Pharm. Sci.* 73, 385–389 (1984).
Bodor et al, *Science* 221, 65–67 (1983).

Primary Examiner—John W. Rollins
Assistant Examiner—James D. Wilson
Attorney, Agent, or Firm—Burns, Doane, Swecker & Mathis

[57] ABSTRACT

Compounds of the formula

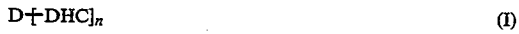

$$D\text{-}[DHC]_n \qquad (I)$$

and the nontoxic pharmaceutically acceptable salt thereof, wherein D is the residue of a centrally acting drug containing at least one reactive functional group selected from the group consisting of amino, hydroxyl, mercapto, carboxyl, amide and imide, said residue being characterized by the absence of a hydrogen atom from at least one of said reactive functional groups in said drug; n is a positive integer equal to the number of said functional groups from which a hydrogen atom is ab- (Abstract continued on next page.)

sent; and [DHC] is the reduced, biooxidizable, blood-brain barrier penetrating lipoidal form of a dihydropyridine⇌pyridinium salt redox carrier, said carrier comprising a bivalent radical of the formula

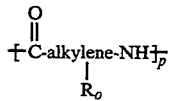

wherein the alkylene group can be straight or branched and can contain 1 to 3 carbon atoms; $R_o$ is a radical identical to the corresponding portion of a natural amino acid; and p is 1 or 2, provided that, when p is 2, then the alkylene groups can be the same or different and the $R_o$ radicals can be the same or different; said bivalent radical being so positioned that the terminal carbonyl function of the bivalent radical is linked to the drug residue while the terminal amino function of the bivalent radical is linked to the remaining portion of the carrier moiety; are adapted for the site-specific/sustained delivery of centrally acting drugs to the brain. The corresponding pyridinium salt type drug/carrier entities $D\ [QC^+]_n\ qY^{-t}$ are also disclosed.

28 Claims, No Drawings

REDOX CARRIERS FOR BRAIN-SPECIFIC DRUG DELIVERY

CROSS-REFERENCE TO RELATED APPLICATIONS

This application is a division of application Ser. No. 07/295,663, filed Jan. 11, 1989, now U.S. Pat. No. 5,087,618, which is a division of application Ser. No. 06/666,210, filed Oct. 29, 1984, now U.S. Pat. No. 4,829,070, which is a continuation-in-part of my earlier applications Ser. No. 06/379,316, filed May 18, 1982, now U.S. Pat. No. 4,479,932; Ser. No. 06/461,543, filed Jan. 27, 1983, abandoned in favor of Ser. No. 06/733,463, filed May 13, 1985, now U.S. Pat. No. 4,727,079; Ser. No. 06/475,493, filed Mar. 15, 1983, now U.S. Pat. No. 4,622,218, and Ser. No. 06/515,382, filed Jul. 22, 1983, now U.S. Pat. No. 4,540,564. Each of said earlier applications is hereby expressly incorporated by reference in its entirely and relied upon.

FIELD OF THE INVENTION

The present invention relates to a dihydropyridine/-pyridinium salt type of redox system for the site-specific or sustained delivery (or both) of a wide variety of drug species to the brain. More especially, this invention relates to the discovery that a biologically active compound coupled to a lipoidal carrier moiety comprising a dihydropyridine nucleus readily and easily penetrates the blood-brain barrier ("BBB") and attains increased levels of concentration in the brain; oxidation of the dihydropyridine carrier moiety in vivo to the ionic pyridinium salt prevents its elimination from the brain, while elimination from the general circulation is accelerated, resulting in significant and prolongedly sustained brain-specific drug activity, whether ascribable to the cleavage of the drug/quaternary entity and sustained release of the drug in the brain and/or to the drug/quaternary itself.

BACKGROUND OF THE INVENTION

The delivery of drug species to the brain is ofttimes seriously limited by transport and metabolism factors and, more specifically, by the functional barrier of the endothelial brain capillary wall deemed the blood-brain barrier, BBB. Site-specific delivery and sustained delivery of drugs to the brain are even more difficult.

It has been previously suggested to deliver a drug species, specifically N-methylpyridinium-2-carbaldoxime chloride (2-PAM), into the brain, the active nucleus of which in and of itself constitutes a quaternary pyridinium salt, by way of the dihydropyridine latentiated prodrug form thereof. Such approach was conspicuously delimited to relatively small molecule quaternary pyridinium ring-containing drug species and did not provide the overall ideal result of brain-specific, sustained release of the desired drug, with concomitant rapid elimination from the general circulation, enhanced drug efficacy and decreased toxicity. Hence, no "trapping" in the brain of the 2-PAM formed in situ resulted, and obviously no brain-specific, sustained delivery occurred as any consequence thereof: the 2-PAM was eliminated as fast from the brain as it was from the general circulation and other organs. Compare U.S. Pat. Nos. 3,929, 813 and 3,962,447; Bodor et al, *J. Pharm. Sci.*, 67, No. 5, pp. 685–687 (1978); Bodor et al, *Science,* Vol. 190 (1975), pp. 155–156; Shek, Higuchi and Bodor, *J. Med. Chem.*, Vol. 19 (1976), pp. 113–117. A more recent extension of this approach is described by Brewster, *Dissertation Abstracts International,* Vol. 43, No. 09, March 1983, p. 2910B. It has a also been speculated to deliver, e.g., an antitumor agent, into the brain by utilizing a dihydropyridine/pyridinium redox carrier moiety therefor, but this particular hypothesis necessarily entails derivatizing the dihydropyridine/-pyridinium carrier with a substituent itself critically designed to control the release rate of the active drug species itself; Bodor et al, *J. Pharm. Sci.,* supra. See also Bodor, "Novel Approaches for the Design of Membrane Transport Properties of Drugs", in *Design of Biopharmaceutical Properties Through Prodrugs and Analogs,* Roche, E. B. (ed.), APhA Academy of Pharmaceutical Sciences, Washington, D.C., pp. 98–135 (1976).

More recently, the present inventor and his coworkers, in Bodor et al, *Science,* Vol. 214, December 18, 1981, pp. 1370–1372, have reported on site-specific sustained release of drugs to the brain. The *Science* publication outlines a scheme for specific and sustained delivery of drug species to the brain, as depicted in the following Scheme:

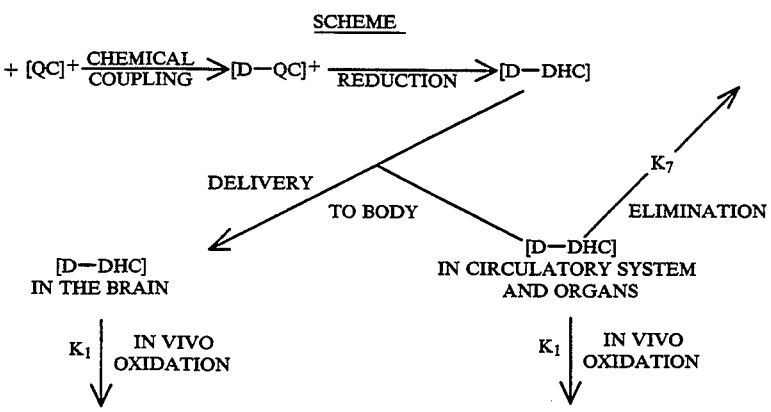

SCHEME

SCHEME -continued

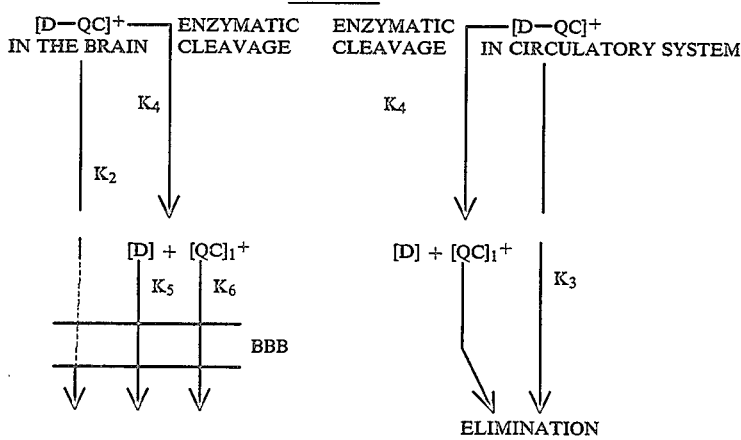

According to the scheme in *Science*, a drug [D] is coupled to a quaternary carrier [QC]+ and the [D-QC]+ which results is then reduced chemically to the lipoidal dihydro form [D-DHC]. After administration of [D-DHC] in vivo, it is rapidly distributed throughout the body, including the brain. The dihydro form [D-DHC] is then in situ oxidized (rate constant, $k_1$) (by the NAD⇌NADH system) to the ideally inactive original [D-QC]+ quaternary salt which, because of its ionic, hydrophilic character, should be rapidly eliminated from the general circulation of the body, while the blood-brain barrier should prevent its elimination from the brain ($k_3 >> k_2$; $k_3 >> k_7$). Enzymatic cleavage of the [D-QC]+ that is "locked" in the brain effects a sustained delivery of the drug species ]D], followed by its normal elimination ($k_5$), metabolism. A properly selected carrier [QC]+ will also be rapidly eliminated from the brain ($k_6 >> K_2$). Because of the facile elimination of [D-QC]+ from the general circulation, only minor amounts of drug are released in the body ($k_3 >> k_4$); [D] will be released primarily in the brain ($k_4 > k_2$). The overall result ideally will be a brain-specific sustained release of the target drug species.

Bodor et al have reported, in *Science*, their work with phenylethylamine as the drug model, which was coupled to nicotinic acid, then quaternized to give compounds of the formula

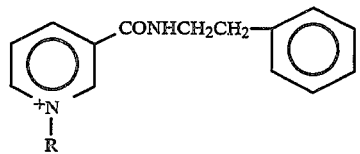

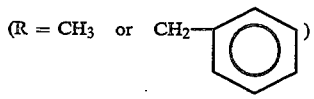

which were subsequently reduced by sodium dithionite to the corresponding compounds of the formula

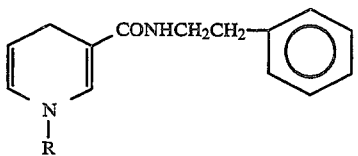

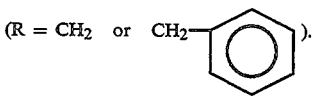

Testing of the N-methyl derivative in vivo supported the criteria set forth in the Scheme. Bodor et al speculated that various types of drugs might possibly be delivered using the depicted or analogous carrier systems and indicated that use of N-methylnicotinic acid esters and amides and their pyridine ring-substituted derivatives was being studied for delivery of amino- or hydroxyl-containing drugs, including small peptides, to the brain. No other possible specific carriers were disclosed.

Other reports of the present inventor's work have appeared in *The Friday Evening Post*, Aug. 14, 1981, Health Center Communications, University of Florida, Gainesville, Fla.; *Chemical & Engineering News*, Dec. 21, 1981, pp. 24–25; and *Science News*, Jan. 2, 1982, Vol. 121, No. 1, page 7. These publications do not suggest any carrier systems other than the specific N-methyl and N-benzyl nicotinic acid-type carriers disclosed in the *Science* publication. Other classes of drugs as well as a few specific drugs are mentioned as possible candidates for derivatization; for example, steroid hormones, cancer drugs and memory enhancers are indicated as targets for possible future work, as are enkephalins, and specifically, dopamine and testosterone. The publications do not suggest how to link such drugs to the carrier except possibly when the drugs are simple structures containing a single $NH_2$ or, perhaps, simple structures containing a single OH, of the primary or secondary type, as is the case with phenylethylamine or testosterone. There is, for example, no suggestion of how one of ordinary skill in the art would form a drug-carrier combination when the drug has a more complicated chemical structure than phenylethylamine, e.g., dopamine or an enkephalin. For further details concerning the work with phenylethylamine, dopamine and testosterone, see also Bodor et al, *J. Med. Chem.*, Vol. 26, March 1983, pp. 313-317; Bodor et al, *J. Med. Chem.*, Vol. 26, April 1983, pp. 528-534; Bodor et al, *Pharmacology and Therapeutics*, Vol. 19, No. 3, pp. 337-386 (April 1983); Bodor et al, *Science*, Vol. 221, July 1983, pp. 65-67; and Bodor et al, *J. Pharm. Sci.*, Vol. 73, No. 3, March 1984, pp. 385-388.

In view of the foregoing, it is apparent that an acutely serious need exists for a truly effective, generic but nonetheless flexible, method for the site-specific or sustained delivery, or both, of drug species to the brain. This need has been addressed by the earlier copending applications referred to hereinabove, and especially by the Ser. Nos. 379,316 and 516,382, now U.S. Pat. Nos. 4,479,932 and 4,540,564, respectively, which provide such a generic method for site-specific, sustained delivery of drugs to the brain utilizing a dihydropyridine⇌pyridinium salt type of redox carrier system. According to those applications, a drug (typically having a reactive hydroxyl, carboxyl or amino group) can be coupled to a dihydropyridine⇌pyridinium carrier; the lipoidal dihydro form of the drug-carrier system readily crosses the blood-brain barrier; the dihydropyridine moiety is then oxidized in vivo to the ideally inactive quaternary form, which is "locked in" the brain, while it is facilely eliminated from the general circulation; enzymatic cleavage of the "locked in" quaternary effects a sustained delivery of the drug itself to the brain, to achieve the desired biological effect. The aforementioned earlier applications disclose a variety of specific carriers for use in site-specific drug delivery. Nevertheless, a need still exists for additional specific carriers which incorporate the dihydropyridine⇌pyridinium salt redox system and which can be coupled to drugs to deliver them in a sustained, site-specific manner. Such additional carriers would enhance the flexibility of the present inventor's dihydropyridine/pyridinium salt redox carrier system as described in his earlier copending applications, since new dihydropyridine/pyridinium salt redox carriers could be used to modify the rate of oxidation of the dihydro form to the corresponding quaternary and/or to modify the rate of release of the drug itself from the "locked in" quaternary form. This need is met by the invention described herein.

SUMMARY OF THE INVENTION

It has now been found that applicant's chemical delivery system as described in his earlier applications can be expanded to include use of new classes of dihydropyridine⇌pyridinium salt type redox carriers; and that this expanded system is well suited for an effective site-specific and/or sustained and/or enhanced delivery of drugs to the brain.

In one aspect, the present invention thus provides, as an effective drug delivery system, novel compounds of the formula $$D\text{-}[DHC]_n \qquad (I)$$

and the nontoxic pharmaceutically acceptable salts thereof, wherein D is the residue of a centrally acting drug containing at least one reactive functional group selected from the group consisting of amino, hydroxyl, mercapto, carboxyl, amide and imide, said residue being characterized by the absence of a hydrogen atom from at least one of said reactive functional groups in said drug; n is a positive integer equal to the number of said functional groups from which a hydrogen atom is absent; and [DHC] is the reduced, biooxidizable, blood-brain barrier penetrating lipoidal form of a dihydropyridine⇌pyridinium salt redox carrier, said carrier comprising a bivalent radical of the formula

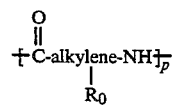

wherein the alkylene group can be straight or branched and can contain 1 to 3 carbon atoms; $R_o$ is a radical identical to the corresponding portion of a natural amino acid; and p is 1 or 2, provided that, when p is 2, then the alkylene groups can be the same or different and the $R_o$ radicals can be the same or different; said bivalent radical being so positioned that the terminal carbonyl function of the bivalent radical is linked to the drug residue while the terminal amino function of the bivalent radical is linked to the remaining portion of the carrier moiety.

In another aspect, the present invention provides, as novel chemical intermediates to the compounds of formula (I), the quaternary salts of the formula $$D\text{-}[QC^+]_n \quad qY^{-t} \qquad (II)$$

wherein D and n are as defined with formula (I); [QC+] is the hydrophilic, ionic pyridinium salt form of a dihydropyridine⇌pyridinium salt redox carrier, said carrier comprising a bivalent radical of the formula

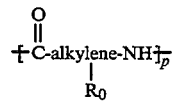

wherein $R_o$, p and the alkylene group are as defined with formula (I), said bivalent radical being positioned as in formula (I); $Y^+$ is the anion of a pharmaceutically acceptable organic or inorganic acid; t is the valence of the acid anion; and q is the number which when multiplied by t is equal to n. The pyridinium salts of formula (II) are not only chemical intermediates to the corresponding compounds of formula (I) but also represent the form of the present chemical delivery system which is "locked in" the brain following administration of the formula (I) dihydro derivatives.

In yet another aspect, the present invention provides a method for specific and/or target enhanced delivery to the brain of a wide variety of centrally acting drug species, such brain-specific drug delivery being effected via the bidirectional transport of the drug species into and out of the brain by means of the particular dihydropyridine⇌pyridinium salt carrier type redox system, (I)⇌(II). Thus, the lipoidal form (I) readily crosses the blood-brain barrier; oxidation of (I) in vivo affords the corresponding pyridinium salt (II) which, because of its hydrophilic, ionic nature, is "locked in" the brain, while it is readily eliminated from the general circulation; and enzymatic cleavage of the "locked in" quaternary effects sustained delivery of the drug itself. The new carriers encompassed by formulas (I) and (II) herein make it possible to modify the rate of oxidation of (I) to (II). Moreover, these new carriers allow more controllable enzymatic cleavage of (II) to release the drug itself, because they are a better substrate for peptidase and esterase than are the corresponding carriers in which a bivalent radical of the formula

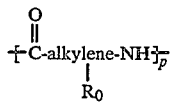

as defined hereinabove does not link the drug to the remainder of the carrier moiety. Cleavage of the bond between the drug portion of the molecule and the terminal carbonyl function of the bivalent radical leads to release of the drug, while the carrier portion of the molecule may be eliminated as such or further cleaved between the terminal amino function of the bivalent radical and the remainder of the carrier. The carrier itself is composed of portions having low toxicity; thus, enhanced drug efficacy and decreased toxicity as compared to administration of the drug itself can be expected from use of the present invention. Moreover, consistent herewith, there is provided enhanced site-specific and sustained delivery to the brain of a wide variety of centrally acting agents which are not themselves able to penetrate the blood-brain barrier to any considerable extent.

DETAILED DESCRIPTION OF THE INVENTION

More particularly, in accord with the present invention, the following definitions are applicable:

The term "drug" as used herein means any substance intended for use in the diagnosis, cure, mitigation, treatment or prevention of disease or in the enhancement of desirable physical or mental development and conditions in man or other animal.

The term "lipoidal" as used herein designates a carrier moiety which is lipid-soluble or lipophilic.

The expression "non-toxic pharmaceutically acceptable salts" as used herein generally includes the non-toxic salts of products of the invention of structure (I) hereinabove formed with non-toxic, pharmaceutically acceptable inorganic or organic acids of the general formula HY. For example, the salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, fumaric, methanesulfonic, toluenesulfonic and the like. The expression "anion of a pharmaceutically acceptable organic or inorganic acid" as used herein, e.g. in connection with structure (II) above, is intended to include anions of such HY acids.

It will be appreciated from the foregoing that a compound of formula (I) may be administered as the free base or in the form of a non-toxic pharmaceutically acceptable salt thereof, i.e. a salt which can be represented by the formula

wherein D, [DHC], n and HY are defined as before; and that, regardless of the actual form in which the compound is administered, it will be converted in vivo to a quaternary salt of formula (II), the anion $Y^-$ being present in vivo. It is not necessary that the anion be introduced as part of the compound administered. Indeed, even when the compound of formula (I) is used in its salt form, the anion of the formula (II) compound in vivo is not necessarily the same as that present in the formula (I) compound. In fact, the exact identity of the anionic portion of the compound of formula (II) is immaterial to the in vivo transformation of (I) to (II).

In the expression "at least one reactive functional group selected from the group consisting of amino, hydroxyl, mercapto, carboxyl, amide and imide" as used herein, the designated reactive functional groups have the following meanings:

The word "amino" means a primary or secondary amino function, i.e. $-NH_2$ or $-NHR$. The secondary amino function is also represented herein as $-NH-$, particularly since the exact identity of the R portion of $-NHR$ is immaterial, R being a part of the drug residue D itself which is left unchanged by this invention.

The word "hydroxyl" means an $-OH$ function.
The word "carboxyl" means a $-COOH$ function.
The word "mercapto" means an $-SH$ function.
The word "amide" means a carbamoyl ($-CONH_2$) or substituted carbamoyl ($-CONHR$) functional group or a sulfamoyl ($-SO_2NH_2$) or substituted sulfamoyl ($-SO_2NHR$) functional group. The $-CONHR$ group may also be represented herein as $-CONH-$, since the exact identity of the R portion of $-CONHR$ is immaterial, R being a part of the drug residue D itself which is left unchanged by this invention. Similarly, the $-SO_2NHR$ group may also be represented herein as $-SO_2NH-$ since the identity of R is likewise immaterial, R being part of the drug residue D itself which is left unchanged by this invention.

The word "imide" means a functional group having the structure

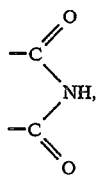

that is, the structure which characterizes imides (i.e. compounds having succinimide-type, or phthalimide-type structures and so forth).

The expression "$R_o$ is a radical identical to the corresponding portion of a natural amino acid" is believed to be self-explanatory. Thus, for example, $R_o$ can be hydrogen, as in glycine; methyl, as in alanine; $-CH(CH_3)_2$, as in valine; $-CH_2-CH(CH_3)_2$, as in leucine; —

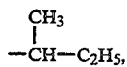

as in isoleucine;

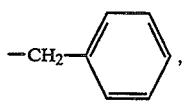

as in phenylalanine;

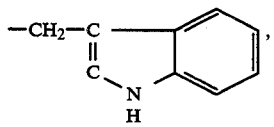

as in tryptophan; —CH$_2$OH, as in serine; —CHOH—CH$_3$, as in threonine; —(CH$_2$)$_2$—SCH$_3$, as in methionine; —CH$_2$—CONH$_2$, as in asparagine; —CH$_2$CH$_2$—CONH$_2$, as in glutamine;

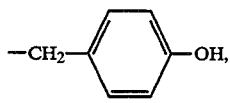

as in tyrosine; —CH$_2$SH, as in cysteine; —CH$_2$COOH, as in aspartic acid; and —CH$_2$CH$_2$COOH, as in glutamic acid. The expression "natural amino acid" as used herein does not encompass dopa or L-DOPA. Preferred amino acids encompassed by the R$_o$ term include glycine, alanine, valine, leucine, phenylalanine, isoleucine, methionine, asparagine and glutamine.

By "centrally acting" drug species, active agent or compound as utilized herein, there is of course intended any drug species or the like, a significant (usually, principal) pharmacological activity of which is CNS and a result of direct action in the brain.

Exemplary such centrally acting drug species are the CNS-amines and other nervous system agents, whether sympathetic or parasympathetic, e.g., phenylethylamine (a stimulant), dopamine (a neurotransmitter and dopaminergic agent used, e.g. in the treatment of Parkinsonism or hyperprolactinemia), tyramine (a stimulant), L-DOPA (a dopamine precursor, used, for example, in the treatment of Parkinsonism); muscle relaxants, tranquilizers and antidepressants, e.g., benzodiazepine tranquilizers such as oxazepam and phenothiazine tranquilizers such as carphenazine, fluphenazine and the like; mild and strong analgesics and narcotics; sedatives and hypnotics; narcotic antagonists; vascular agents; stimulants; anesthetics; antiepileptic and anticonvulsant drugs generally, including hydantoins such as phenytoin and ethotoin; barbituates such phenobarbital; hormones, such as the steroid hormones, e.g., estradiol, testosterone, 17 α-ethynyl testosterone (ethisterone), and the like (recent studies on histological mapping of hormone-sensitive and specific steroid binding cells in the brain have underscored the importance of the steroid action in the brain on sexual behavior); amphetamine-like drugs; anticancer and anti-Parkinsonism agents; antihypertensives; agents to enhance learning capacity and the memory processes, including treatment of dementias, such as Alzheimer's disease; antibacterials; growth promoters; centrally active hypotensive agents; centrally acting prostaglandins; diagnostic agents, such as radiopharmaceuticals ; monoamine oxidase (MAO) inhibitor drugs; and any like centrally acting compounds.

Other illustrative ultimate species of centrally active drug entities are: amphetamine, dextroamphetamine, levamphetamine, aletamine, cypenamine, fencamfamin, fenozolone, zylofuramine, methamphetamine, phenmetrazine and phentermine, which are sympathomimetic amines/cerebral stimulants and appetite suppressants; etryptamine, a cerebral stimulant; codeine, oxycodone, pentazocine, anileridine, hydromorphone, morphine and oxymorphone, which are natcotic analgesics; desipramine, nortriptyline, octriptyline, maprotiline, opipramol and protriptyline, which are cerebral stimulants/tricyclic antidepressants of the dibenzazapine-type used, e.g., in endogenous depressions; clonidine and methyldopa, which are sympatholytic agents used, e.g., in hypertension; biperiden, cycrimine and procyclidine, which are centrally acting anticholinergics; tranylcypromine, a sympathomimetic cerebral stimulant/MAO inhibitor and antidepressant; acetophenazine, carphenazine, fluphenazine, perphenazine and piperacetazine, which are phenothiazine-type tranquilizers; benzoctamine, a sedative/muscle relaxant which structurally is an analogue of the phenothiazine tranquilizers; chlordiazepoxide, clorazepate, nitrazepam and temazepam, which are benzodiazepine-type tranquilizers; noracymethadol, a narcotic analgesic of the methadone-type; piminodine, a narcotic analgesic of the meperidine type; tracazolate, a sedative/hypnotic; tileramine, an anticonvulsant; prizidilol, a centrally acting hypotensive; sulpiride, an antidepressant/psychotropic; haloperidol and clopenthixol, which are tranquilizers; norepinephrine, a sympathetic stimulant/adrenergic agent; nalorphine and naloxone, narcotic antagonists; hydralazine, a hypotensive; ethotoin, phenobarbital and aminoglutethimide, anticonvulsants; epinephrine, an adrenergic agent; ethamivan, a medullary stimulant; bemegride, a barbiturate antagonist; amiphenazole, a stimulant; iopydol, iodopyracet, iodouppurate (o-iodohippuric acid), iodamide and iopanoic acid, which are radiodiagnostics; ephedrine; pseudoephedrine, oxymetazoline and phenylephrine, which are sympathomimetic amines and decongestants; estradiol, estrone and estriol, the natural estrogens; amoxicillin, oxacillin, carbenicillin, benzylpenicillin, phenoxymethylpenicillin, methicillin, nafcillin, ticarcillin, bacampicillin, epicillin, hetacillin, pivampicillin, the methoxymethylester of hetacillin and ampicillin, which are penicillin-type antibiotics; amobarbital, a sedative; trihexyphenidyl, a centrally acting anticholinergic; hydroxyzine, a tranquilizer; chlortetracycline, demeclocycline, minocycline, doxycycline, oxytetracycline, tetracycline and methacycline, which are tetracycline-type antibiotics; clindamycin, lincomycin, nalidixic acid, oxolinic acid and phenazopyridine, antibacterials/antibiotics; bromazepam, demoxepam and lorazepam, benzodtazeptne tranquilizers; phenytoin, an anticonvulsant; glutethimide, a mild hypnotic/sedative; bethanidine and guanethidine, hypotensives/sympatholytics; captopril, a hypotensive; methyprylon, a mild hypnotic; amedalin, bupropion, cartazolate, daledalin, difluanine, fluoxetine and nisoxetine, which are cerebral stimulants; dicloxacillin, a penicillin-type antibacterial; butalbital, a barbiturate sedative; γ-vinyl GABA and γ-acetylenic GABA, derivatives of the neurotransmitter GABA for possible use in epilepsy; valproic acid and its metabolites such as 5-hydroxy-2-n-propylpentanoic acid, 4-hydroxy-2-n-propylpentanoic acid and 3-hydroxy-2-n-propylpentanoic acid, also for use as anticonvulsants; valpromide, a valproic acid derivative for use as an anticonvulsant; apomorphine, a narcotic depressant/emetic, which has been used in the treatment of photosensitive epilepsy; pholcodine, a narcotic antitussive; methotrexate, mitoxantrone, podophyllotoxin derivatives (etopside, teniposide), doxorubicin, daumamycin and cyclophosphamide, anticancer/antitumor agents; methylphenidate, a stimulant; thiopental, an anesthetic;

ethinyl estradiol and mestranol, estrogens; meptazinol, cyclazocine, phenazocine, profadol, metopon, drocode and myfadol, which are narcotic analgesics; buprenorphine, nalbuphine, butorphanol, levallorphan, naltrexone, alazocine, oxilorphan and nalmexone, which are narcotic antagonists or agonist-antagonists; norgestrel and norethindrone, progestins; cephalothin, cephalexin, cefazolin, cefoxitln, moxalactam, ceforanide, cefroxadine and cephapirin, cephalosporin antibiotics; atenolol, propranolol, nadolol, timolol and metoprolol, β-blockers/hypotensives; sulfadiazine and other sulfonamide antibiotics; ribavarin and acyclovir, antiviral agents; chlorambucil and melphalan, nitrogen mustard-type antlcancer/antitumor agents; methotrexate and aminopterin, which are folic acid antagonist-type anticancer-/antitumor agents; platinum coordination complexes, i.e. cisplatin analogue-type anticancer/antitumor agents; dactinomycin and mitomycin C, used in cancer chemotherapy; thioguanine, a purine/pyrimidine antagonist used in cancer treatment; vincristine and vinblastine, anticancer alkaloids; hydroxyurea and DON, anticancer urea derivatives; N,N'-bis(dichloracetyl)-1,8-octamethylenediamine (fertilysin), an agent for male fertility inhibition; levorphanol, a narcotic, analgesic; benzestrol and diethylstilbestrol, synthetic estrogens; ethyl β-carboline-3-carboxylate, a benzodiazepine antagonist; furosemide, a diuretic/antihypertensive; dipyridamole and nifedipine, coronary vasodilators; progabide, a GABA-agonist and prodrug of GABA. Yet other ultimate species include nonsteroidal antiinflammatory agents/non-narcotic analgesics, e.g., propionic acid derivatives, acetic acid derivatives, fenamic acid derivatives and biphenylcarboxylic acid derivatives. Specific NSAID's/nonnarcotic analgesics contemplated for use herein include ibuprofen, naproxen, flurbiprofen, zomepirac, sulindac, indomethacin, fenbufen, fenoprofen, indoprofen, ketoprofen, fluprofen, bucloxic acid, tolmetin, alclofenac, fenclozic acid, ibufenac, flufenisal, pirprofen, flufenamic acid, mefenamic acid, clonixeril, clonixin, meclofenamic acid, flunixin, diclofenac, carprofen, etodolac, fendosal, prodolic acid, sermetacin, indoxole, tetrydamine, diflunisal, naproxol, piroxicam, metazamide, flutiazin and tesicam.

Preferred classes of centrally acting drugs for use herein are the central neurotransmitters, steroids, anticancer and antitumor agents, antiviral agents, tranquilizers, memory enhancers, hypotensives, sedatives, antipsychotics and cerebral stimulants (especially tricyclic antidepressants). Among the neurotransmitters, there can be mentioned catecholamines, such as doramine, norepinephrine and epinephrine; serotonin, histamine and tryptamine. Among the steroids, there can be mentioned antiinflammatory adrenal cortical steroids such as hydrocortisone, betamethasone, cortisone, dexamethasone, flumethasone, fluprednisolone, meprednisone, methyl prednisolone, prednisolone, prednisone, triamcinolone, cortodoxone, fludrocortisone, flurandrenolone acetonide (flurandrenolide), paramethasone and the like; male sex hormones (androgens), such as testosterone and its close analogues, e.g. methyl testosterone (17-methyltestosterone); and female sex hormones, both estrogens and progestins, e.g., progestins such as norgestrel, norethindrone, norethynodrel, ethisterone, dimethisterone, allylestrenol, cingestol, ethynerone, lynestrenol, norgesterone, norvinisterone, hydroxethynodiol, oxogestone and tigestol, and estrogens such as ethinyl estradiol, mestranol, estradiol, estriol, estrone and quinestrol and the like. Among the anticancer and antitumor agents, there can be mentioned Ara-AC, pentostatin (2'-deoxycoformycin), Ara-C (cytarabine), 3-deazaguanine, dihydro-5-azacytidine, tiazofurin, sangivamycin, Ara-A (vidarabine), 6-MMPR, PCNU, spiromustine, btsbenzimtdazole, L-alanosine, DON (6-diazo-5-oxo-L-norleucine), L-ICRF, trimethyl TMM, 5-methyltetrahydrohomofolic acid, glyoxylic acid sulfonylhydrazone, DACH, SR-2555, SR-2508, desmethylmisonidazole, mitoxantrone, menogarol, aclacinomycin A, phyllanthoside, bactobolin, aphidocolin, homoharringtonine, levonantradol, acivicin, streptozotocin, hydroxyurea, chlorambucil, cyclophosphamide, uracil mustard, melphalan, 5-FUDR (floxuridine), vincristine, vinblastine, cytosine arabinoside, 6-mercaptopurine, hioguanine, 5-azacytidne, methotrexate, adriamycin (doxorubicin), daunomycin (daunorubicin), largomycine polypeptide, aminopterin, dactinomycin, mitomycin C and podophyllotoxin derivatives, such as etoposide (VP-16) and teniposide. Among the antiviral agents, there can be mentioned ribavarin; acyclovir (ACV); amantadine (also of possible value as an anti-Parkinsonism agent); diarylamidines such as 5-amidino-2-(5-amidino-2-benzofuranyl)indole and 4',6-diimidazolino-2-phenylbenzo(b)thiophene; 2-aminoxazoles such as 2-guanidino-4,5-di-n-propyloxazole and 2-guanidino-4,5-diphenyloxazole; benzimidazole analogues such as the syn and anti isomers of 6-[[(hydroxyimino)phenyl]-methyl]-1-[(1-methylethyl)sulfonyl]-1H-benzimidazol-2-amine; bridgehead C-nucleosides such as 5,7-dimethyl-2-β-D-ribofuranosyl-s-triazole(1,5-a)pyrimidine; glycosides such as 2-deoxy-D-glycose, glycosamine, 2-deoxy-2-fluoro-D-mannose and 6-amino-6-deoxy-D-glucose; phenyl glucoside derivatives such as phenyl-6-chloro-6-deoxy-β-D-glycopyranoside; (S)-9-(2,3-dihydroxy-propyl)adenine; 6-azauridine; idoxuridine; trifluridine; BDVU (bisdihydroxyvinyluridine); and 5,6-dichloro-1-β-D-ribofuranosylbenzimidazole. Among the tranquilizers, there can be mentioned benzodiazepine tranquilizers such as oxazepam, lorazepam, chlordiazepoxide, bromazepam, chlorazepate, nitrazepam and temazepam; hydantoin-type tranquilizers/anticonvulsants such as phenytoin, ethotoin and mephenytoin; phenothiazine-type tranquilizers such as acetophenazine, carphenazine, fluphenazine, perphenazine and piperacetazine; and others. Among the hypotensives, there can be mentioned clonidine, methyldopa, bethanidine, debrisoquin, hydralazine, and guanethidine and its analogues. Among the sedatives, tranquilizers and antipsychotics, there can be mentioned the many specific compounds of this type already disclosed above, especially the phenothiazines and benzodiazepines and their analogues. Among the cerebral stimulants, there can also be mentioned the many specific compounds set forth hereinabove, particularly the sympathomimtic amine-type cerebral stimulants and the tricyclic antidepressants, especially preferred tricyclics being the dibenzazepines and their analogues.

Also illustrative of the centrally acting drug species contemplated by this invention are centrally active metabolites of centrally acting drugs. Such metabolites are typified by hydroxylated metabolites of tricyclic antidepressants, such as the E- and Z-isomers of 10-hydroxynortriptyline, 2-hydroxyimipramine, 2-hydroxydesipramine and 8-hydroxychlorimipramine; hydroxylated metabolites of phenothiazine tranquilizers, e.g. 7-hydroxychlorpromazine; and desmethyl metabolites of N-methyl benzodiazepine tranquilizers, e.g. desmethyldiazepam. Other CNS active metabolites for use herein will be apparent to those skilled in the art, e.g. SL75102, which is an active metabolite of progabide, a GABA agonist. Typically, these CNS active metabolites have been identified as such in the scientific literature but have not been administered as drugs themselves. In many cases, the active metabolites are believed to be comparable in CNS activity to their parent drugs; frequently, however, the metabolites have not been administered per se because they are not themselves able to penetrate the blood-brain barrier.

As indicated hereinabove, diagnostic agents, including radiopharmaceuticals, are encompassed by the expression "centrally acting drug" or the like as used herein. Any diagnostic agent which can be derivatized to afford a compound of formula (I) which will penetrate the BBB and concentrate in the brain in its quaternary form (II) and can be detected therein is encompassed by this invention. The diagnostic may be "cold" and be detected by X-ray (e.g. radiopaque agents) or other means such as mass spectrophotometry, NMR or other non-invasive techniques (e.g., when the compound includes stable isotopes such as C 13, N 15, O 18, S 33 and S 34). The diagnostic alternatively may be "hot", i.e. radiolabeled, such as with radioactive iodine (I 123, I 125, I 131) and detected/imaged by radiation detection/imaging means. Typical "cold" diagnostics for derivation herein include o-iodohippuric acid, iothalamic acid, iopydol, iodamide and iopanoic acid. Typical radiolabeled diagnostics include diohippuric acid (I 125, I 131), diotyrosine (I 125, I 131), o-iodohippuric acid (I 131), iothalamic acid (I 125, I 131), thyroxine (I 125, I 131), iotyrosine (I 131) and iodometaraminol (I 123), which has the structural formula

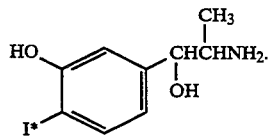

In the case of diagnostics, unlike the drugs which are for treatment or prevention of disease, the "locked in" quaternary form will be the form that is imaged or detected, not the original diagnostic itself. Moreover, any of the centrally acting drugs encompassed by this invention which are intended for the treatment or prevention of medical disorders or the like which can be radiolabeled, e.g. with a radioisotope such as iodine, or labeled with a stable isotope, can thus be converted to a diagnostic for use herein. Put another way, any compound of formula (I) of this invention which can have incorporated into its structure such a radioactive or stable isotope [either directly or through incorporation of the isotope into the structure of the corresponding compound of formula (IX)] can be used for diagnostic purposes.

Specifically excluded from the scope of the expression "centrally acting" drug species, compound or the like as used herein are amino acids, small peptides, such as di-, tri-, tetra- and pentapeptides, and other small 2-20 amino acid unit containing peptides, e.g. enkephalins and endorphins, as well as larger peptides. The specifically excluded amino acids include tryptophan, GABA, glycine, glutamic acid, tyrosine, aspartic acid and other natural amino acids such as those typically incorporated into protein. However, dopa, or L-DOPA, is not classified as an amino acid according to this application or its parent Ser. Nos. 379,316 and 516,382, now U.S. Pat. Nos. 4,479,932 and 4,540,564, respectively, but rather as a CNS amine and dopaminergic agent used, for example, in the treatment of Parkinsonism; thus, L-DOPA is not intended to be excluded from derivation according to this invention, but on the contrary is a particularly significant centrally acting drug encompassed hereby.

It will be apparent from the known structures of the many drug species exemplified above, that in many cases the selected drug will possess more than one reactive functional group, and, in particular, that the drug may contain hydroxyl or carboxyl or amino or other functional groups in addition to the groups to which the carrier will be linked and that these additional groups will at times benefit from being protected during synthesis and/or during administration. The nature of such protection is described in more detail below. Obviously, such protected drug species are encompassed by the definition of "drug" set forth hereinabove.

The expression "hydroxyl protective group" as used hereinbelow is intended to designate a group which is inserted in place of the hydrogen atom(s) of an OH group or groups in order to prevent premature metabolism of said OH group or groups prior to the compound's reaching the desired site in the body. Typical hydroxyl protective groups contemplated by the present invention are acyl groups and carbonates.

When the hydroxyl protective group is acyl (i.e., when it is an organic radical derived from a carboxylic acid by removal of the hydroxyl group), it preferably represents an acyl radical select ed from the group consisting of alkanoyl having 2 to 8 carbon atoms; alkenoyl having one or two double bonds and 3 to 8 carbon atoms;

wherein the cycloalkyl portion contains 3 to 7 ring atoms and r is zero, one, two or three; phenoxyacetyl; pyridinecarbonyl; and

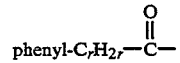

wherein r is zero, one, two or three and phenyl is unsubstituted or is substituted by 1 to 3 alkyl each having 1 to 4 carbon atoms, alkoxy having 1 to 4 carbon atoms, halo, trifluoromethyl, dialkylamino having 2 to 8 carbon atoms or alkanoylamino having 2 to 6 carbon atoms.

When the acyl group is alkanoyl, there are included both unbranched and branched alkanoyl, for example, acetyl, propionyl, butyryl, isobutyryl, valeryl, isovaleryl 2-methylbutanoyl, pivalyl (pivaloyl), 3-methylpentanoyl, 3,3 -dimethylbutanoyl, 2,2-dimethylpentanoyl and the like. Pivalyl, isobutyryl and isovaleryl are especially preferred.

When the acyl group is alkenoyl, there are included, for example, crotonyl, 2,5-hexadienoyl and 3,6-octadienoyl.

When the acyl group is

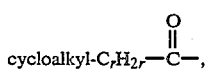

there are included cycloalkanecarbonyl and cycloalkanealkanoyl groups wherein the cycloalkane portion can optionally near 1 or 2 alkyl groups as substituents, e.g. cyclopropanecarbonyl, 1-methylcyclopropanecarbonyl, cyclopropaneacetyl, α-methylcyclopropaneacetyl, 1-methylcyclopropaneacetyl, cyclopropanepropionyl, α-methylcyclopropanepropionyl, 2-isobutylcyclopropanepropionyl, cyclobutanecarbonyl, 3,3-dimethylcyclobutanecarbonyl, cyclobutaneacetyl, 2,2-dimethyl-3-ethylcyclobutaneacetyl, cyclopentanecarbonyl, cyclohexaneacetyl, cyclohexanecarbonyl, cycloheptanecarbonyl and cycloheptanepropionyl. Cyclohexanecarbonyl is especially preferred.

When the acyl group is pyridinecarbonyl, there are included picolinoyl (2-pyridinecarbonyl), nicotinoyl (3-pyridinecarbonyl) and isonicotinoyl (4-pyridinecarbonyl).

When the acyl group is

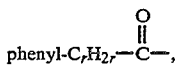

there are included, for example, benzoyl, phenylacetyl, α-phenylpropionyl, β-phenylpropionyl, p-toluyl, m-toluyl, o-toluyl, o-ethylbenzoyl, p-tert-butylbenzoyl, 3,4-dimethylbenzoyl, 2-methyl-4-ethylbenzoyl, 2,4,6-trimethylbenzoyl, m-methylphenylacetyl, p-isobutylphenylacetyl, β(p-ethylphenyl)propionyl, p-anisoyl, m-anisoyl, o-anisoyl, m-isopropoxybenzoyl, p-methoxyphenylacetyl, m-isobutoxyphenylacetyl, m-diethylaminobenzoyl, 3-methoxy-4-ethoxybenzoyl, 3,4,5-trimethoxybenzoyl, p-dibutylaminobenzoyl, 3,4-diethoxyphenylacetyl, β-(3,4,5-trimethoxyphenyl)propionyl, o-iodobenzoyl, m-bromobenzoyl, p-chlorobenzoyl, p-fluorobenzoyl, 2-bromo-4-chlorobenzoyl, 2,4,6-trichlorobenzoyl, p-chlorophenylacetyl, α-(m-bromophenyl)propionyl, p-trifluoromethylbenzoyl, 2,4-di(trifluoromethyl)benzoyl, m-trifluoromethylphenylacetyl, β-(3-methyl-4-chlorophenyl)propionyl, p-dimethylaminobenzoyl, p-(N-methyl-N-ethylamino)benzoyl, o-acetamidobenzoyl, m-propionamidobenzoyl, 3-chloro-4-acetamidophenylacetyl, p-n-butoxybenzoyl, 2,4,6-triethoxybenzoyl, β-(p-trifluoromethylphenyl)propionyl, 2-methyl-4-methoxybenzoyl, p-acetamidophenylpropionyl and 3-chloro-4-ethoxybenzoyl.

When the hydroxyl protective group is a carbonate grouping, it has the structural formula

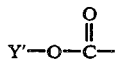

i.e., it is an organic radical which can be considered to be derived from a carbonic acid by removal of the hydroxyl group from the COOH portion. Y' preferably represents alkyl having 1 to 7 carbon atoms; alkenyl having one or two double bonds and 2 to 7 carbon atoms;

cycloalkyl—C$_r$H$_{2r}$— wherein the cycloalkyl portion contains 3 to 7 ring atoms and r is zero, one, two or three; phenoxy; 2-, 3-, or 4-pyridyl; or phenyl—C$_r$H$_{2r}$— wherein r is zero, one, two or three and phenyl is unsubstituted or is substituted by 1 to 3 alkyl each having 1 to 4 carbon atoms, alkoxy having 1 to 4 carbon atoms, halo, trifluoromethyl, dialkylamino having 2 to 8 carbon atoms or alkanoylamino having 2 to 6 carbon atoms. Most preferably, Y' is C$_1$-C$_7$ alkyl, particularly ethyl or isopropyl.

Similarly, the expression "carboxyl protective group" as used hereinbelow is intended to designate a group which is inserted in place of the hydrogen atom(s) of a COOH group or groups in order to prevent premature metabolism of said COOH group or groups prior to the compound's reaching the desired site in the body. Typical carboxyl protective groups are the groups encompassed by Y' above, especially C$_1$-C$_7$ alkyl, particularly ethyl, isopropyl and t-butyl. While such simple alkyl esters and the like are often useful, other carboxyl protecting groups may be selected in order to achieve greater control over the rate of in vivo hydrolysis of the ester back to the acid and thus enhance drug delivery. To that end, carboxyl protecting groups such as the following may be used to replace the hydrogen of the —COOH group:

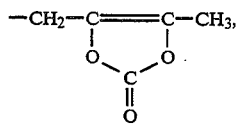

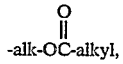
-alk-OC-alkyl,

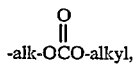
-alk-OCO-alkyl, or

-alk-O-alkyl, wherein alk is C$_1$-C$_6$ straight or branched alkylene and the alkyl radical is straight or branched and contains 1 to 7 carbon atoms

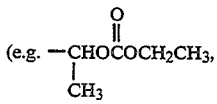

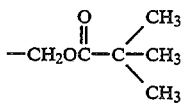

and

—CH$_2$OCH$_3$).

The expression "amino protective group" as used hereinbelow is intended to designate a group which is inserted in place of the hydrogen atom(s) of an amino group or groups in order to prevent unwanted reaction of the amino function(s) during chemical synthesis.

Such protective groups are well-known in the art and include t-butoxycarbonyl and carbobenzoxy (i.e. benzyloxycarbonyl). Other appropriate amino protective groups will be apparent to those skilled in the art. Unlike the instant hydroxyl and carboxyl protective groups described above, which not only prevent unwanted chemical reaction but also protect those hydroxyl and carboxyl functions from premature metabolism in vivo, the amino protective groups are primarily intended for use during synthesis and are typically removed by well-known procedures at an appropriate stage of the synthetic pathway after they have achieved their protective function and are no longer needed. Occasionally, however, an amino protective function will be retained in the compound of formula (I) to also protect the amino group in vivo.

In accord with the present invention, the sustained delivery of a drug to the brain in sufficient concentrations to achieve the desired pharmacological effect can be accomplished with much lower concentrations in the peripheral circulation and other tissues. The present invention of course will allow such treatment of any other organs or glands in which sufficient drug accumulates. Thus, for example, it is expected that the quaternary form (II) which is locked in the brain will be locked in the testes as well. See my earlier copending application Ser. No. 475,493 now U.S. Pat. No. 4,622,218.

The novel chemical delivery system of this invention begins with the preparation of the novel quaternary intermediates of formula (II). The preparation of those intermediates will be tailored to the particular drug portion and carrier portion to be combined, and especially to the nature of the chemical bond between them, e.g. whether the linkage is an ester or amide linkage, as well as to the presence or absence of other reactive functional groups (amino, mercapto, carboxyl, hydroxy) in either the drug or carrier portion. Typically, if such other reactive groups are present, they are found in the drug portion or in the $R_o$ portion of the carrier. In any event, when such groups are present and it is desired to protect them, a step that introduces appropriate protecting groups can be incorporated at a suitable stage of the synthetic pathway. Typical protective groups are well known in the art and have been defined hereinabove. When carbonate protecting groups for alcoholic hydroxyl radicals are desired, the step of introducing the protecting groups will involve reacting the alcohol with a halocarbonate of the type ROCOCl or ROCOBr (formed by reaction of ROH with $COCl_2$ or $COBr_2$, R typically being lower alkyl). For acyl protecting groups, the alcoholic hydroxyl is reacted with an acyl halide RCl or RBr, R being —$COCH_3$ or —$COC(CH_3)_3$. Yet other reaction schemes and reactants will be readily apparent to those skilled in the art as will the appropriate means for removing such protective groups after they have achieved their function and are no longer needed. As already explained above, carboxyl and hydroxyl protecting groups are typically retained in the compounds of formula (I) and (II) rather than being removed, so that they can perform their protective function in vivo as well.

In forming the intermediates of formula (II), at least one amino, hydroxy,l mercapto, carboxyl, amide or imide group in a drug will be bonded to $[QC]^+$, the hydrophilic, ionic pyridinium salt form of a dihydropyridine⇌pyridinium salt redox carrier comprising a divalent radical as defined hereinabove.

It too will be appreciated that by "dihydropyridine carrier" or "[DHC]", there is intended any nontoxic carrier moiety comprising, containing or including the dihydropyridine nucleus, whether or not a part of any larger basic nucleus, and whether substituted or unsubstituted, the only criteria therefor being (1) capacity for BBB penetration and in vivo oxidation thereof to the corresponding quaternary pyridinium salt carrier $[QC^+]$, and (2) incorporation therein of the bivalent radical

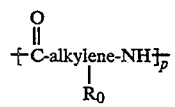

wherein the structural variables are defined as hereinabove. As aforesaid, the ionic pyridinium salt drug/carrier prodrug entity $D\text{+}QC^+]$ which results from such in vivo oxidation is prevented from efflux from the brain, while elimination from the general circulation is accelerated. Subsequently, the bond coupling the drug species to the quaternary carrier $[QC^+]$ is metabolically cleaved which results in sustained delivery of the drug in the brain and facile elimination of the carrier moiety $[QC^+]$. And the cleavage of the quaternary compound (II) to sustainedly deliver the drug species in the brain with concomitant facile elimination of the carrier moiety $[QC^+]$ is characteristically enzymatic cleavage, e.g., by esterase, peptidase, amidase, cholinesterase or hydrolytic enzyme, albeit any type of in brain cleavage which might result, whether enzymatic, metabolic or otherwise, of course remains within the ambit of this invention. Thus, the drug release rate controlling parameter of the compounds of this invention is imparted via the clearable bonding between drug and carrier, and not by any release rate controlling substituent(s).

Dihydropyridine⇌pyridinium salt redox carrier moieties for use herein include the following quaternaries and the corresponding dihydro forms:

(1) For linkage to a drug having at least one hydroxyl or mercapto or primary or secondary amino functional grouping, replacing a hydrogen atom from at least one of said functional groupings with one of the following $[QC^+]$ groupings:

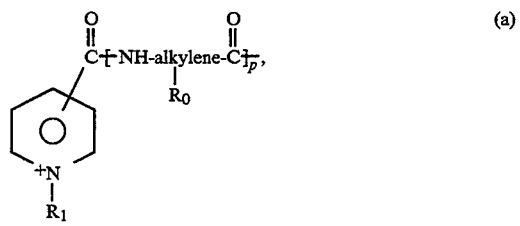

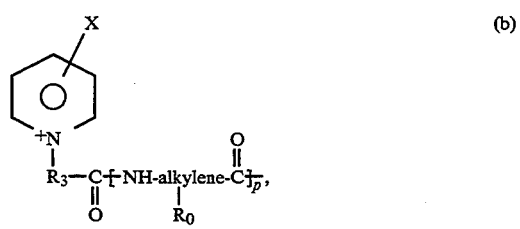

-continued

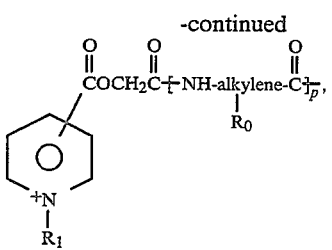 (c)

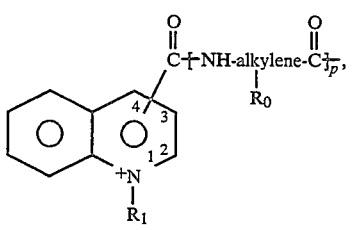 (d)

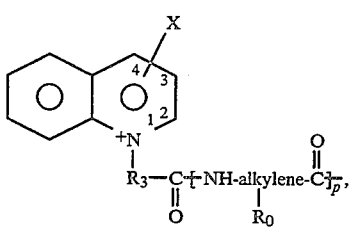 (e)

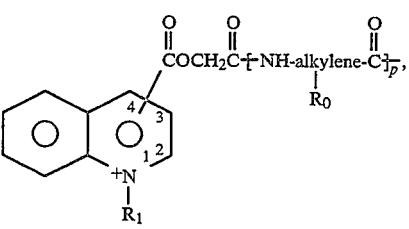 (f)

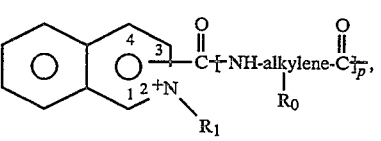 (g)

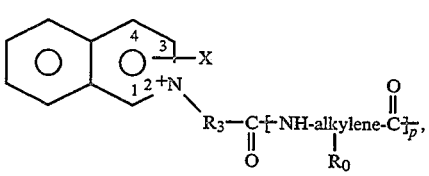 (h)

or

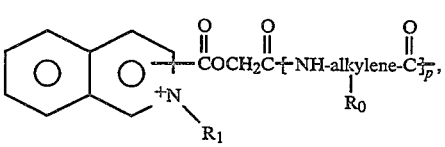 (j)

wherein alkylene, $R_o$ and p are as defined with formula (I) hereinabove; $R_1$ is $C_1$-$C_7$ alkyl, $C_1$-$C_7$ haloalkyl or $C_7$-$C_{10}$ aralkyl; $R_3$ is $C_1$ to $C_3$ alkylene; X is —CONR'R" wherein R' and R", which can be the same or different, are each H or $C_1$-$C_7$ alkyl, or X is —CH=NOR''' wherein R''' is H or $C_1$-$C_7$ alkyl; the carbonyl-containing groupings in formulas (a) and (c) and the X substituent in formula (b) can each be attached at the 2, 3 or 4 position of the pyridinium ring; the carbonyl-containing groupings in formulas (d) and (f) and the X substituent in formula (e) can each be attached at the 2, 3 or 4 position of the quinolinium ring; and the carbonyl-containing groupings in formulas (g) and (j) and the X substituent in formula (h) can each be attached at the 1, 3 or 4 position of the isoquinolinium ring;

(2) For, the linkage to a drug having at least one carboxyl functional grouping, replacing a hydrogen atom from at least one of said carboxyl groupings with one of the following [QC+] groupings:

(a) When there are one or more —COOH groups to be derivatized:

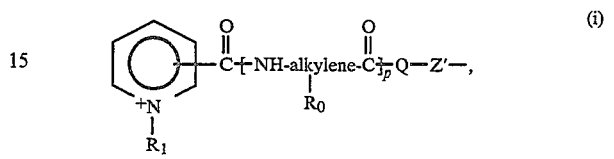 (i)

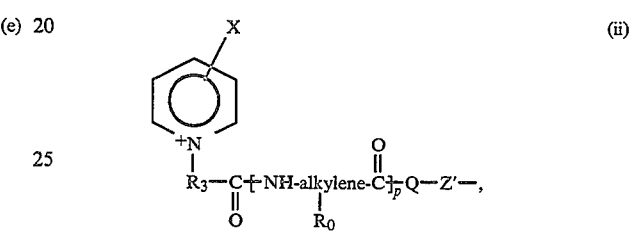 (ii)

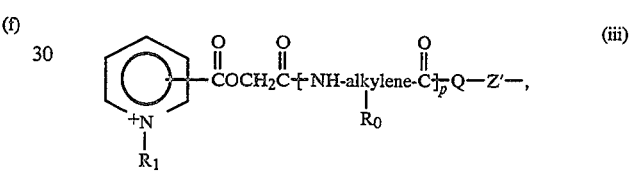 (iii)

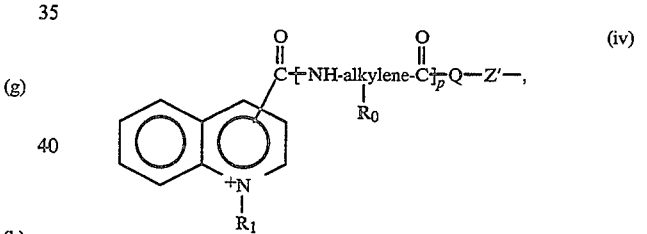 (iv)

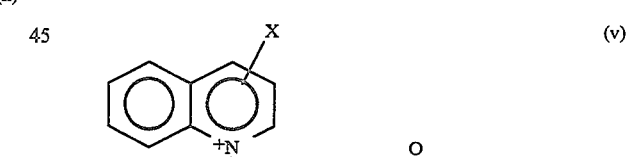 (v)

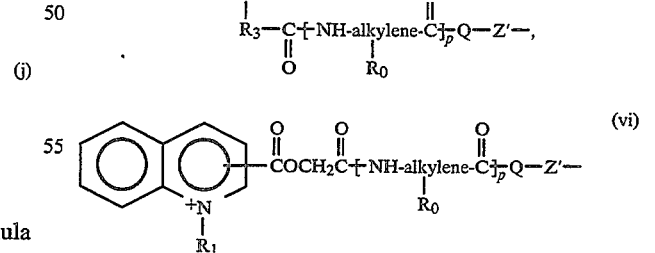 (vi)

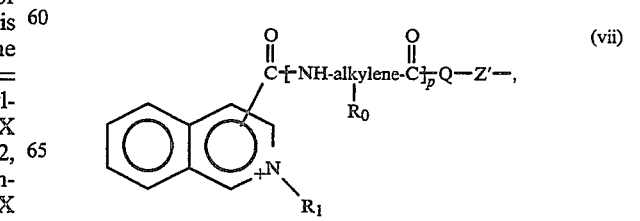 (vii)

-continued

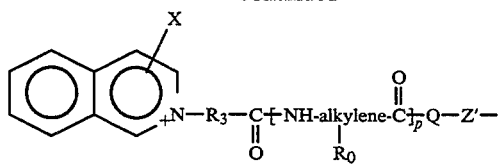
(viii)

or

(ix)

wherein alkylene, $R_o$ and p are as defined with formula (I) hereinabove; $Z'$ is $C_1$-$C_8$ straight or branched alkylene, preferably $C_1$-$C_3$ straight or branched alkylene; Q is —O— or —NH—; $R_1$ is $C_1$-$C_7$ alkyl, $C_1$-$C_7$ haloalkyl or $C_7$-$C_{10}$ aralkyl; $R_3$ is $C_1$-$C_3$ alkylene; X is —CONR'R'' wherein R' and R'', which can be the same or different, are each H or $C_1$-$C_7$ alkyl, or X is —CH=NOR''' where in R''' is H or $C_1$-$C_7$ alkyl; the X substituent in formula (ii) and the carbonyl-containing groupings in formulas (i) and (iii) can each be attached at the 2, 3 or 4 position of the pyridinium ring; the X substituent in formula (v) and the carbonyl-containing groupings, in formulas (iv) and (vi) can each be attached at the 2, 3 or 4 position of the quinolinium ring; and the X substituent in formula (viii) and carbonyl-containing groupings in formulas (vii) and (ix) can each be attached at the 1, 3 or 4 position of the isoquinolinium ring;

(b) Alternatively when there is only one —COOH group to be derivatized:

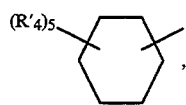
(x)

(xi)

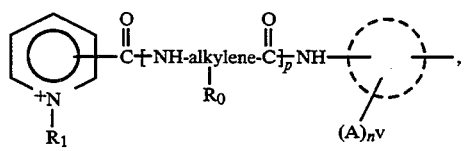
(xii)

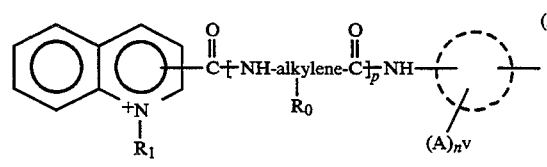
(xiii)

or

-continued

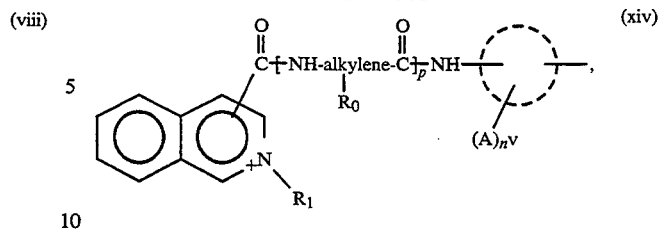
(xiv)

wherein ⌬ is the skeleton of a sugar molecule; $n^{iv}$ is a positive integer equal to the total number of —OH functions in the sugar molecule from which said skeleton is derived; $n^v$ is a positive integer one less than the total number of —OH functions in the sugar molecule from which said skeleton is derived; each A in each of structures (xii), (xiii) and (xiv) can independently be hydroxy or D', D' being the residue of a centrally acting drug containing one reactive carboxyl functional group, said residue being characterized by the absence of a hydrogen atom from said carboxyl functional group in said drug; and each $R'_4$ in each of structures (x) and (xi) can independently be hydroxy,

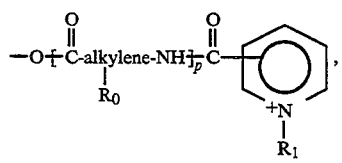

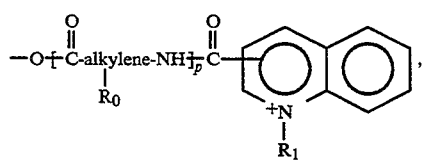

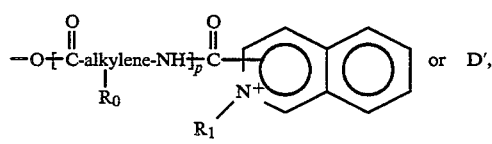
or D', wherein alkylene, $R_o$ and p are defined as with formula (I); D' is defined as with structure (xii), (xiii) and (xiv); $R_1$ is $C_1$-$C_7$ alkyl, $C_1$-$C_7$ haloalkyl or $C_7$-$C_{10}$ aralkyl; and the depicted carbonyl-containing groupings can be attached at the 2, 3 or 4 position of the pyridinium or quinolinium ring, or at the 1, 3 or 4 position of the isoquinolinium ring; with the proviso that at least one $R'_4$ in each of structures (x) and (xi) is

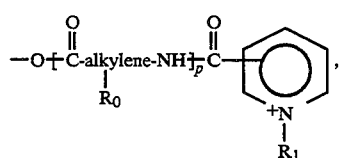

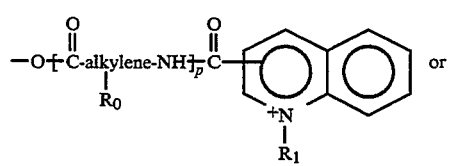
or

-continued

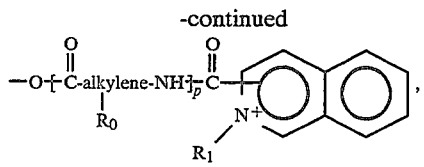

wherein alkylene, $R_o$, p and $R_1$ and the position of the carbonyl-containing groupings are defined as above; and with the further proviso that when more than one of the $R'_4$ radicals in a given compound are the aforesaid carbonyl-containing groupings, then all such carbonyl-containing groupings in said compound are identical.

(3) For linkage to a drug having at least one —NH— functional group which is part of an amide or imide structure or at least one low pKa primary or secondary amine functional group, replacing a hydrogen atom from at least one of said functional groupings with one of the following [QC+] groupings:

(k)
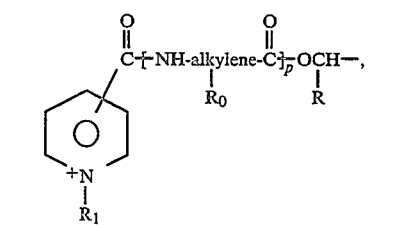

(l)
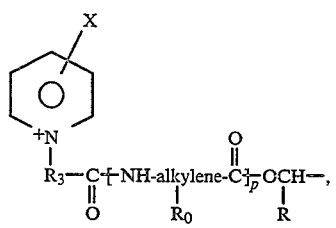

(m)
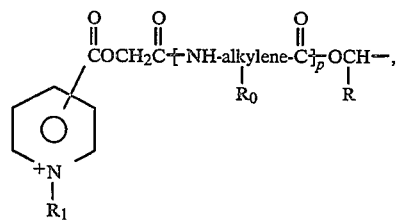

(n)
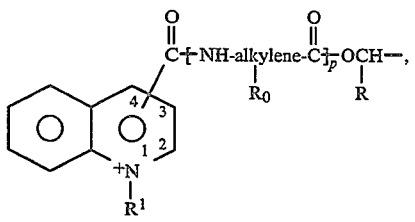

(o)
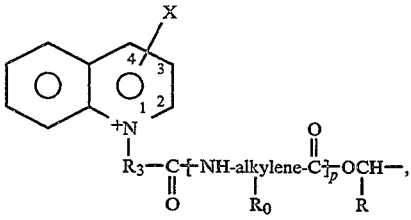

-continued (p)
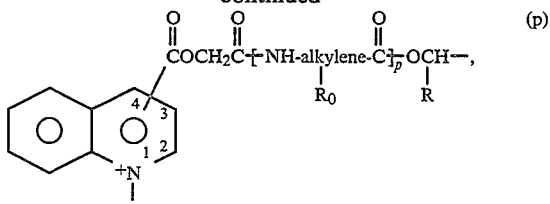

(q)
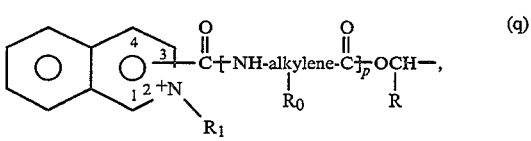

(r)
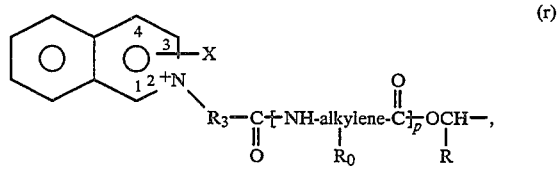

or (s)
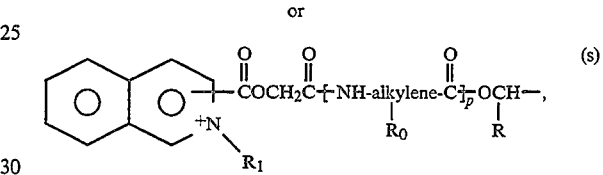

wherein alkylene, $R_o$ and p are as defined with formula (I); $R_1$ is $C_1$-$C_7$ alkyl, $C_1$-$C_7$ haloalkyl or $C_7$-$C_{10}$ aralkyl; R is hydrogen, $C_1$-$C_7$ alkyl, $C_3$-$C_8$ cycloalkyl, $C_1$-$C_7$ haloalkyl, furyl, phenyl, or phenyl substituted by one or more halo, lower alkyl, lower alkoxy, carbamoyl, lower alkoxycarbonyl, lower alkanoyloxy, lower haloalkyl, mono(lower alkyl)carbamoyl, di(lower alkyl)carbamoyl, lower alkylthio, lower alkylsulfinyl or lower alkylsulfonyl; $R_3$ is $C_1$ to $C_3$ alkylene; X is —CONR'R" wherein R' and R", which can be the same or different, are each H or $C_1$-$C_7$ alkyl, or X is —CH=NOR''' wherein R''' is H or $C_1$-$C_7$ alkyl; the carbonyl-containing groupings in formulas (k) and (m) and the X substituent in formula (l) can each be attached at the 2, 3 or 4 position of the pyridinium ring; the carbonyl containing groupings in formulas (n) and (p) and the X substituent in formula (o) can each be attached at the 2, 3 or 4 position of the quintolinium ring; and the carbonyl-containing groupings in formulas (q) and (s) and the X substituent in formula (r) can each be attached at the 1, 3 or 4 position of the isoquinolinium ring. Here and throughout this application, the expression "$C_1$-$C_7$ haloalkyl" means $C_1$-$C_7$ alkyl substituted by one or more halogen atoms. Also here and throughout this application, the alkyl radicals, including alkyl and alkylene portions of other radicals, can be straight or branched unless otherwise specified.

Drugs containing secondary or tertiary hydroxyl functional groups can be linked to any of the [QC]+ groupings (k) through (s) above in which the

portion is derived from an aldehyde $RCH_2O$ capable of reacting with said drug to form the corresponding hemiacetal, as discussed in more detail in Method K' hereinafter.

The dihydro forms [DHC] corresponding to the aforementioned quaternaries are as follows:

(1') For Group (1) above:

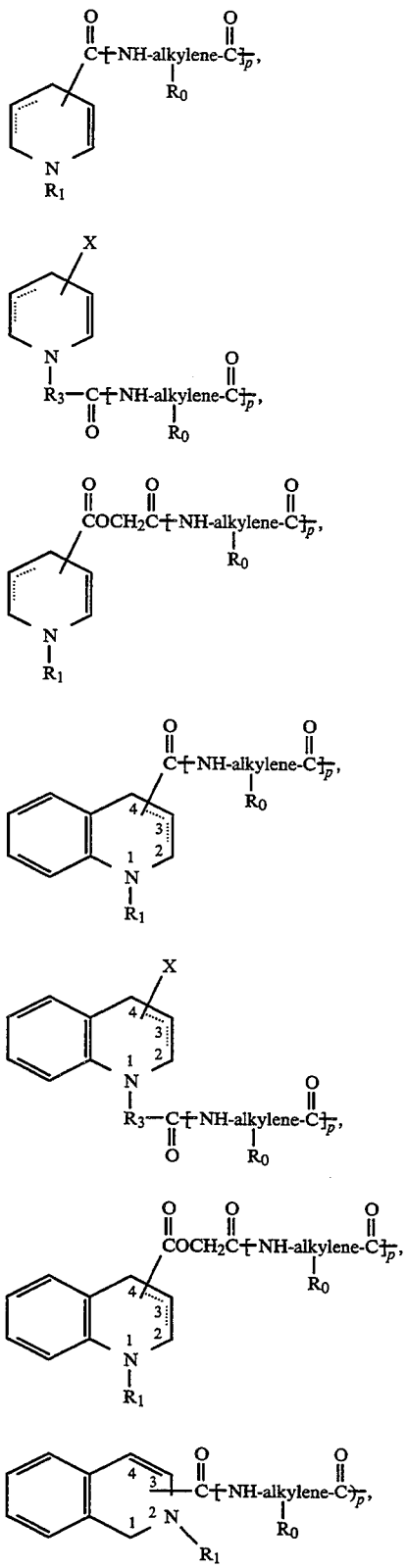

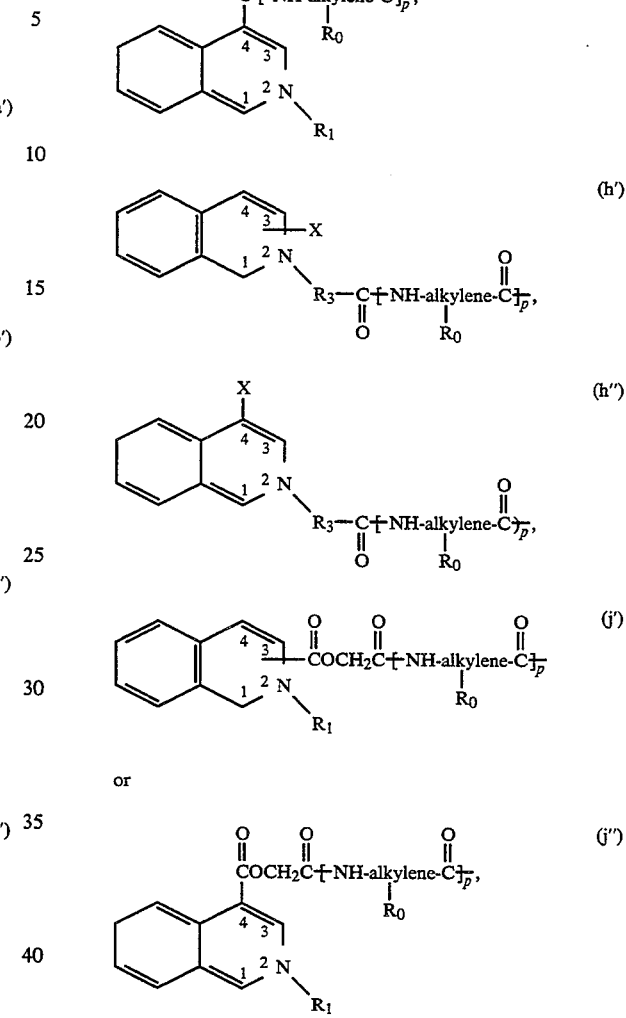

wherein alkylene, $R_o$ and p are as defined with formula (I); the dotted line in formulas (a'), (b') and (c') indicates the presence of a double bond in either the 4 or 5 position of the dihydropyridine ring; the dotted line in formulas (d'), (e') and (f') indicates the presence of a double bond in either the 2 or 3 position of the dihydroquinoline ring; $R_1$ is $C_1$–$C_7$ alkyl, $C_1$–$C_7$ haloalkyl or $C_7$–$C_{10}$ aralkyl; $R_3$ is $C_1$ to $C_3$ alkylene; X is —CONR'R" wherein R' and R", which can be the same or different, are each H or $C_1$–$C_7$ alkyl, or X is —CH=NOR''' wherein R''' is H or $C_1$–$C_7$ alkyl; the carbonyl-containing groupings in formulas (a') and (c') and the X substituent in formula (b') can each be attached at the 2, 3 or 4 position of the dihydropyridine ring; the carbonyl-containing groupings in formulas (d') and (f') and the X substituent in formula (e') can each be attached at 2, 3 or 4 position of the dihydroquinoline ring; and the carbonyl-containing groupings in formulas (g') and (j') and the X substituent in formula (h') can each be attached at 1, 3 or 4 position of the dihydroisoquinoline ring;

(2') For Group (2) (a) above:

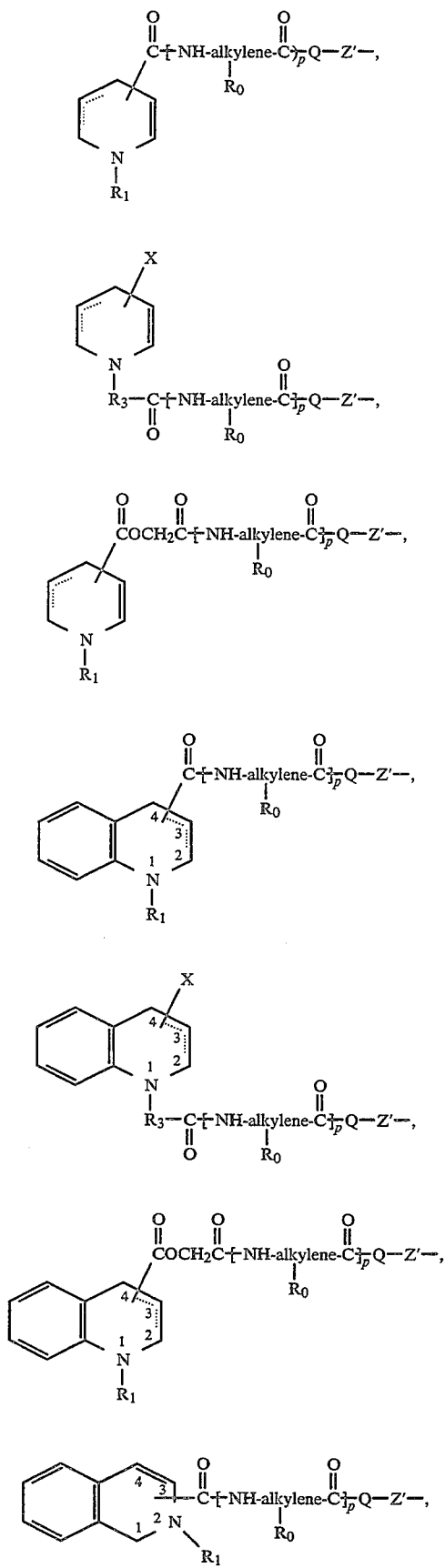
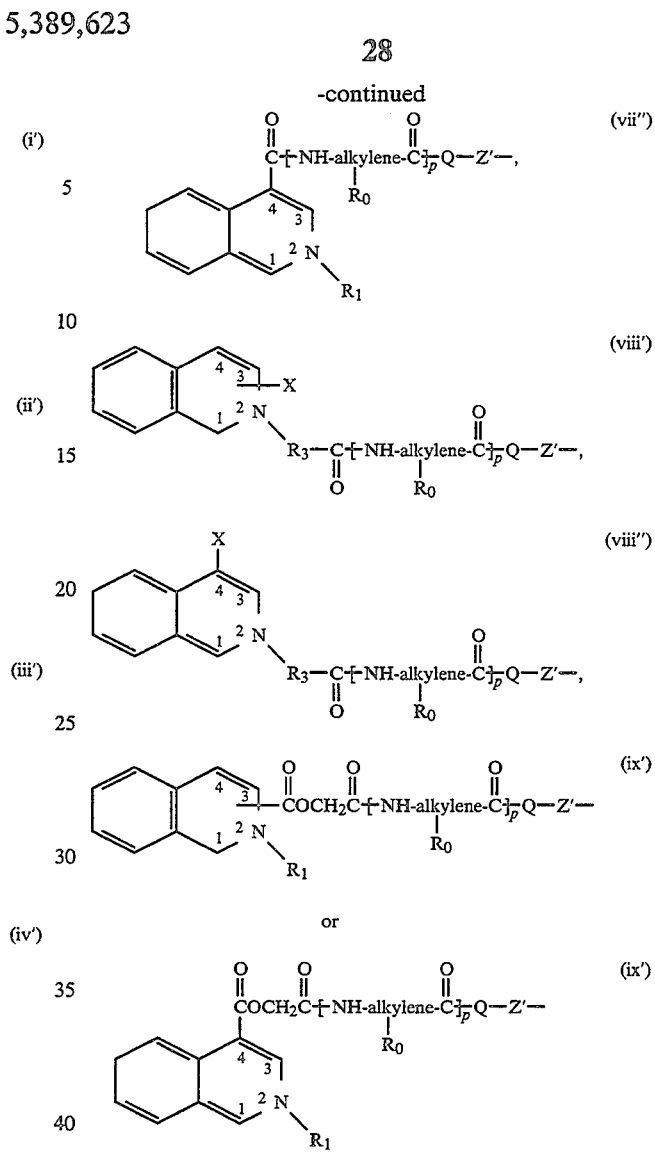

wherein alkylene, $R_o$ and p are as defined with formula (I) hereinabove; the dotted line in formulas (i'), (ii') and (iii') indicates the presence of a double bond in either the 4 or 5 position of the dihydropyridine ring; the dotted line in formulas (iv'), (v') and (vi') indicates the presence of a double bond in either the 2 or 3 position of the dihydroquinoline ring; Z' is $C_1$-$C_8$ straight or branched alkylene, preferably $C_1$-$C_3$ straight or branched alkylene; Q is —O— or —NH—; $R_1$ is $C_1$-$C_7$ alkyl, $C_1$-$C_7$ haloalkyl or $C_7$-$C_{10}$ aralkyl; $R_3$ is $C_1$-$C_3$ alkylene; X is —CONR'R" wherein R' and R", which can be the same or different, are each H or $C_1$-$C_7$ alkyl; or X is —CH=NOR'" wherein R'" is H or $C_1$-$C_7$ alkyl; the X substituent in formula (ii') and the carbonyl-containing grouping in formulas (i') and (iii') can each be attached at the 2, 3 or 4 position of the dihydropyridine ring; the X substituent in formula (v') and the carbonyl-containing grouping in formulas (iv') and (vi') can each be attached at the 2, 3 or 4 position of the dihydroquinoline ring; and the X substituent in formula (viii') and the carbonyl-containing groupings in formulas (vii') and (ix') can each be attached at the 1, 3 or 4 position of the dihydroisoquinoline ring.

(3') For Group (2) (b) above:

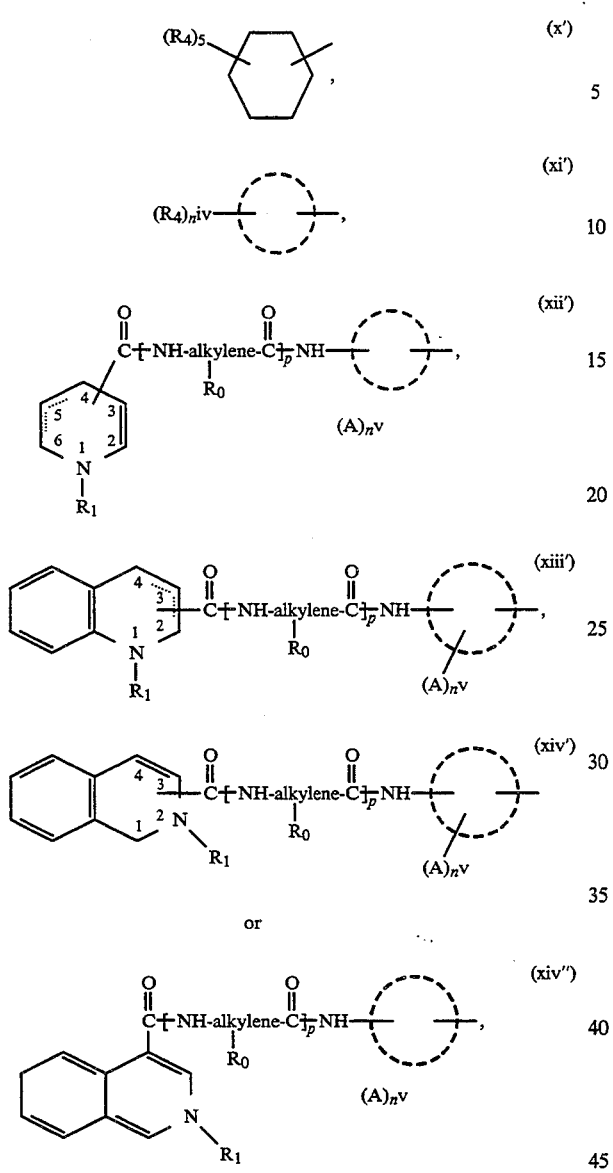

wherein alkylene, $R_o$ and p are as defined with formula (I) above; the dotted line in formula (xii') indicates the presence of a double bond in either the 4 or 5 position of the dihydropyridine ring; the dotted line in formula (xiii') indicates the presence of a double bond in either the 2 or 3 position of the dihydroquinoline ring; ⬡ is the skeleton of a sugar molecule; $n^{iv}$ is a positive integer equal to the total number of —OH functions in the sugar molecule from which said skeleton is derived; $n^v$ is a positive integer one less than the total number of —OH functions in the sugar molecule from which said skeleton is derived; each A in each of structures (xii'), (xiii'), (xiv') and (xiv'') can independently be hydroxy or D', D' being the residue of a centrally acting drug containing one reactive carboxyl functional group, said residue being characterized by the absence of a hydrogen atom from said carboxyl functional group in said drug; and each $R_4$ in each of structures (x') and (xi') can independently be hydroxy, wherein alkylene, $R_o$ and p are defined as with formula (I); the dotted line is defined as with structures (xii') and (xiii'); D' is defined as with structures (xii'), (xiii'), (xiv') and (xiv''); $R_1$ is $C_1$-$C_7$ alkyl, $C_1$-$C_7$ haloalkyl or $C_7$-$C_{10}$ aralkyl; and the depicted carbonyl groupings can be attached at the 2, 3 or 4 position of the pyridinium or quinolinium ring or, except where otherwise specified, at the 1, 3 or 4 position of the isoquinolinium ring; with the proviso that at least one $R_4$ in each of structures (x') and (xi') is wherein alkylene, $R_o$, p, $R_1$, the dotted lines and the position of the carbonyl-containing groupings are defined as above; and with the further proviso that when more than one of the $R_4$ radicals in a given compound are the aforesaid carbonyl-containing groupings, then all such carbonyl-containing groupings in said compound are identical.

(4') For Group (3) above:

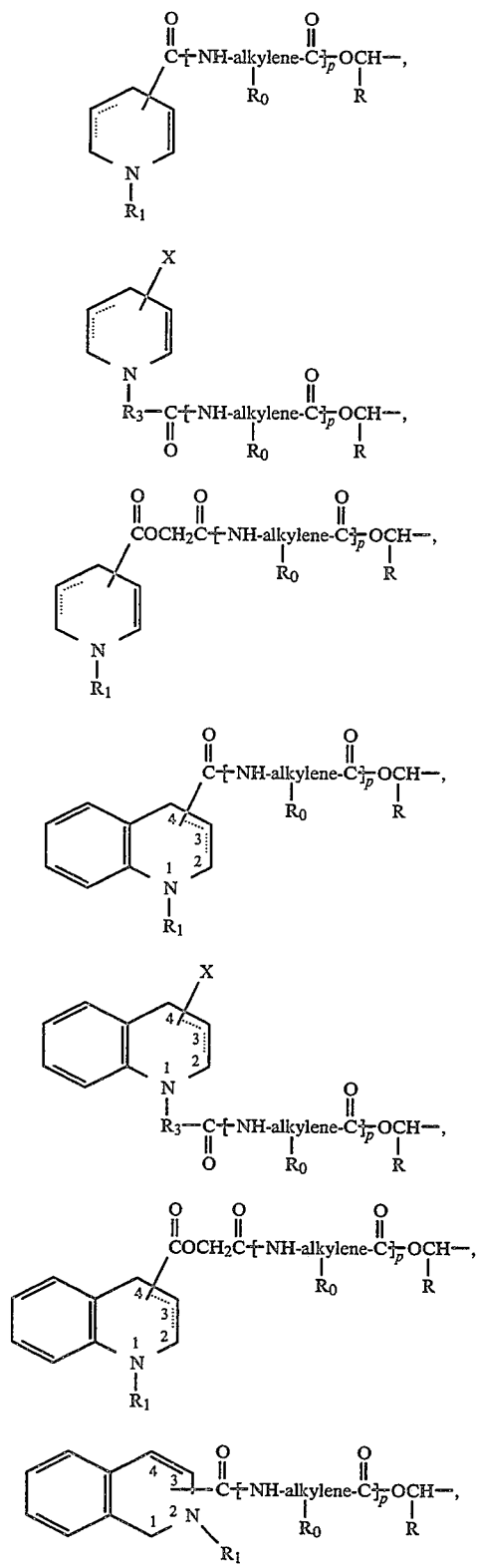

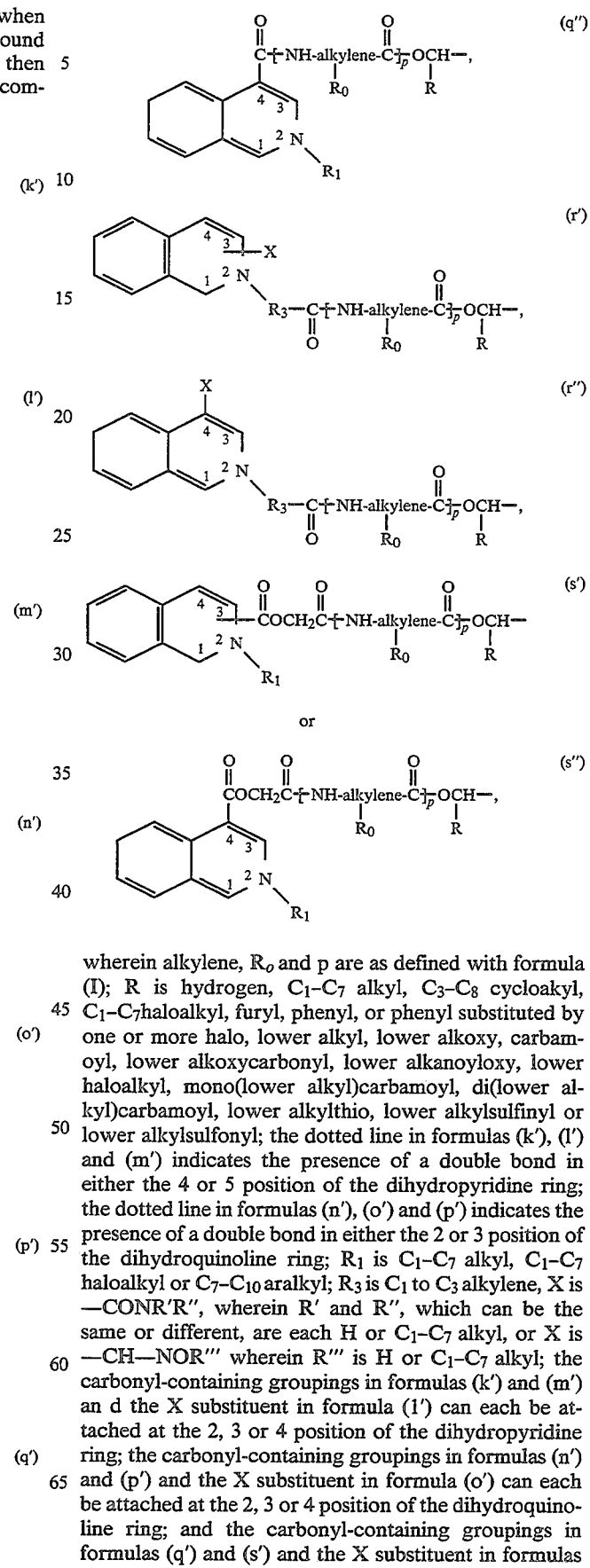

wherein alkylene, $R_o$ and p are as defined with formula (I); R is hydrogen, $C_1$-$C_7$ alkyl, $C_3$-$C_8$ cycloakyl, $C_1$-$C_7$haloalkyl, furyl, phenyl, or phenyl substituted by one or more halo, lower alkyl, lower alkoxy, carbamoyl, lower alkoxycarbonyl, lower alkanoyloxy, lower haloalkyl, mono(lower alkyl)carbamoyl, di(lower alkyl)carbamoyl, lower alkylthio, lower alkylsulfinyl or lower alkylsulfonyl; the dotted line in formulas (k'), (l') and (m') indicates the presence of a double bond in either the 4 or 5 position of the dihydropyridine ring; the dotted line in formulas (n'), (o') and (p') indicates the presence of a double bond in either the 2 or 3 position of the dihydroquinoline ring; $R_1$ is $C_1$-$C_7$ alkyl, $C_1$-$C_7$ haloalkyl or $C_7$-$C_{10}$ aralkyl; $R_3$ is $C_1$ to $C_3$ alkylene, X is —CONR'R", wherein R' and R", which can be the same or different, are each H or $C_1$-$C_7$ alkyl, or X is —CH—NOR''' wherein R''' is H or $C_1$-$C_7$ alkyl; the carbonyl-containing groupings in formulas (k') and (m') an d the X substituent in formula (l') can each be attached at the 2, 3 or 4 position of the dihydropyridine ring; the carbonyl-containing groupings in formulas (n') and (p') and the X substituent in formula (o') can each be attached at the 2, 3 or 4 position of the dihydroquinoline ring; and the carbonyl-containing groupings in formulas (q') and (s') and the X substituent in formulas (r') can each be attached at the 1, 3 or 4 position of the dihydroisoquinoline ring.

The presently preferred dihydropyridine⇌pyridinium salt redox carrier moieties of this invention are those wherein alkylene is —CH₂—; p is 1; R_o is H, —CH₃, —CH(CH₃)₂, —CH₂—CH(CH₃)₂,

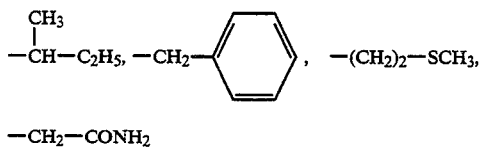

—CH₂—CONH₂ or —CH₂CH₂—CONH₂; R₁, when present, is —CH₃; R₃, when present, is —CH₂CH₂—; X when present, is —CONH₂; the depicted carbonyl -containing groupings in formulas (a) and (c) and the X substituent in formula (b) are attached at the 3-position; the depicted carbonyl-containing groupings in formulas (d) and (f) and the X substituent in formula (e) are attached at the 3-position; the depicted carbonyl-containing groupings formulas (g) and (j) and the X substituent in formula (h) are attached at the 4-position; Z', when present, is C₂ or C₃ straight or branched alkylene; Q, when present, is —NH—; the X substituent in formulas (ii) and (v) and the depicted carbonyl-containing groupings in formulas (i), (iii), (iv) and (vi) are attached at the 3-position; the X substituent in formula (viii) and the depicted carbonyl-containing groupings is formulas (vii) and (ix) are attached at the 4-position; and the depicted carbonyl-containing groupings encompassed by formulas (x), (xi), (xii), (xiii) and (xiv) are in the 3-position of the pyridinium or quinolinium ring and in the 4-position of the isoquinolinium ring; all R'₄'s in structures (x) and (xi) are —OH except for the one R₄ in each structure which must be the carrier moiety; all A's in structures (xii), (xiii) and (xiv) are —OH; ◯ is skeleton of a glucose molecule; R in formulas the (k), (l) and (m) is hydrogen, methyl or CCl₃; and the depicted carbonyl-containing groupings in formulas (k) through (s) are in the 3-position of the pyridinium or quinolinium ring and in the 4-position of the isoquinolinium ring; and the corresponding dihydro moieties.

Especially preferred dihydropyridine⇌pyridinium salt redox carrier moieties are the quaternaries of Group (1), structures (a), (b), (d), (e), (g) and (h); those of Group (2), structures (i), (ii), (iv), (v), (vii), (viii), (x) and (xii); and those of Group 3, structures (k), (l), (n), (o), (q) and (r); and the corresponding dihydro forms, most especially when they contain the preferred structural variables identified in the preceding paragraph.

The following synthetic schemes illustrate various approaches to the preparation of the compounds of this invention.

SCHEME 1

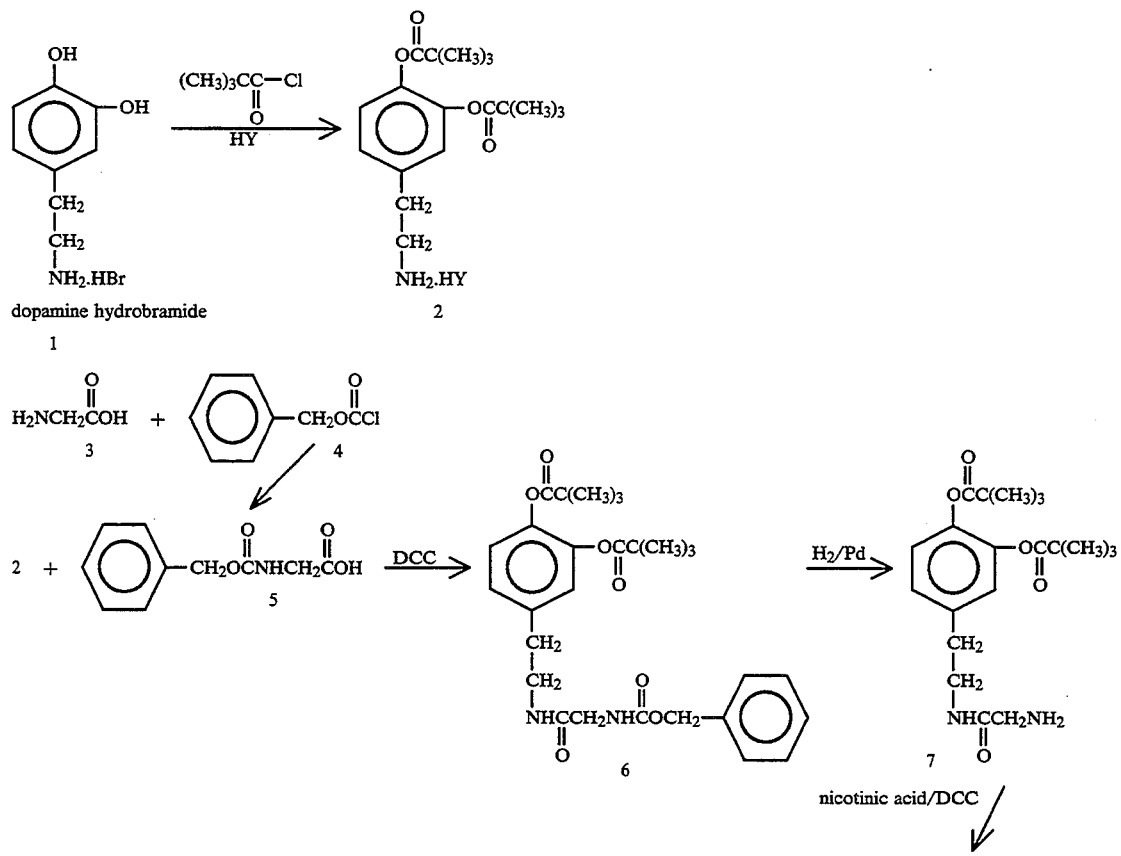

SCHEME 1
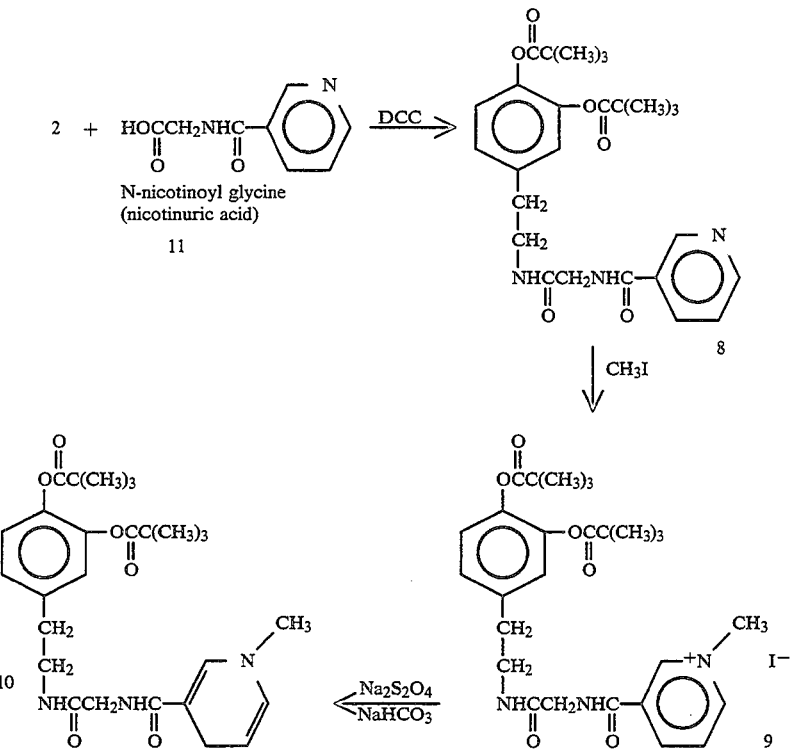
SCHEME 2
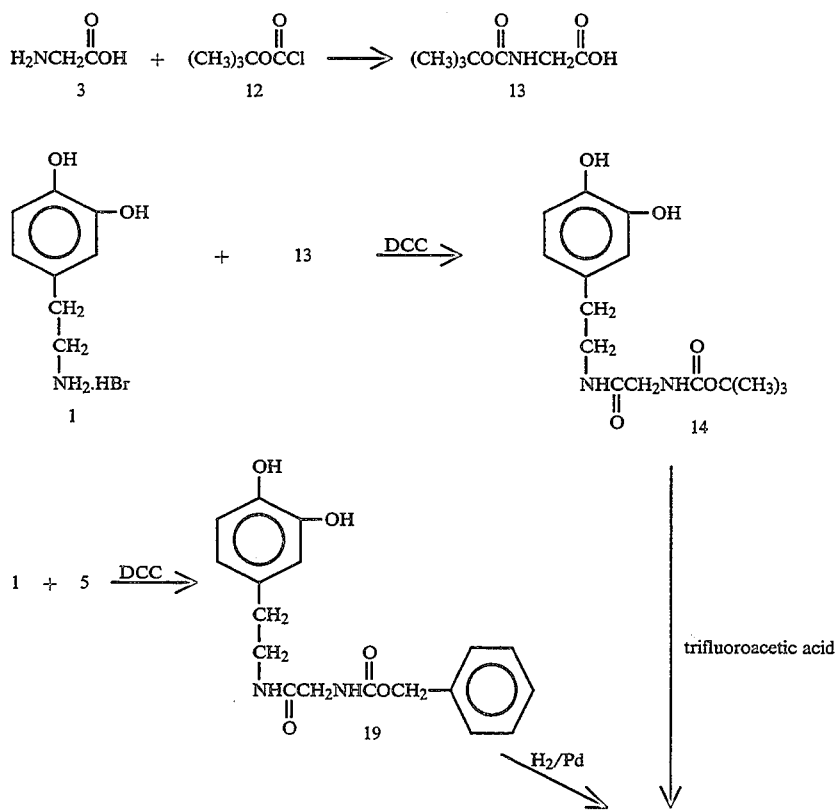

-continued
SCHEME 2
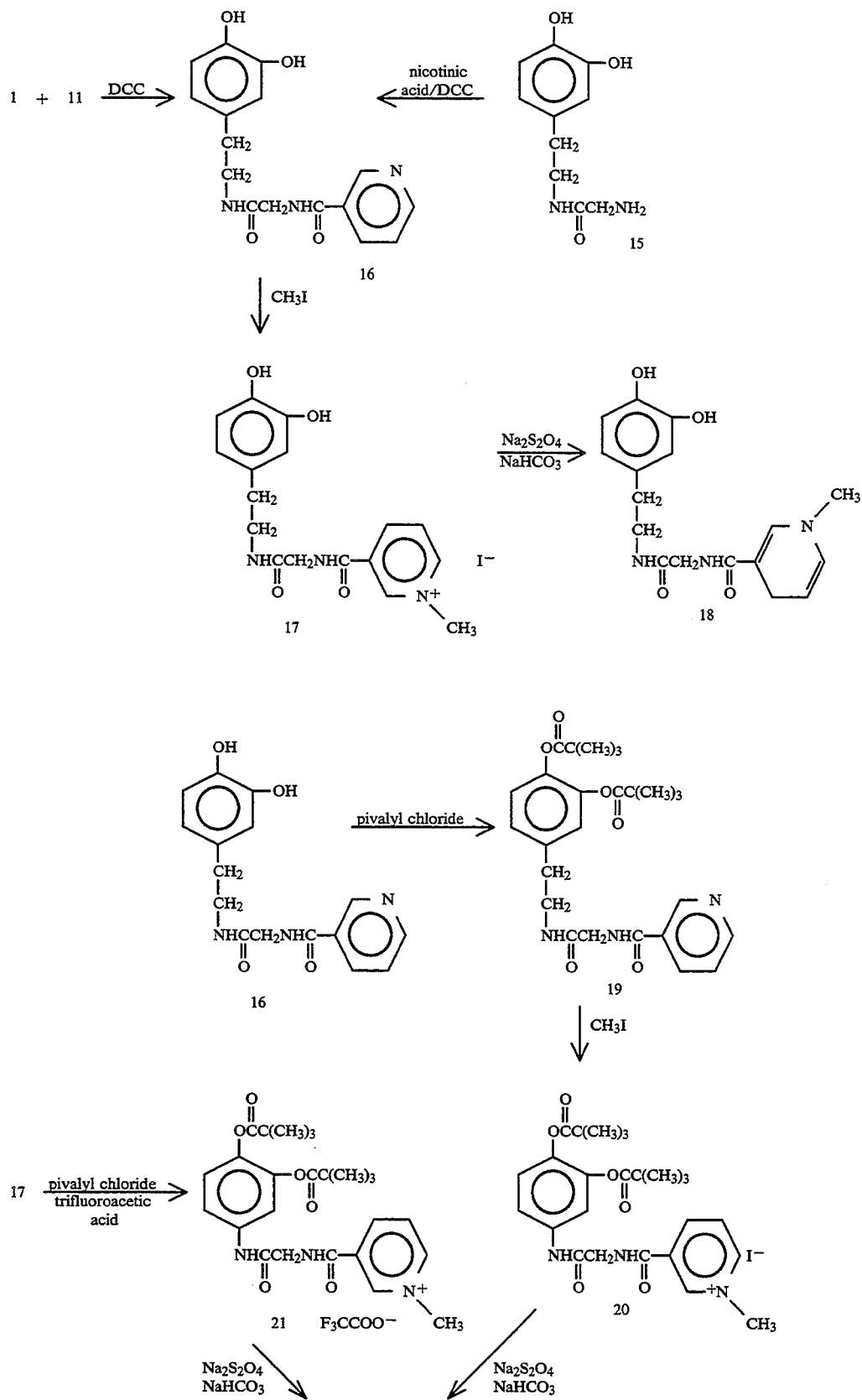

SCHEME 2
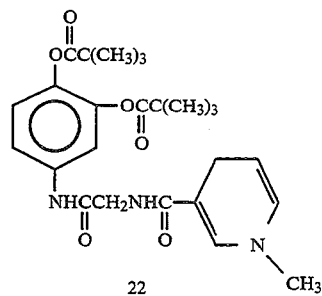
SCHEME 3
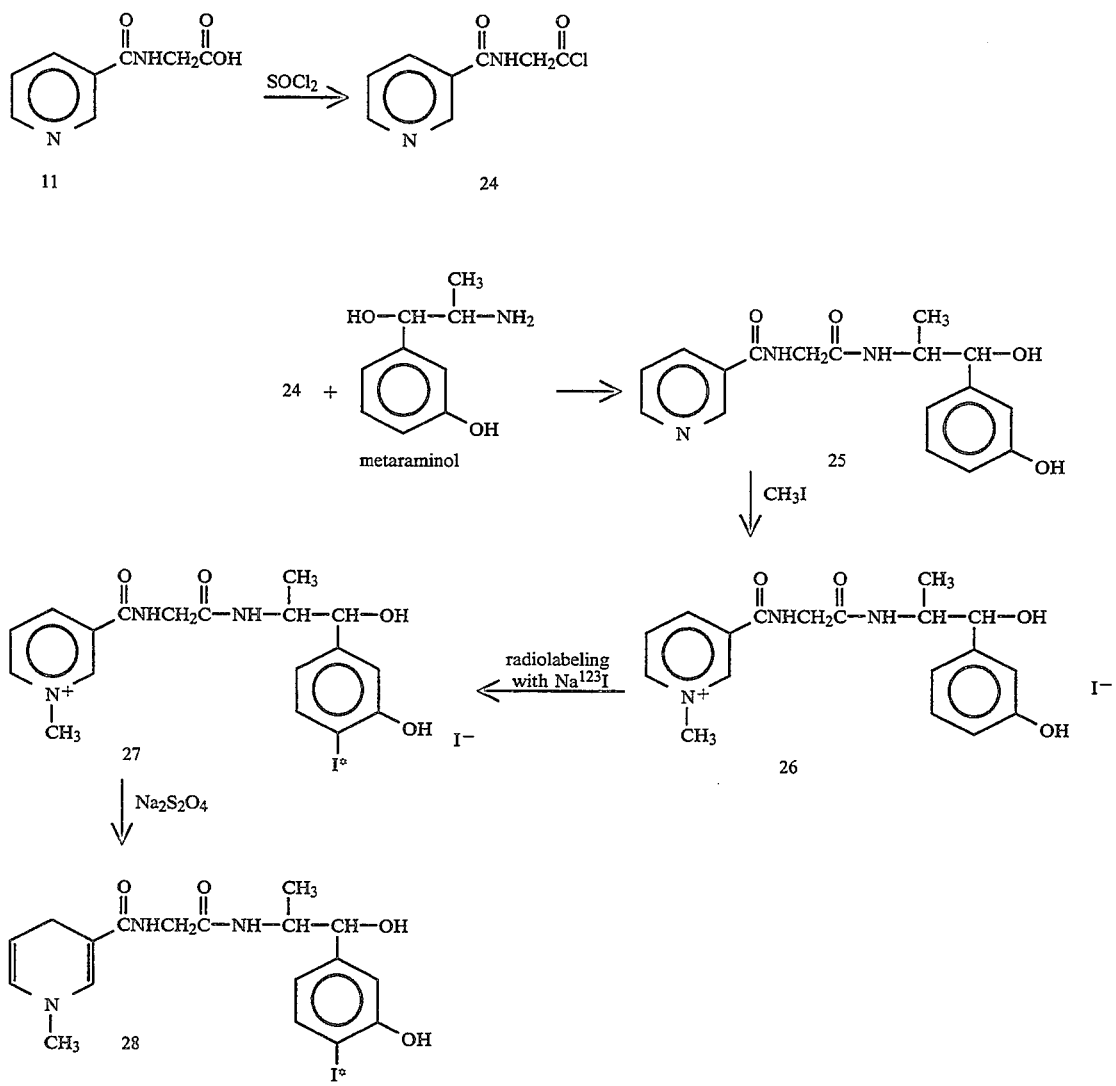

SCHEME 4

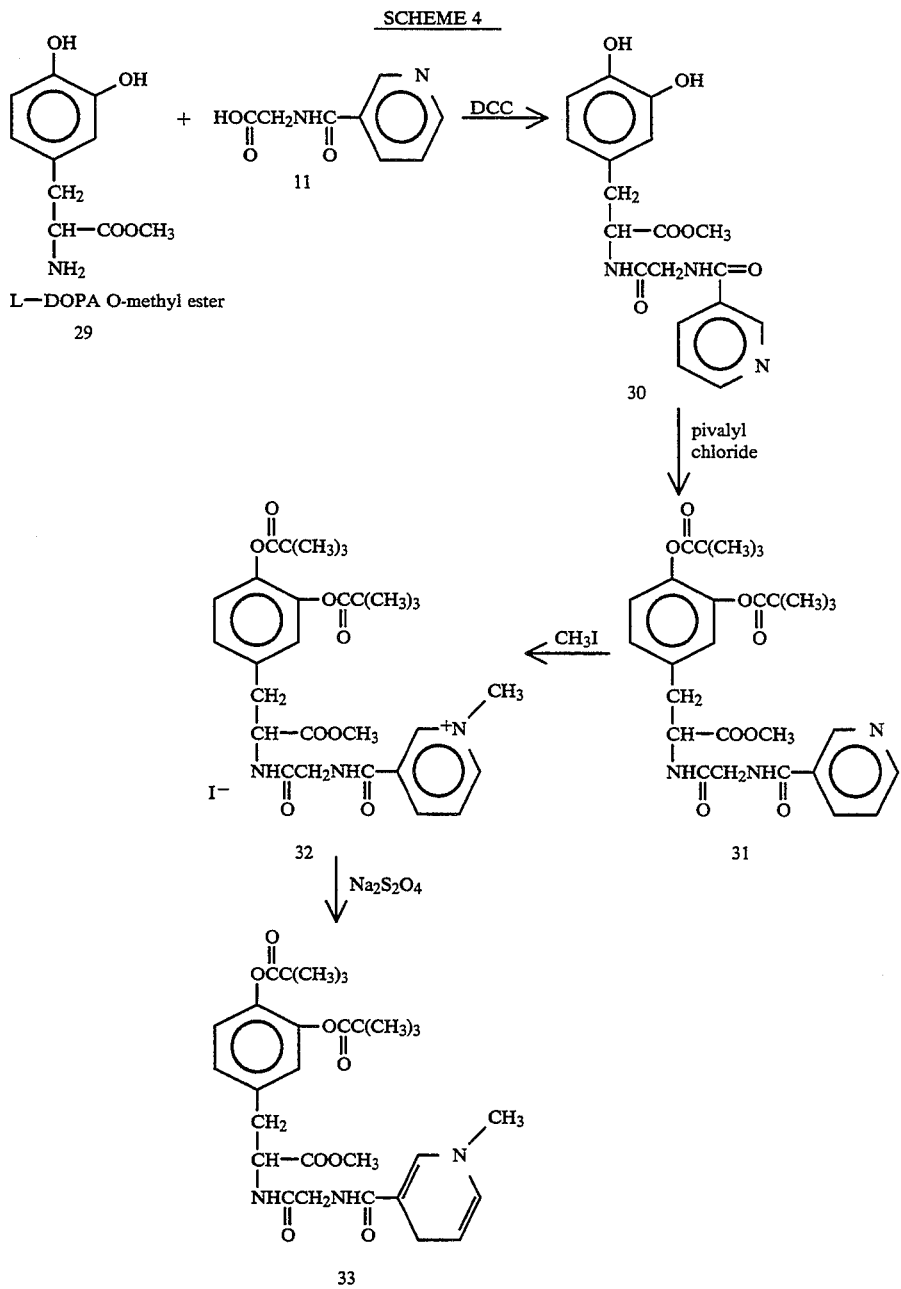

Similar schemes can be shown for the preparation of the other compounds of the invention. The acylation steps which introduce the hydroxyl protecting groups in Scheme 1, 2 and 4, for example, are only needed when there are hydroxyl groups which it is desired to protect. Moreover, carbonate rather than acyl protecting groups could be introduced instead, as already discussed hereinabove. Also, as shown in Schemes 2 and 3, the order of steps may be altered; quaternization, followed by reduction, need not always constitute the final two steps but may be carried out earlier in the reaction sequence. Yet other reaction schemes, reactants, solvents, reaction conditions, etc. (e.g. using an anhydride rather than an acyl halide for the acylation step, or preparing a different acyl derivative, e.g. the acetyl rather than the pivalyl derivative, or using a different amino acid or nicotinoyl derivative thereof in place of glycine or nicotinuric acid, respectively) will be readily apparent to those skilled in the art. Also, insofar as concerns the quaternary compounds, when an anion different from that obtained is desired, the anion in the quaternary salt may be subjected to anion exchange via an anion exchange resin or, more conveniently, by use of the method of Kaminski et al, *Tetrahedron*, Vol. 34, pp. 2857–2859 (1978). According to the Kaminski et al method, a methanolic solution of an HY acid will react with a quaternary ammonium halide to produce the methyl halide and the corresponding quaternary.Y salt. Moreover, the manner in which the ultimate compound is prepared should be tailored to the presence of any other reactive groups in the molecule. For example, when the parent drug contains an —OH or —NH$_2$ group to be derivatized as well as one or more carboxy functions, such carboxy functions will typically be esterified, e.g. converted to the corresponding ethyl ester, or otherwise suitably protected, usually prior to formation of the quaternary compound. Thus, a wide variety of synthetic approaches can be utilized, depending on the desired structure of the final product. And compounds containing more than one category of reactive functional groups may be derivatized in a variety of ways; for example, a compound containing reactive hydroxyl and carboxyl groups may have the hydroxyl group(s) protected and the carboxyl group(s) linked to the carrier, or the hydroxyl(s) may be linked to the carrier and the carboxyl(s) protected.

Various illustrative synthetic schemes as applied to specific compounds of the invention are set forth below in the section entitled "Illustrative Synthetic Methods". While the sequence of reaction steps can be varied in many cases, in general the final step (except in the case of optional salt formation or possibly in the case of radiolabeling) will be reduction of a quaternary compound of formula (II) to the corresponding dihydro compound of formula (I). The reduction is usually conducted at a temperature from about $-10°$ C. to room temperature, for a period of time from about 10 minutes to 2 hours, conveniently at atmospheric pressure. Typically, a large excess of reducing agent is employed, e.g. a 1:5 molar ratio of reducing agent to starting compound of formula (II). The process is conducted in the presence of a suitable reducing agent, preferably an alkali metal dithionite such as sodium dithionite or an alkali metal borohydride such as sodium borohydride or lithium aluminum borohydride, in a suitable solvent. Sodium dithionite reduction is conveniently carried out in an aqueous solution; the dihydro product of formula (I) is usually insoluble in water and thus can be readily separated from the reaction medium. In the case of sodium borohydride reduction, an organic reaction medium is employed, e.g. a lower alkanol such as methanol, an aqueous alkanol or other protic solvent.

In a presently preferred embodiment of the present invention, the centrally acting drug of which D is the residue is dopamine or L-DOPA or a protected counterpart thereof, and the instant redox system is thus designed to elicit a sustained and brain-specific dopaminergic (e.g. anti-Parkinsonism or anti-hyperprolactinemia) response in the animal to which the formula (I) derivative is administer ed. In analogous fashion, the instant redox carrier system I⇌II in which D is the residue of any other centrally acting drug as defined herein is designed to elicit the kind of pharmacological response which would be obtained by delivery of the drug itself to the brain, i.e. when the centrally acting parent drug is an antitumor/anticancer agent, the instant redox system is employed to elicit an antitumor-/anticancer response; when the parent drug is a sympathetic stimulant, the instant redox system is used to elicit a sympathetic stimulant or amphetamine-like response; when the parent drug is an anticonvulsant compound, the instant redox system is used to elicit an anticonvulsant response; when the parent drug is a tranquilizer, the instant system is used to elicit a tranquilizing response; when the parent drug is an antidepressant, the instant system is used to elicit an antidepressant response; and so forth.

Suitable nontoxic pharmaceutically acceptable carriers for use with the topic compounds of formula (I), e.g. those less toxic than the target drug species themselves, will be apparent to those skilled in this art. Compare, for example, Remington's Pharmaceutical Sciences, 4th Edition (1970). Obviously, the choice of suitable carriers will depend upon the exact nature of the particular dosage form selected, as well as upon the identity of the compound to be administered. The therapeutic dosage range for administration of a compound according to this invention will generally be the same as, or less than, those which would characteristically be used in this art for administration of the parent drug itself. Naturally, such therapeutic dosage ranges will vary with the size of the patient, the condition for which the compound is administered, the particular dosage form employed, route of administration and the like. The quantity of given dosage form needed to deliver the desired dose will of course depend upon the concentration of the compound of formula (I) in any given pharmaceutical composition/dosage form thereof. Obviously, in the case of diagnostic agents, the dosage of formula (I) compound used will be a quantity sufficient to deliver to the target body area an amount of radioisotope, stable isotope or the like which can be effectively detected by radio-imaging or other detection means. The amount of radioisotope, stable isotope or the like present in the dosage form will be within or below the ranges conventionally used for diagnostic purposes.

The ability of the topic compounds to cross the BBB and to be "locked into" the brain allows administration in a site-specific manner. A combination of the present dihydropyridine⇌pyridinium salt redox carrier system with a sustained release system will further enhance this site-specificity. Thus, a preferred embodiment of the invention comprises formulating the compound of formula (I) or its salt utilizing a sustained release carrier system and/or route of administration capable of slowly releasing the chemical, e.g. sustained release tablets and capsules for oral administration; subcutaneous injection, or implantation of drugs in solid pellet form (for example, distributed in a biodegradable polymer); intramuscular injection of the compound in solution in oil or suspended in a repository vehicle; a transdermal delivery device or form such as an ointment to be applied locally to the desired site (when the drug is susceptible of delivery through the skin), slow intravenous infusion and the like. The rate of release of compound from the sustained release system should be comparable to the rate of in vivo oxidation of the dihydro form of the redox system in order to achieve the greatest degree of enhancement of specificity.

In applicant's copending application Ser. No. 632,314, filed Jul. 19, 1984 (itself a continuation-in-part of the earlier Ser. No. 379,316, now U.S. Pat. No. 4,479,932; Ser. No. 461,543, abandoned in favor of Ser. No. 733,463, filed May 13, 1985, now U.S. Pat. No. 4,727,079; Ser. No. 475,493 now U.S. Pat. No. 4,622,218; and Ser. No. 516,382 now U.S. Pat. No. 4,540,564), Ser. No. 632,314 being abandoned in favor of Ser. No. 879,120, filed Mar. 19, 1986, in turn abandoned in favor of Ser. No. 088,523, filed Aug. 21, 1987, now U.S. Pat. No. 4,963,688), the concept of applicant's redox carrier system was expanded to provide novel carrier-containing chelating agents, precursors thereto and radiopharmaceuticals derived therefrom, utilizing the dihydropyridine⇌pyridinium salt type carriers disclosed in the four earlier applications. The teachings of Ser. No. 632,314, which is incorporated by reference herein in its entirety and relied upon, can be readily combined with the teachings of the present application to expand the classes of chelating agents, precursors and radiopharmaceuticals defined therein to specifically include dihydropyridine⇌pyrdinium salt redox carriers comprising a bivalent radical of the formula

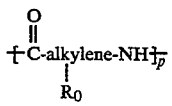

as defined herein.

ILLUSTRATIVE SYNTHETIC METHODS

I. Methods for Derivatizing —NH$_2$ or —NH— Functions in Drugs

Method A

The drug is reacted with nicotinuric acid chloride, with nicotinuric acid anhydride, or with nicotinuric acid in the presence of a suitable coupling agent such as dicyclohexylcarbodiimide, in an appropriate organic solvent, to afford the corresponding glycylnicotinamide, or nicotinuramide. The nicotinuramide is then quaternized, typically by treatment with methyl iodide in a suitable organic solvent, to afford the quaternary derivative of formula (II), which is then reduced by treatment with sodium dithionite or sodium borohydride as generally described hereinabove to afford the desired compound of formula (I). The representative drugs depicted below may be derivatized in this manner to the corresponding compounds of formulas (II) and (I). Bupropion, difluamine, propranolol, ethyl β-carboline-3-carboxylate, prizidilol, pseudoephedrine, 5-amidino-2-(5-amidino-2-benzofuranyl)indole, 4',6-diimidazolino-2-phenylbenzo(b)thiophene, 2-guanidino-4,5-di-n-propyloxazole, 2-guanidino-4,5-diphenyloxazole, glucosamine, 6-amino-6-deoxy-D-glucose and 6[[(hydroxyimino)phenyl]methyl]-1-[(methylethyl)sulfonyl-1H-benzimidazol-2-amine may be similarly derivatized.

Alternatively, glycine may be first reacted with a reagent capable of introducing an amino protecting group such as benzyloxycarbonyl or t-butoxycarbonyl (e.g. as in Scheme 1 or 2 hereinabove) and the N-protected glycine then reacted with the drug in the presence of a coupling agent such as dicyclohexylcarbodiimide, followed by removal of the N-protecting group, followed by reaction with nicotinoyl chloride or nicotinic anhydride, or with nicotinic acid in the presence of dicyclohexylcarbodiimide or other suitable coupling agent, to afford the nicotinuramide. The nicotinuramide may then be quaternized and the quaternary reduced as described in the preceding paragraph.

The procedure of the second paragraph of this method may be repeated using picolinic acid or its acid chloride or anhydride, or isonicotinic acid or its acid chloride or anhydride, in place of nicotinic acid or its acid chloride or anhydride, respectively, to convert drugs such as those specifically mentioned for derivatizing by this method to the corresponding glycyl picolinamides and glycyl isonicotinamides and then to the corresponding compounds of formula (II) and (I). The procedure of the first paragraph of this method may be similarly adapted. Moreover, any of these procedures may be repeated, substituting a different amino acid or nicotinic acid derivative thereof for the glycine or nicotinuric acid used above, e.g. replacing glycine with alanine, valine, leucine, phenylalanine, isoleucine, methionine, asparagine or glutamine.

Alternatively, the drug may be reacted with an activated ester of nicotinuric acid or the like, e.g. a sucinimidyl ester such as

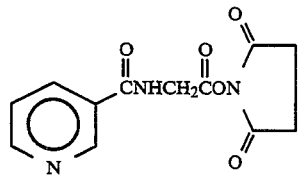

and the product quaternized and then reduced as described in the first paragraph of this method to afford the identical products. As yet another alternative, the activated ester, e.g. the succinimidyl ester depicted above, may be quaternized (e.g. by treatment with methyl iodide) and the quaternized activated ester then reacted with the drug. The quaternary compound of formula (II) thus obtained may then be reduced as described in the first paragraph of this method to give the corresponding compound of formula (I).

| STARTING MATERIAL | QUATERNARY INTERMEDIATE (CATION) | DIHYDRO DERIVATIVE |
|---|---|---|
| phenethylamine | | |
| dopamine | | |
| tyramine | | |

-continued
| STARTING MATERIAL | QUATERNARY INTERMEDIATE (CATION) | DIHYDRO DERIVATIVE |
|---|---|---|
| 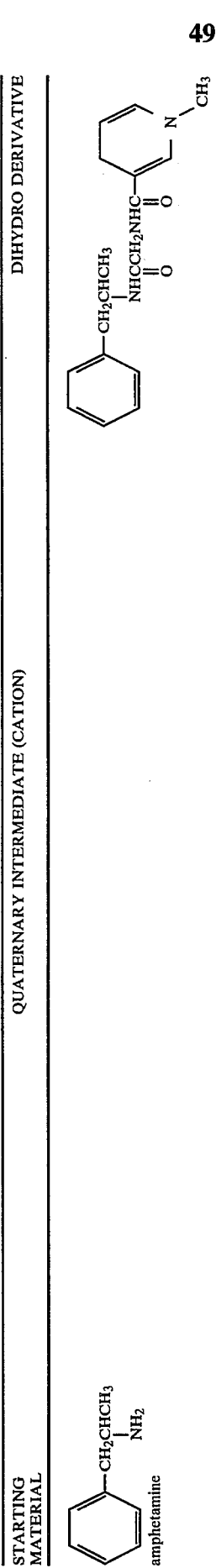 amphetamine | |  |
| 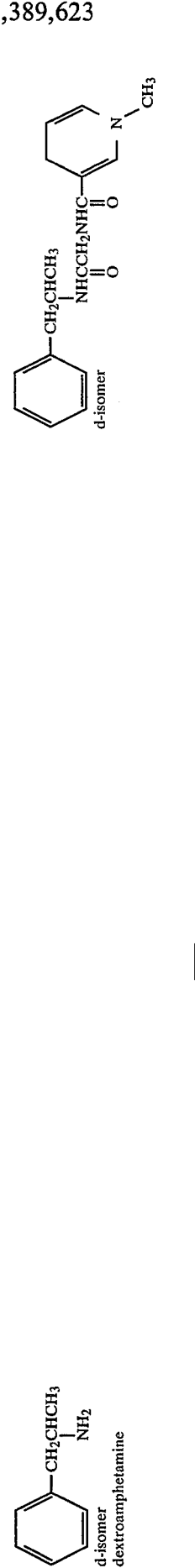 d-isomer dextroamphetamine | 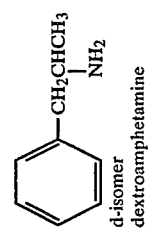 d-isomer | 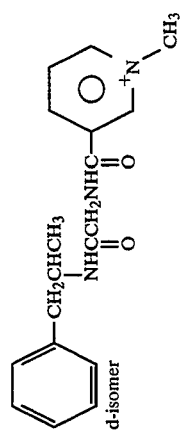 d-isomer |
| 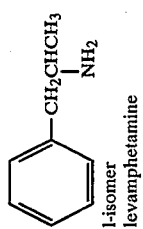 l-isomer levamphetamine | 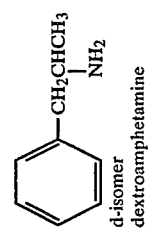 d-isomer | l-isomer |

-continued
| STARTING MATERIAL | QUATERNARY INTERMEDIATE (CATION) | DIHYDRO DERIVATIVE |
|---|---|---|
| 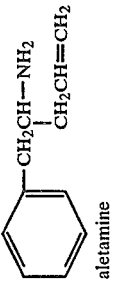 aletamine | 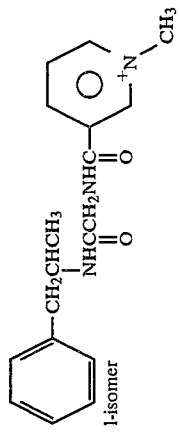 l-isomer <br><br> 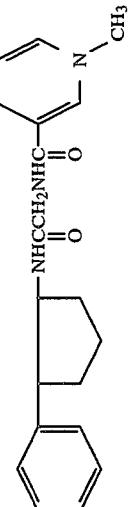 | 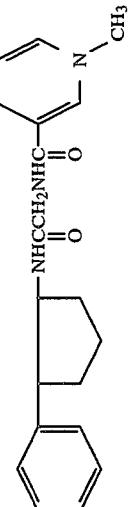 |
| 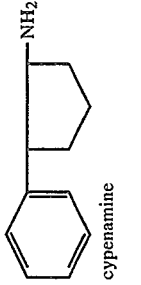 cypenamine | | |

| STARTING MATERIAL | QUATERNARY INTERMEDIATE (CATION) | DIHYDRO DERIVATIVE |
|---|---|---|
| 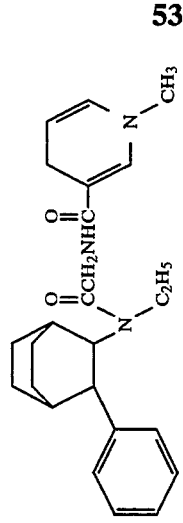 fencomfomin | 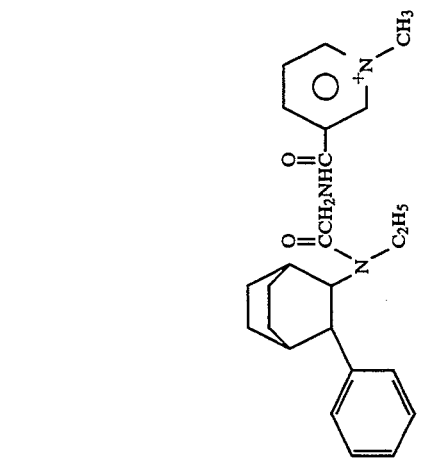 |  |
| 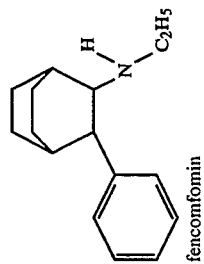 zylofuramine |  |  |
| 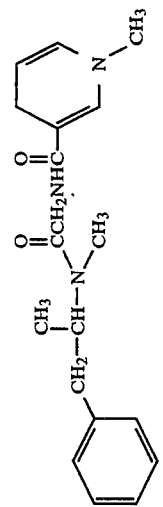 methamphetamine | | |

-continued
| STARTING MATERIAL | QUATERNARY INTERMEDIATE (CATION) | DIHYDRO DERIVATIVE |
|---|---|---|
| | 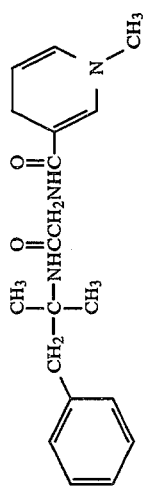 | 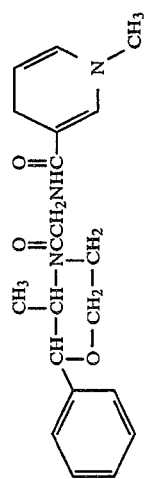 |
| | 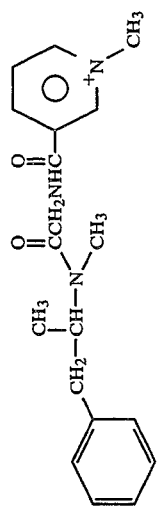 | |
| | 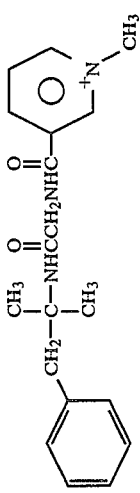 | 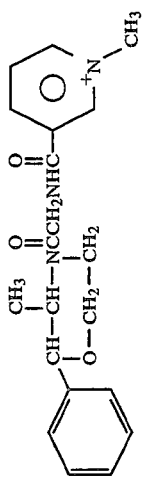 |
| 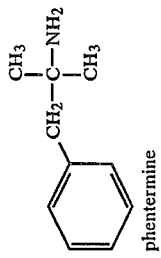
phentermine | | |
| 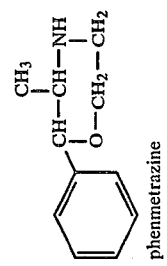
phenmetrazine | | |

-continued
| STARTING MATERIAL | QUATERNARY INTERMEDIATE (CATION) | DIHYDRO DERIVATIVE |
|---|---|---|
| 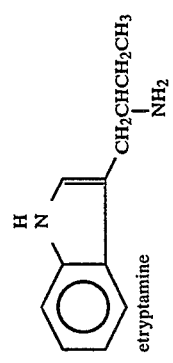 etryptamine | 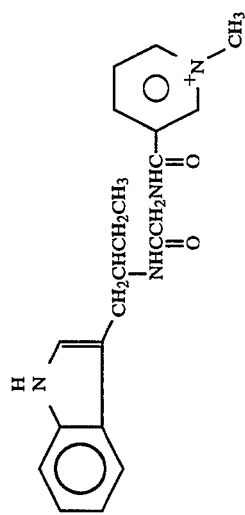 | 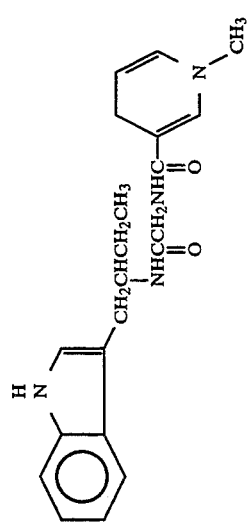 |
| 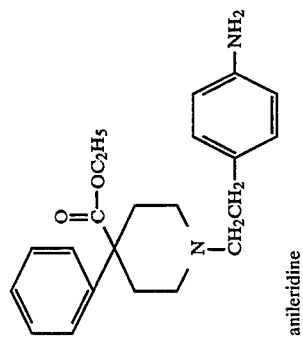 anileridine | | 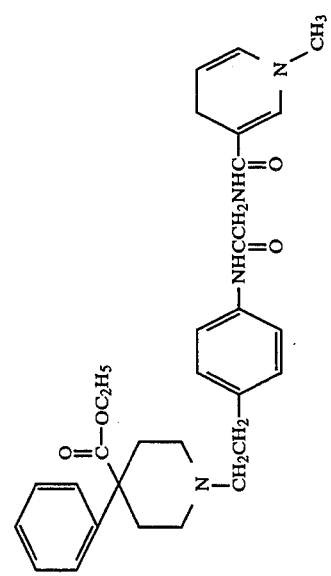 |

-continued
| STARTING MATERIAL | QUATERNARY INTERMEDIATE (CATION) | DIHYDRO DERIVATIVE |
|---|---|---|
| 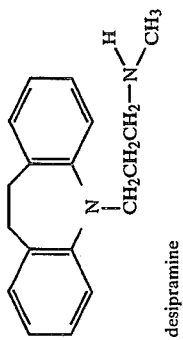 desipramine | 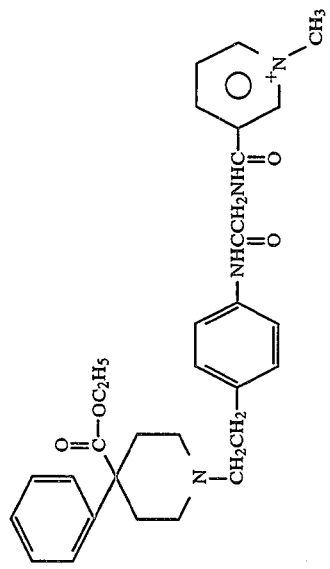 | 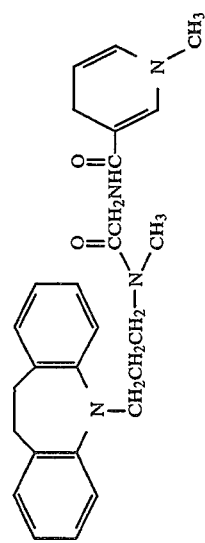 |
| 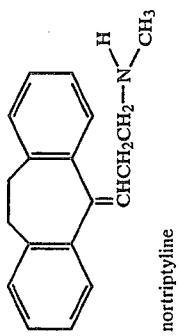 nortriptyline | 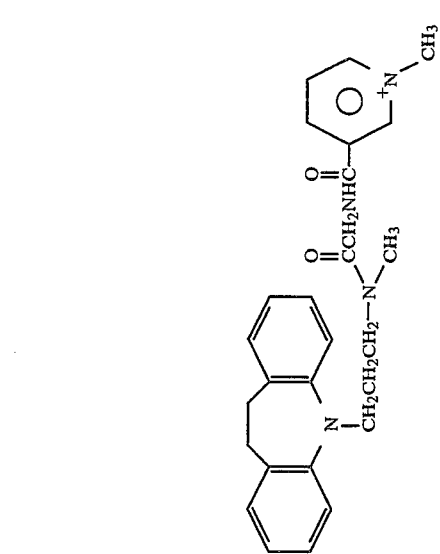 | 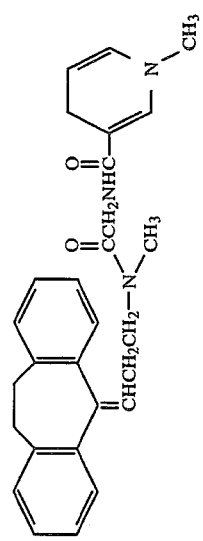 |

-continued
| STARTING MATERIAL | QUATERNARY INTERMEDIATE (CATION) | DIHYDRO DERIVATIVE |
|---|---|---|
| 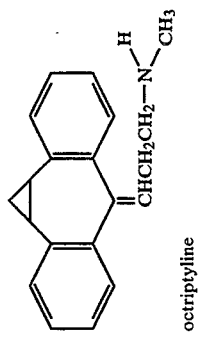<br>octriptyline | 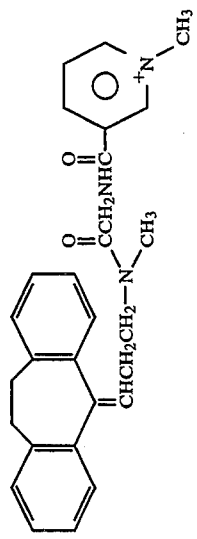 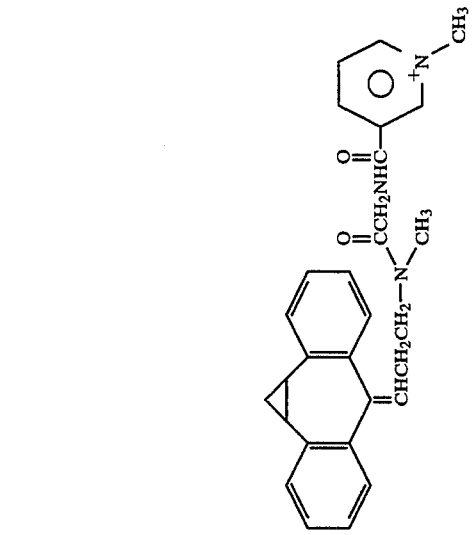 | 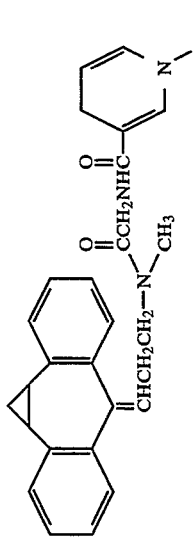 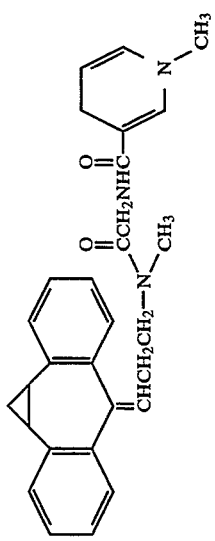 |
| 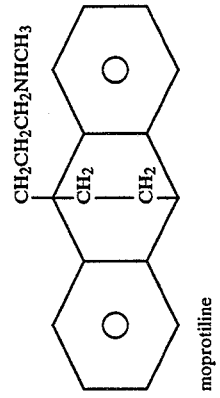<br>moprotiline | | 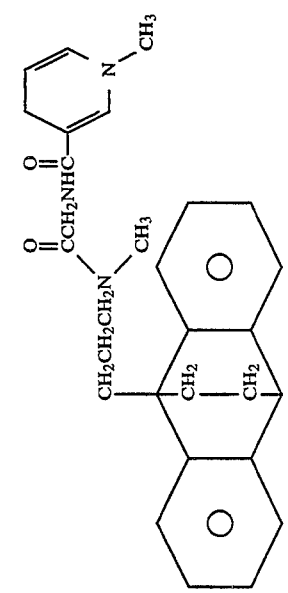 |

-continued
| STARTING MATERIAL | QUATERNARY INTERMEDIATE (CATION) | DIHYDRO DERIVATIVE |
|---|---|---|
| 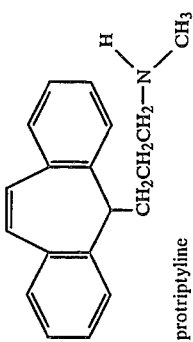 protriptyline | 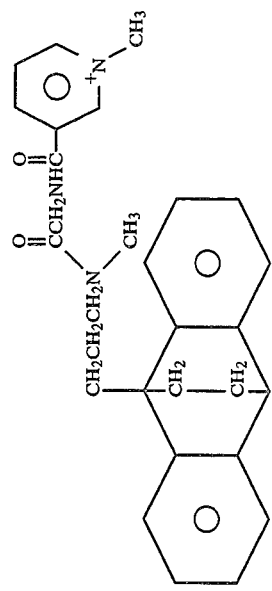 | 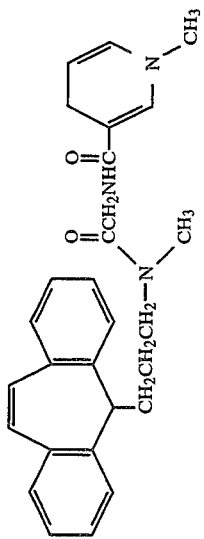 |
| 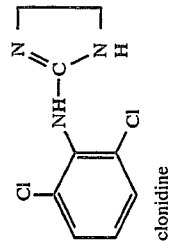 clonidine | 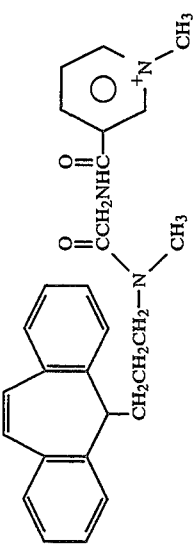 | 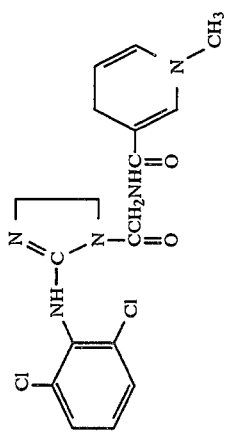 |

| STARTING MATERIAL | QUATERNARY INTERMEDIATE (CATION) | DIHYDRO DERIVATIVE |
|---|---|---|
|  tranylcypromine | 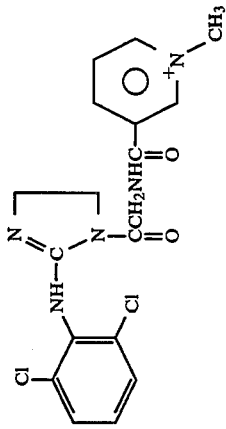 | 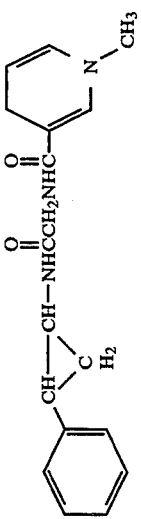 |
| | 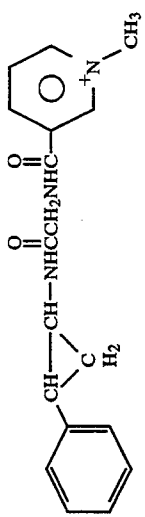 | |
| 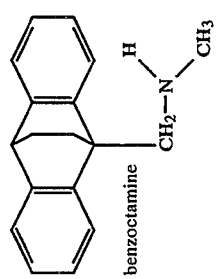 benzoctamine | | 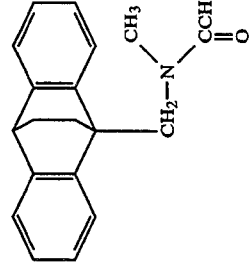 |

| STARTING MATERIAL | QUATERNARY INTERMEDIATE (CATION) | DIHYDRO DERIVATIVE |
|---|---|---|
| | 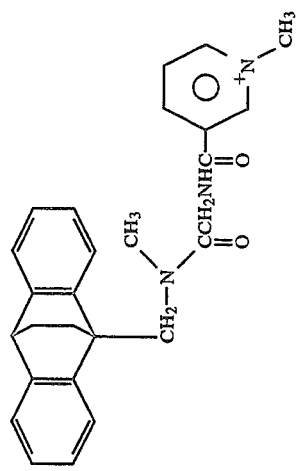 | 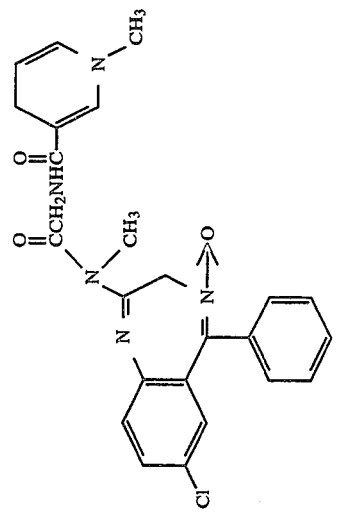 |
| 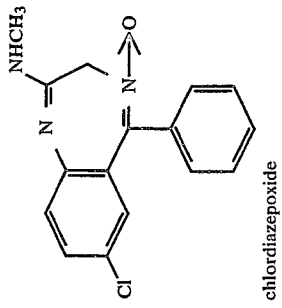<br>chlordiazepoxide | | 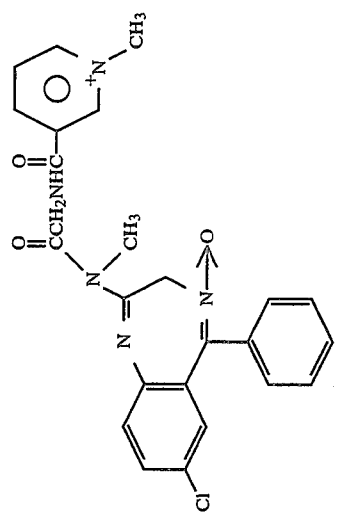 |

| STARTING MATERIAL | QUATERNARY INTERMEDIATE (CATION) | DIHYDRO DERIVATIVE |
|---|---|---|
| 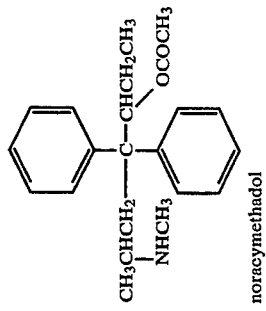 noracymethadol | 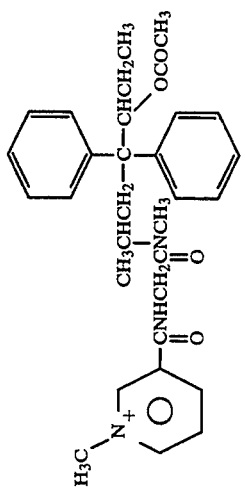 | 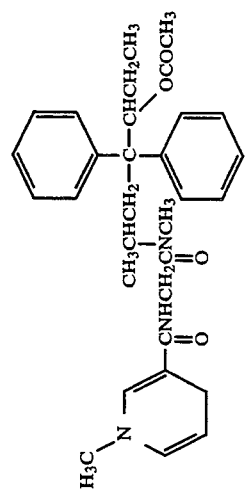 |
| 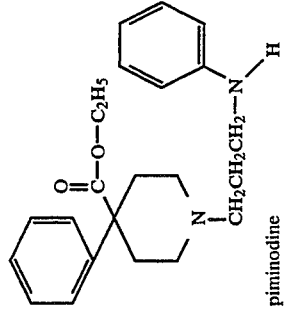 piminodine | | 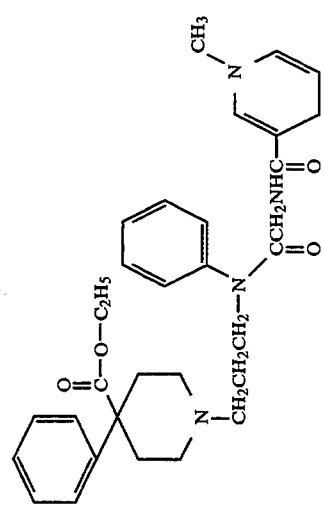 |

| STARTING MATERIAL | QUATERNARY INTERMEDIATE (CATION) | DIHYDRO DERIVATIVE |
|---|---|---|
| | 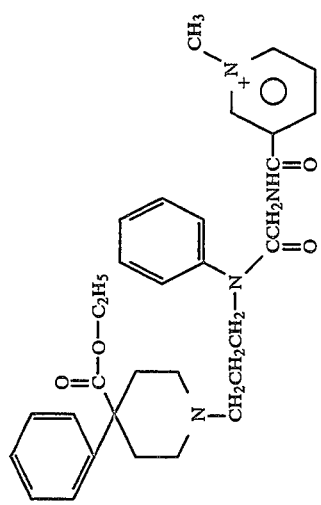 | 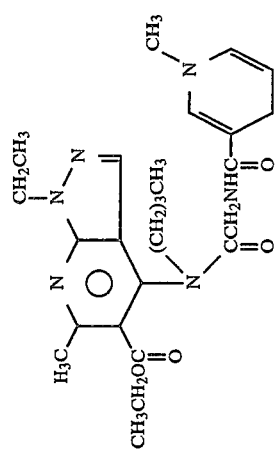 |
| 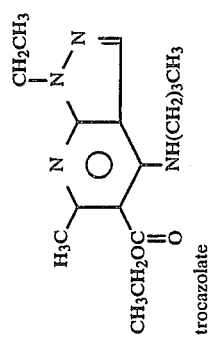
trocazolate | | 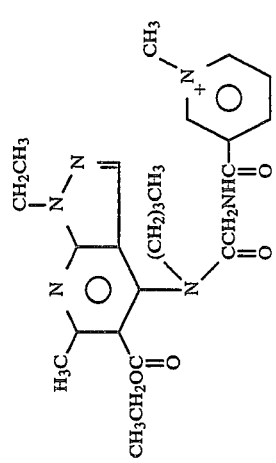 |

-continued
| STARTING MATERIAL | QUATERNARY INTERMEDIATE (CATION) | DIHYDRO DERIVATIVE |
|---|---|---|
| 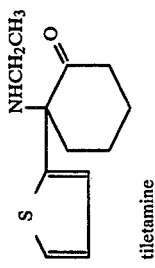 tiletamine | 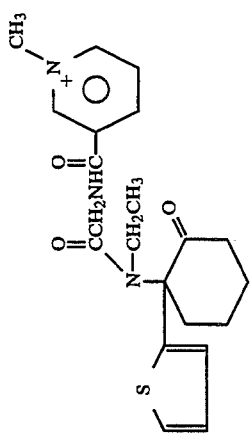 | 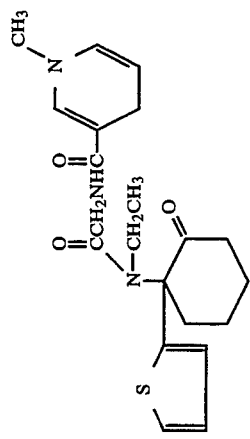 |
| 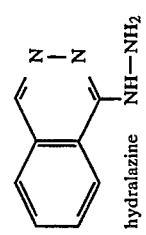 hydralazine | 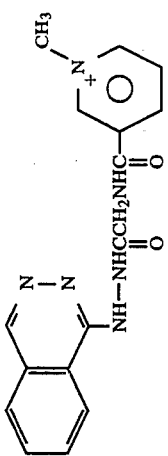 | 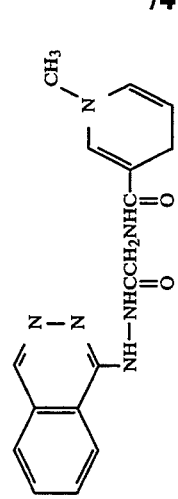 |

-continued
| STARTING MATERIAL | QUATERNARY INTERMEDIATE (CATION) | DIHYDRO DERIVATIVE |
|---|---|---|
| 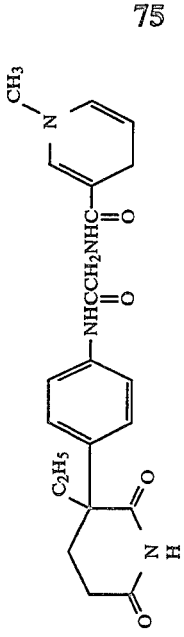 aminoglutethimide | 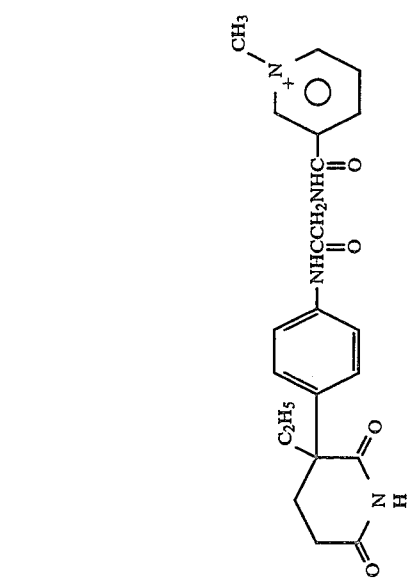 | 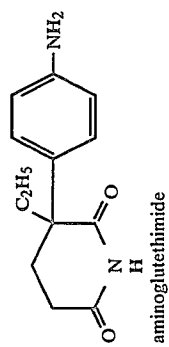 |
| 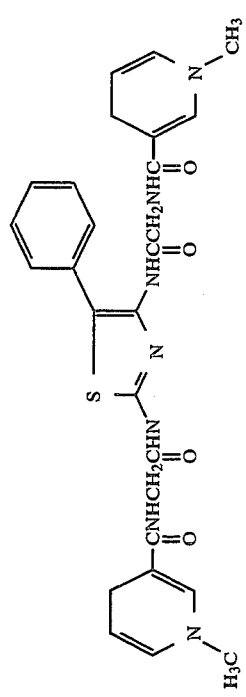 amiphenazole | 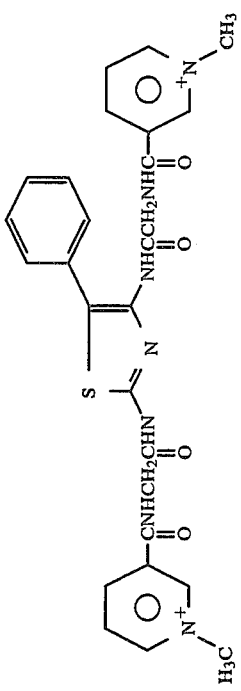 | 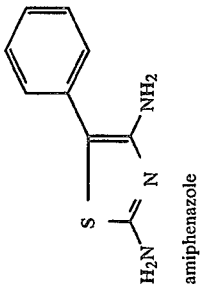 |

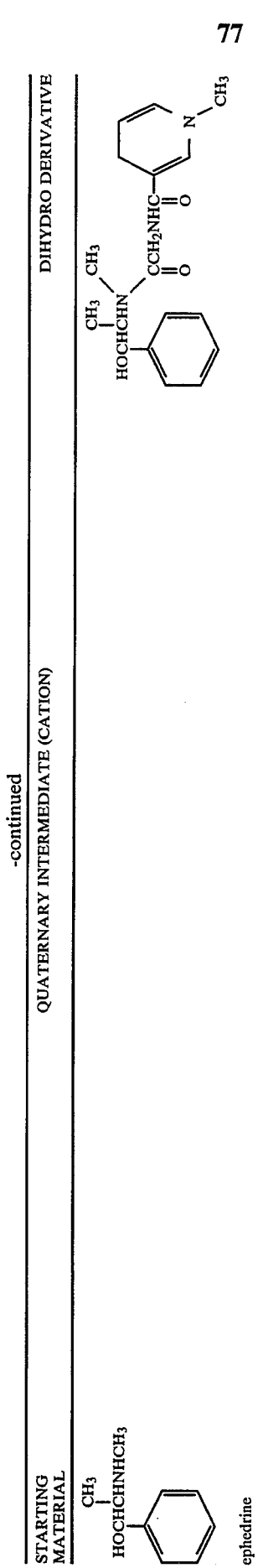
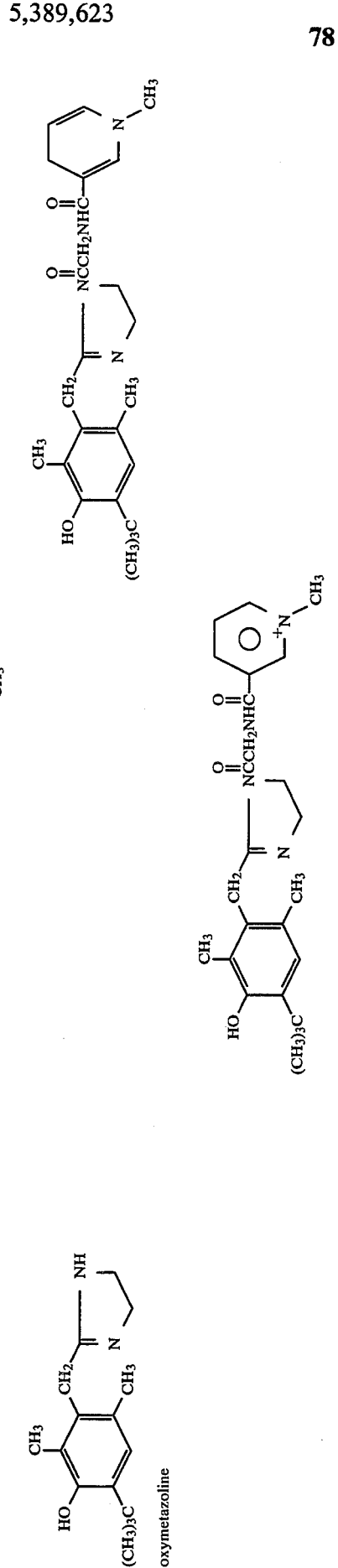

| STARTING MATERIAL | QUATERNARY INTERMEDIATE (CATION) | DIHYDRO DERIVATIVE |
|---|---|---|
| 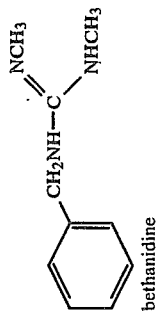 bethanidine | 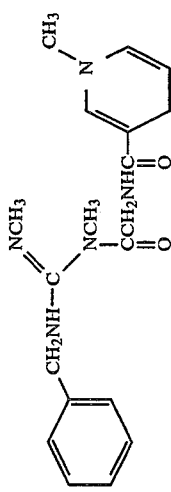 | 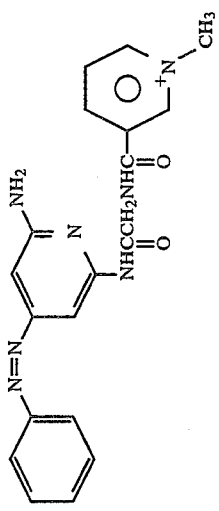 |
| | 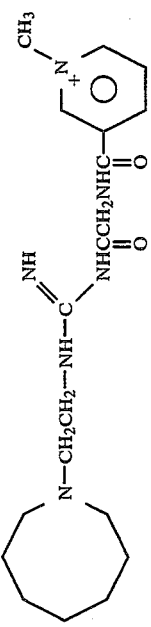 | |
| 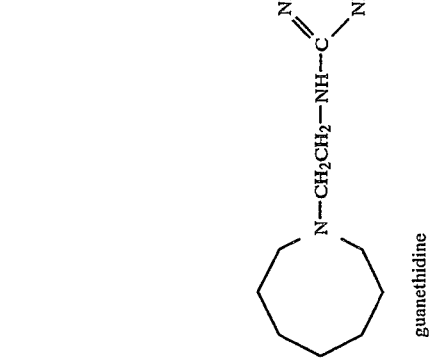 guanethidine | 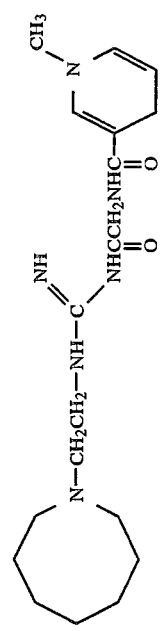 |  |

-continued
| STARTING MATERIAL | QUATERNARY INTERMEDIATE (CATION) | DIHYDRO DERIVATIVE |
|---|---|---|
| 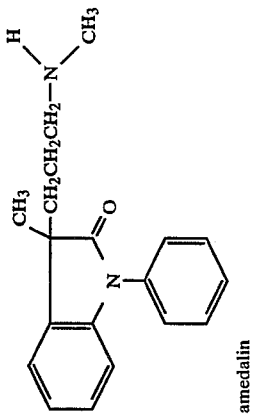 amedalin | 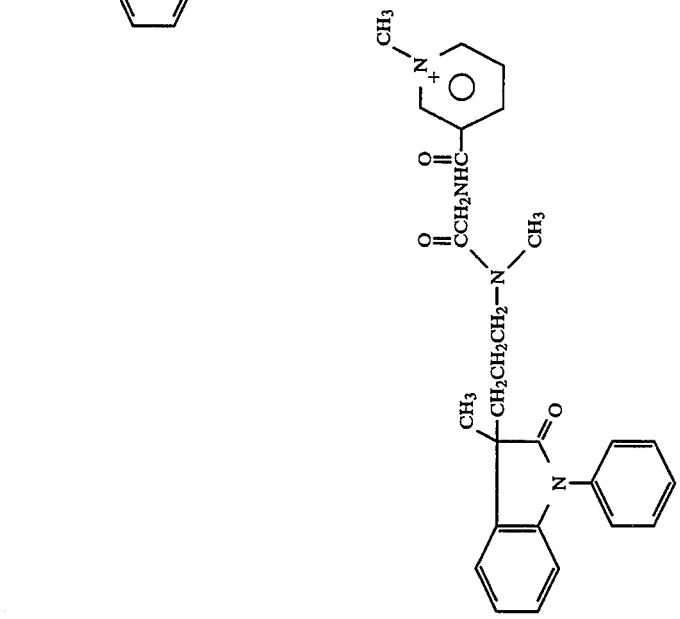 | 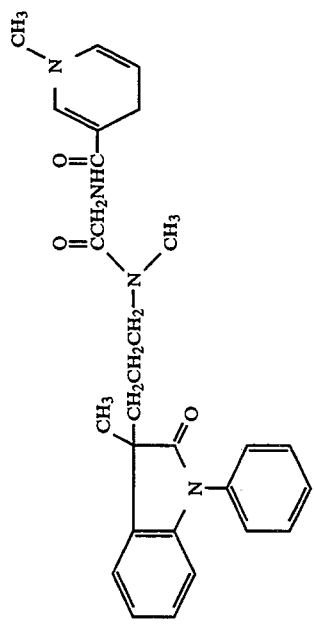 |
| 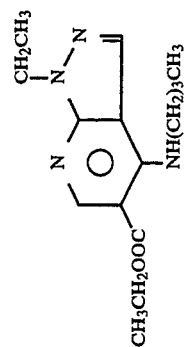 cartazolate | | |

-continued
| STARTING MATERIAL | QUATERNARY INTERMEDIATE (CATION) | DIHYDRO DERIVATIVE |
|---|---|---|
| 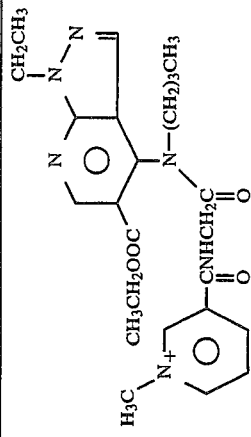 daledalin | 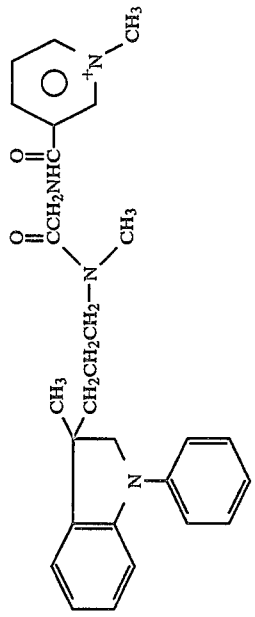 | 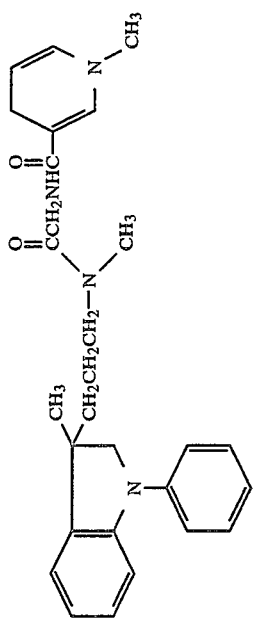 |
| 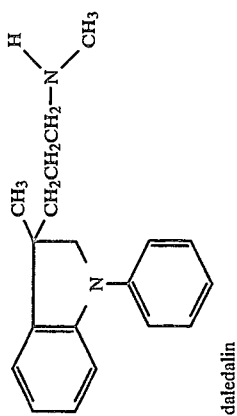 fluoxetine | | 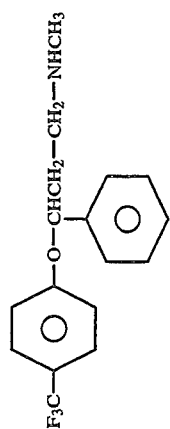 |

-continued
| STARTING MATERIAL | QUATERNARY INTERMEDIATE (CATION) | DIHYDRO DERIVATIVE |
|---|---|---|
| 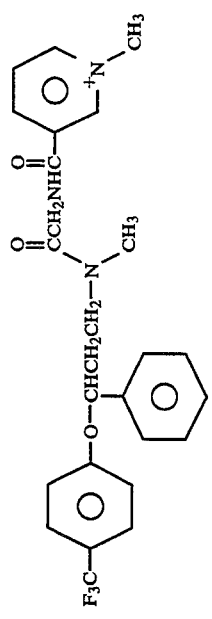<br>nisoxetine | 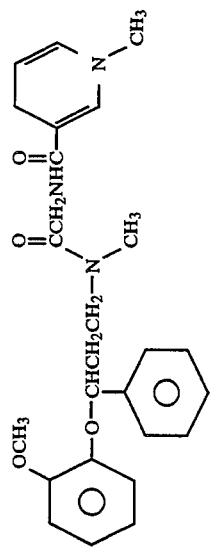 | 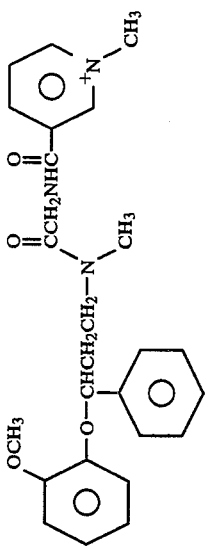 |
| 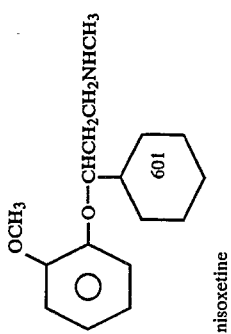<br>amantadine | | 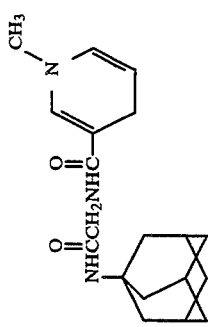 |
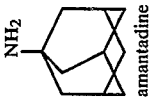

| STARTING MATERIAL | QUATERNARY INTERMEDIATE (CATION) | DIHYDRO DERIVATIVE |
|---|---|---|
| 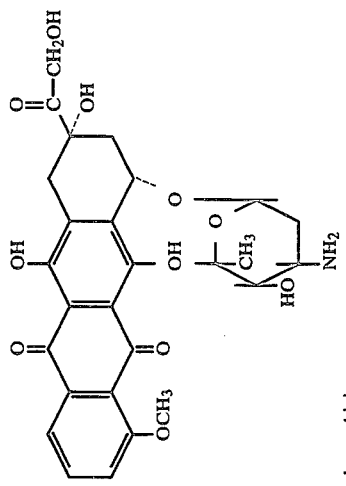 doxorubicin (odriamycin) | 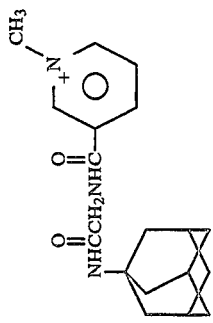 | 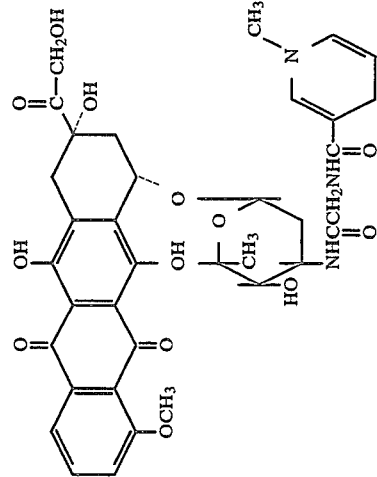 |
| | | 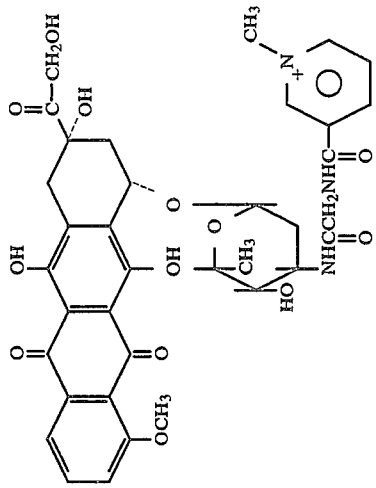 |

| STARTING MATERIAL | QUATERNARY INTERMEDIATE (CATION) | DIHYDRO DERIVATIVE |
|---|---|---|
| 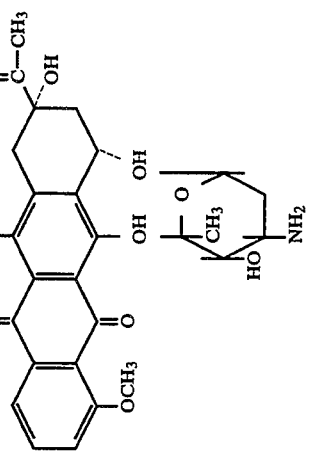
daunamycin (daunorubicin) | 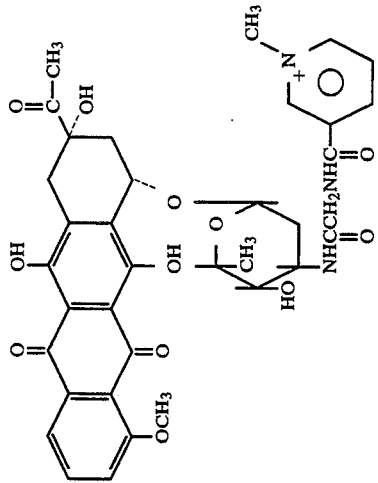 | 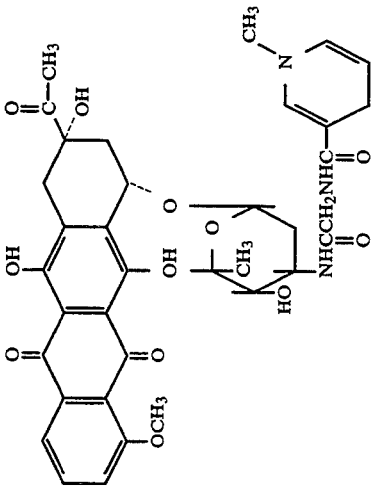 |
| 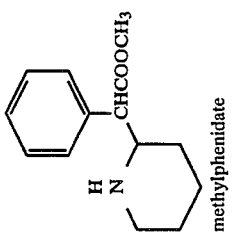
methylphenidate | |  |

| STARTING MATERIAL | QUATERNARY INTERMEDIATE (CATION) | DIHYDRO DERIVATIVE |
|---|---|---|
| 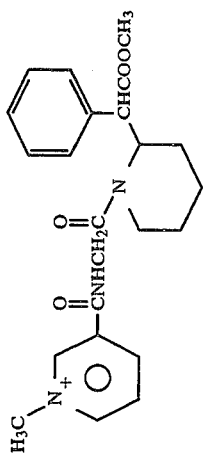 tryptamine | 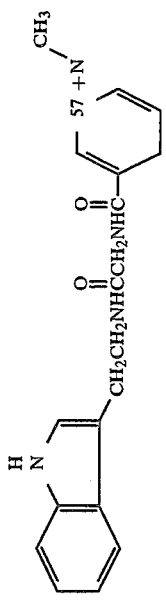  | 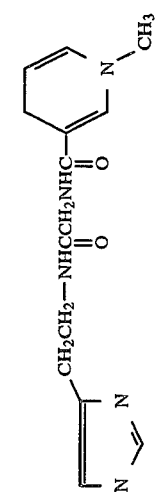 57 |
| 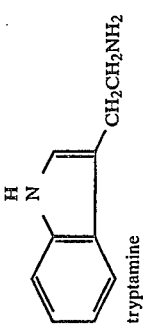 histamine | 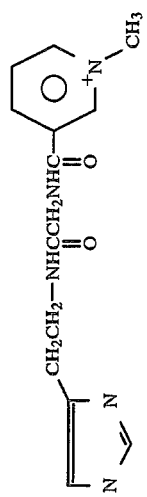 | 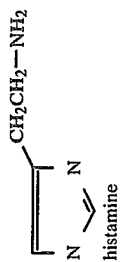 |

-continued
| STARTING MATERIAL | QUATERNARY INTERMEDIATE (CATION) | DIHYDRO DERIVATIVE |
|---|---|---|
| 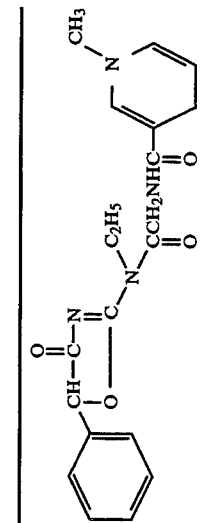 fenzolone | 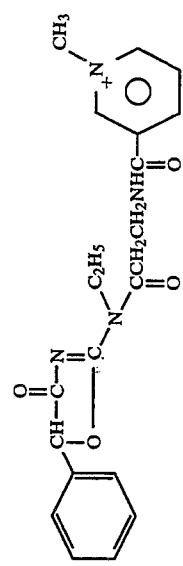 | 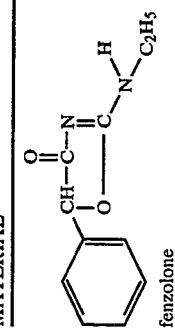 |
| 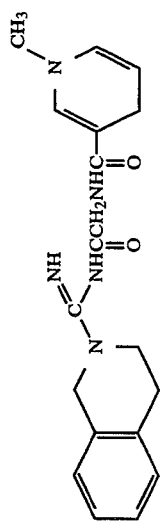 debrisoquin | 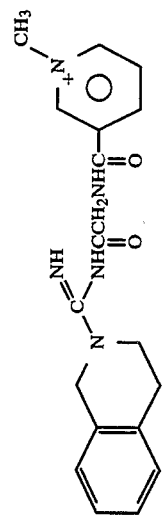 | 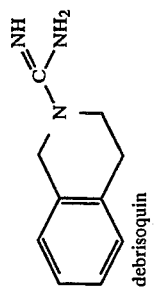 |
| 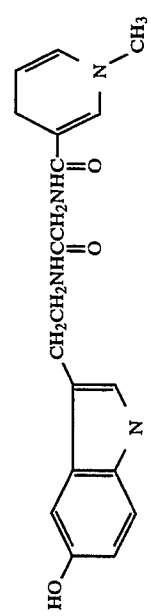 serotonin | 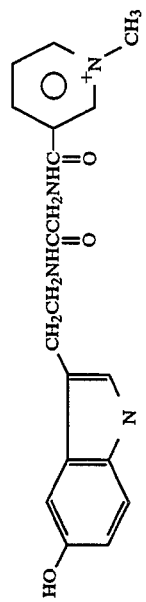 | 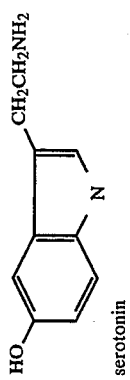 |

| STARTING MATERIAL | QUATERNARY INTERMEDIATE (CATION) | DIHYDRO DERIVATIVE |
|---|---|---|
| 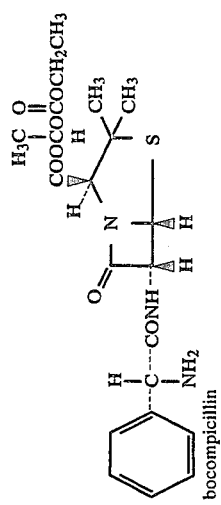 bocompicillin | 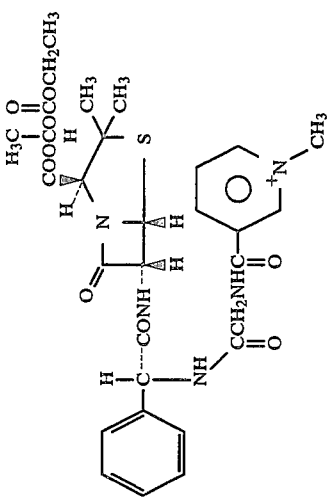 | 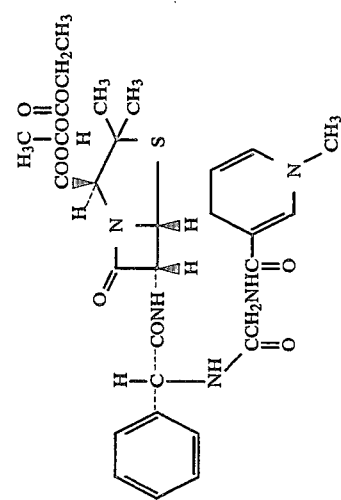 |
| 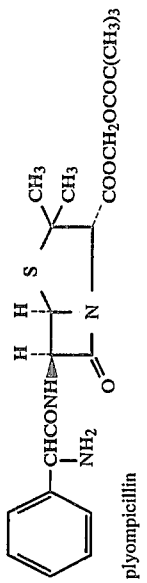 plyompicillin | | 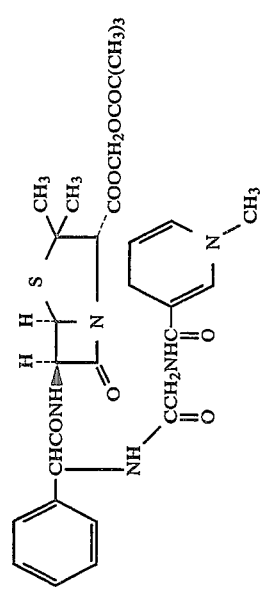 |

| STARTING MATERIAL | QUATERNARY INTERMEDIATE (CATION) | DIHYDRO DERIVATIVE |
|---|---|---|
| | 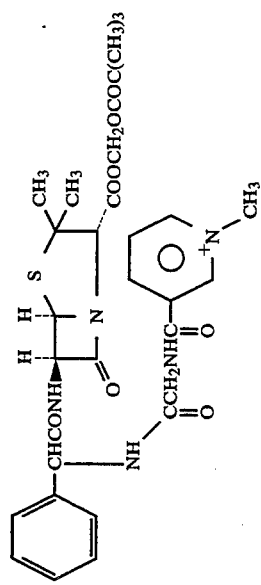 | |

Method B

This is a variation of Method A used when the drug contains at least one —COOH function which is to be protected.

The drug is first converted to the corresponding t-butyl ester by conventional esterification techniques. That ester is then used as the starting material and Method A is repeated.

Obviously, other esters may be similarly prepared in the first step by use of other esterifying agents.

The representative drugs depicted below may be derivatized in this manner to the corresponding compounds of formulas (II) and (I). Ceforanide, furosemide and acivicin may be similarly derivatized.

The glycyl picolinamide and glycyl isonicotinamide quaternary and dihydro derivatives of the drugs specifically mentioned for derivatizing according to this method may be similarly prepared, as may derivatives of other amino acids. See Method A, last paragraph.

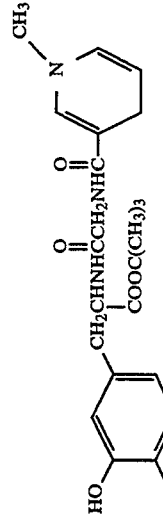

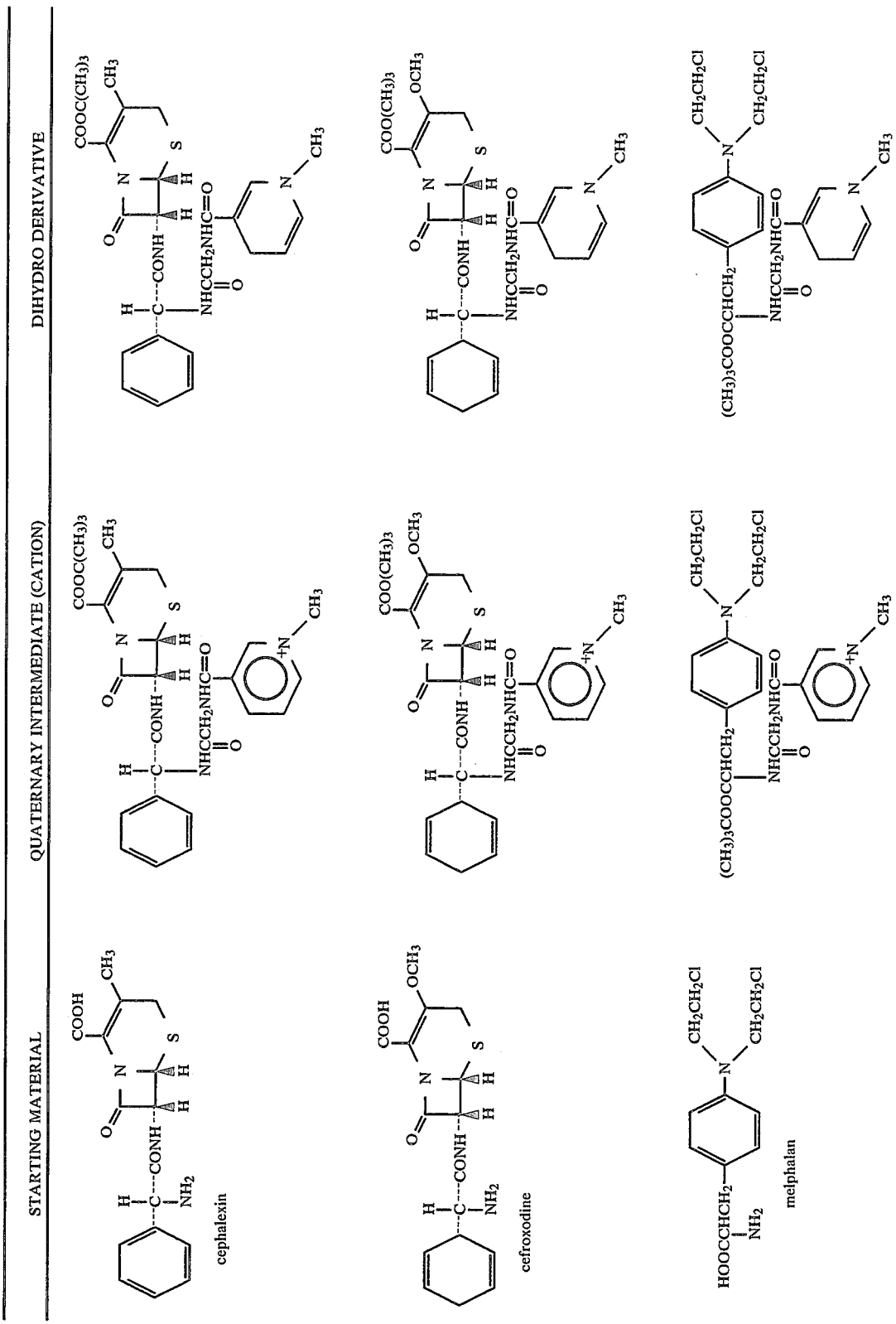

| STARTING MATERIAL | QUATERNARY INTERMEDIATE (CATION) | DIHYDRO DERIVATIVE |
|---|---|---|
| N=N=CHCCH$_2$CH$_2$CHCOH, NH$_2$ (DON) | N=N=CHCCH$_2$CH$_2$CHCOC(CH$_3$)$_3$, NHCCH$_2$NHC=O, N$^+$-CH$_3$ (pyridinium) | N=N=CHCCH$_2$CH$_2$CHCOC(CH$_3$)$_3$, NHCCH$_2$NHC=O, N-CH$_3$ (dihydropyridine) |
| HOOC-CH(NH$_2$)-CH$_2$-N(NO)-OH (L-alanosine) | (CH$_3$)$_3$COOC-CH(NHCCH$_2$NH-)-CH$_2$-N(NO)-OH, pyridinium-N$^+$-CH$_3$ | (CH$_3$)$_3$COOC-CH(NHCCH$_2$NH-)-CH$_2$-N(NO)-OH, dihydropyridine-N-CH$_3$ |

Method C

This is a variation of Method A used when the drug contains one or more OH functions which are to be protected.

The drug is first reacted with excess trimethylacetyl chloride to convert the hydroxy group(s) to pivalyloxy group(s). (This process is generally conducted in the presence of a base; however, strongly acid conditions are used when an amine function is present.) That protected derivative is then used as the starting material and subjected to Method A. Alternatively, the first two steps may be reversed, i.e. the drug may be first converted to the nicotinuramide, which may then be reacted with trimethylacetyl chloride to form the protected nicotinuramide.

Various other hydroxy protecting groups may be introduced in similar fashion.

The representative drugs depicted be low may be derivatized in this manner to the corresponding compounds of formulas (II) and (I). The corresponding glycyl picolinamide and glycyl isonicotin amide quaternary and dihydro derivatives may be similarly prepared, as may derivatives of amino acids other than glycine. See Method A, last paragraph. Moreover, drugs such as norepiniphrine, epinephrine, phenylephrine, atenolol, metoprolol, pentostatin (2'-deoxycoformycin), glucosamine, 6-amino-6-deoxy-D-glucose and pseudoephedrine may be similarly derivatized.

| STARTING MATERIAL | QUATERNARY INTERMEDIATE (CATION) | DIHYDRO DERIVATIVE |
|---|---|---|
| dopamine | | |
| tyramine | | |
| ephedrine | | |
| serotonin | | |

Method D

This variation of Method A can be used when the drug contains one or more OH and COOH functions which are to be protected. The protecting groups, for example, the t-butyl ester and pivalyloxy groups, are introduced as described in Methods B and C, in the sequence considered most convenient. Obviously, other protecting groups can be introduced instead. The amine function is derivatized according to Method A.

The representative drugs listed below may be derivatized in this manner to the corresponding compounds of formulas (II) and (I). The corresponding glycyl picolinamide and glycyl isonicotinamide quaternary and dihydro derivatives may be similarly prepared, as may derivatives of amino acids other than glycine. See Method A, last paragraph.

| STARTING MATERIAL | QUATERNARY INTERMEDIATE (CATION) | DIHYDRO DERIVATIVE |
|---|---|---|
| methyldopa | | |
| levodopa (L-DOPA) | | |

Method E

This method is of particular use when the —NH— function is part of an amide or imide or a very low pKa primary or secondary amine.

The drug is first reacted with an aldehyde [e.g. formaldehyde, benzaldehyde, acetaldehyde or chloral (Cl₃CCHO)]; for example, in the case of formaldehyde, one converts the —NH— function to a

function and thus forms a suitable bridging group. The resultant compound is then reacted with nicotinuric acid in the presence of a suitable dehydrating agent, or with nicotinuric acid chloride or nicotinuric acid anhydride, to form the corresponding nicotinuric acid ester of the partial formula

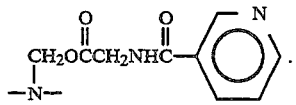

The resultant intermediate is then quaternized and reduced as in Method A. The alternative process utilizing an activated ester or quaternary derivative thereof which is described in Method A may be utilized here as well.

The representative starting drugs depicted below may be derivatized in this manner to the corresponding compounds of formulas (II) and (I). Drugs such as minocycline, doxycycline, oxytetracycline, tetracycline, methacycline, atenolol, sulfadiazine, cyclophosphamide, dactinomycin, mitomycin, 3-deazaguanine, progabide and 6-mercaptopurine may be similarly derivatized.

Alternatively, the steps subsequent to formation of the

function may be replaced with steps analogous to those detailed in the second paragraph of Method A.

The procedure of the preceding paragraph may be repeated using picolinic acid or its acid chloride or anhydride, or isonicotinic acid or its acid chloride or anhydride, in place of nitotinic acid or its acid chloride or anhydride, respectively (as called for in the second paragraph of Method A), to convert drugs such as those specifically mentioned for derivatizing according to this Method to the corresponding glycyl picolinic acid esters and glycyl isonicotinic acid esters and then to the corresponding compounds of formulas (II) and (I). Derivatives of amino acids other than glycine may be similarly prepared. See Method A, last paragraph.

As yet another alternative, the intermediate compound containing the

group or the like may be reacted with thionyl chloride to afford the corresponding compound containing a

or similar group. That derivative may then be reacted with a metallic salt (especially a silver or thallous salt) of nicotinuric acid or the like (formed, e.g. by reacting nicotinuric acid or the like with fresh silver hydroxide or oxide or with thallous ethoxide). The resultant nicotinuric acid ester of the partial formula

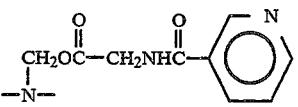

or like derivative is then quaternized and subsequently reduced as in Method A.

| STARTING MATERIAL | QUATERNARY INTERMEDIATE (CATION) | DIHYDRO DERIVATIVE |
|---|---|---|
| oxazepam | | |
| phenytoin | | |
| ethotoin | | |
| phenobarbital | | |

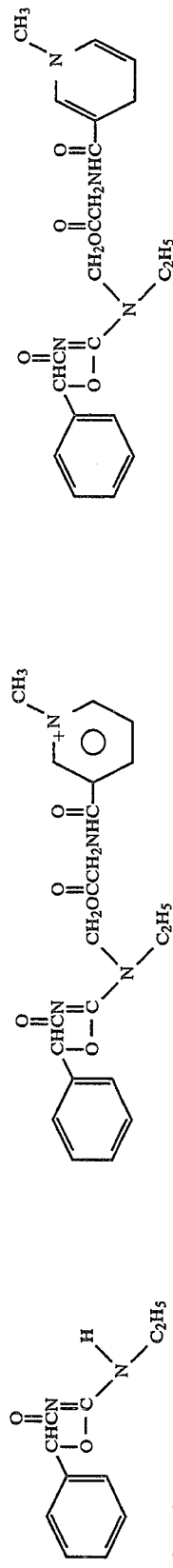
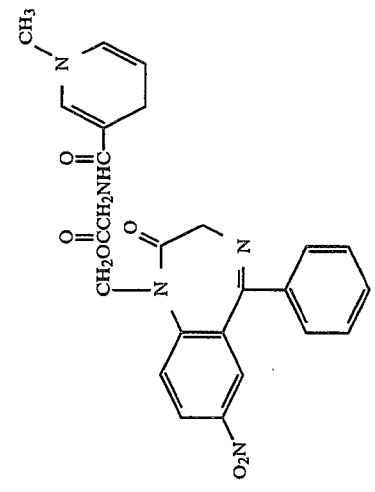
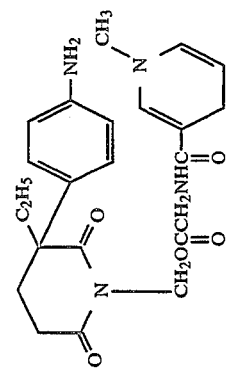
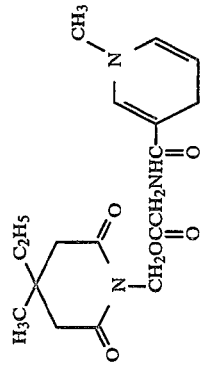
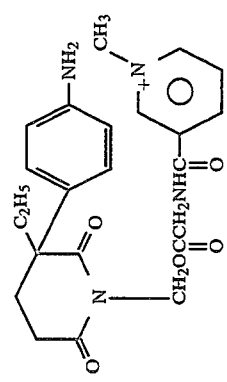
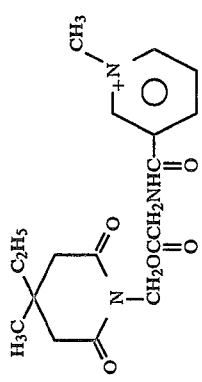
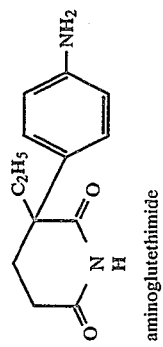
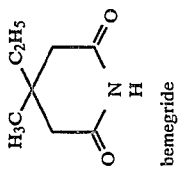

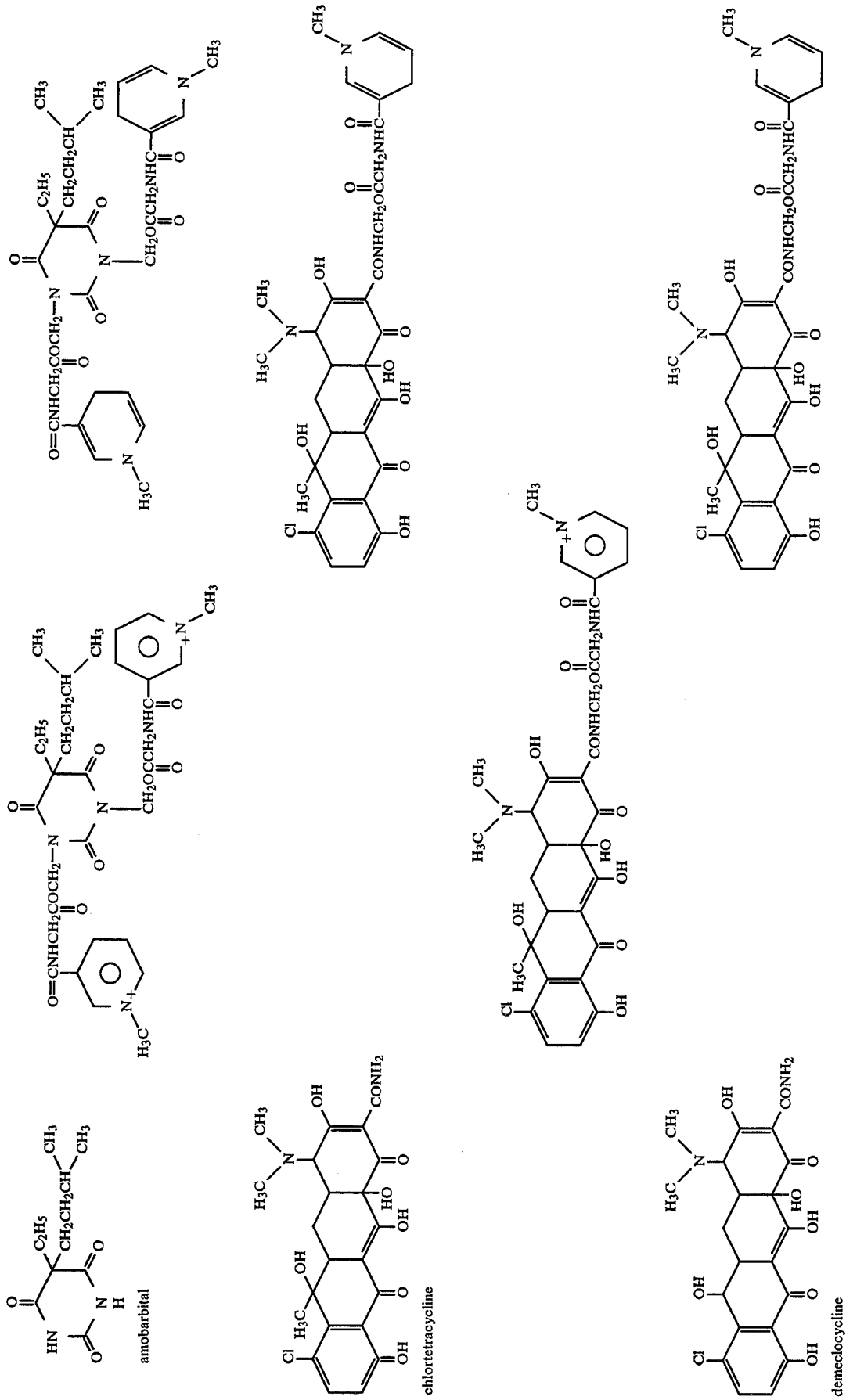

-continued
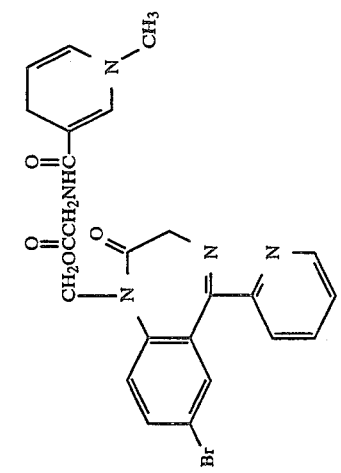
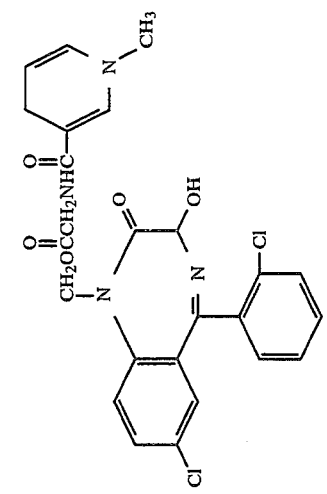
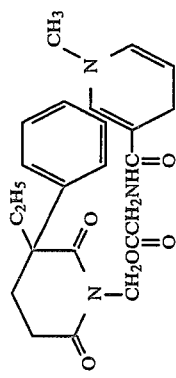
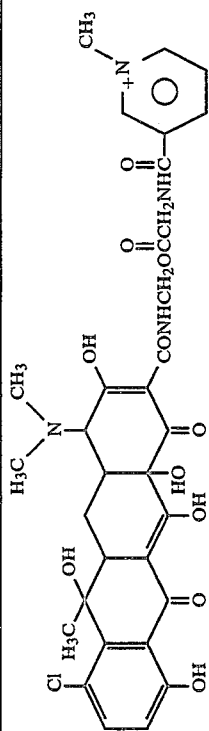
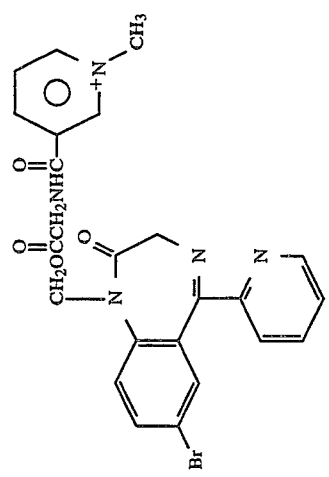
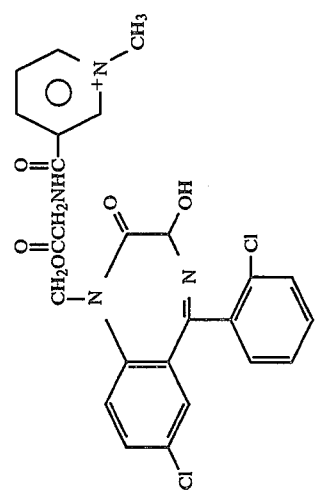
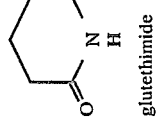
bromozepam
lorazepam
glutethimide -continued
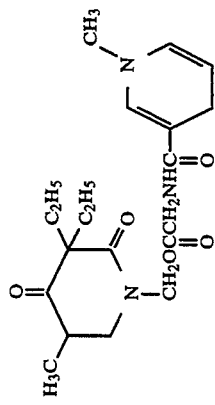
methyprylon
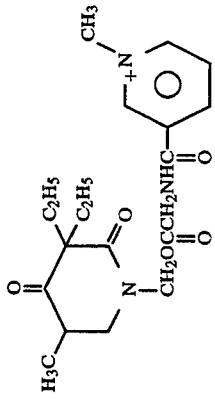
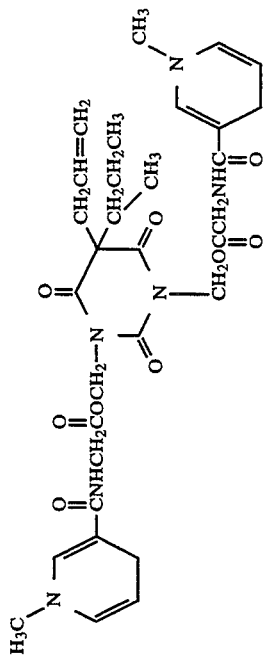
butalbital
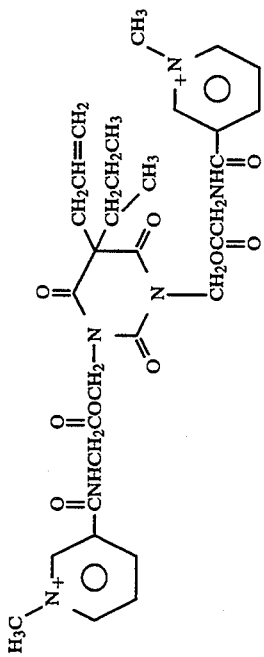
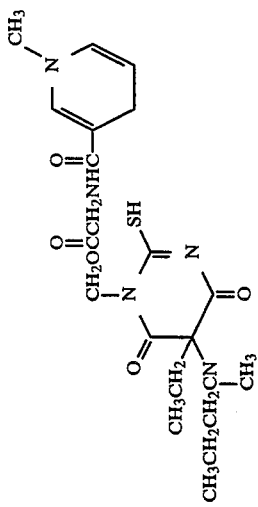
thiopental
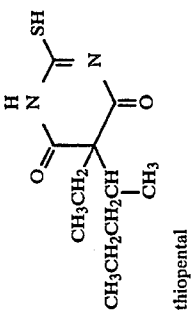
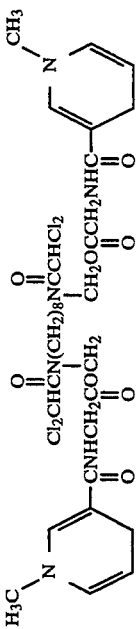
fertilysin
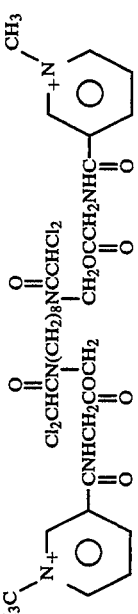

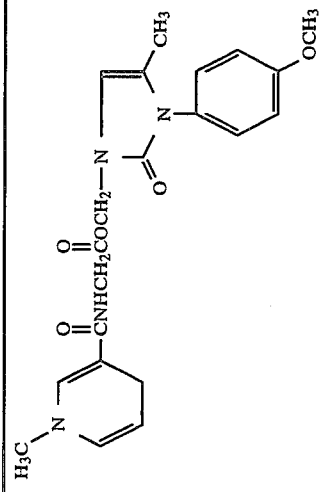 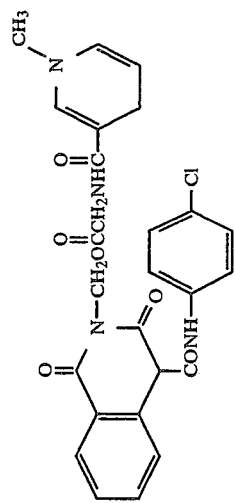 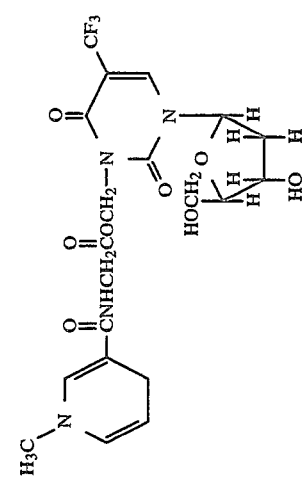 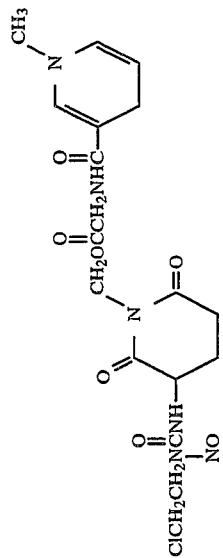
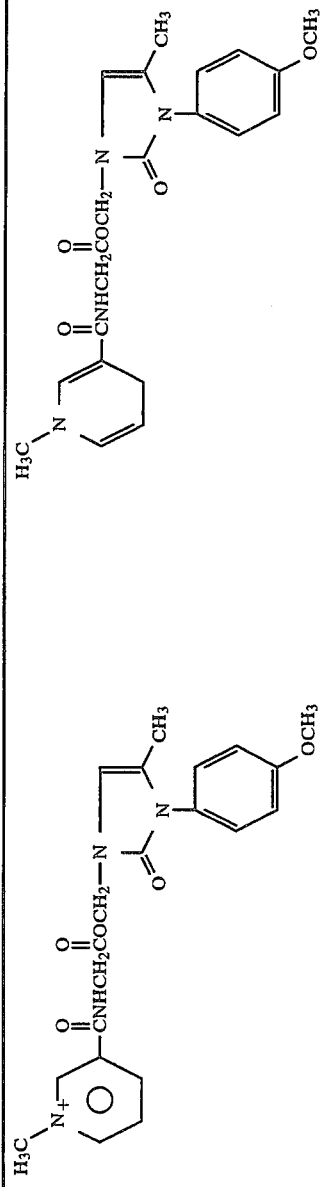 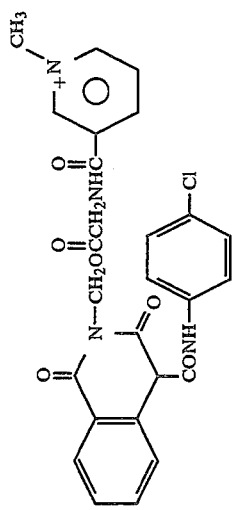 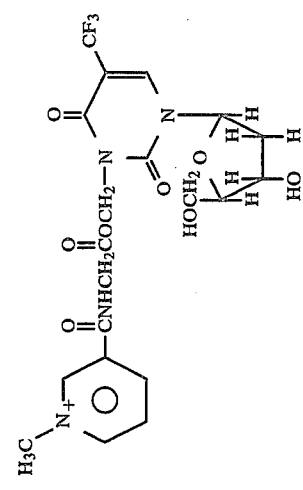 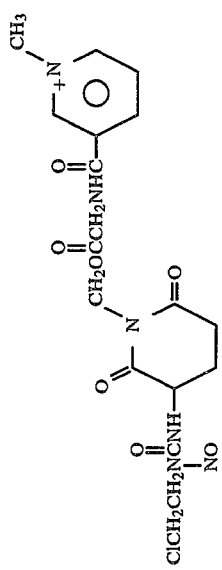
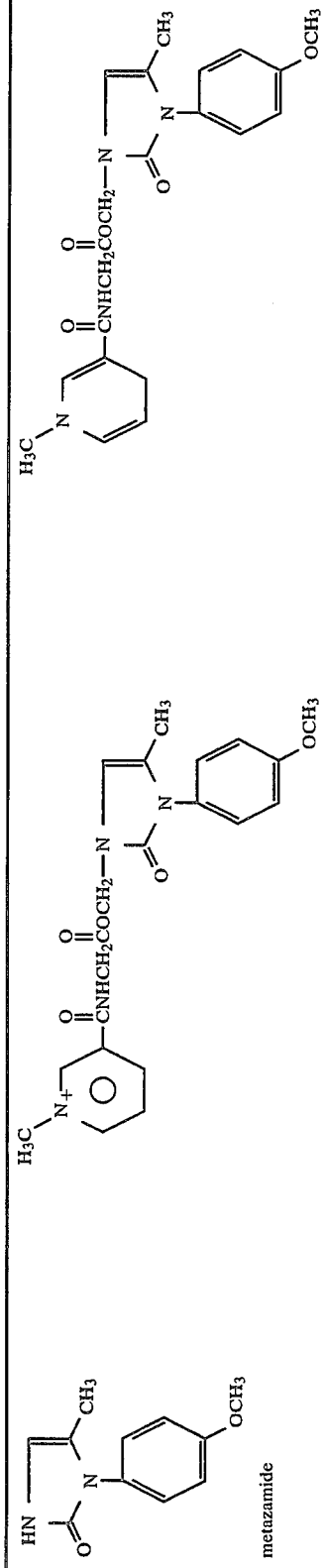 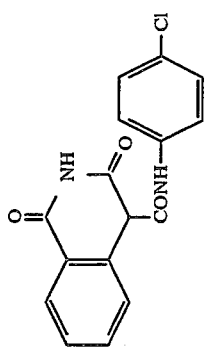 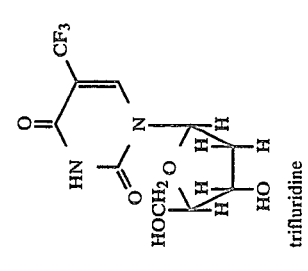 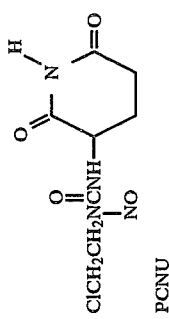

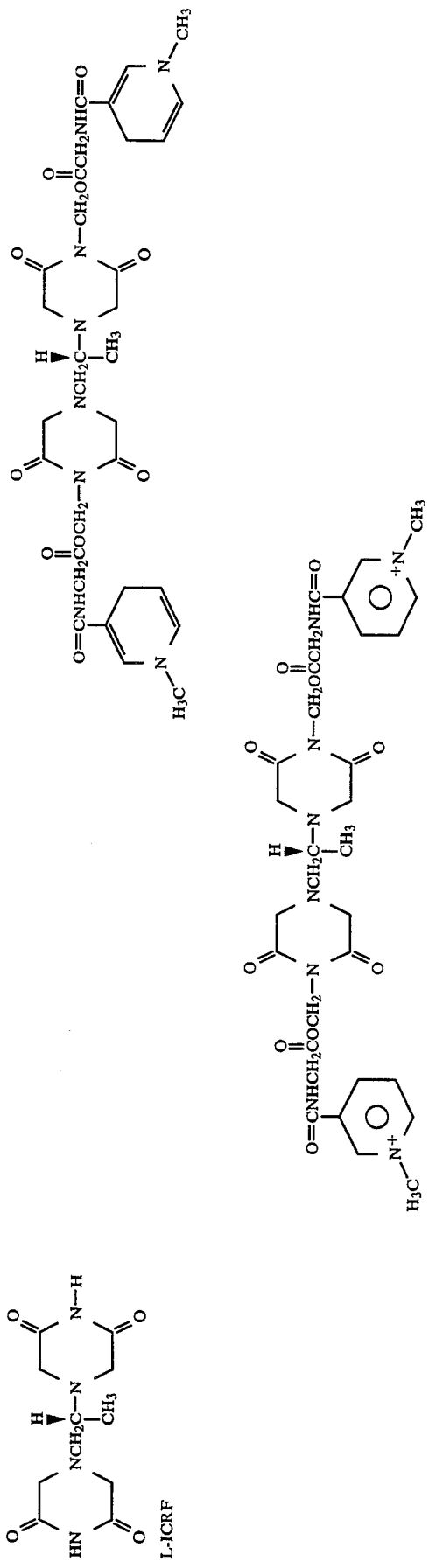
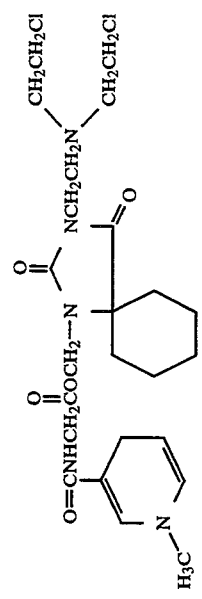
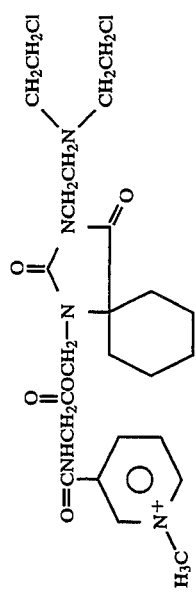
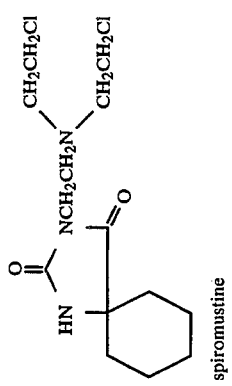
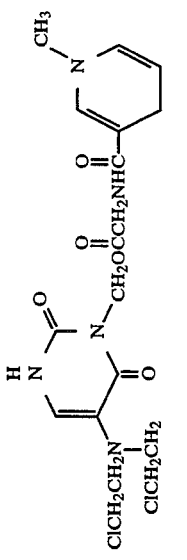

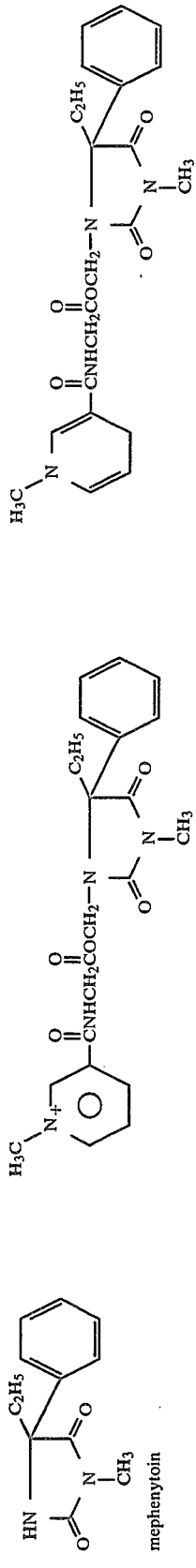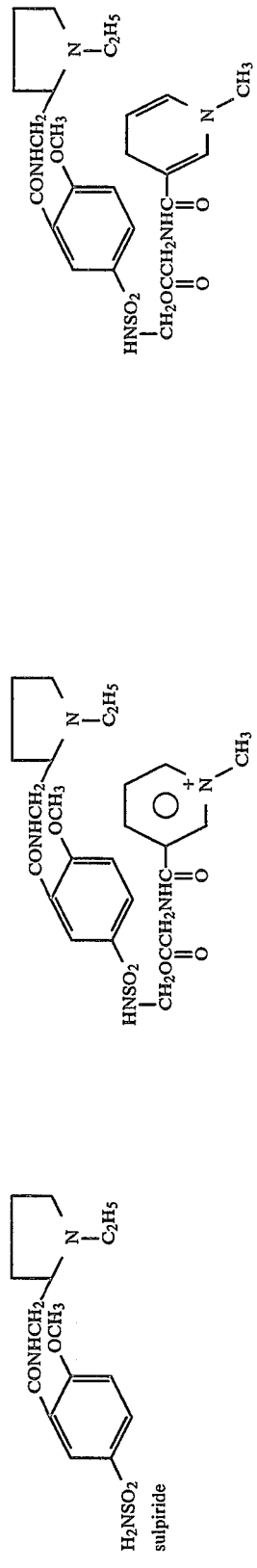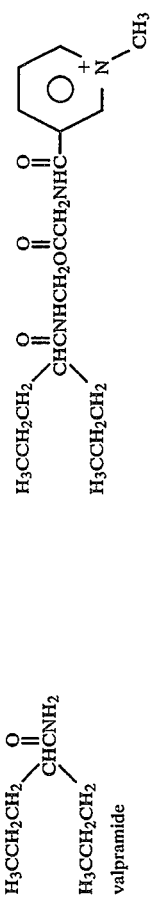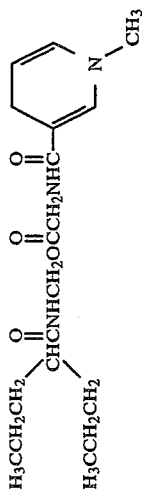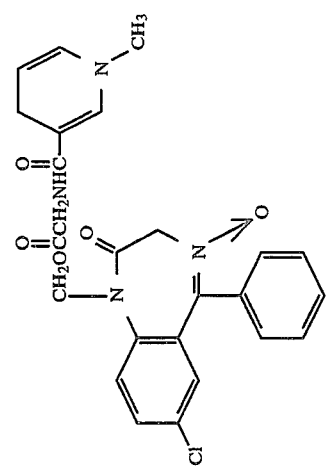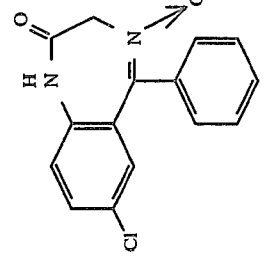

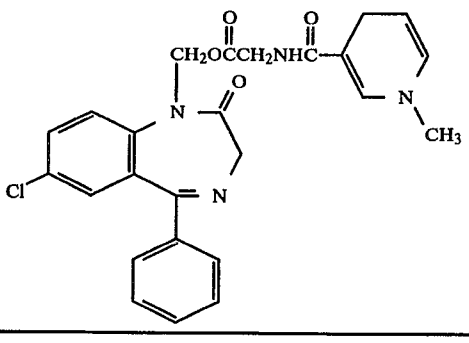
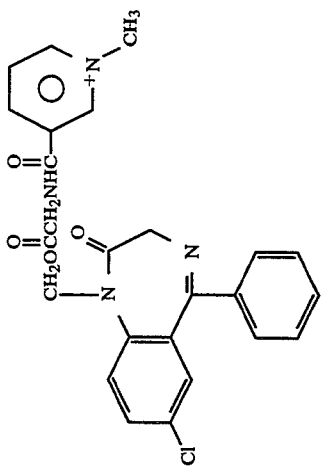
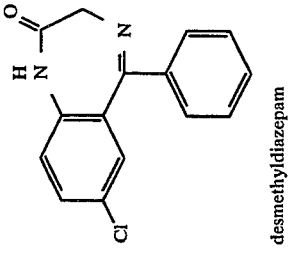
desmethyldiazepam

Method F

This method is a variation of Method E which can be used when the —NH— function is part of an amide or imide or low pKa primary or secondary amine and the drug contains one or more —COOH functions which is/are to be protected. Typically, the carboxyl group or groups is/are first converted to the corresponding pivaloyloxymethyl ester by known esterification techniques. Obviously, other esters may be similarly prepared. The ester is then used as the starting material and Method E is repeated.

The representative starting drugs depicted below may be derivatized in this manner to the corresponding compounds of formulas (II) and (I). Drugs such as carbenicillin, phenoxymethylpenicillin, methicillin, nafcillin, ticarcillin, dicloxacillin, cefazolin, cefoxitin, moxalactam, aminopterin, furosemide, and 5-methyltetrahydrohomofolic acid may be similarly derivatized.

The alternative procedures described in Method E, last paragraph, may be used in Method F also.

| STARTING MATERIAL | QUATERNARY INTERMEDIATE (CATION) | DIHYDRO DERIVATIVE |
|---|---|---|
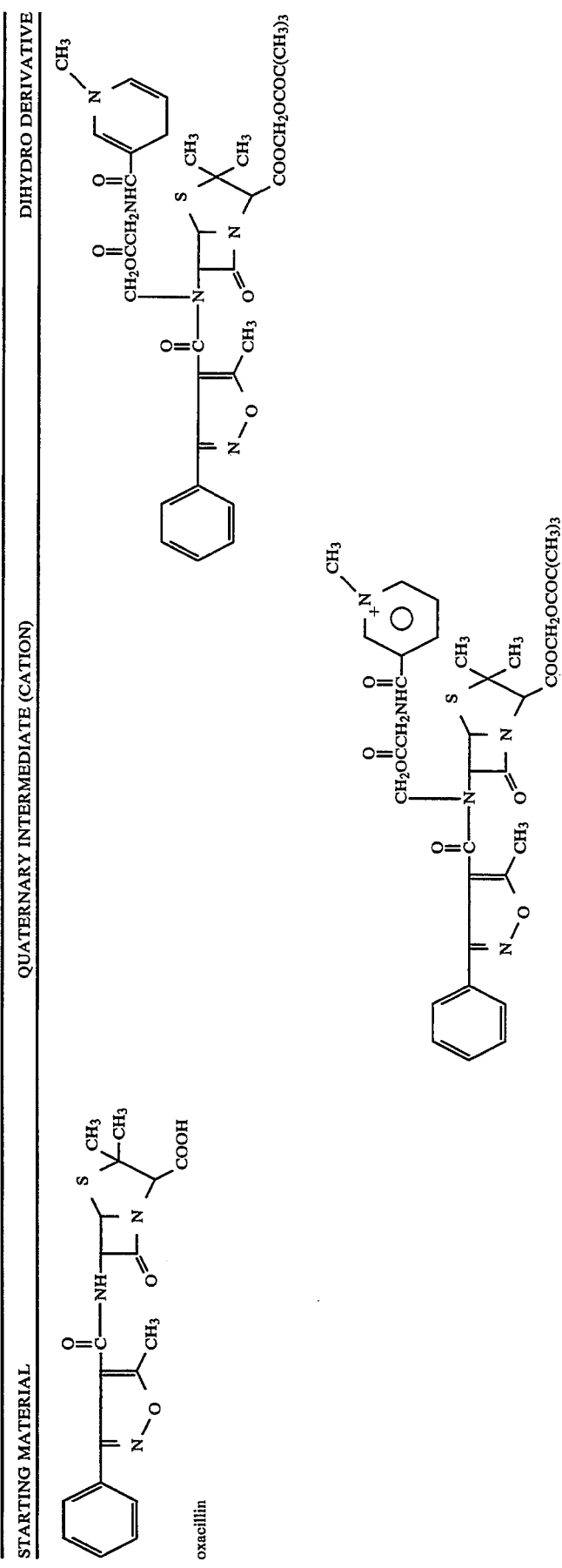

-continued
| STARTING MATERIAL | QUATERNARY INTERMEDIATE (CATION) | DIHYDRO DERIVATIVE |
|---|---|---|
| | 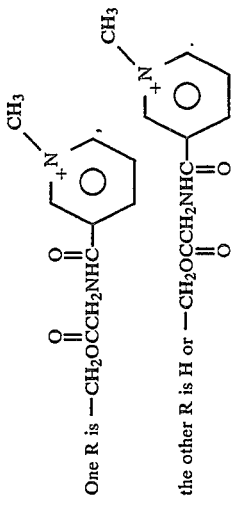 | 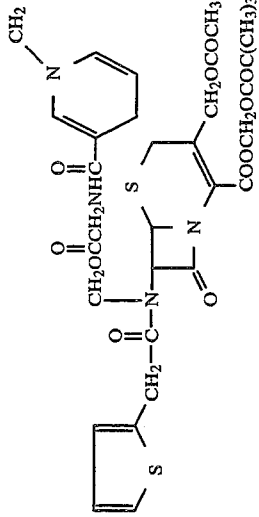 |
| 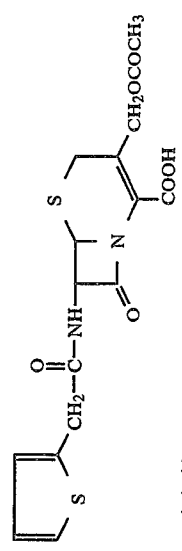 cephalothin | 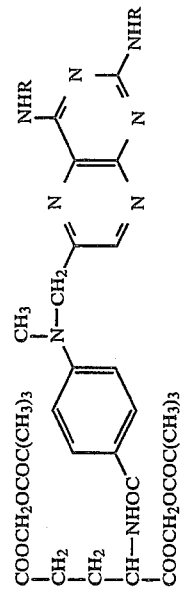 One R is —CH$_2$OCOCH$_2$NHC(O)—<br>the other R is H or —CH$_2$OCOCH$_2$NHC(O)— | 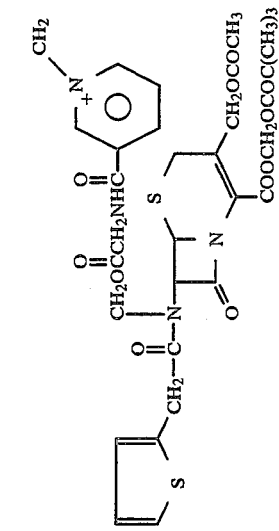 |

-continued
| STARTING MATERIAL | QUATERNARY INTERMEDIATE (CATION) | DIHYDRO DERIVATIVE |
|---|---|---|
| 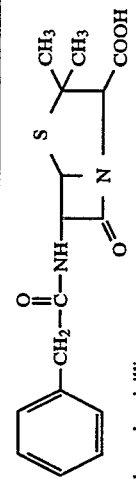 benzylpenicillin | 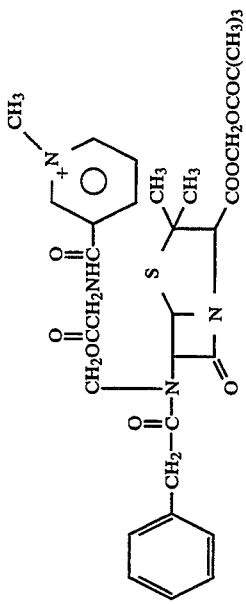 | 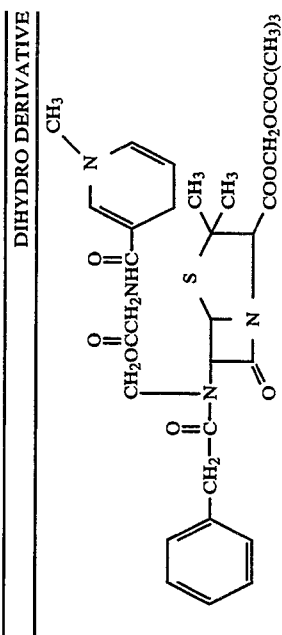 |

Method G

This is a variation of Method E used when the drug also contains one or more hydroxy functions which are to be protected. Typically, the drug is first reacted with excess trimethylacetyl chloride to convert the hydroxy group(s) to pivalyloxy group(s). That protected derivative is then used as the starting material and subjected to Method E.

Other hydroxy protecting groups may be introduced in similar fashion.

The representative drugs depicted below may be derivatized in this manner to the corresponding compounds of formulas (II) and (I).

The alternative procedures described in Method E, last paragraph, may be used in Method G also.

| STARTING MATERIAL | QUATERNARY INTERMEDIATE (CATION) | DIHYDRO DERIVATIVE |
|---|---|---|
| oxazepam | | |
| trifluridine | | |

Method H

The procedure of the second paragraph of Method A is followed, except that removal of the N-protecting group is followed by reaction with 3-quinolinecarboxylic acid or its acid chloride or anhydride instead of nicotinic acid or its acid chloride or anhydride.

The representative drugs depicted below may be derivatized in this manner to the corresponding compounds of formulas (II) and (I), as may the remaining drugs mentioned with Method A.

The procedure of the first paragraph of Method A may be similarly adapted to the production of the 3-quinolinecarboxylic acid derivatives. Moreover, Method H may be combined with Methods B, C, D, E, F or G to afford the corresponding 3-quinolinecarboxylic acid derivatives of the drugs mentioned with those methods.

The procedure of the first paragraph of this method may be repeated using 4-isoquinolinecarboxylic acid or its acid chloride or anhydride to convert drugs such as those mentioned with Methods A, B, C, D, E, F or G to the corresponding 4-isoquinolinecarboxylic acid derivatives.

The procedure of the first or fourth paragraph of this method may be repeated, substituting a different amino acid, e.g. alanine, valine, leucine, phenylalanine, isoleucine, methionine, asparagine or glutamine, for the glycine used in the first step. (See Method A, second paragraph).

The general procedures described above may be utilized to provide the 1,2-dihydro derivatives as well as the depicted 1,4-dihydros.

| STARTING MATERIAL | QUATERNARY INTERMEDIATE (CATION) | DIHYDRO DERIVATIVE |
|---|---|---|
| nortriptyline | | |
| tranylcypramine | | |
| amantadine | | |
| amphetamine | | |
| phenethylamine | | |

| STARTING MATERIAL | QUATERNARY INTERMEDIATE (CATION) | DIHYDRO DERIVATIVE |
|---|---|---|
| hydrolazine | | |
| phentermine | | |
| desipramine | | |
| chlordiazepoxide | | |

Method I

The procedure of the second paragraph of Method is followed, except that a reactant of the formula

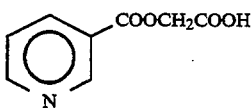

is used place of nicotinic acid. (That starting material may be prepared by reacting nicotinic anhydride, nicotinoyl chloride or nicotinic acid with glycolic acid.)

The representative drugs depicted below may be derivatized in this manner to the corresponding compounds of formulas (II) and (I), as may the remaining drugs listed with Method A.

Similarly, Method I may be combined with Methods B, C or D to afford the corresponding derivatives, e.g. of the drugs mentioned with those methods.

The foregoing procedure can be repeated using picolinic acid or its acid chloride or anhydride, or isonicotinic acid or its acid chloride or anhydride, in place of nicotinic acid or its acid chloride or anhydride, respectively, in the preparation of the reactant depicted above. This variation affords a reactant of the formula

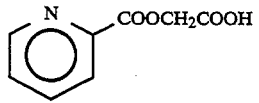 or

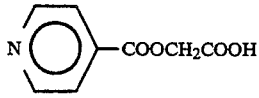

which can then be used in place of nicotinic acid to prepare derivatives of drugs such as those mentioned with Methods A, B, C or D.

The procedure of the first or fourth paragraph of this method may be repeated, substituting a different amino acid, e.g. alanine, valine, leucine, phenylalanine, isoleucine, methionine, asparagine or glutamine, for the glycine used in the first step. (See Method A, second paragraph).

| STARTING MATERIAL | QUATERNARY INTERMEDIATE (CATION) | DIHYDRO DERIVATIVE |
|---|---|---|
| 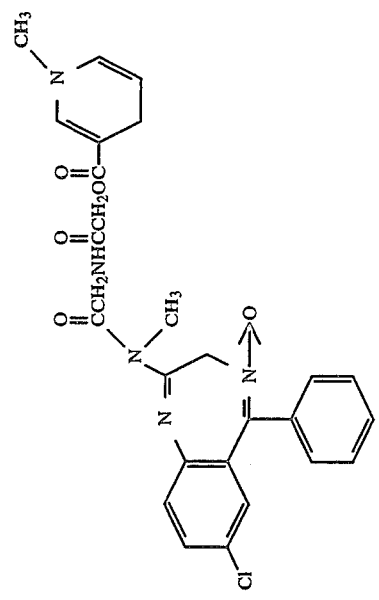 chlordiazepoxide | 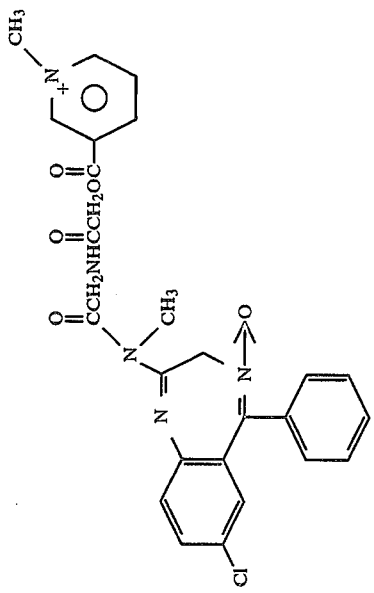 | 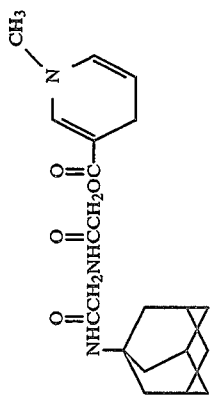 |
| 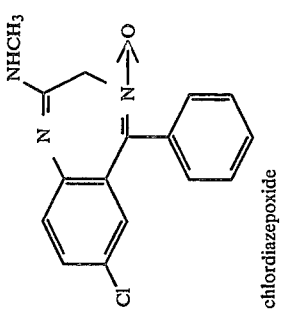 amantadine | | 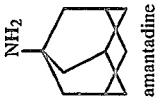 |

| STARTING MATERIAL | QUATERNARY INTERMEDIATE (CATION) | DIHYDRO DERIVATIVE |
|---|---|---|
| 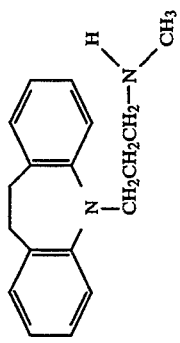 desipramine | 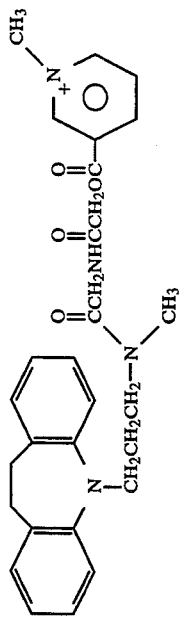 | 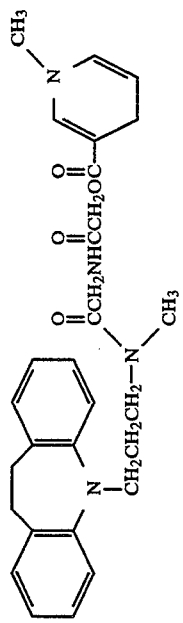 |
| 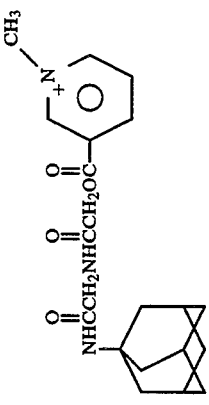 noracymethadol | 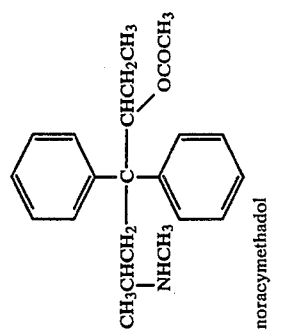 | 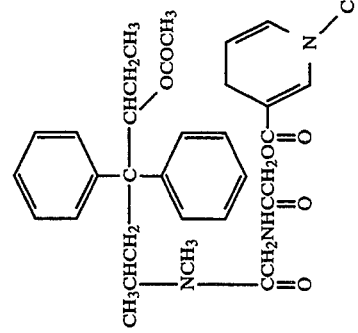 |

| STARTING MATERIAL | QUATERNARY INTERMEDIATE (CATION) | DIHYDRO DERIVATIVE |
|---|---|---|
| 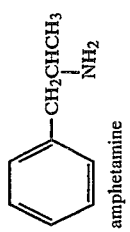<br>amphetamine | 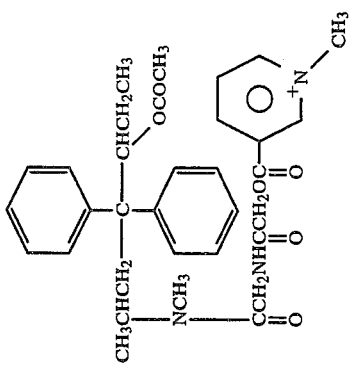 | 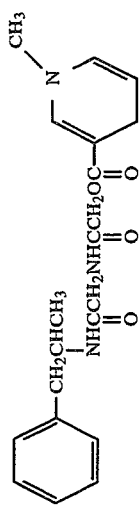 |
| 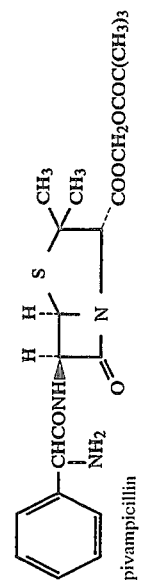<br>pivampicillin | 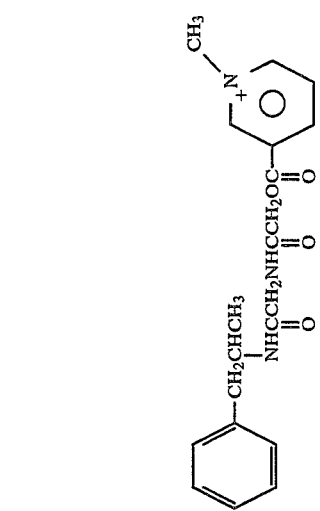 | 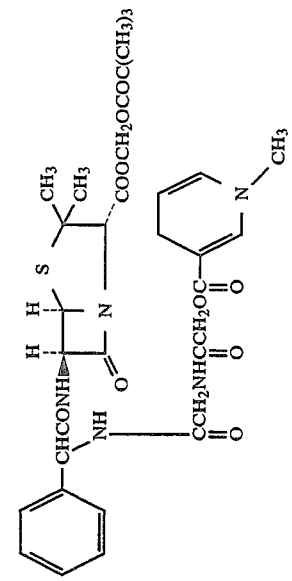 |

| STARTING MATERIAL | QUATERNARY INTERMEDIATE (CATION) | DIHYDRO DERIVATIVE |
|---|---|---|
| | 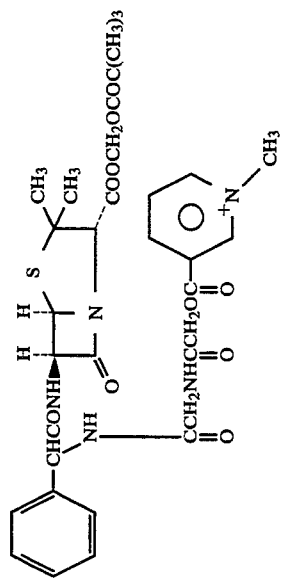 | |

Method J

The procedure of the second paragraph of Method A is followed, except that a reactant of the formula

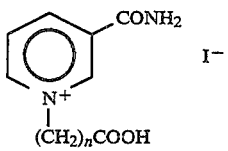

wherein n=1–3, preferably 2, is used in place of nicotinic acid. (That reactant may be prepared from nicotinamide, e.g. when n=2, by reacting 3-iodopropionic acid with nicotinamide.) The quaternary salt of formula (II) thus obtained may then be reduced as described in Method A.

The drugs depicted below may be derivatized in this manner to the corresponding compounds of formulas (II) and (I), as may the remaining drugs mentioned with Method A.

Similarly, Method j may be combined with Methods B, C or D to afford the corresponding derivatives, e.g. of the drugs mentioned with those methods.

The procedure described above can be repeated using picolinamide or isonicotinamide in place of nicotinamide in the preparation of the reactant depicted above. This variation affords a reactant of the formula

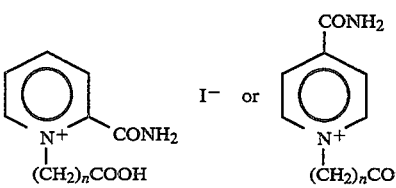

which can then be used in place of nicotinic acid in the procedure of the first paragraph of this method, to afford the corresponding derivatives, e.g. of the drugs mentioned with Methods A, B, C or D.

The procedure of the first or fourth paragraph of this method can be repeated, substituting a different amino acid, e.g. alanine, valine, leucine, phenylalanine, isoleucine, methionine, asparagine or glutamine, for the glycine used in the first step. (See Method A, second paragraph).

| STARTING MATERIAL | QUATERNARY INTERMEDIATE (CATION) | DIHYDRO DERIVATIVE |
|---|---|---|
| amphetamine | | |
| phentermine | | |
| desipramine | | |

| STARTING MATERIAL | QUATERNARY INTERMEDIATE (CATION) | DIHYDRO DERIVATIVE |
|---|---|---|
| bacampicillin | | |

II. Methods for Derivatizing —OH and —SH Functions in Drugs

Method K

The drug is reacted with nicotinuric acid chloride, with nicotinuric acid anhydride, or with nicotinuric acid in the presence of a suitable coupling agent such as dicyclohexyl carbodiimide, in an appropriate organic solvent, to afford the corresponding glycylnicotinate, or nicotinurate. The nicotinurate is then quaternized and subsequently reduced as described above in Method A. When the drug contains more than one reactive hydroxyl or thiol function, reaction conditions may be varied so that more than one hydroxyl or thiol function will be converted to nicotinurate groupings. The alternative process utilizing an activated ester or quaternary derivative thereof which is described in Method A may be utilized here as well.

Alternatively, glycine may be first reacted with a reagent capable of introducing an amino protecting group such as benzyloxycarbonyl or t-butylcarbonyl (e.g. as in Scheme 1 or 2 hereinabove) and the N- protected glycine then reacted with the drug in the presence of a coupling agent such as dicyclohexylcarbodiimide, followed by removal of the N- protecting group, followed by reaction with nicotinoyl chloride or nicotinic anhydride, or with nicotinic acid in the presence of dicyclohexylcarbodiimide or other suitable coupling agent, to afford the nicotinurate. The nicotinurate may then be quaternized and the quaternary reduced as described in the preceding paragraph.

The representative drugs depicted below may be derivatized in this manner to the corresponding compounds of formulas (II) and (I). Estriol, lincomycin, apomorphine, meptazinol, cyclazocine, phenazocine, metopon, myfadol, naltrexone, alazocine, oxilorphan, nalmexone, thioguanine, levorphanol, benzestrol, diethylstilbestrol, pentostatin (2'-deoxycoformycin), tiazofurin, sangivamycin, 2 -deoxy-D-glucose, 2-deoxy-2-fluoro-D-mannose and phenyl-6-chloro-6-deoxy-$\beta$-D-glucopyranoside may be similarly derivatized.

The procedure of the second paragraph of this method may be repeated using picolinic acid or its acid chloride or anhydride, or isonicotinic acid or its acid chloride or anhydride, in place of nicotinic acid or its acid chloride or anhydride, respectively, to convert drugs such as those specifically mentioned for derivatizing by this method to the corresponding glycyl picolinic acid esters or glycyl isonicotinic acid esters and then to the corresponding compounds of formulas (II) and (I). The procedure of the first paragraph of this method may be similarly adapted. Moreover, any of these procedures may be repeated, substituting a different amino acid or nicotinic acid derivative thereof for the glycine or nicotinuric acid used above, e.g. replacing glycine with alanine, valine, leucine, phenylalanine, isoleucine, methionine, asparagine or glutamine.

| STARTING MATERIAL | QUATERNARY INTERMEDIATE (CATION) | DIHYDRO DERIVATIVE |
|---|---|---|
| oxazepam | | |
| carphenazine | | |

| STARTING MATERIAL | QUATERNARY INTERMEDIATE (CATION) | DIHYDRO DERIVATIVE |
|---|---|---|
| 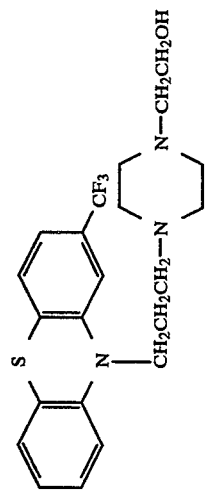<br>fluphenazine | 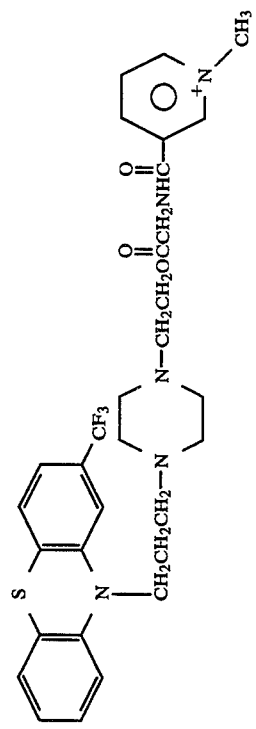 | 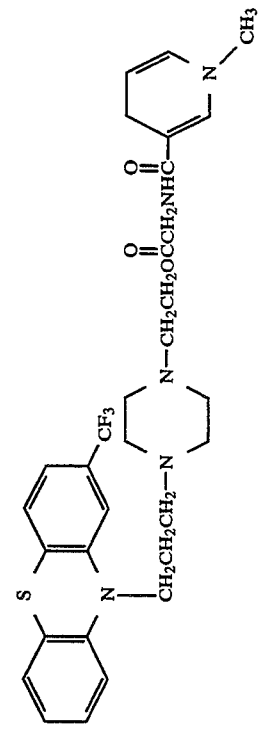 |
| 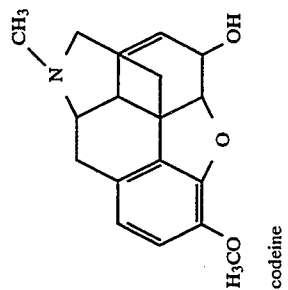<br>codeine | 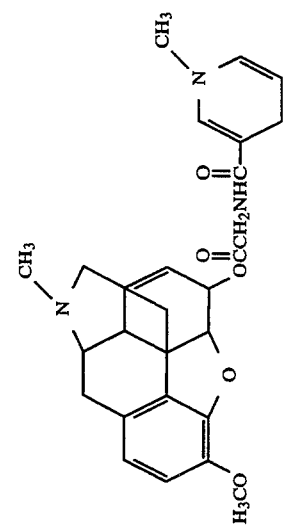 | |

-continued
| STARTING MATERIAL | QUATERNARY INTERMEDIATE (CATION) | DIHYDRO DERIVATIVE |
|---|---|---|
| 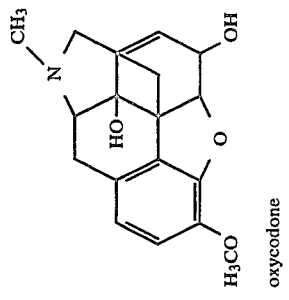<br>oxycodone | 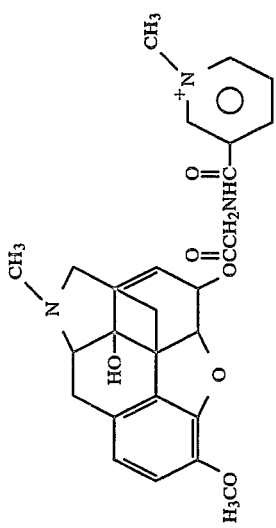 | 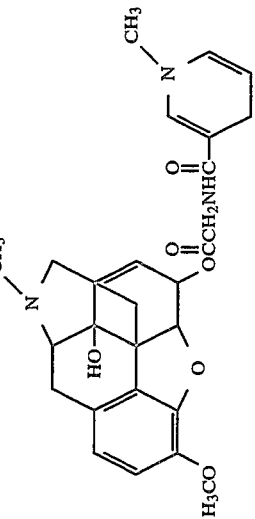 |
| pentazocine | | 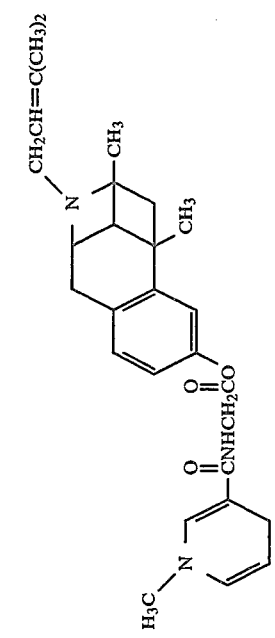 |

| STARTING MATERIAL | QUATERNARY INTERMEDIATE (CATION) | DIHYDRO DERIVATIVE |
|---|---|---|
| 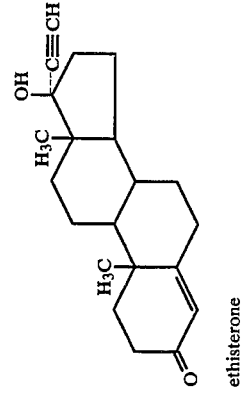
ethisterone | 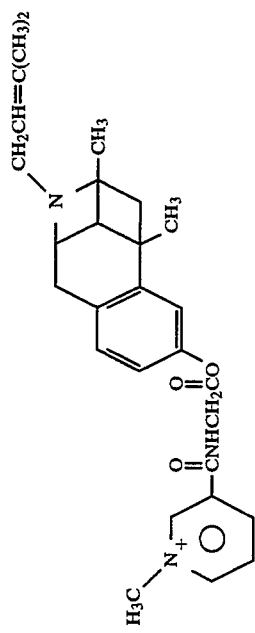 | 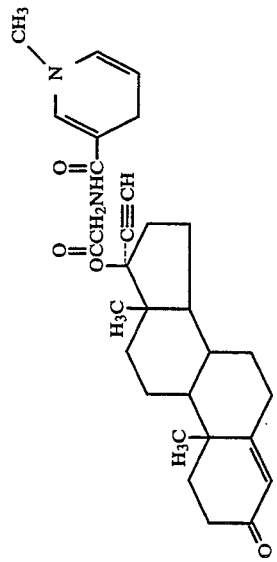
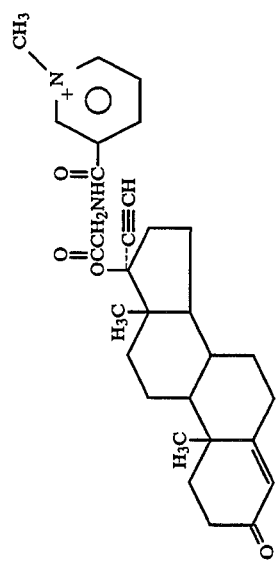 |

| STARTING MATERIAL | QUATERNARY INTERMEDIATE (CATION) | DIHYDRO DERIVATIVE |
|---|---|---|
| 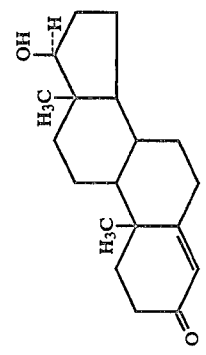 testosterone | 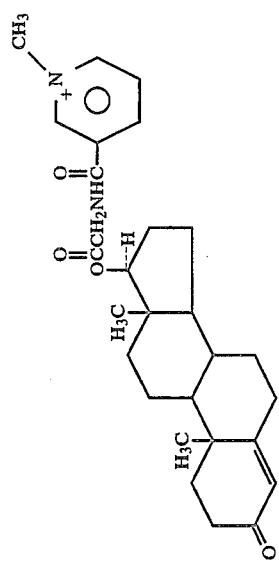 | 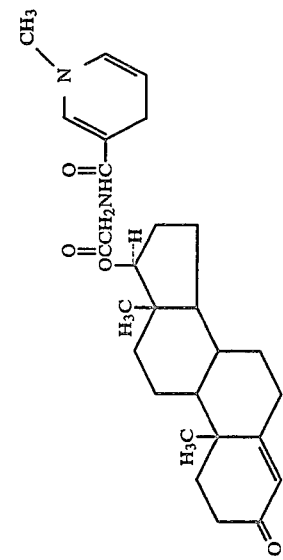 |
| 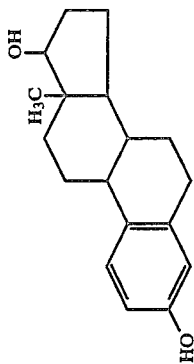 estradiol | | 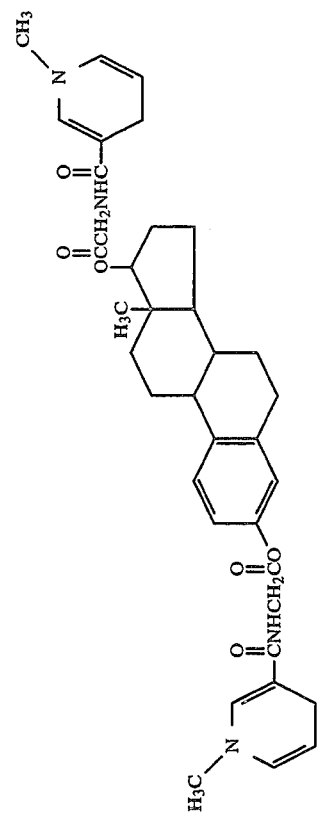 |

| STARTING MATERIAL | QUATERNARY INTERMEDIATE (CATION) | DIHYDRO DERIVATIVE |
|---|---|---|
| 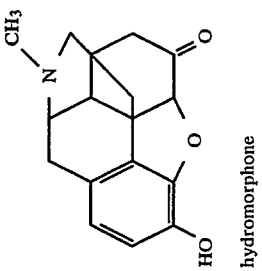
hydromorphone | 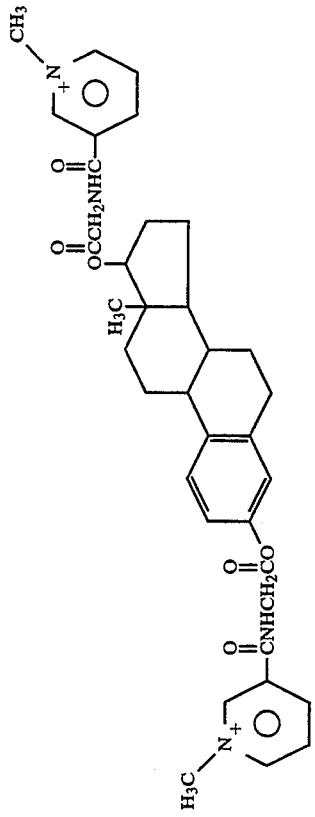 | 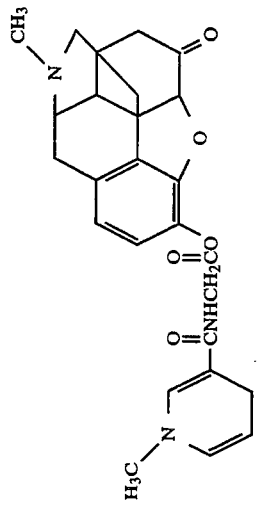<br><br>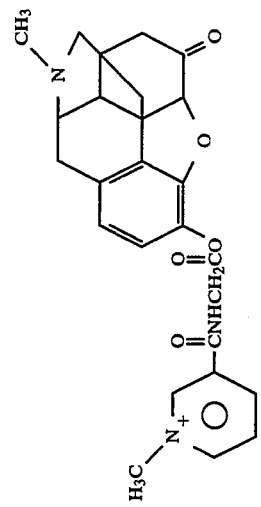 |
This compound can be subsequently selectively hydrolyzed by known methods to the corresponding 17-monoester of formula (II), which can be reduced to the corresponding preferred 17-monoester of formula (I).

| STARTING MATERIAL | QUATERNARY INTERMEDIATE (CATION) | DIHYDRO DERIVATIVE |
|---|---|---|
| 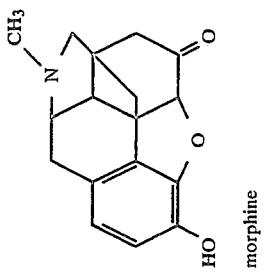
morphine | 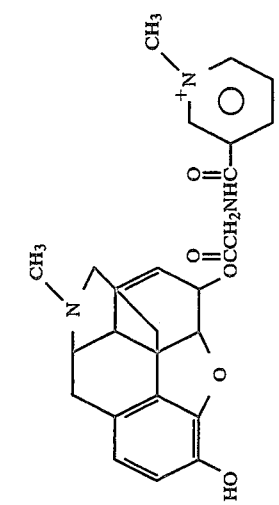 | 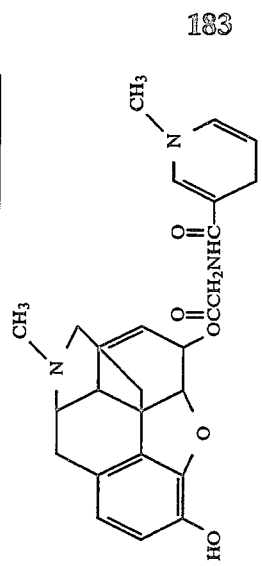 |
| 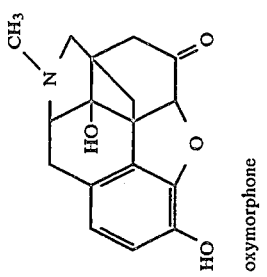
oxymorphone | 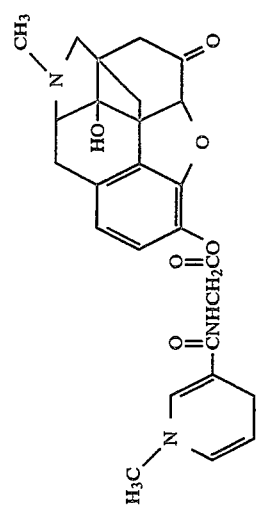 | |

-continued
| STARTING MATERIAL | QUATERNARY INTERMEDIATE (CATION) | DIHYDRO DERIVATIVE |
|---|---|---|
| 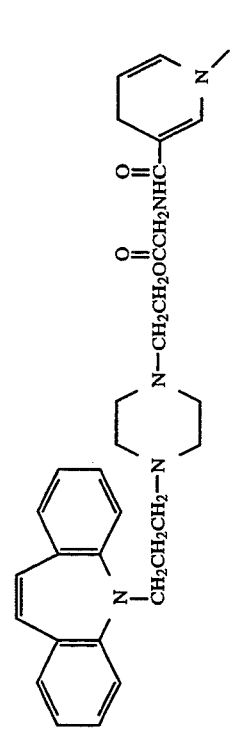 opipromol |  | 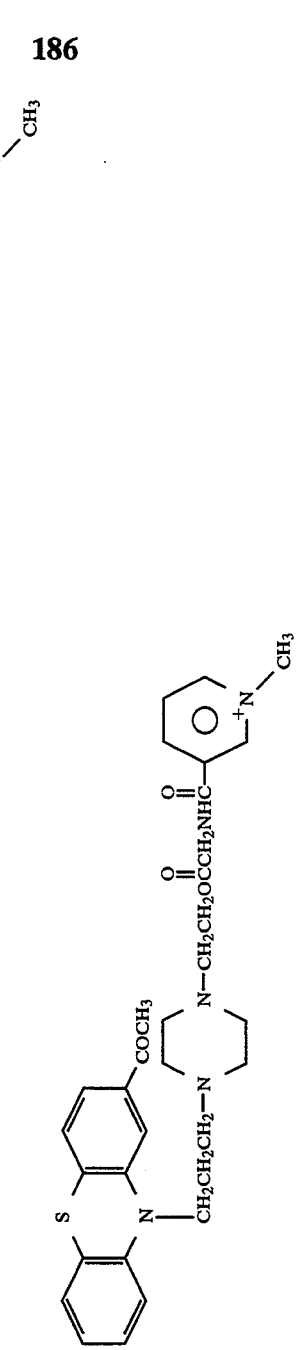 |
|  acetophenazine | 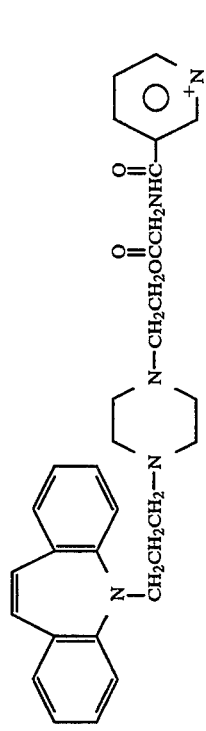 |  |

-continued
| STARTING MATERIAL | QUATERNARY INTERMEDIATE (CATION) | DIHYDRO DERIVATIVE |
|---|---|---|
| 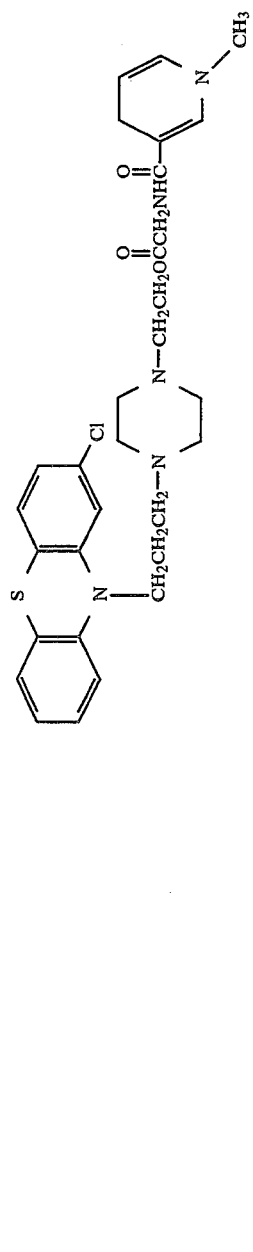 perphenazine | 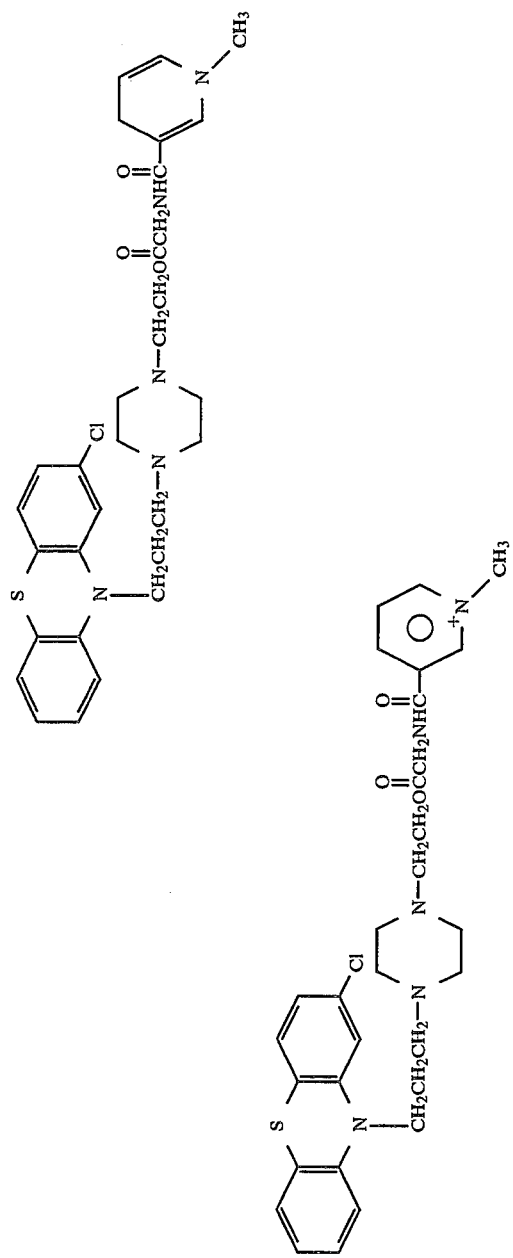 | |
| 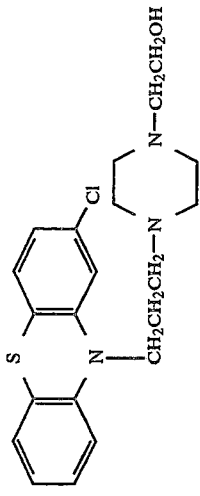 piperacetazine | 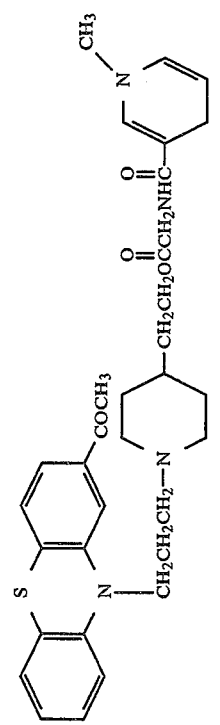 | 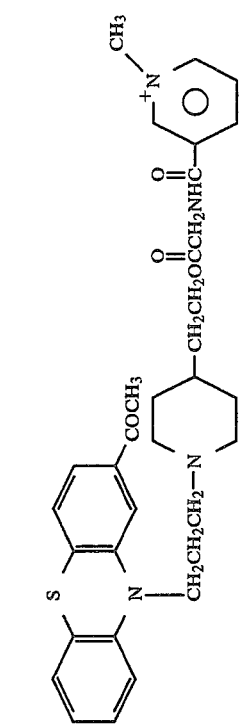 |

| STARTING MATERIAL | QUATERNARY INTERMEDIATE (CATION) | DIHYDRO DERIVATIVE |
|---|---|---|
| 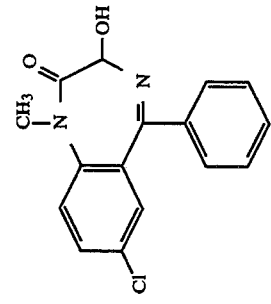<br>temazepam | 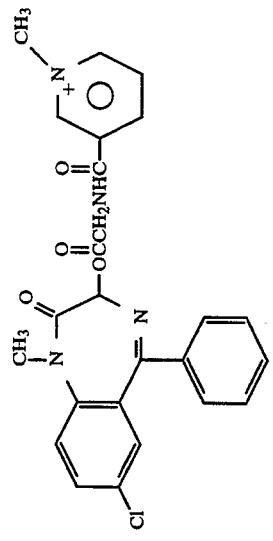 | |
| 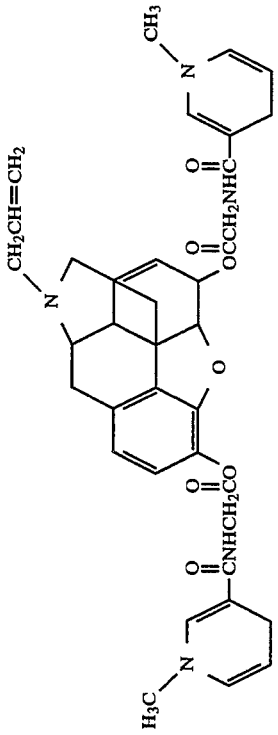nalorphine | | |

| STARTING MATERIAL | QUATERNARY INTERMEDIATE (CATION) | DIHYDRO DERIVATIVE |
|---|---|---|
| 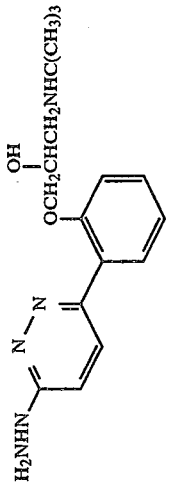 prizidilol | 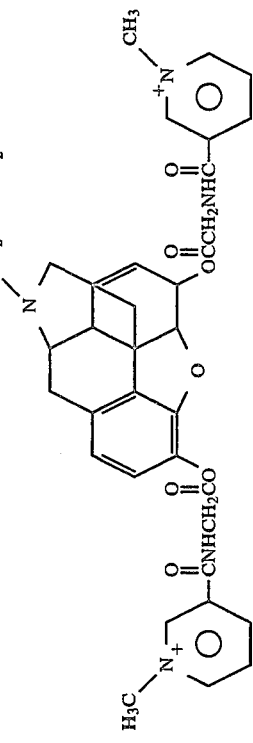 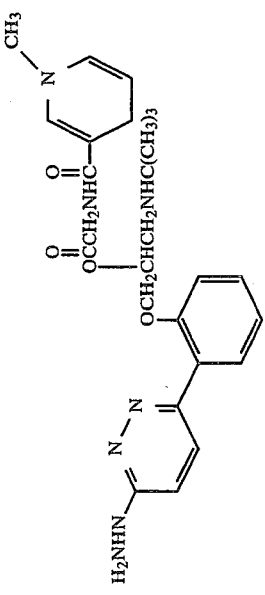 | 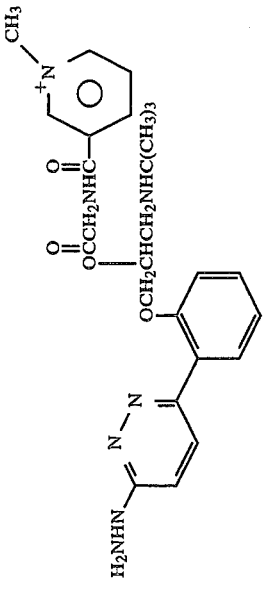 |
| 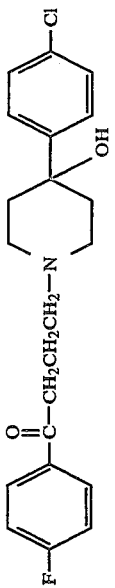 haloperidol | | 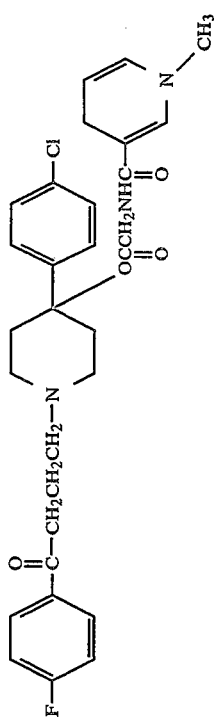 |

-continued
| STARTING MATERIAL | QUATERNARY INTERMEDIATE (CATION) | DIHYDRO DERIVATIVE |
|---|---|---|
| 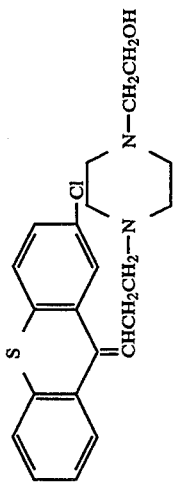 clopenthixol | 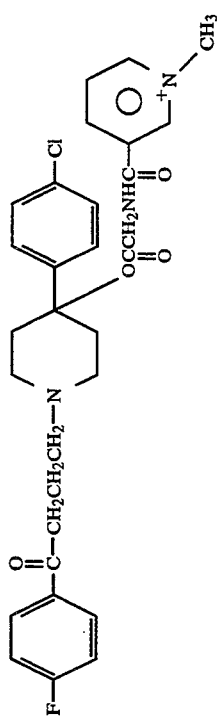 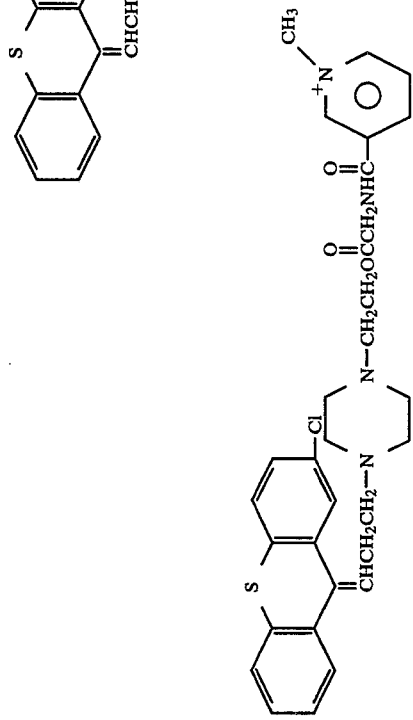 | 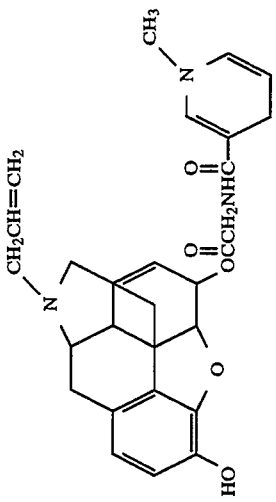 |
| 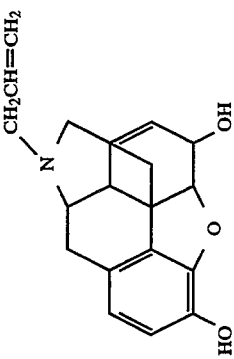 nalorphine | | |

| STARTING MATERIAL | QUATERNARY INTERMEDIATE (CATION) | DIHYDRO DERIVATIVE |
|---|---|---|
| 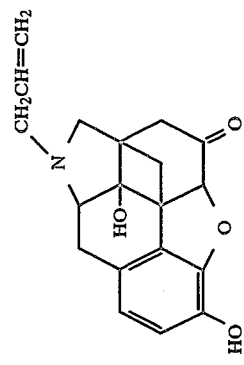<br>naloxane | 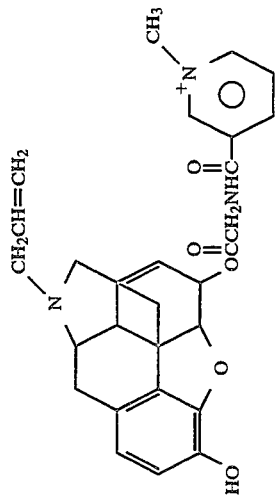 | 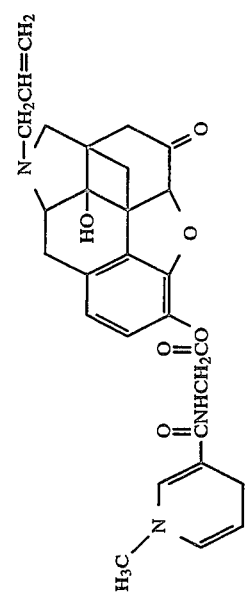 |
| 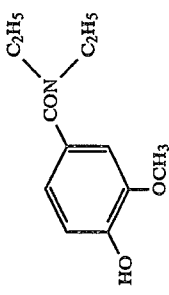<br>ethamivan | 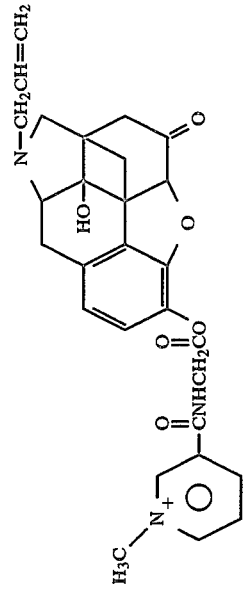 | |

| STARTING MATERIAL | QUATERNARY INTERMEDIATE (CATION) | DIHYDRO DERIVATIVE |
|---|---|---|
| 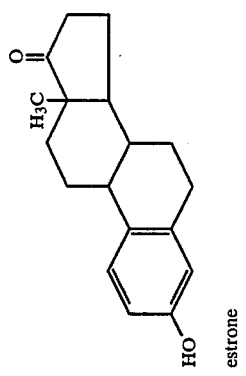<br>estrone | 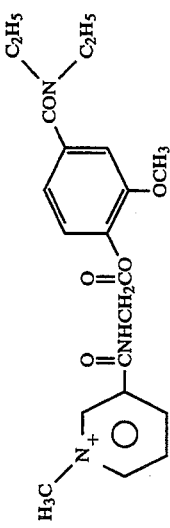 | 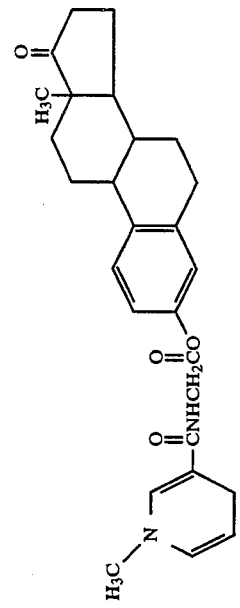 |
| | 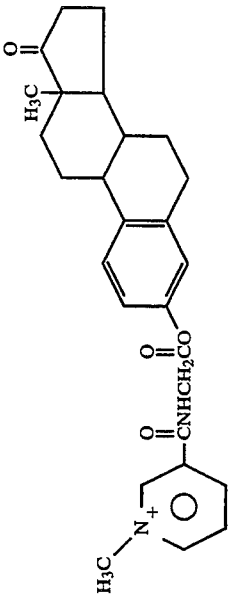 | |
| 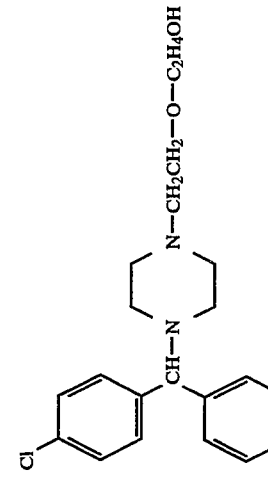<br>hydroxyzine | | 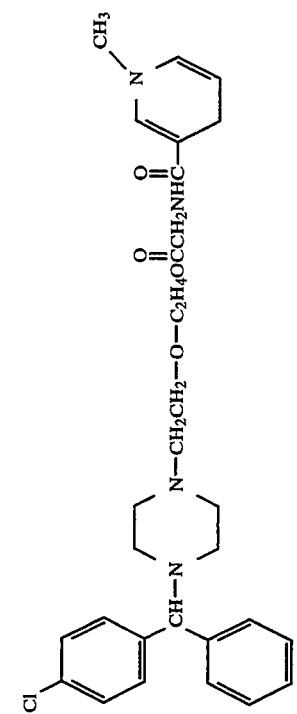 |
197 198

-continued
| STARTING MATERIAL | QUATERNARY INTERMEDIATE (CATION) | DIHYDRO DERIVATIVE |
|---|---|---|
| 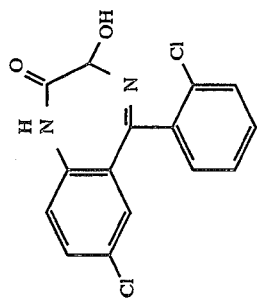
lorazepam | 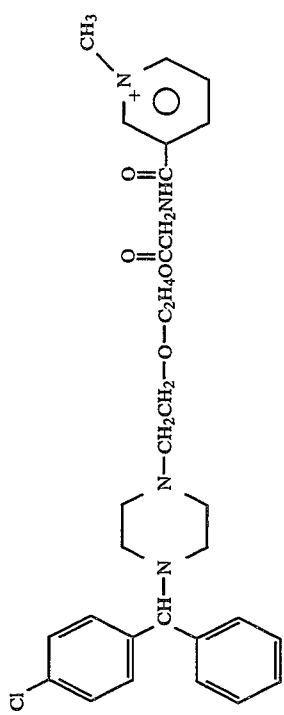 | 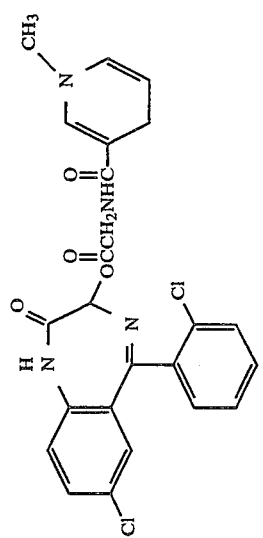<br>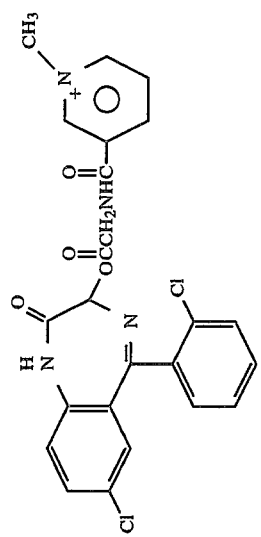 |

-continued
| STARTING MATERIAL | QUATERNARY INTERMEDIATE (CATION) | DIHYDRO DERIVATIVE |
|---|---|---|
| 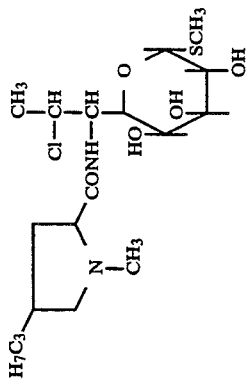 clindamycin | 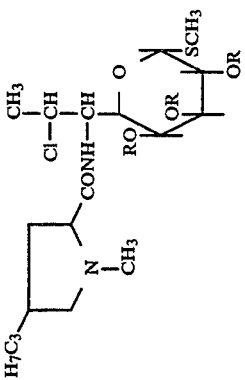 | 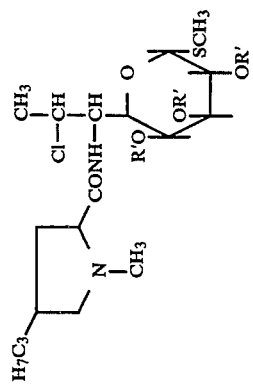  Each R' is H or —CCH$_2$NHC=O provided at least one R' is —CCH$_2$NHC=O |

| STARTING MATERIAL | QUATERNARY INTERMEDIATE (CATION) | DIHYDRO DERIVATIVE |
|---|---|---|
| 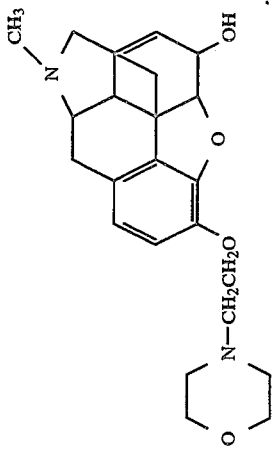pholcodine | 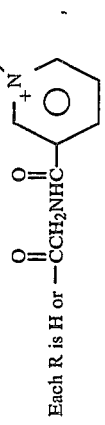 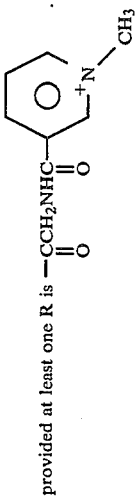<br>Each R is H or —CCH$_2$NHC(=O)-Py-CH$_3$<br>provided at least one R is —CCH$_2$NHC(=O)-Py-CH$_3$ | 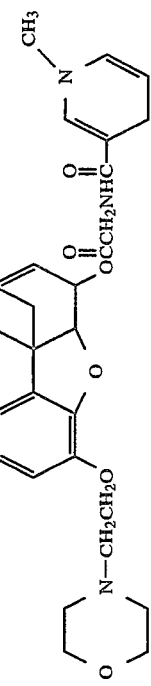<br>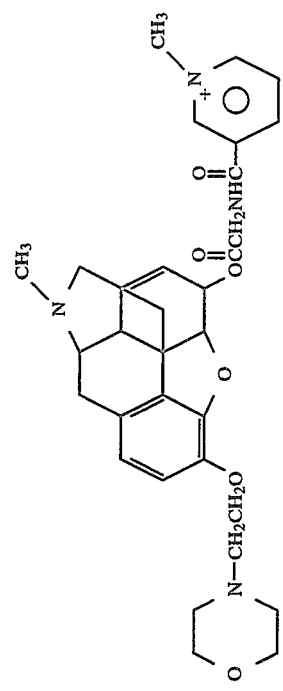 |

| STARTING MATERIAL | QUATERNARY INTERMEDIATE (CATION) | DIHYDRO DERIVATIVE |
|---|---|---|
| 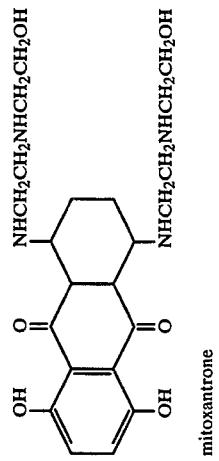 mitoxantrone | 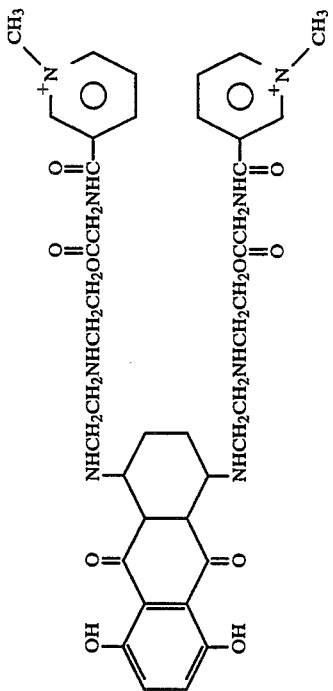 | 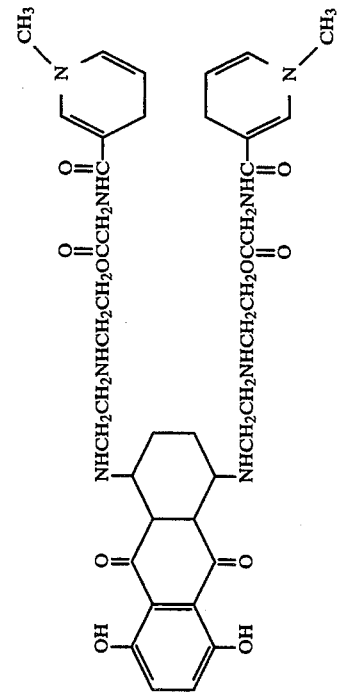 |

-continued
| STARTING MATERIAL | QUATERNARY INTERMEDIATE (CATION) | DIHYDRO DERIVATIVE |
|---|---|---|
| 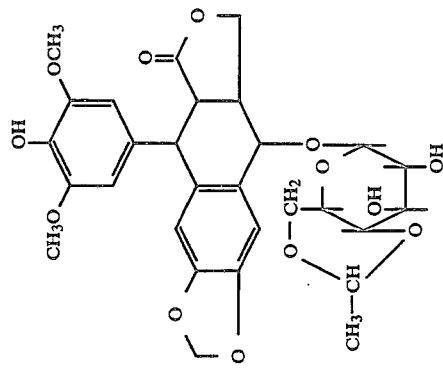  VP-16 (etoposide) | | 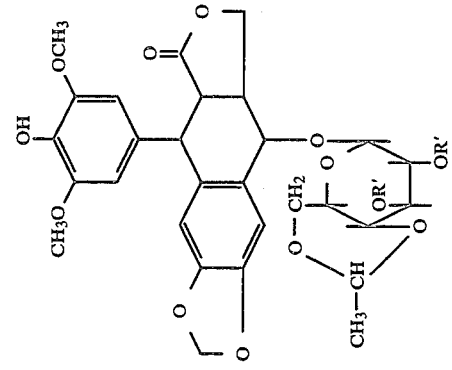 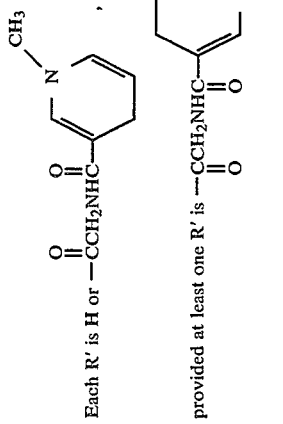  Each R' is H or —CCH$_2$NHC—  provided at least one R' is —CCH$_2$NHC— |

| STARTING MATERIAL | QUATERNARY INTERMEDIATE (CATION) | DIHYDRO DERIVATIVE |
|---|---|---|
| | 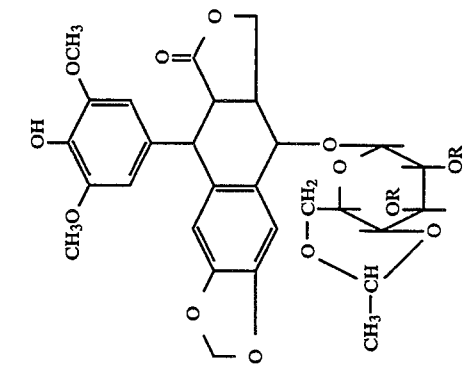 | 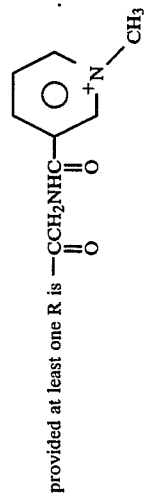 Each R is H or —CCH$_2$NHC— provided at least one R is —CCH$_2$NHC— |
-continued

| STARTING MATERIAL | QUATERNARY INTERMEDIATE (CATION) | DIHYDRO DERIVATIVE |
|---|---|---|
| 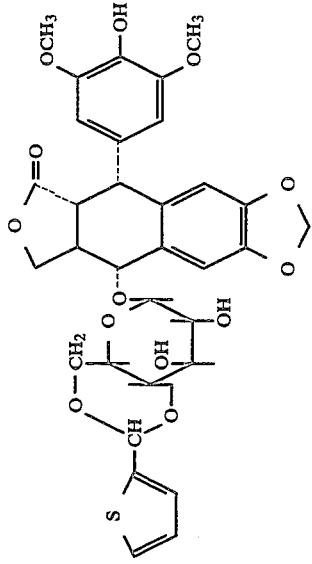<br>teniposide | 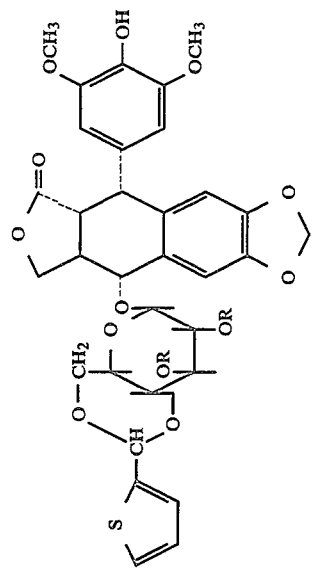 | 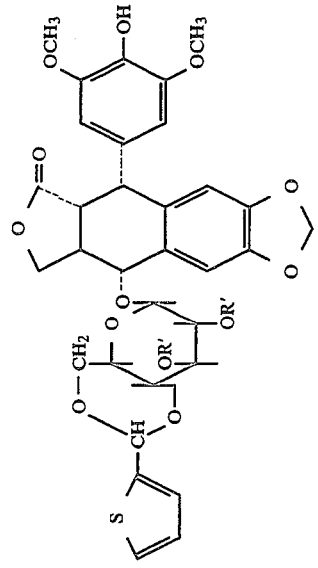<br>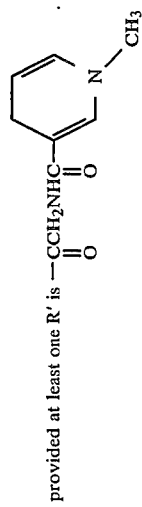<br>Each R' is H or —CCH₂NHC=O<br>provided at least one R' is —CCH₂NHC=O |

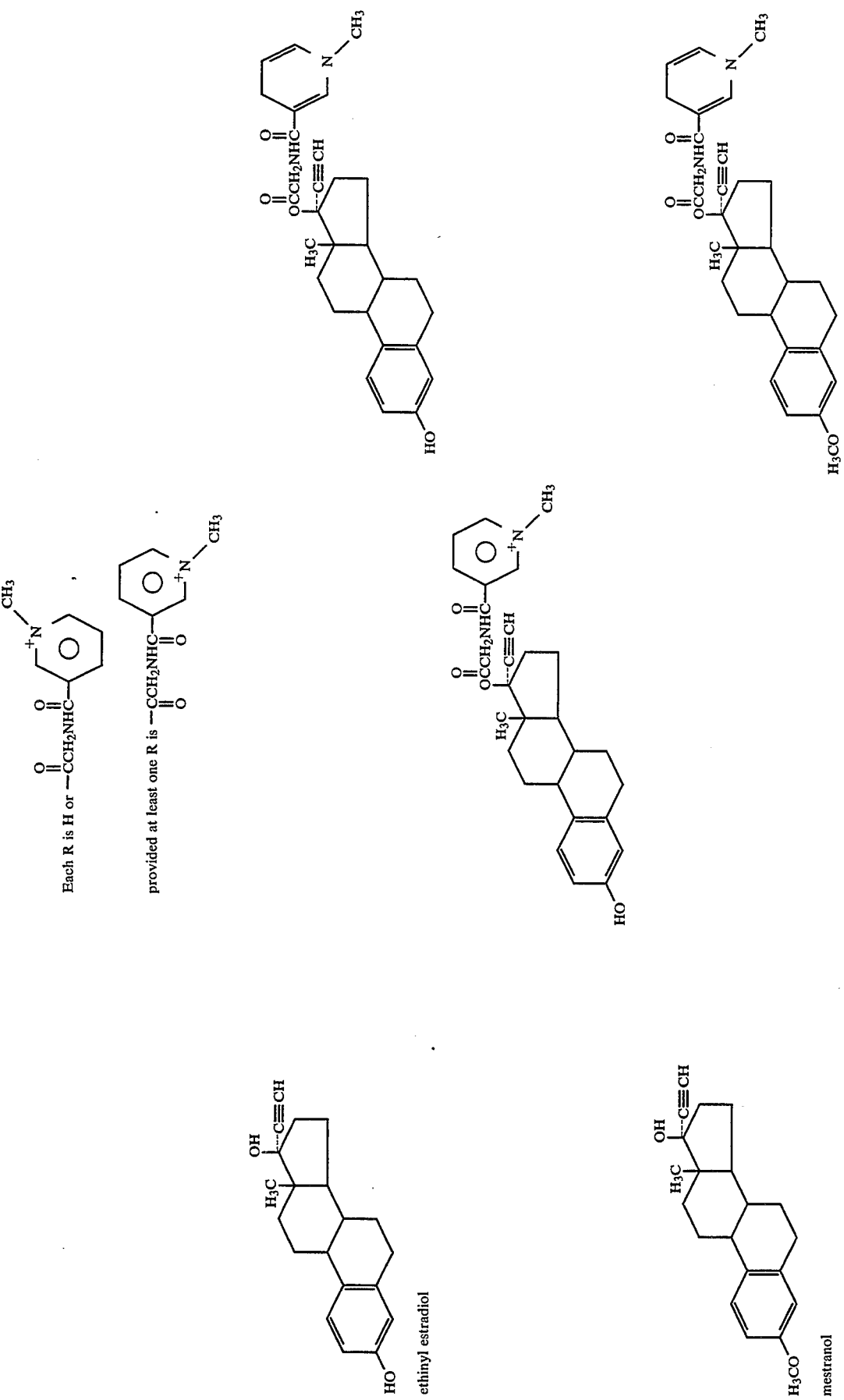

-continued
| STARTING MATERIAL | QUATERNARY INTERMEDIATE (CATION) | DIHYDRO DERIVATIVE |
|---|---|---|
| 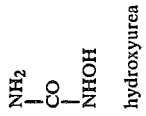<br>hydroxyurea | 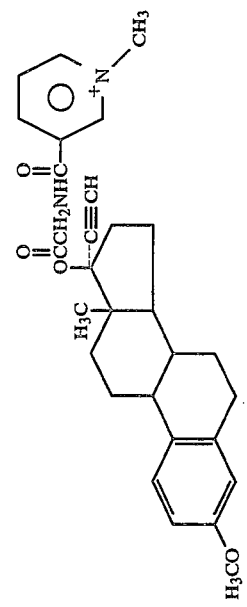 | 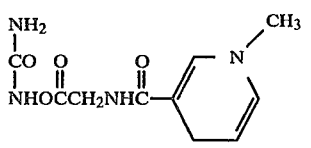 |
| 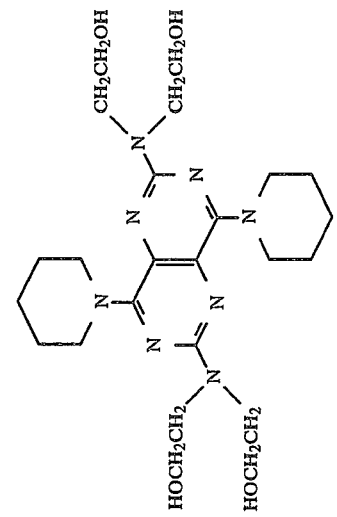<br>dipyridamole |  | 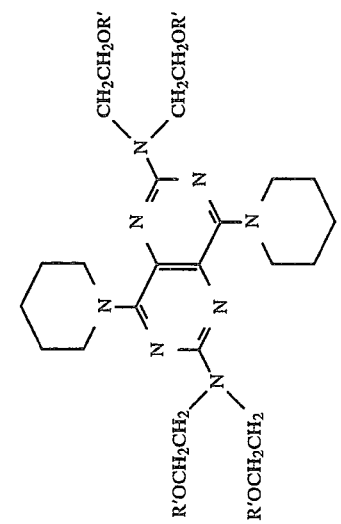 |

| STARTING MATERIAL | QUATERNARY INTERMEDIATE (CATION) | DIHYDRO DERIVATIVE |
|---|---|---|
| | | 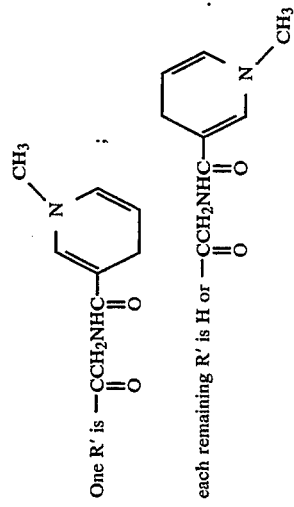<br>One R' is —CCH₂NHC=O / =O ;<br>each remaining R' is H or —CCH₂NHC=O / =O |
| | 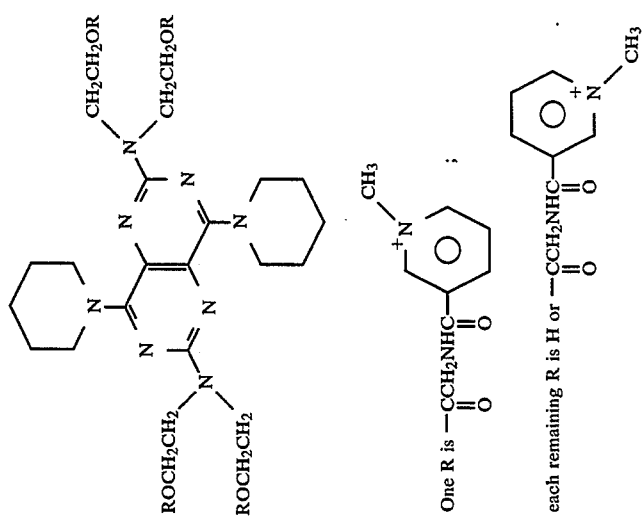<br>One R is —CCH₂NHC=O / =O ;<br>each remaining R is H or —CCH₂NHC=O / =O | |

| STARTING MATERIAL | QUATERNARY INTERMEDIATE (CATION) | DIHYDRO DERIVATIVE |
|---|---|---|
| 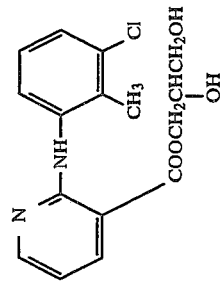 clonixeril | 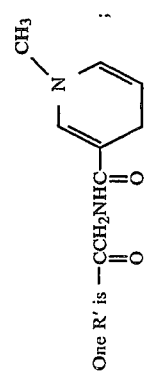 | 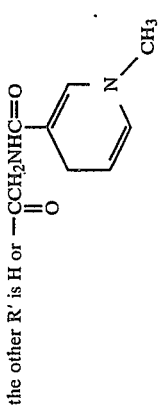 One R' is —CCH$_2$NHC=O ; the other R' is H or —CCH$_2$NHC=O 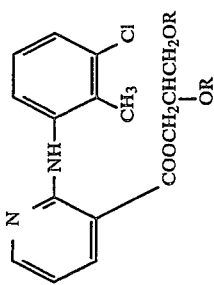 |

-continued
| STARTING MATERIAL | QUATERNARY INTERMEDIATE (CATION) | DIHYDRO DERIVATIVE |
|---|---|---|
| <br>naproxol | 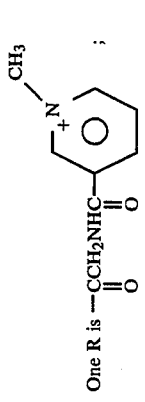<br>One R is —CCH₂NHC=O<br><br>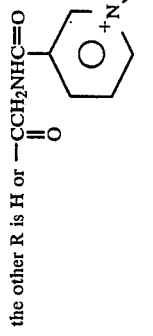<br>the other R is H or —CCH₂NHC=O |  |
| | 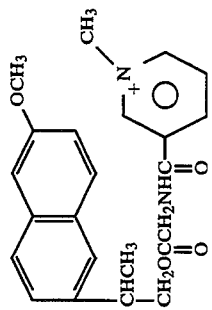 | |

| STARTING MATERIAL | QUATERNARY INTERMEDIATE (CATION) | DIHYDRO DERIVATIVE |
|---|---|---|
| 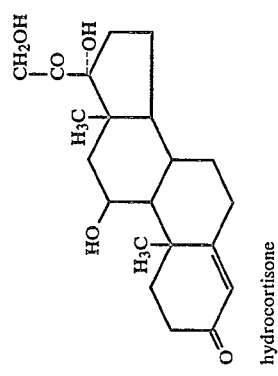 hydrocortisone | 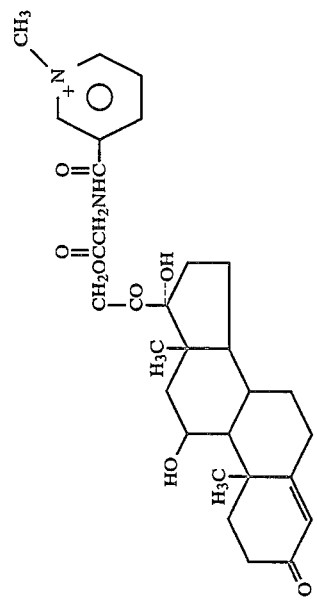 | 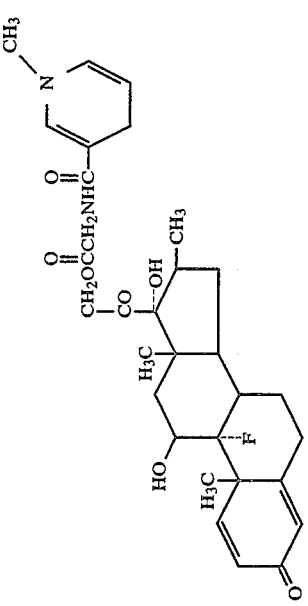 |
| betamethasone | | |

| STARTING MATERIAL | QUATERNARY INTERMEDIATE (CATION) | DIHYDRO DERIVATIVE |
|---|---|---|
| | 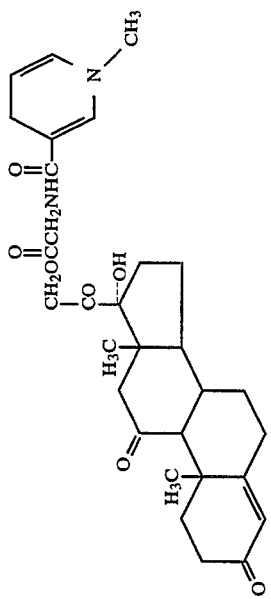 | 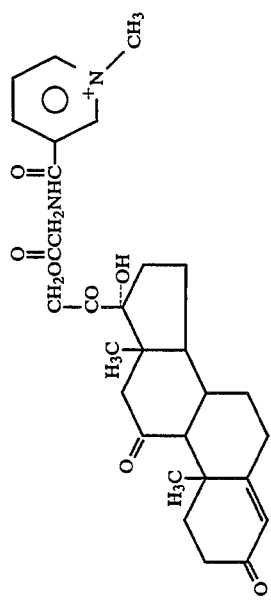 |
| | 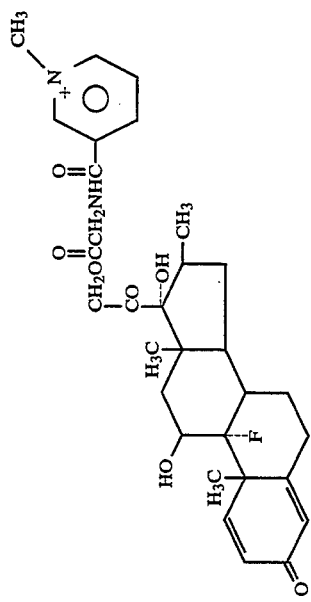 | |
| 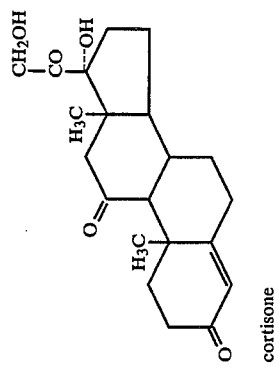cortisone | | |

| STARTING MATERIAL | QUATERNARY INTERMEDIATE (CATION) | DIHYDRO DERIVATIVE |
|---|---|---|
| 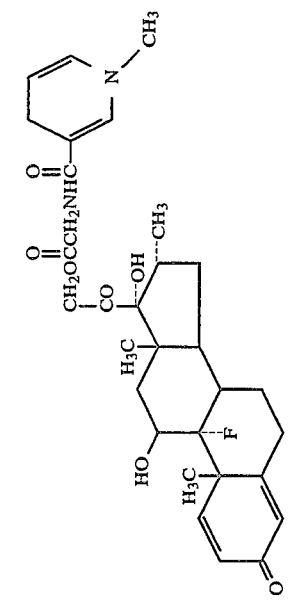<br>dexamethasone | 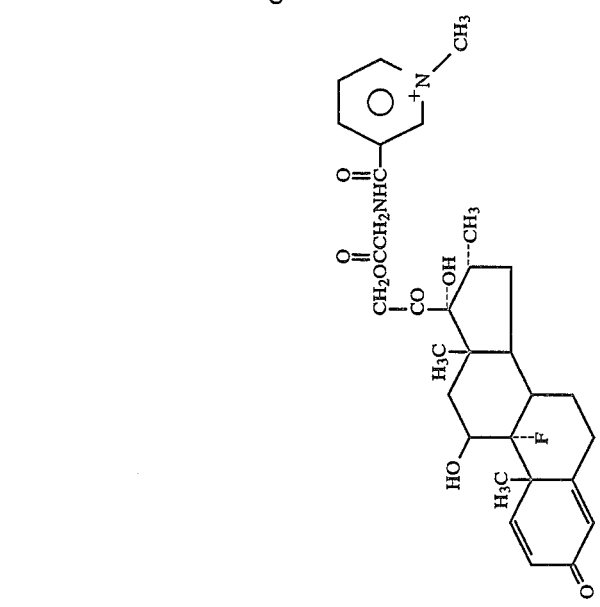 | 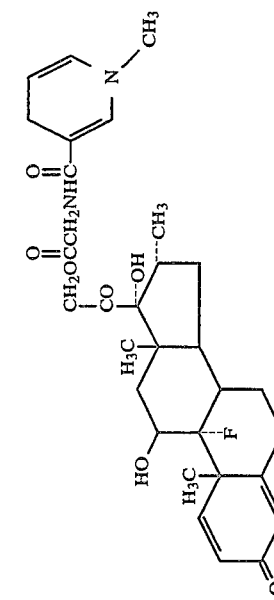 |
| 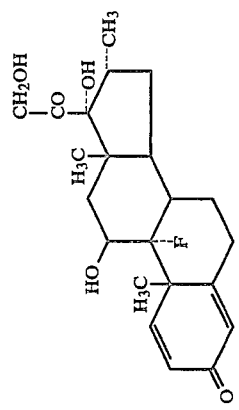<br>flumethasone | | 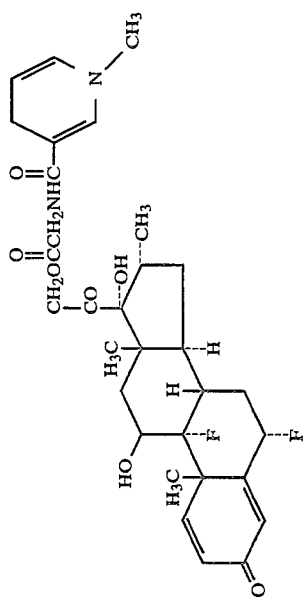 |

-continued
| STARTING MATERIAL | QUATERNARY INTERMEDIATE (CATION) | DIHYDRO DERIVATIVE |
|---|---|---|
| 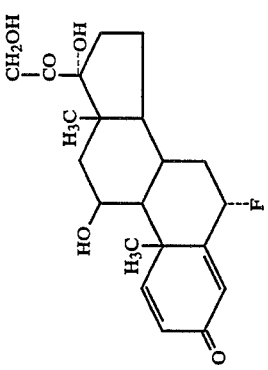<br>fluprednisolone | 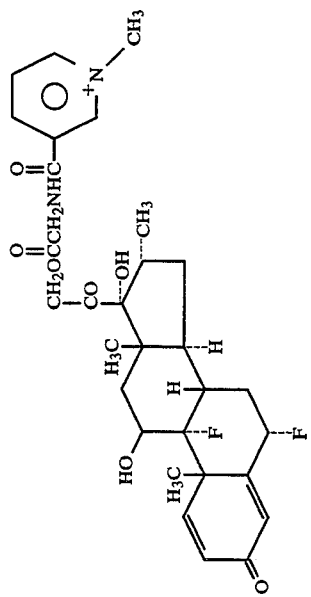 | 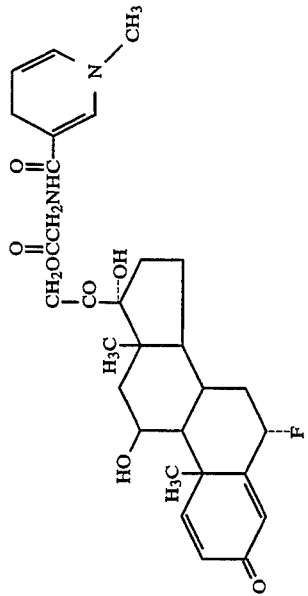 |
| | 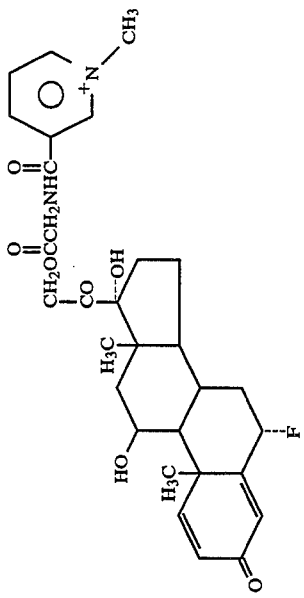 | |

| STARTING MATERIAL | QUATERNARY INTERMEDIATE (CATION) | DIHYDRO DERIVATIVE |
|---|---|---|
| 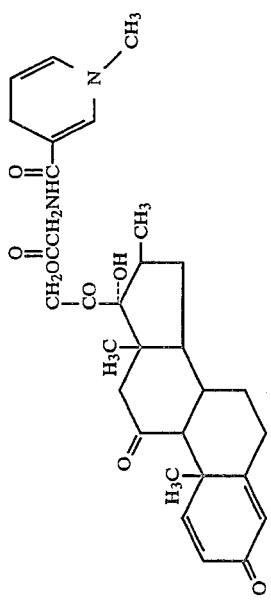 meprednisone | 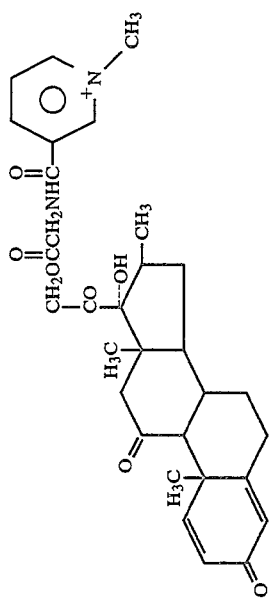 | 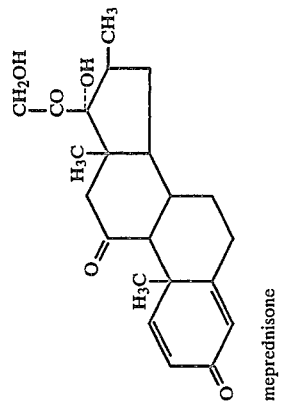 231 |
| 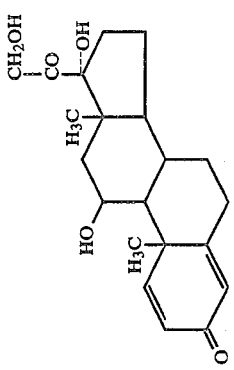 methylprednisolone | |  232 |

| STARTING MATERIAL | QUATERNARY INTERMEDIATE (CATION) | DIHYDRO DERIVATIVE |
|---|---|---|
| 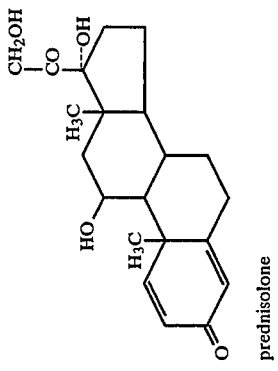<br>prednisolone | 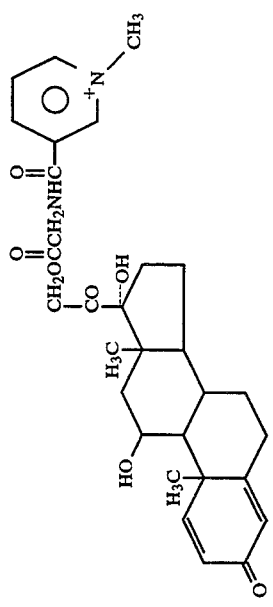 | 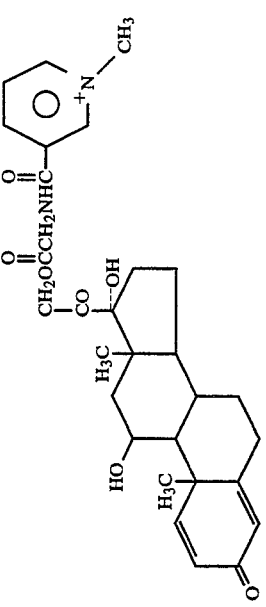 |

| STARTING MATERIAL | QUATERNARY INTERMEDIATE (CATION) | DIHYDRO DERIVATIVE |
|---|---|---|
| 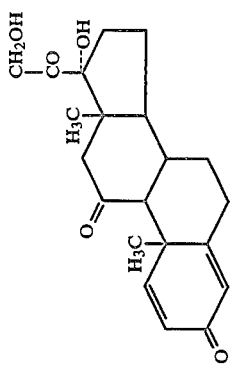<br>prednisone | 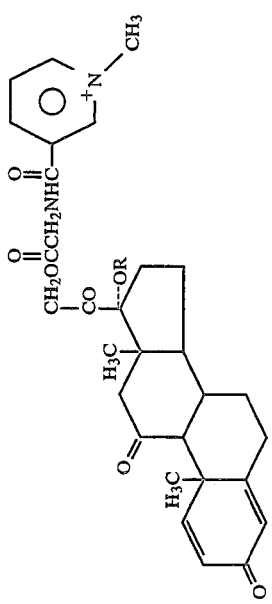 | 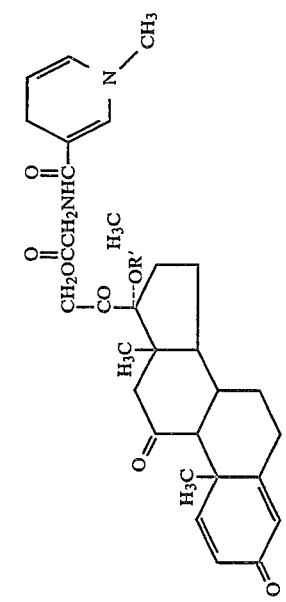 |
| 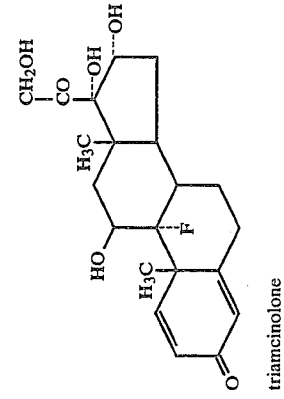<br>triamcinolone | | |

-continued
| STARTING MATERIAL | QUATERNARY INTERMEDIATE (CATION) | DIHYDRO DERIVATIVE |
|---|---|---|
| 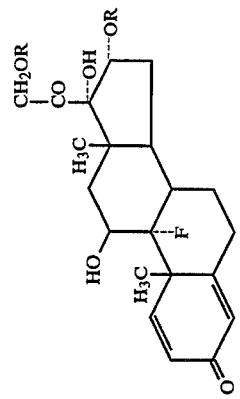 | 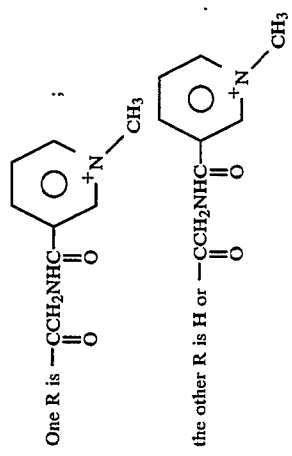<br>One R is —CCH₂NHC(=O)—<br>the other R is H or —CCH₂NHC(=O)— | 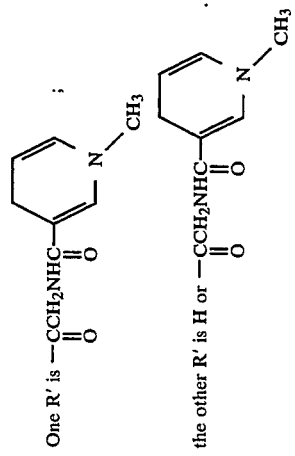<br>One R' is —CCH₂NHC(=O)—<br>the other R' is H or —CCH₂NHC(=O)— |

-continued
| STARTING MATERIAL | QUATERNARY INTERMEDIATE (CATION) | DIHYDRO DERIVATIVE |
|---|---|---|
| 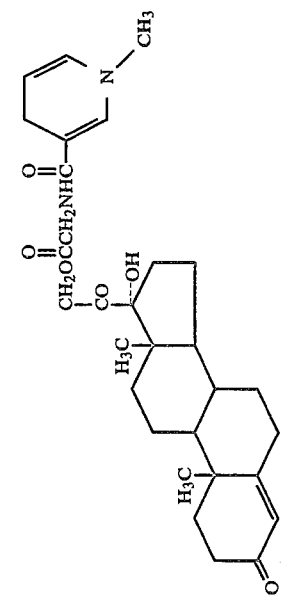<br>cortodoxone | 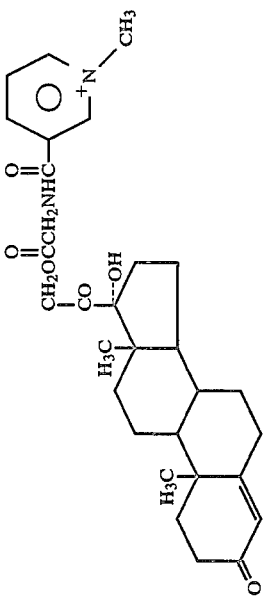 | 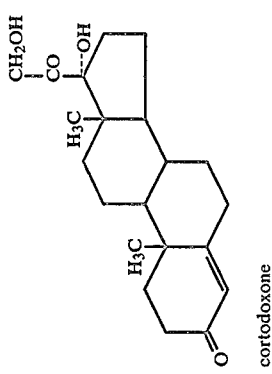 |
| 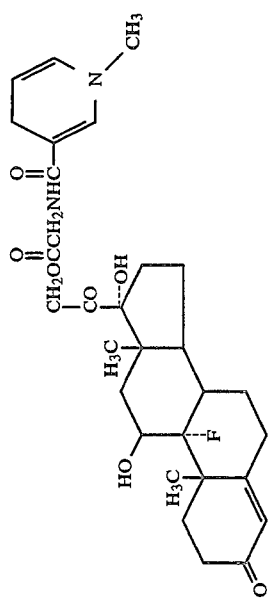<br>fludrocortisone | | |

-continued
| STARTING MATERIAL | QUATERNARY INTERMEDIATE (CATION) | DIHYDRO DERIVATIVE |
|---|---|---|
| 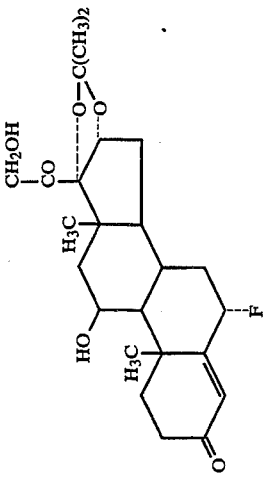flurandrenolide | 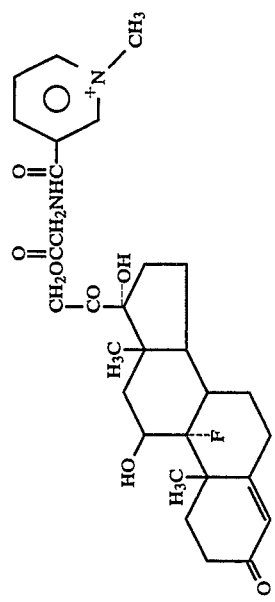 | 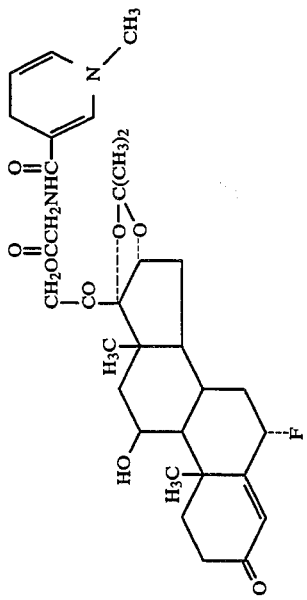<br>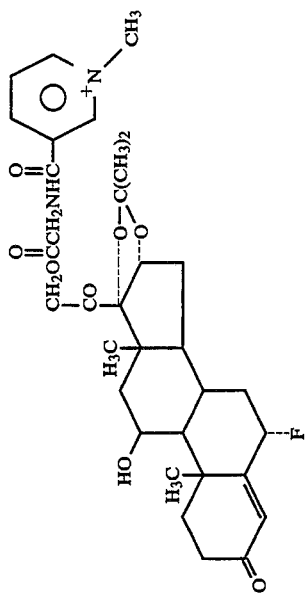 |

-continued
| STARTING MATERIAL | QUATERNARY INTERMEDIATE (CATION) | DIHYDRO DERIVATIVE |
|---|---|---|
| 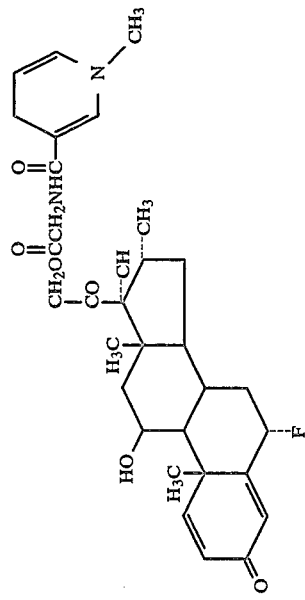<br>paramethasone | 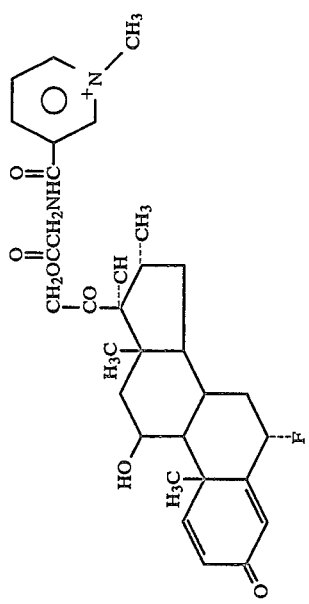 | 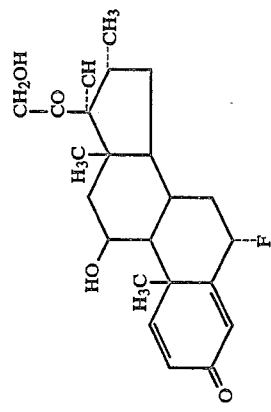 |
| 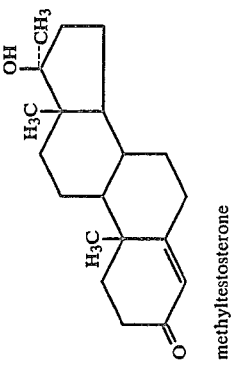<br>methyltestosterone | | 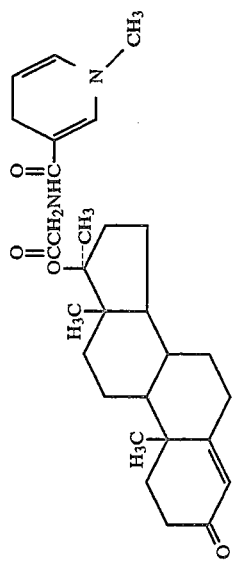 |

| STARTING MATERIAL | -continued<br>QUATERNARY INTERMEDIATE (CATION) | DIHYDRO DERIVATIVE |
|---|---|---|
| 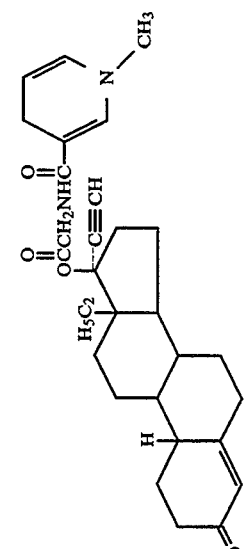
norgestrel | 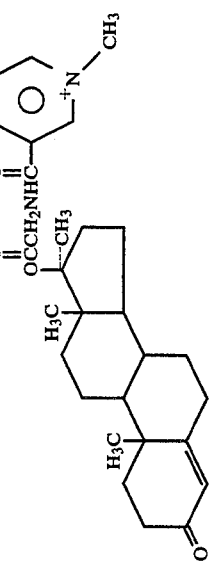 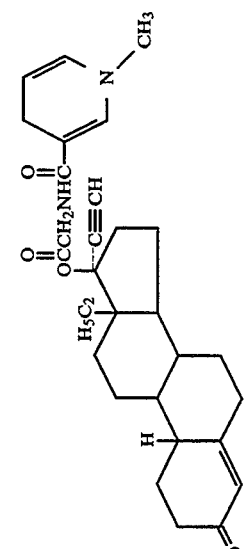 | 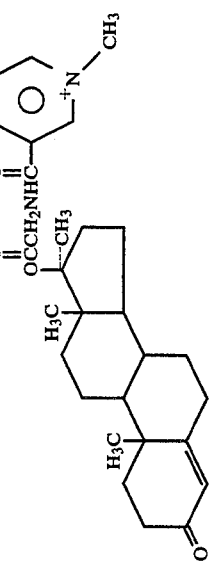 |

| STARTING MATERIAL | QUATERNARY INTERMEDIATE (CATION) | DIHYDRO DERIVATIVE |
|---|---|---|
| 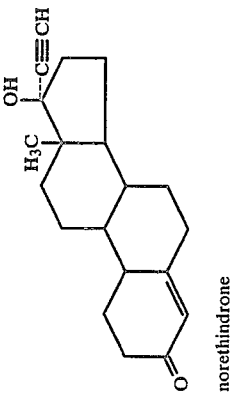 norethindrone | 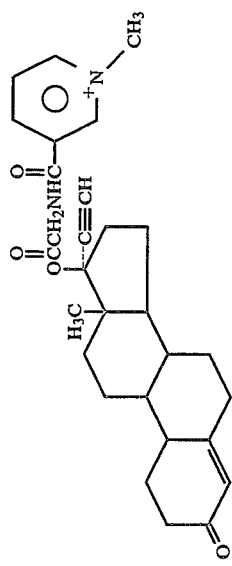 | 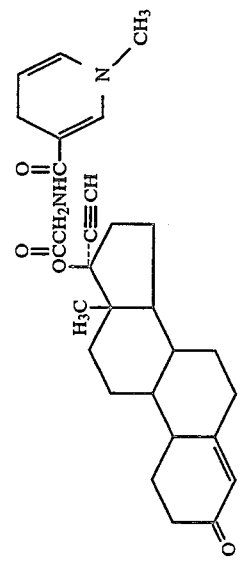 |
| 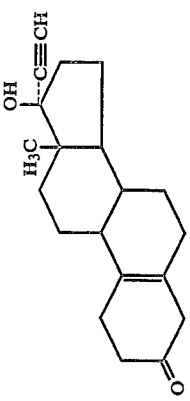 norethynodrel | 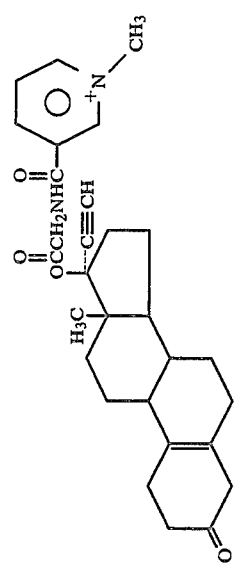 | 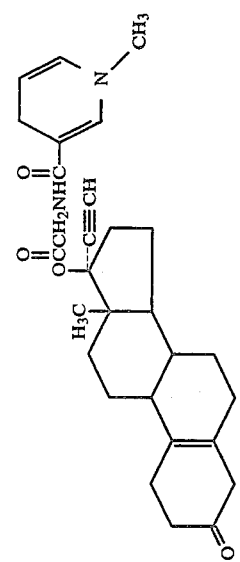 |

| STARTING MATERIAL | QUATERNARY INTERMEDIATE (CATION) | DIHYDRO DERIVATIVE |
|---|---|---|
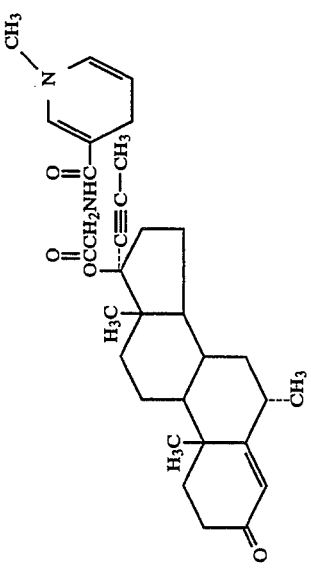
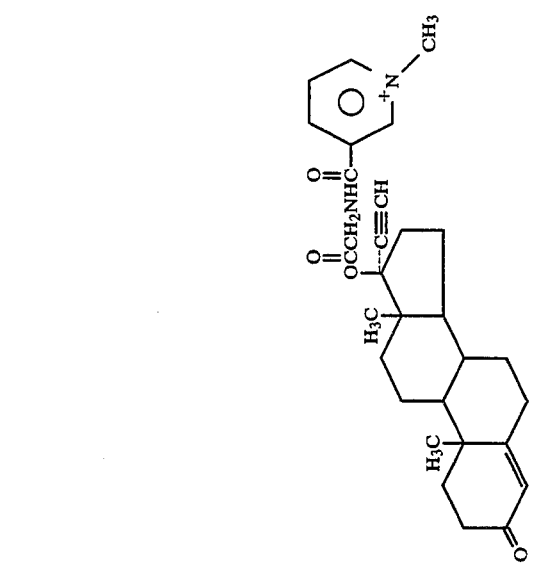
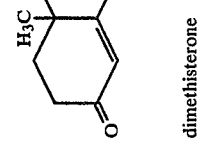

| STARTING MATERIAL | QUATERNARY INTERMEDIATE (CATION) | DIHYDRO DERIVATIVE |
|---|---|---|
| | | 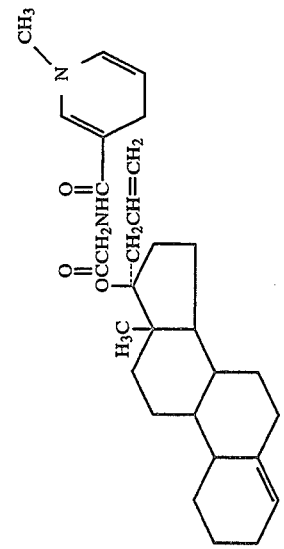 |
| | 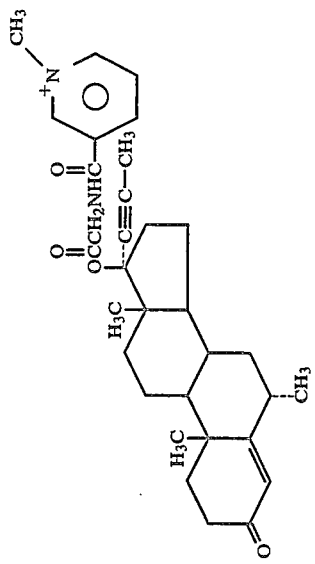 | 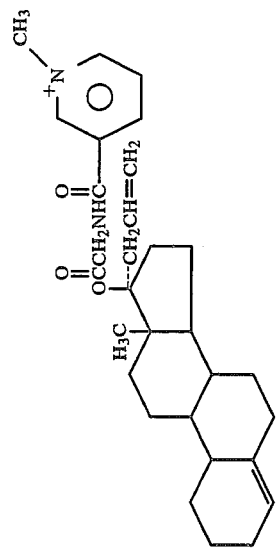 |
| 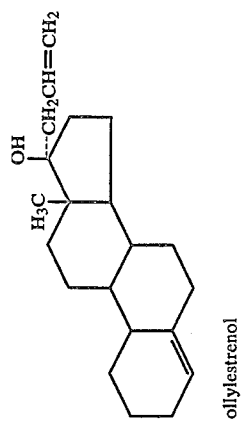
ollyestrenol | | |

| STARTING MATERIAL | QUATERNARY INTERMEDIATE (CATION) | DIHYDRO DERIVATIVE |
|---|---|---| cingestol ethynerone

| STARTING MATERIAL | QUATERNARY INTERMEDIATE (CATION) | DIHYDRO DERIVATIVE |
|---|---|---|
| 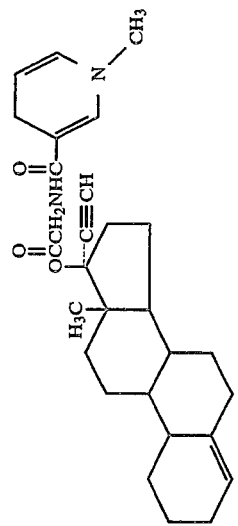<br>lynestrenol | 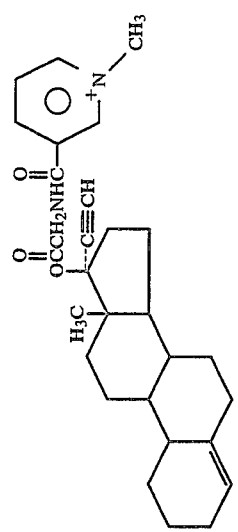 | 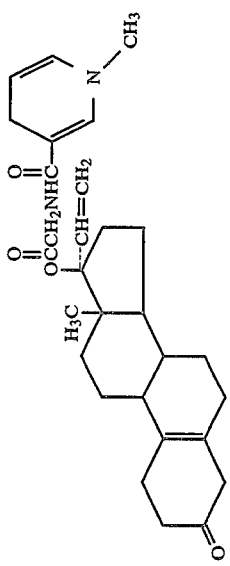 |
| 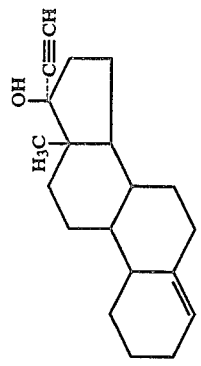<br>norgesterone | 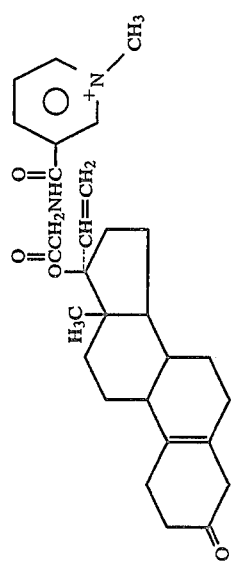 | 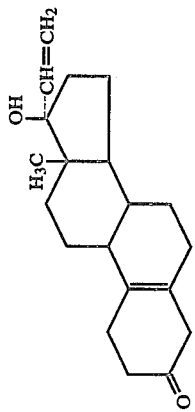 |

| STARTING MATERIAL | QUATERNARY INTERMEDIATE (CATION) | DIHYDRO DERIVATIVE |
|---|---|---|
| 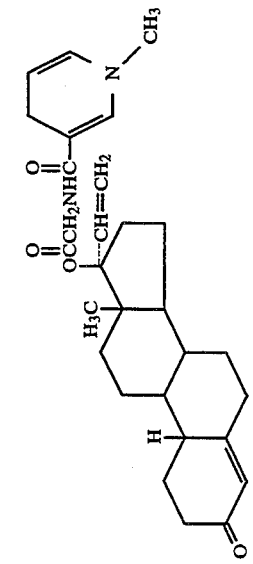<br>norvinisterone | 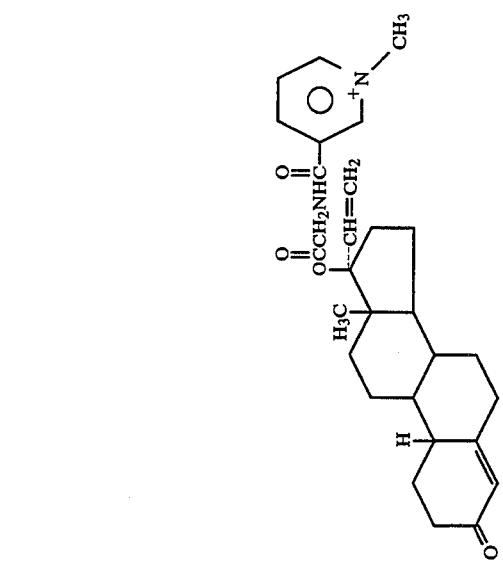 | 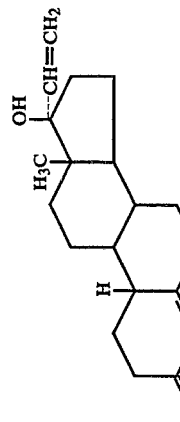 |
| 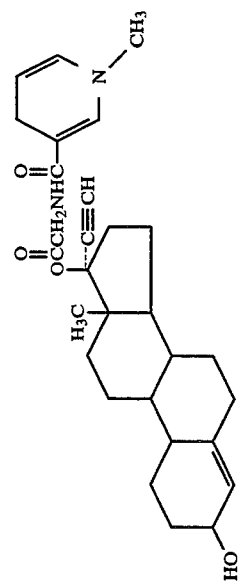<br>ethynodiol | 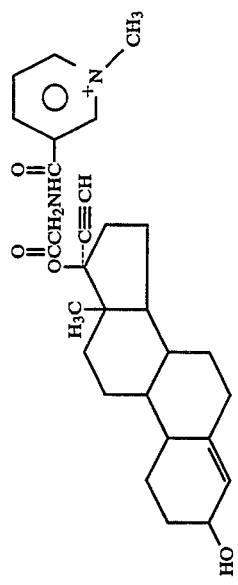 | 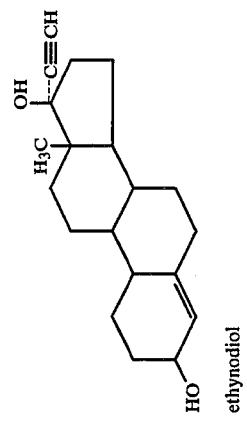 |

| STARTING MATERIAL | QUATERNARY INTERMEDIATE (CATION) | DIHYDRO DERIVATIVE |
|---|---|---|
| 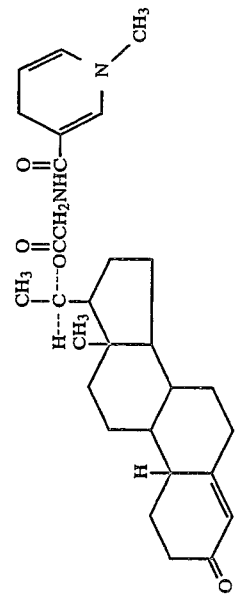 oxogestone | 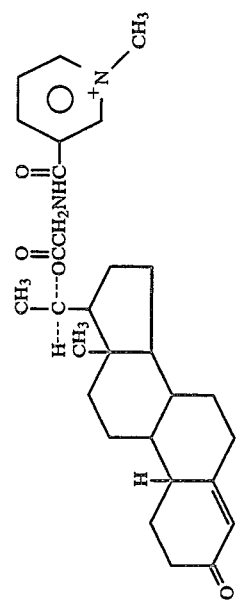 | 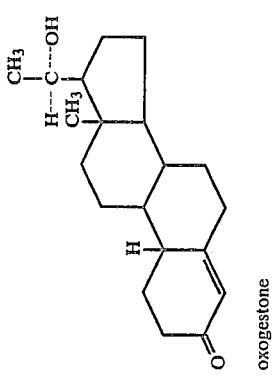 |
| 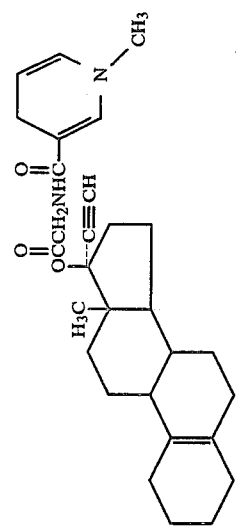 tigestol | 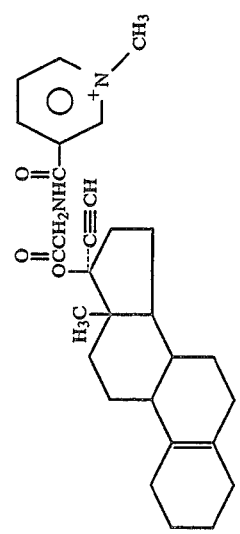 | 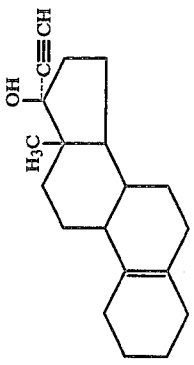 |

| STARTING MATERIAL | QUATERNARY INTERMEDIATE (CATION) | DIHYDRO DERIVATIVE |
|---|---|---|
| 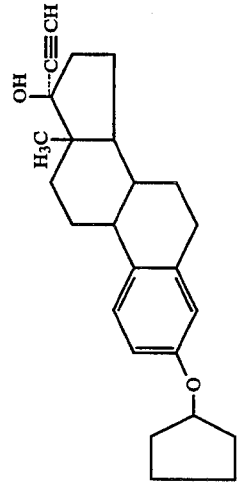<br>quinestrol | 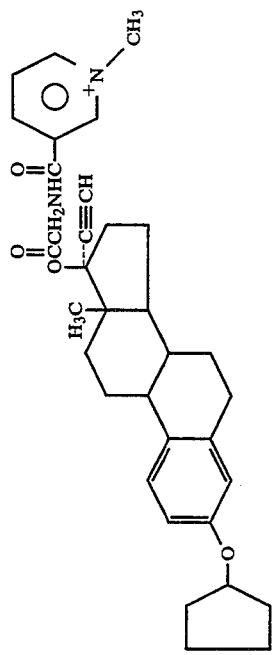 | 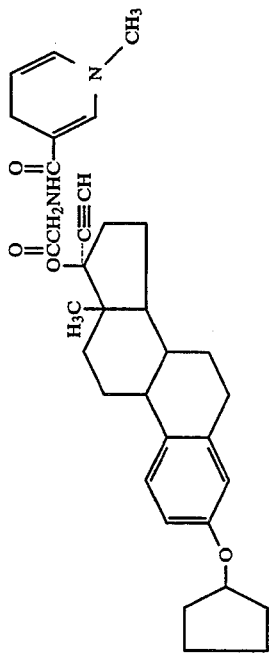 |
| Ara—AC | | 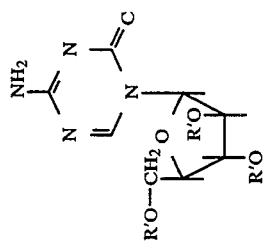 |

| STARTING MATERIAL | QUATERNARY INTERMEDIATE (CATION) | DIHYDRO DERIVATIVE |
|---|---|---|
| -continued | 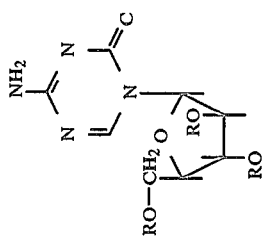 | 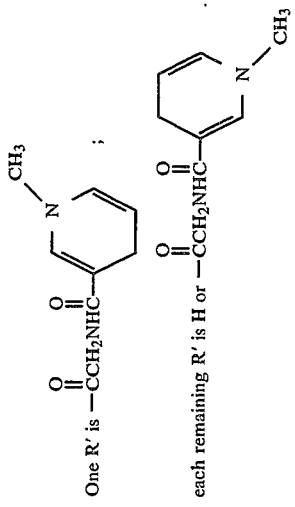 |
| | 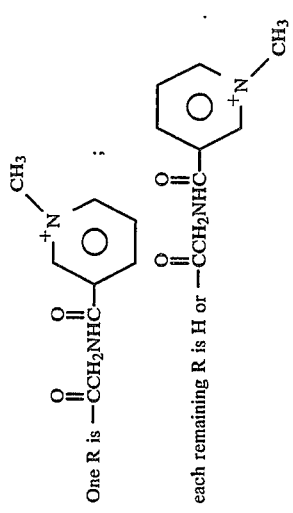 | |

| STARTING MATERIAL | QUATERNARY INTERMEDIATE (CATION) | DIHYDRO DERIVATIVE |
|---|---|---|
| 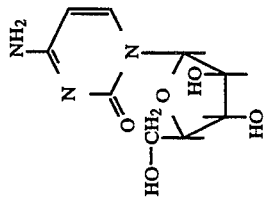<br>Ara—C(cytarobine) | 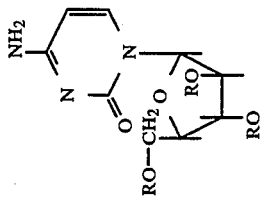 | 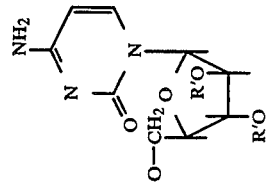<br>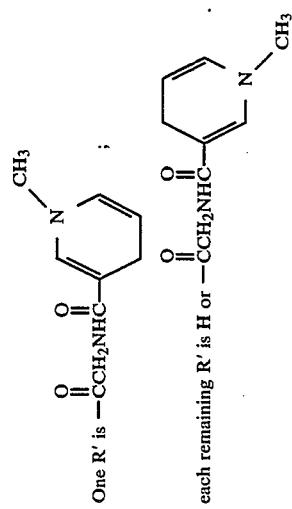<br>One R' is $-\text{CCH}_2\text{NHC}$ with two =O, or $-\text{CCH}_2\text{NHC}$ with two =O;<br>each remaining R' is H or $-\text{CCH}_2\text{NHC}$ (with =O, =O, N-CH$_3$) |

-continued
| STARTING MATERIAL | QUATERNARY INTERMEDIATE (CATION) | DIHYDRO DERIVATIVE |
|---|---|---|
| 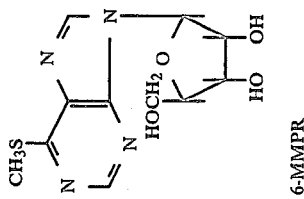<br>6-MMPR | 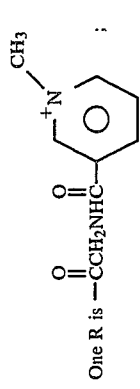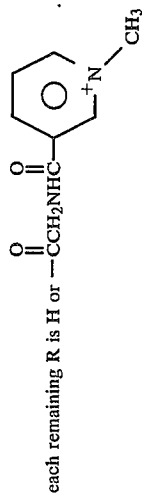<br>One R is —CCH$_2$NHC<br>each remaining R is H or —CCH$_2$NHC | 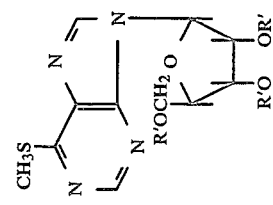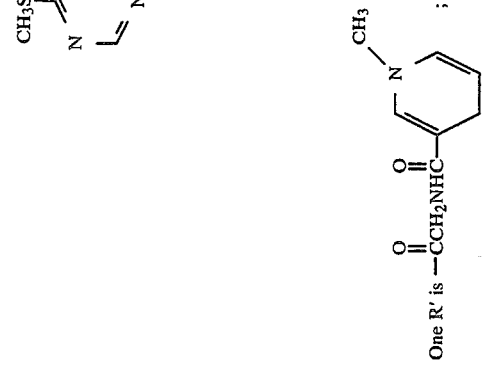<br>One R' is —CCH$_2$NHC<br>each remaining R' is H or —CCH$_2$NHC |

| STARTING MATERIAL | QUATERNARY INTERMEDIATE (CATION) | DIHYDRO DERIVATIVE |
|---|---|---|
| 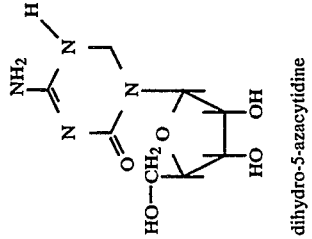 dihydro-5-azacytidine | 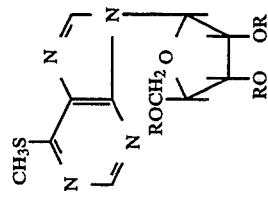 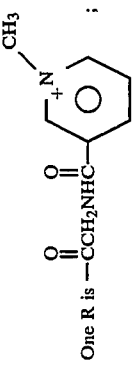 ; 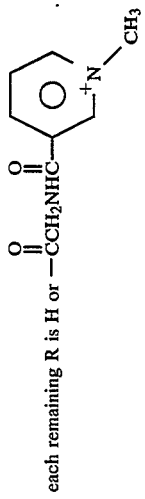 One R is —CCH₂NHC   each remaining R is H or —CCH₂NHC | 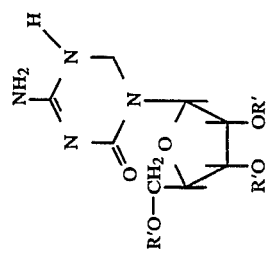 |

| STARTING MATERIAL | QUATERNARY INTERMEDIATE (CATION) | DIHYDRO DERIVATIVE |
|---|---|---|
| 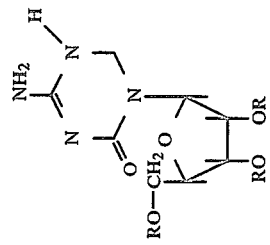 | 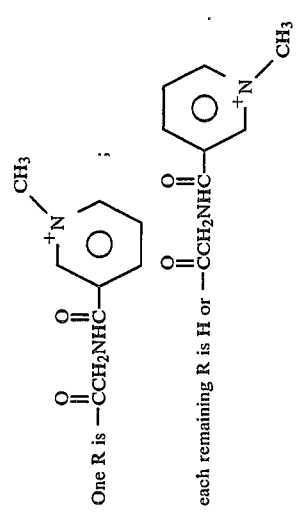
One R is —CCH$_2$NHC—
each remaining R is H or —CCH$_2$NHC— | 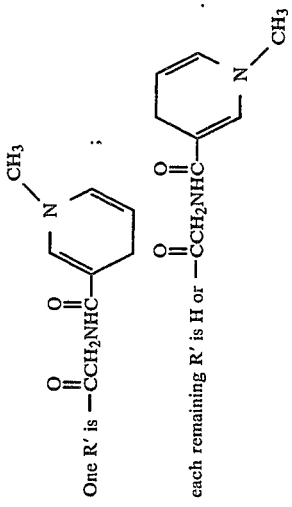
One R' is —CCH$_2$NHC—
each remaining R' is H or —CCH$_2$NHC— |

| STARTING MATERIAL | QUATERNARY INTERMEDIATE (CATION) | DIHYDRO DERIVATIVE |
|---|---|---|
| 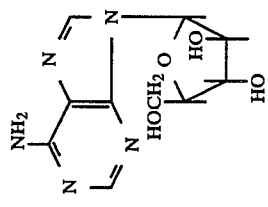<br>Ara—A(vidarobine) | 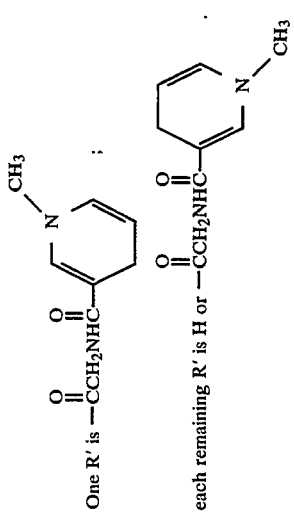<br>One R' is —CCH₂NHC=O—<br>each remaining R' is H or —CCH₂NHC=O— | 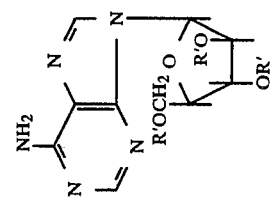 |

| STARTING MATERIAL | QUATERNARY INTERMEDIATE (CATION) | DIHYDRO DERIVATIVE |
|---|---|---|
| 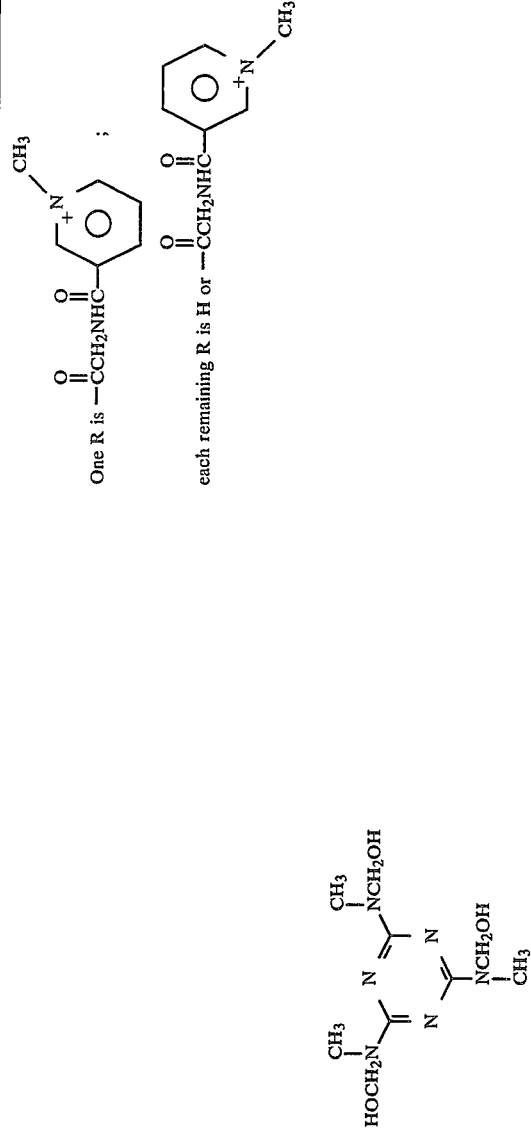 trimethyl TMM | 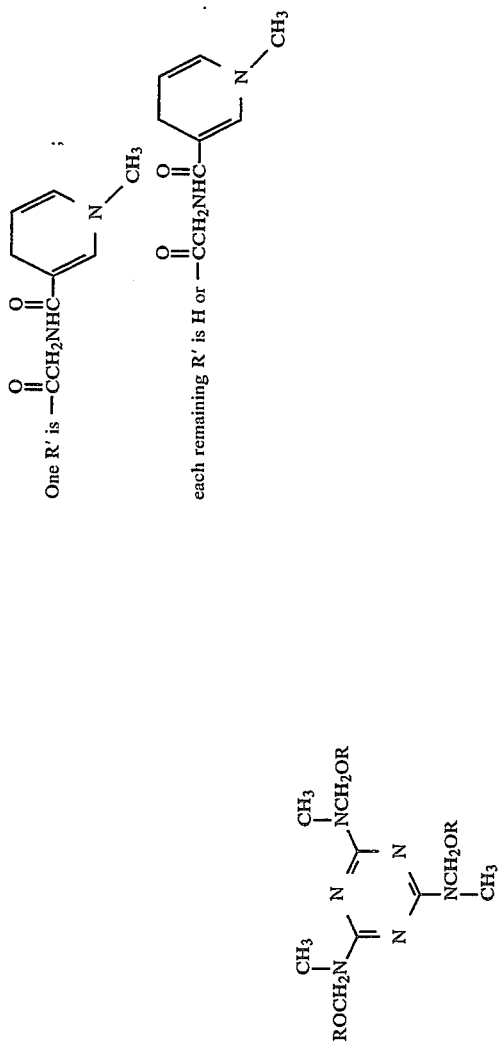 | |

-continued
| STARTING MATERIAL | QUATERNARY INTERMEDIATE (CATION) | DIHYDRO DERIVATIVE |
|---|---|---|
| 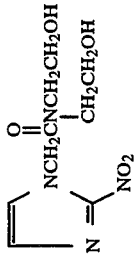<br>SR-2555 | 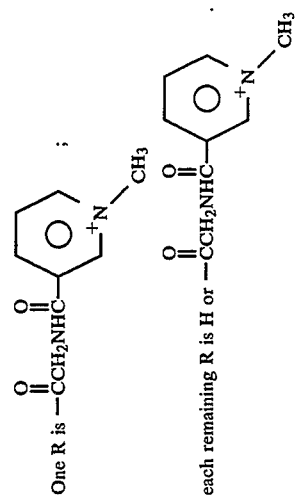<br>One R is —CCH$_2$NHC<br>each remaining R is H or —CCH$_2$NHC | 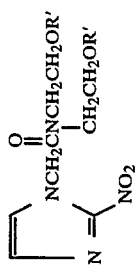<br>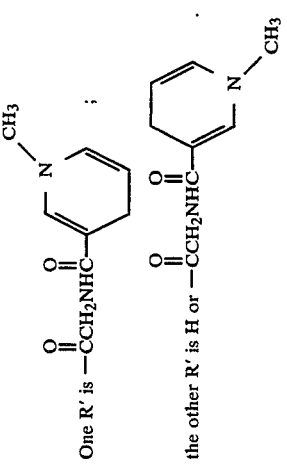<br>One R' is —CCH$_2$NHC<br>the other R' is H or —CCH$_2$NHC<br>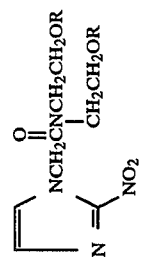 |

-continued
| STARTING MATERIAL | QUATERNARY INTERMEDIATE (CATION) | DIHYDRO DERIVATIVE |
|---|---|---|
| 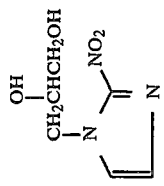desmethylisonidazole | 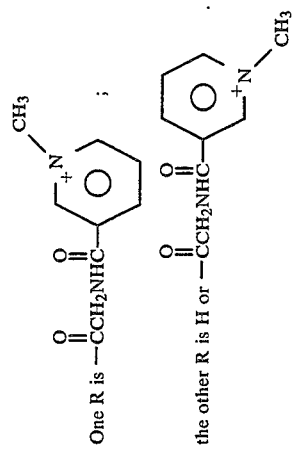One R is —CCH₂NHC the other R is H or —CCH₂NHC | 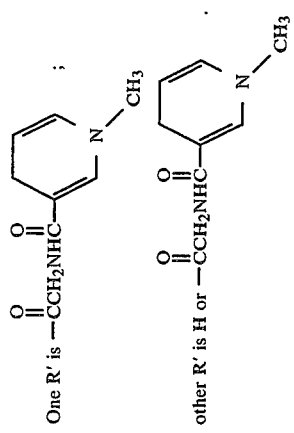One R' is —CCH₂NHC other R' is H or —CCH₂NHC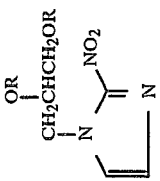 |

| STARTING MATERIAL | QUATERNARY INTERMEDIATE (CATION) | DIHYDRO DERIVATIVE |
|---|---|---|
| | 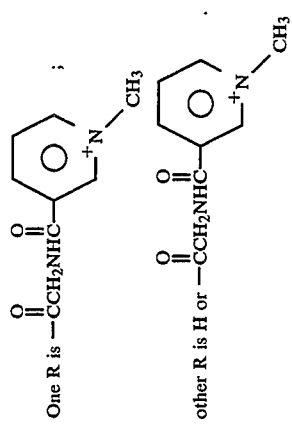<br>One R is —CCH$_2$NHC<br>other R is H or —CCH$_2$NHC | 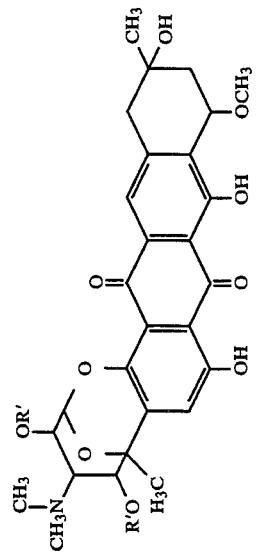 |
| 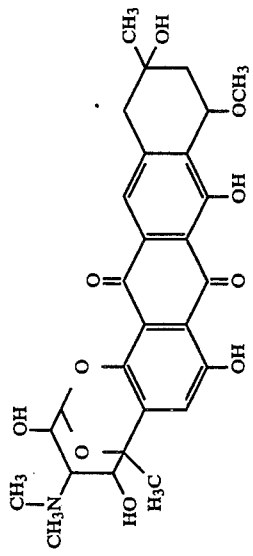<br>menogarol | | 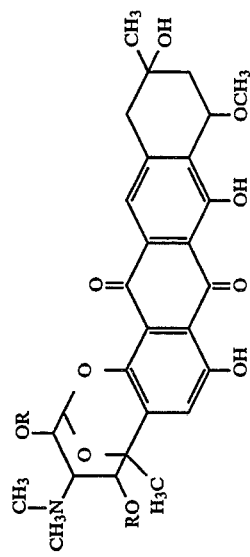 |

| STARTING MATERIAL | -continued<br>QUATERNARY INTERMEDIATE (CATION) | DIHYDRO DERIVATIVE |
|---|---|---|
| 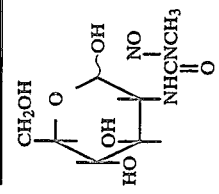<br>streptozotocin | 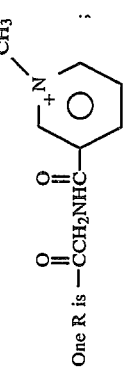<br>One R is —CCH$_2$NHC<br>each remaining R is H or —CCH$_2$NHC | 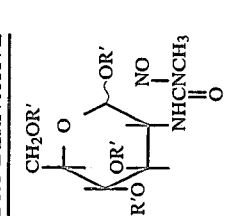<br>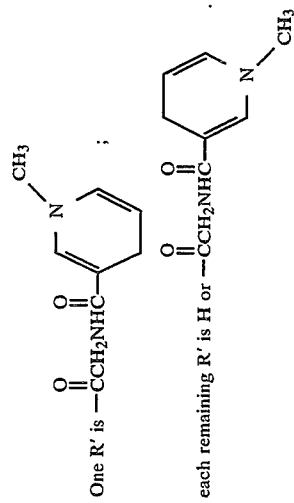<br>One R' is —CCH$_2$NHC<br>each remaining R' is H or —CCH$_2$NHC |

| STARTING MATERIAL | QUATERNARY INTERMEDIATE (CATION) | DIHYDRO DERIVATIVE |
|---|---|---|
| 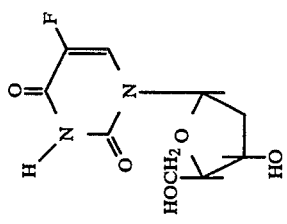<br>5-FUDR(floxuridine) | 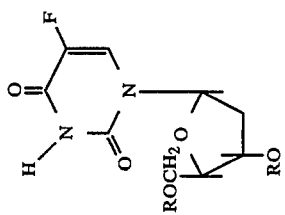 | 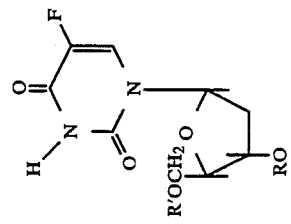<br>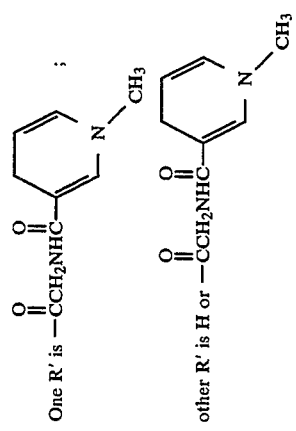  One R' is —CCH₂NHC(=O)— ; other R' is H or —CCH₂NHC(=O)— |

| STARTING MATERIAL | QUATERNARY INTERMEDIATE (CATION) | DIHYDRO DERIVATIVE |
|---|---|---|
| 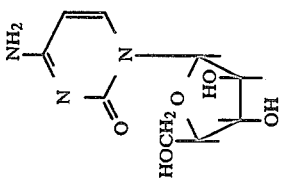 cytosine arobinoside | 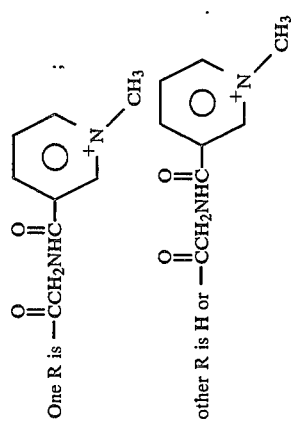 One R is —CCH₂NHC... other R is H or —CCH₂NHC... | (structure with R'OCH₂O, HO, OR') and (structure with ROCH₂O, HO, OR) |

| STARTING MATERIAL | QUATERNARY INTERMEDIATE (CATION) | DIHYDRO DERIVATIVE |
|---|---|---|
| 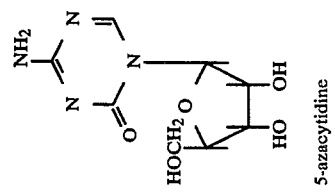<br>5-azacytidine | 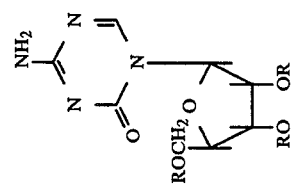 | 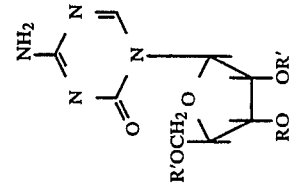<br>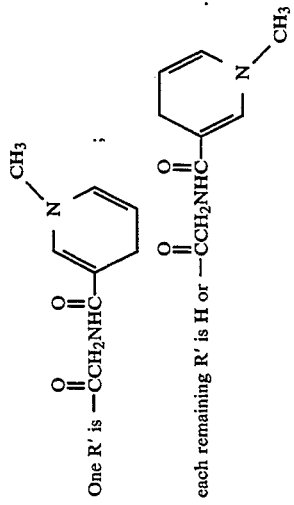<br>One R' is —CCH₂NHC(=O)— ;<br>each remaining R' is H or —CCH₂NHC(=O)— |

| STARTING MATERIAL | QUATERNARY INTERMEDIATE (CATION) | DIHYDRO DERIVATIVE |
|---|---|---|
| 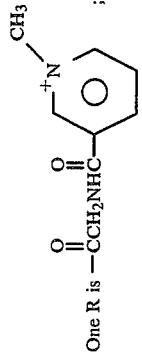<br>5,7-dimethyl-2-β-D-ribofuranosyl-s-triazole(1,5-a)pyrimidine | <br>One R is —CCH$_2$NHC<br>each remaining R is H or —CCH$_2$NHC<br>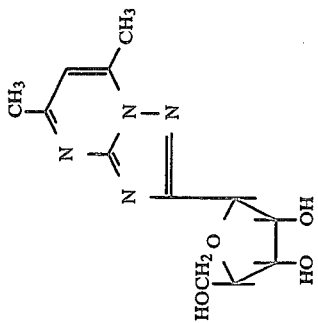 | 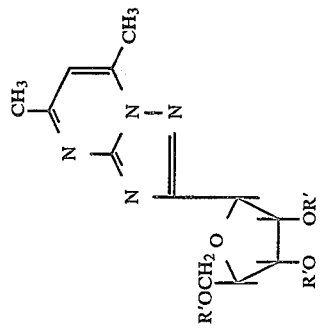<br>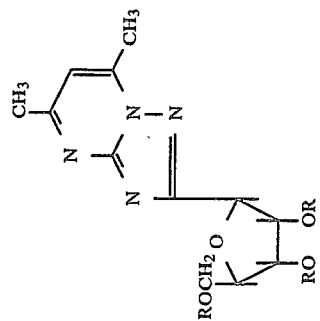 |

| STARTING MATERIAL | QUATERNARY INTERMEDIATE (CATION) | DIHYDRO DERIVATIVE |
|---|---|---|
| 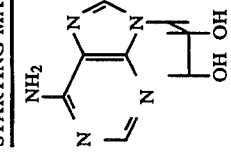<br>(S)-9-(2,3-dihydroxypropyl)-adenine | 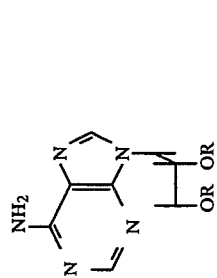<br>One R is —CCH$_2$NHC<br>other R is H or —CCH$_2$NHC | 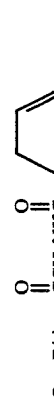 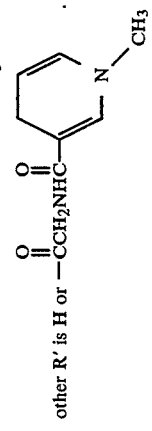<br>One R' is —CCH$_2$NHC<br>other R' is H or —CCH$_2$NHC |

-continued
| STARTING MATERIAL | QUATERNARY INTERMEDIATE (CATION) | DIHYDRO DERIVATIVE |
|---|---|---|
| 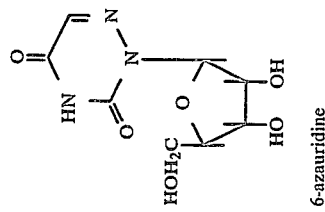<br>6-azauridine | 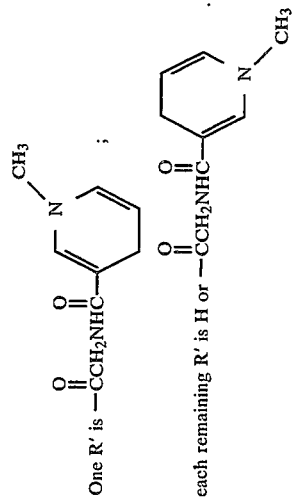<br>One R' is —CCH$_2$NHC—<br>each remaining R' is H or —CCH$_2$NHC— | 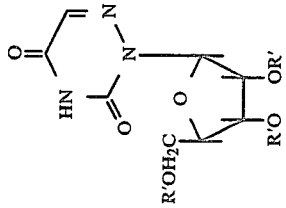<br><br>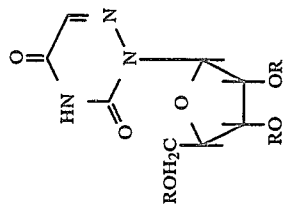 |

-continued
| STARTING MATERIAL | QUATERNARY INTERMEDIATE (CATION) | DIHYDRO DERIVATIVE |
|---|---|---|
| 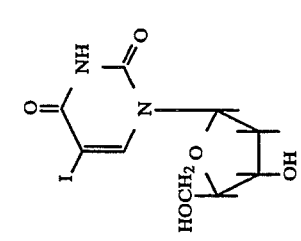<br>idoxuridine | 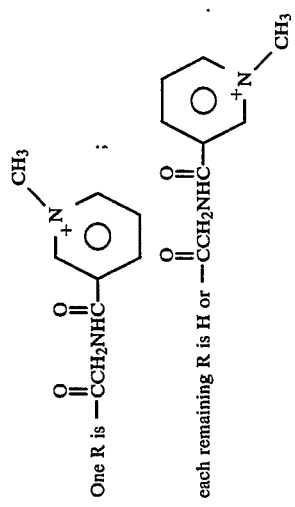<br>One R is —CCH$_2$NHC<br>each remaining R is H or —CCH$_2$NHC | 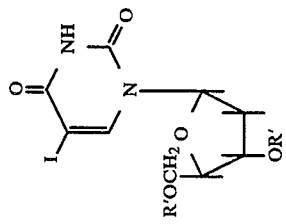<br>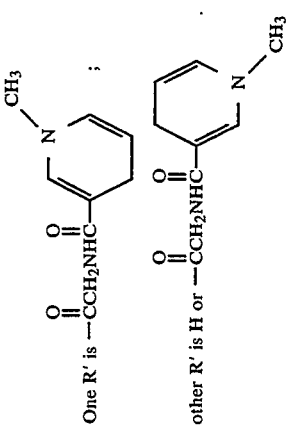<br>One R' is —CCH$_2$NHC<br>other R' is H or —CCH$_2$NHC |

| STARTING MATERIAL | QUATERNARY INTERMEDIATE (CATION) | DIHYDRO DERIVATIVE |
|---|---|---|
| 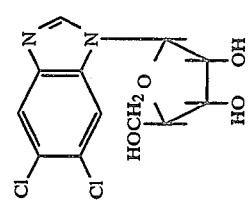<br>5,6-dichloro-1-β-D-ribo-furanosylbenzimidazole | 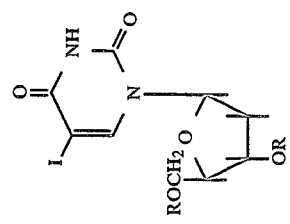<br>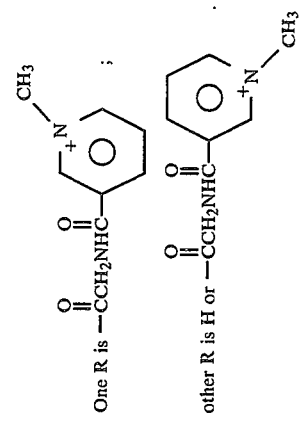<br>One R is —CCH₂NHC; other R is H or —CCH₂NHC | 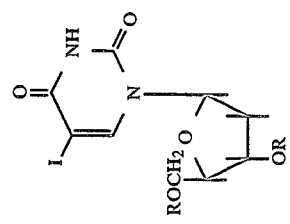 |

-continued
| STARTING MATERIAL | QUATERNARY INTERMEDIATE (CATION) | DIHYDRO DERIVATIVE |
|---|---|---|
| | 301 | |
| | 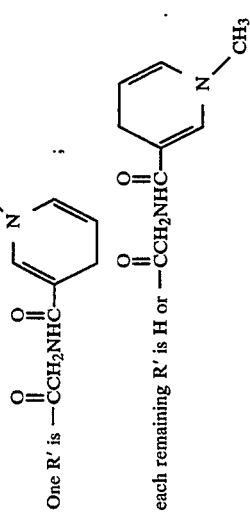 One R' is —CCH₂NHC each remaining R' is H or —CCH₂NHC | |
| | 302 | |
| | 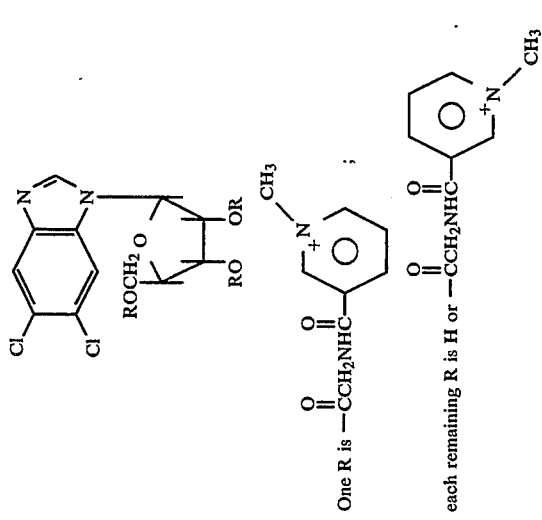 One R is —CCH₂NHC each remaining R is H or —CCH₂NHC | |
| 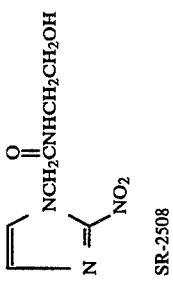 SR-2508 | | |

| STARTING MATERIAL | QUATERNARY INTERMEDIATE (CATION) | DIHYDRO DERIVATIVE |
|---|---|---|
| 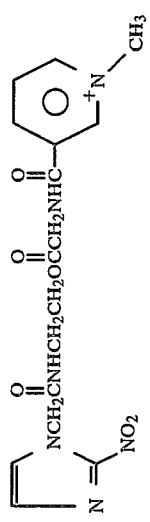<br>Iopydol | 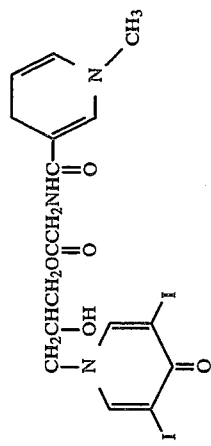 | 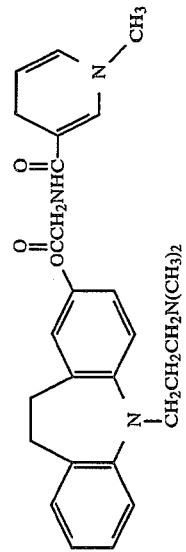 |
| 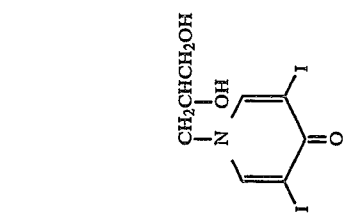<br>2-hydroxyimipramine | 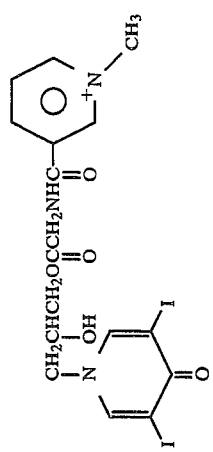<br>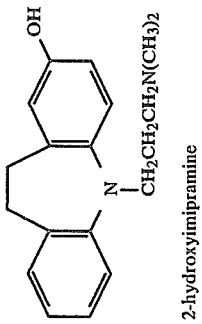 | 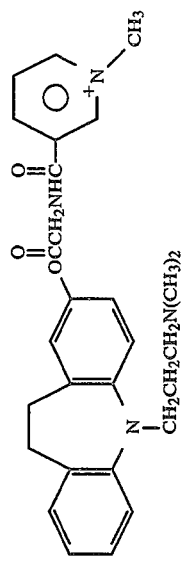 |

| STARTING MATERIAL | QUATERNARY INTERMEDIATE (CATION) | DIHYDRO DERIVATIVE |
|---|---|---|
| 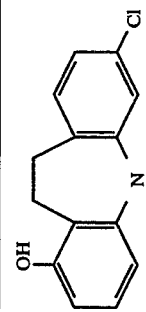<br>8-hydroxychlorimipramine(8-hydroxyclomipamine) | 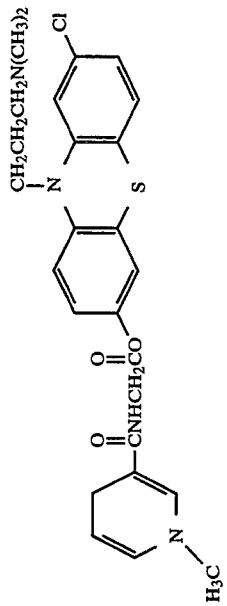 | 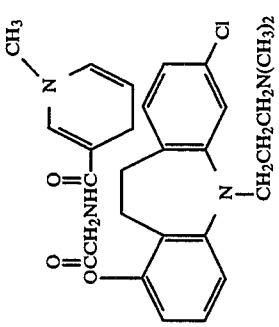 |
| 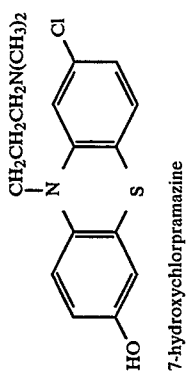<br>7-hydroxychlorpramazine | 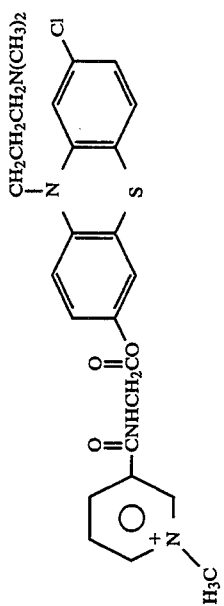 | |

| STARTING MATERIAL | QUATERNARY INTERMEDIATE (CATION) | DIHYDRO DERIVATIVE |
|---|---|---|
| 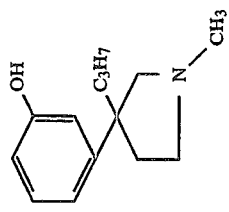<br>profadol | 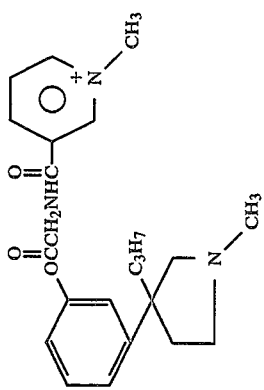 | 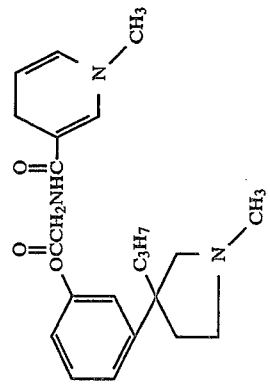 |
| 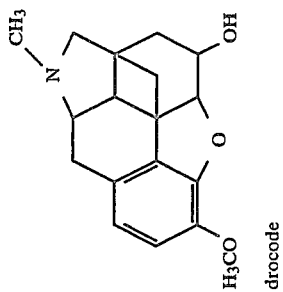<br>drocode | | 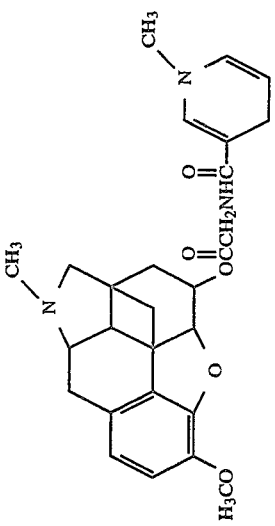 |

| STARTING MATERIAL | QUATERNARY INTERMEDIATE (CATION) | DIHYDRO DERIVATIVE |
|---|---|---|
| 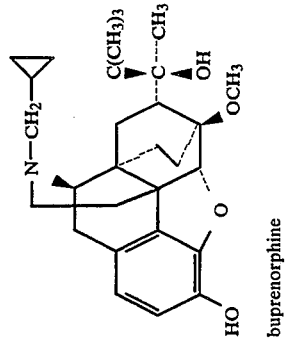<br>buprenorphine | 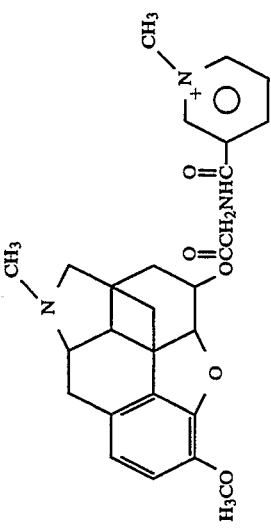 | 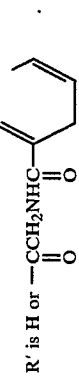<br>R' is H or —CCH$_2$NHC— |

| STARTING MATERIAL | QUATERNARY INTERMEDIATE (CATION) | DIHYDRO DERIVATIVE |
|---|---|---|
| 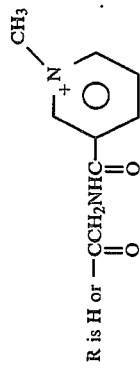 nalbuphine | 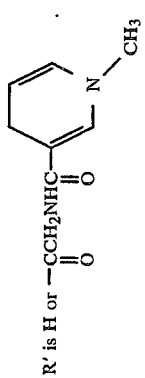 R is H or —CCH$_2$NHC— (with =O, =O) | 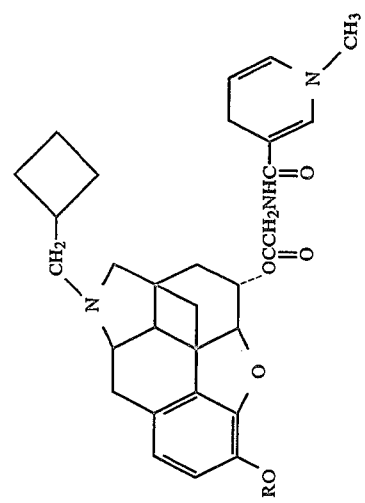 R' is H or —CCH$_2$NHC— (with =O, =O) |
| | 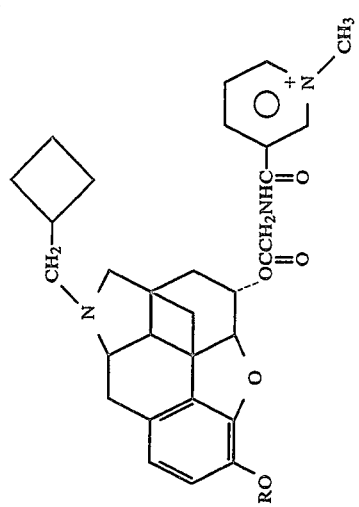 | |

-continued
| STARTING MATERIAL | QUATERNARY INTERMEDIATE (CATION) | DIHYDRO DERIVATIVE |
|---|---|---|
| 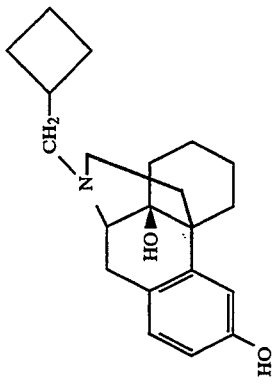<br>butorphanol | 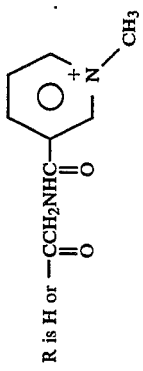<br>R is H or —CCH$_2$NHC— | 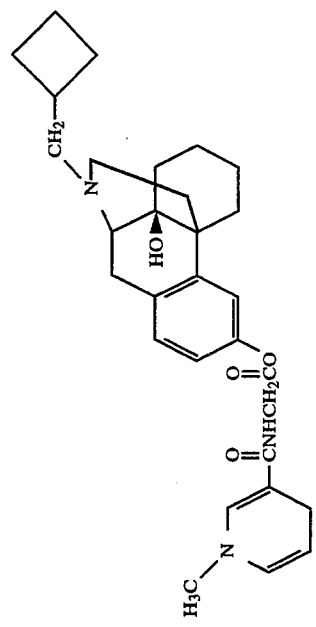<br><br>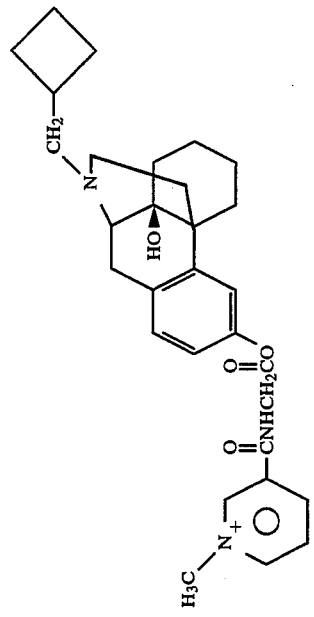 |

| STARTING MATERIAL | QUATERNARY INTERMEDIATE (CATION) | DIHYDRO DERIVATIVE |
|---|---|---|
| 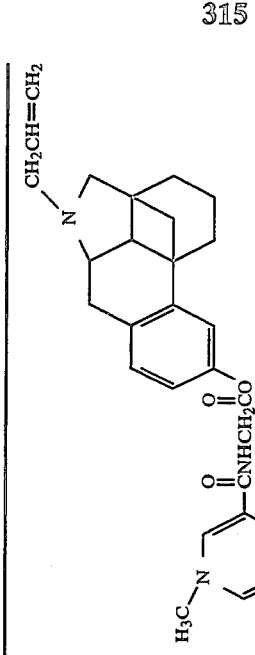<br>levallorphan | 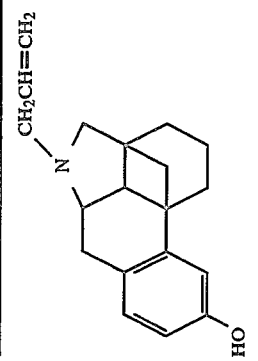 | 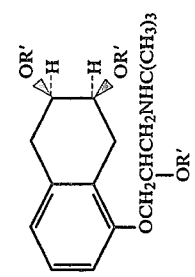 |
| 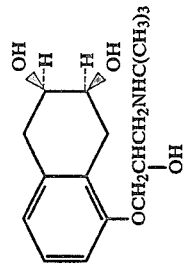<br>nodolol | | 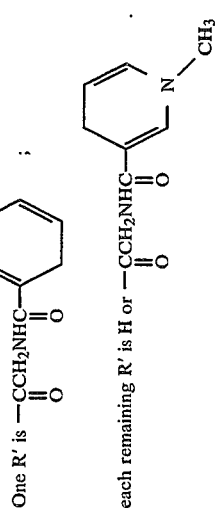<br>One R' is —CCH$_2$NHC=O<br>;<br>each remaining R' is H or —CCH$_2$NHC=O |

| STARTING MATERIAL | QUATERNARY INTERMEDIATE (CATION) | DIHYDRO DERIVATIVE |
|---|---|---|
| | 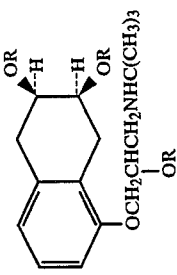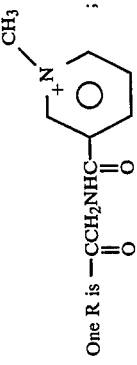  One R is —CCH₂NHC=O ; each remaining R is H or —CCH₂NHC=O | 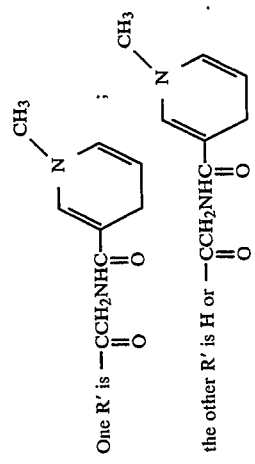  One R' is —CCH₂NHC=O ; the other R' is H or —CCH₂NHC=O |
| 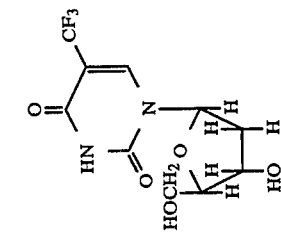 trifluridine | | |

-continued
| STARTING MATERIAL | QUATERNARY INTERMEDIATE (CATION) | DIHYDRO DERIVATIVE |
|---|---|---|
| 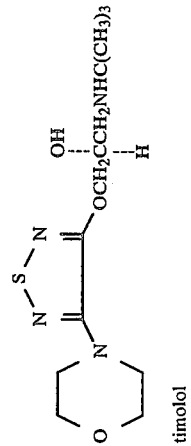
timolol | 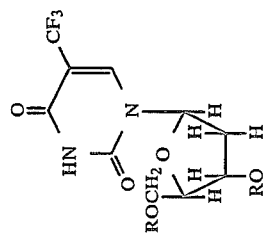
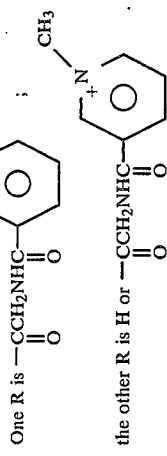
One R is —CCH₂NHC=O
the other R is H or —CCH₂NHC=O | 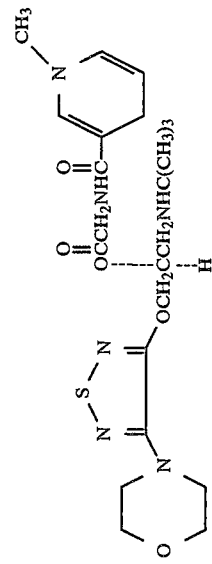 |

| STARTING MATERIAL | QUATERNARY INTERMEDIATE (CATION) | DIHYDRO DERIVATIVE |
|---|---|---|
| 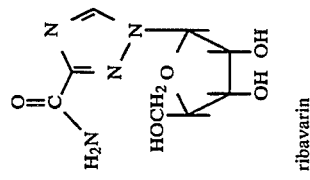 ribavarin | 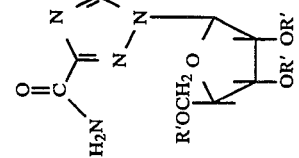 | 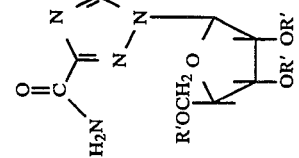 |
| | 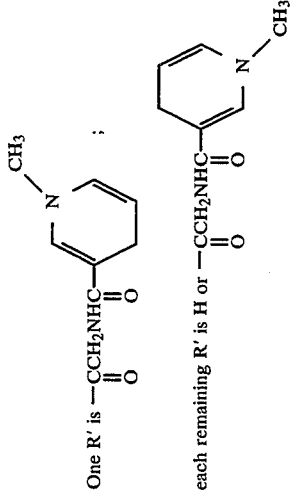 One R' is —CCH₂NHC— ‖ ‖ O O ; each remaining R' is H or —CCH₂NHC— ‖ ‖ O O | 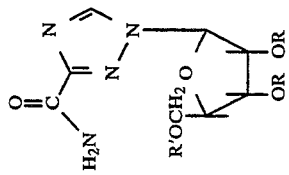 |

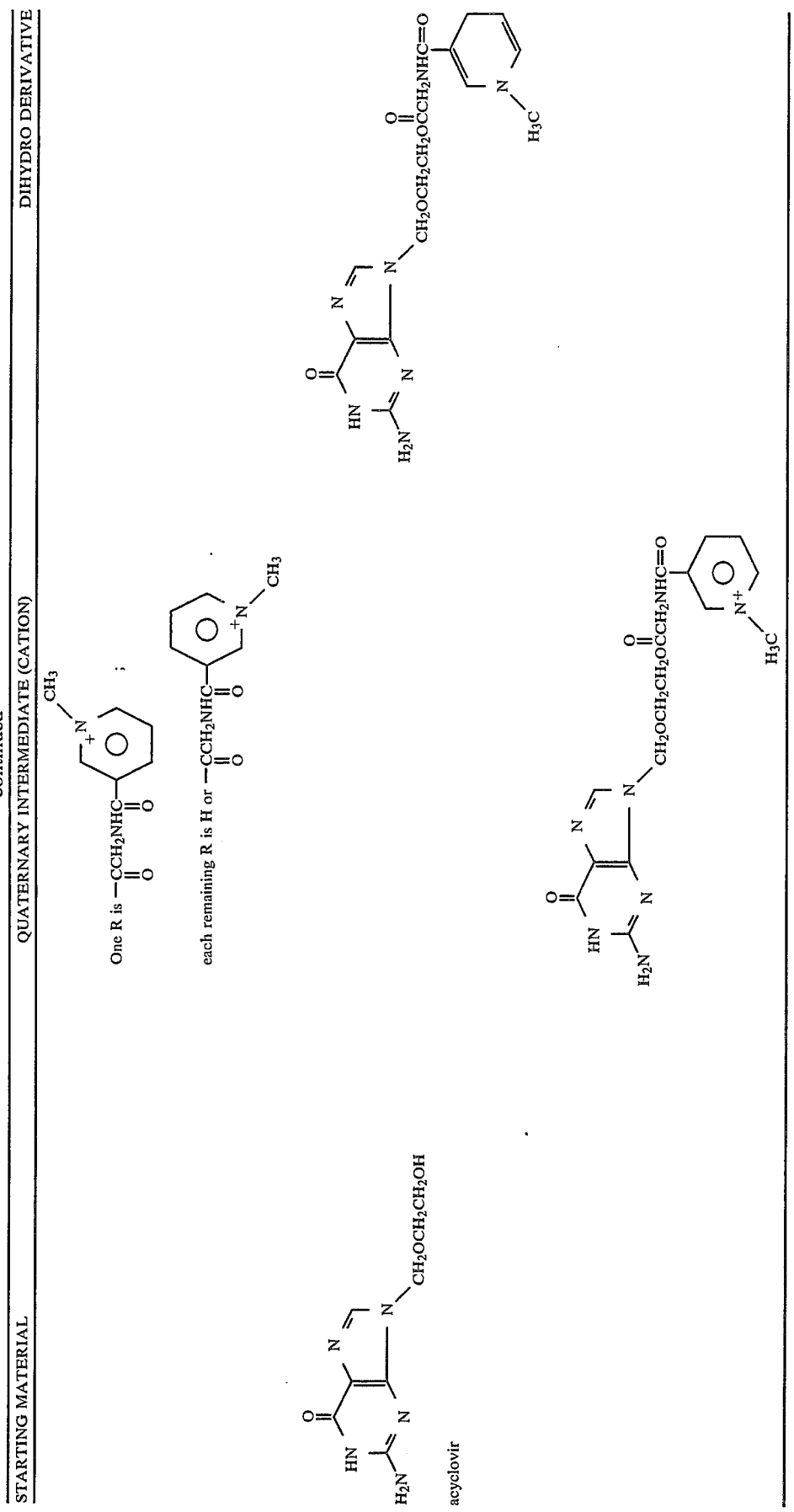

Method K

This is an alternate process for derivatizing drugs containing secondary or tertiary hydroxyl functional groups. According to this process, the drug is reacted with chloral or other aldehyde capable of forming a hemiacetal therewith. In the case of chloral, this converts the —OH function(s) to

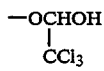

groupings. The —OH function(s) of the resultant hemiacetal can then be derivatized by any of the methods for derivatizing —OH groups disclosed herein, e.g. by reaction with nicotinuric acid or its acid chloride or anhydride as described in Method K.

This process is of particular value when the —OH group(s) in the drug is/are sterically hindered and/or when it is desired to alter the rate of release of the drug from that obtained when the carrier is hooked directly to the drug's hydroxy function(s).

The representative drugs depicted below may be derivatized in this manner to the corresponding compounds of formulas (II) and (I). Other drugs containing secondary or tertiary —OH groups which are disclosed herein, e.g. in connection with Method K, may be similarly derivatized. This method is of special interest for derivatizing steroids containing secondary or tertiary 17 β-hydroxy substituents, especially steroid sex hormones, and most especially such hormones bearing a bulky 17 α-substituent such as a 17 α-ethynyl grouping.

| STARTING MATERIAL | QUARTERNARY INTERMEDIATE (CATION) | DIHYDRO DERIVATIVE |
|---|---|---|
| 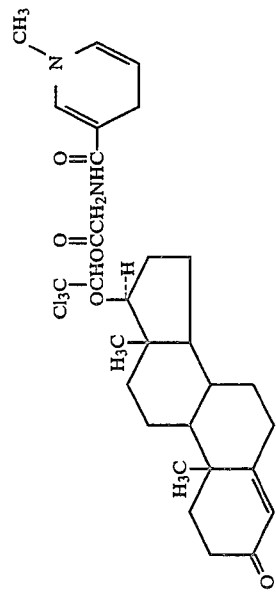 testosterone | 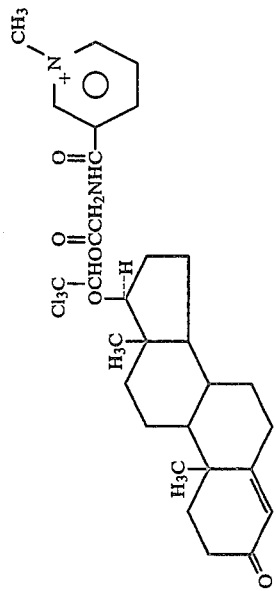 | 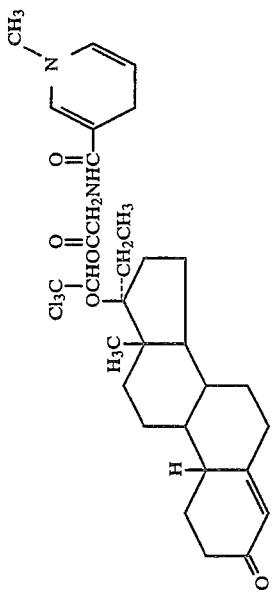 |
| 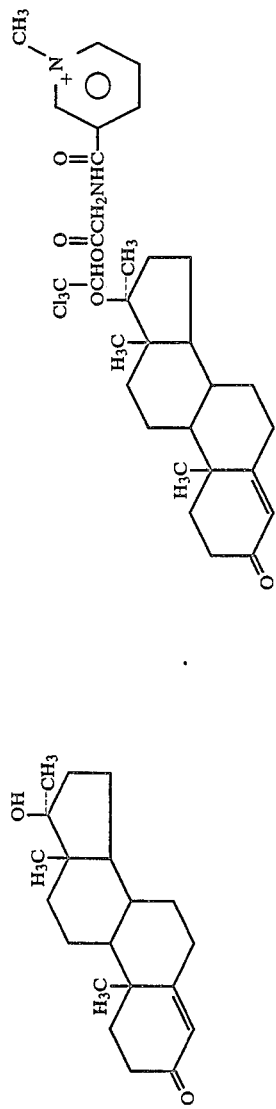 methyltestosterone | | 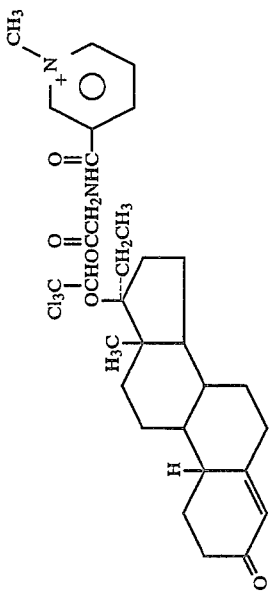 |
| 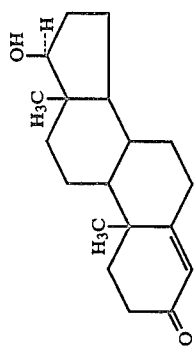 norethandrolone | 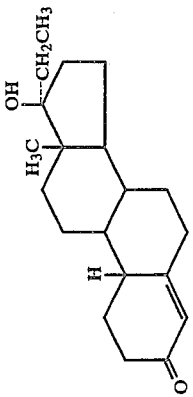 | |

| STARTING MATERIAL | QUARTERNARY INTERMEDIATE (CATION) | DIHYDRO DERIVATIVE |
|---|---|---|
| norethindrone | | |
| norethynodrel | | |
| procyclidine | | |

Method L

This variation of Method K can be used when the drug contains an amino group which needs to be protected. Generally, the amino group is protected prior to any reaction of the hydroxyl function; typically, a benzyloxycarbonyl group is introduced in conventional manner to protect the amino function and then the process described in the first, second or fourth paragraph of Method K is followed. Removal of the protecting group, also in conventional manner, takes place after protection is no longer needed, be it at the end of the synthetic pathway or earlier. Generally, the protecting group is removed before formation of the formula (II) quaternary. Occasionally, an amino protecting group will be utilized which need not be removed, for example, in the case of trifluoroacetyldoxorubicin below.

The representative N- protected drugs depicted below may be derivatized in this manner to the corresponding compounds of formulas (II) and (I). Norepinephrine, epinephrine, glucosamine, 6-amino-6-deoxy-D-glucose and pseudoephedrine may be similarly derivatized.

| STARTING MATERIAL | QUARTERNARY INTERMEDIATE (CATION) | DIHYDRO DERIVATIVE |
|---|---|---|
| 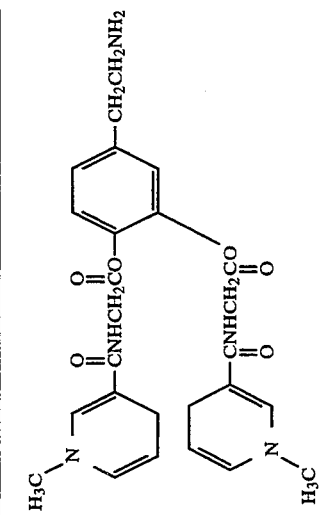 N-benzyloxycarbonyldopamine | | |
| N-benzyloxycarbonyltyramine | | |
| 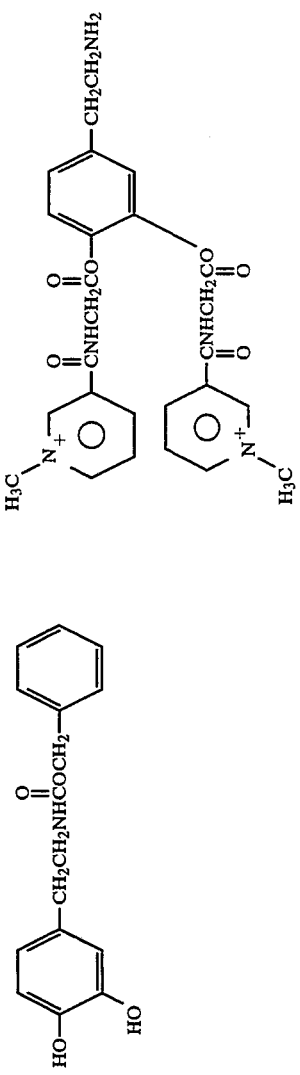 trifluoroacetyldoxorubicin | | 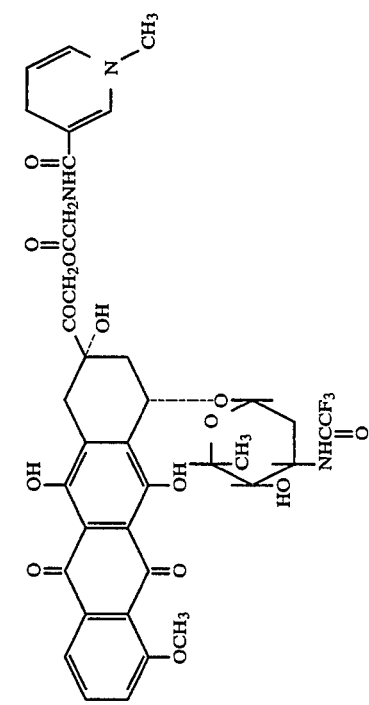 |

| STARTING MATERIAL | QUARTERNARY INTERMEDIATE (CATION) | DIHYDRO DERIVATIVE |
|---|---|---|
| 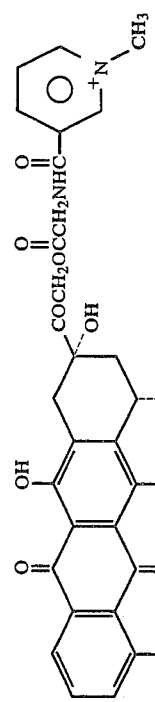<br>N-benzyloxycarbonyl-10-hydroxynortriptyline (E or Z isomer) | 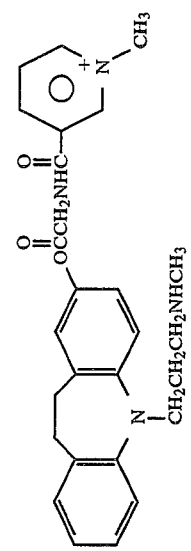 | 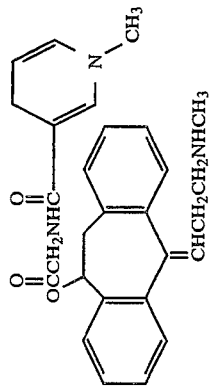 |
| 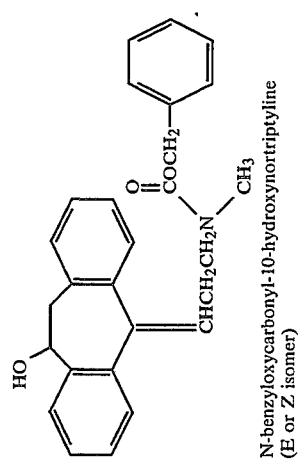<br>N-benzyloxycarbonyl-2-hydroxydesipramine | | 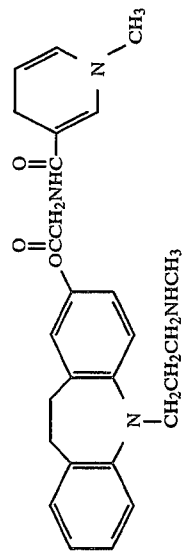 |

Method M

This is a variation of Method K used when the drug contains a —COOH function which is to be protected.

The drug is first converted to the corresponding t-butyl ester by conventional esterification techniques. That ester is then used as the starting material and the procedure of Method K, first, second or fourth paragraph, is repeated. The —COOH group may be similarly converted to other ester groups.

The representative drugs depicted be low may be derivatized in this manner to the corresponding compounds of formulas (II) and (I). Clorazepate and captopril may be similarly derivatized.

| STARTING MATERIAL | QUARTERNARY INTERMEDIATE (CATION) | DIHYDRO DERIVATIVE |
|---|---|---|
| 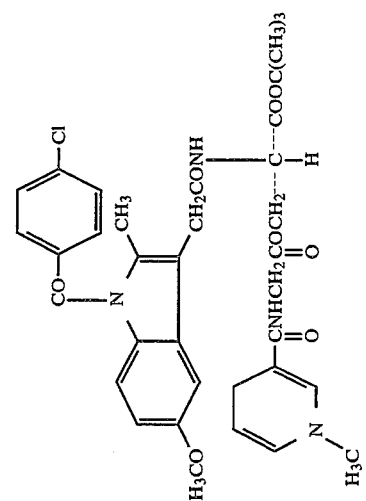 | 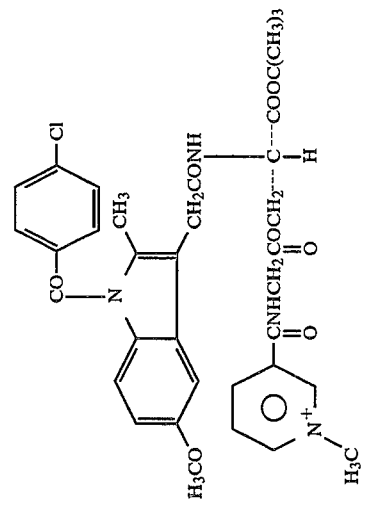 | |
| sermetacin | | |
| 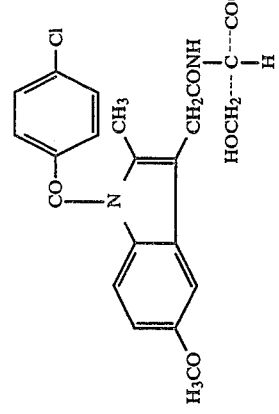 | 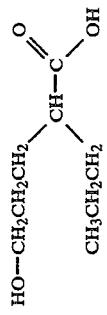 | 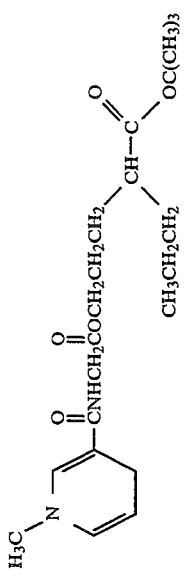 |
| 5-hydroxy-2-n-propylpentanoic acid | | |
| 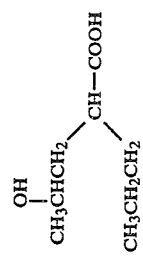 | 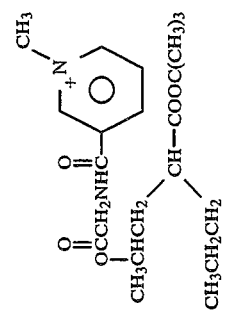 | 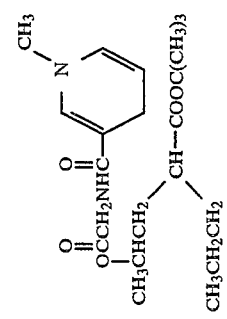 |
| 4-hydroxy-2-n-propylpentanoic acid | | |

| STARTING MATERIAL | QUARTERNARY INTERMEDIATE (CATION) | DIHYDRO DERIVATIVE |
|---|---|---|
| OH<br>\|<br>CH₃CH₂CH—CH—COOH<br>\|<br>CH₃CH₂CH₂ | [chemical structure] | [chemical structure] |
| 3-hydroxy-2-n-propylpentanoic acid | | |
| [PGD₂ structure]<br>PGD₂ | [chemical structure] | [chemical structure] |

Method N

The procedure of the second paragraph of Method K is followed, except that a reactant of the formula

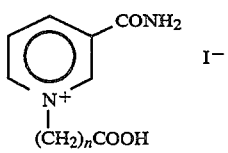

wherein n=1-3, preferably 2 (prepared as described in Method J), is used in place of nicotinic acid. The quaternary salt of formula (II) thus obtained may then be reduced as described in Method A.

The representative drugs depicted below may be derivatized in this manner to the corresponding compounds of formulas (II) and (I), as may the remaining drugs listed with Method K.

Similarly, Method N may be combined with Method L or M to afford the corresponding derivatives, e.g. of the drugs listed with those methods.

A starting material of the formula set forth immediately above can also be substituted for nicotinic acid in the procedure of Method E, third paragraph, to afford the corresponding derivatives, e.g. of the drugs listed with that method. The drugs mentioned with Methods F and G may be similarly derivatized.

Method N is of particular use in preparing derivatives of drugs in which the hydroxy function is hindered, e.g., biperiden, cycrimine, procyclidine and trihexyphenidyl.

Alternatively, Method N may follow Method K, second paragraph, except that it employs a reactant of the formula

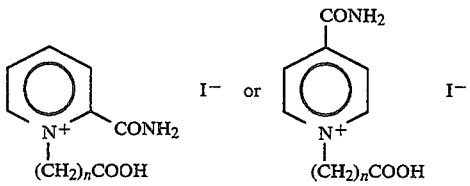

(prepared as described in Method J) in place of nicotinic acid, to afford derivatives of the drugs indicated with Method K. This alternative form of Method N may also be combined with Method L or M, to afford the corresponding derivatives of the drugs listed with Method L or M, respectively. Also, these alternative Method N starting materials may be substituted for nicotinic acid in Method E, third paragraph, to give the corresponding derivatives of the drugs listed with that method.

The procedures of this method may be repeated, substituting a different amino acid, e.g. alanine, valine, leucine, phenylalanine, isoleucine, methionine, asparagine or glutamine, for the glycine used in the first step. (See Method A, second paragraph).

| STARTING MATERIAL | QUARTERNARY INTERMEDIATE (CATION) | DIHYDRO DERIVATIVE |
|---|---|---|

-continued
| STARTING MATERIAL | QUARTERNARY INTERMEDIATE (CATION) | DIHYDRO DERIVATIVE |
|---|---|---|
| 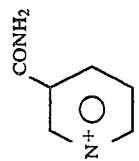<br>oxazepam | 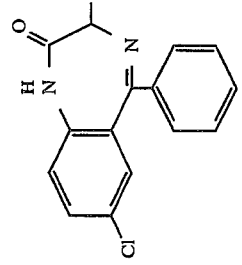 | 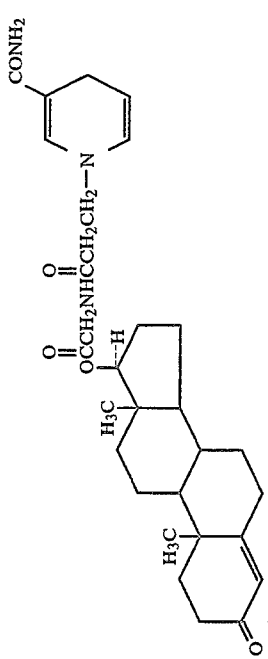 |
| 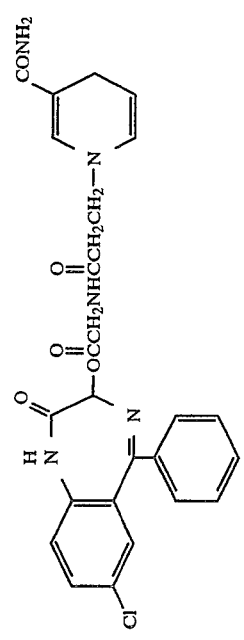<br>testosterone | 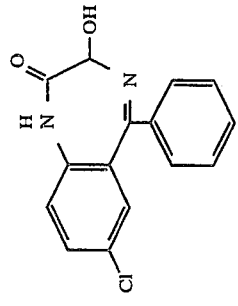 | 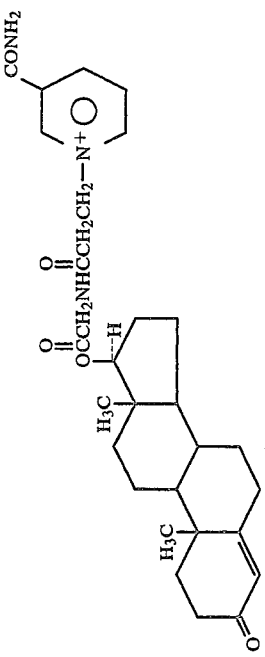 |
| | | 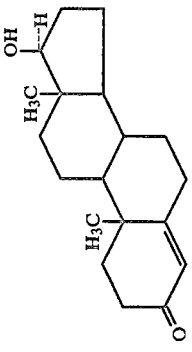 |

This compound can be subsequently selectively hydrolyzed by known methods to the corresponding 17-monoester of formula (II), which can be reduced to the corresponding preferred 17-monoester of formula (I).

| STARTING MATERIAL | QUARTERNARY INTERMEDIATE (CATION) | DIHYDRO DERIVATIVE |
|---|---|---|
| cycrimine | 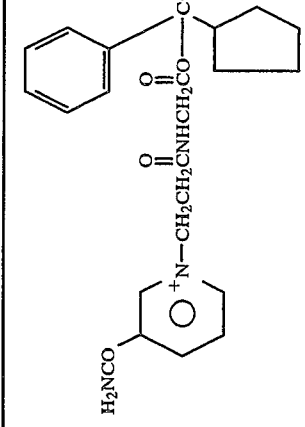 | |
| procyclidine | 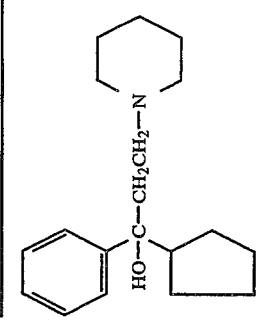 | 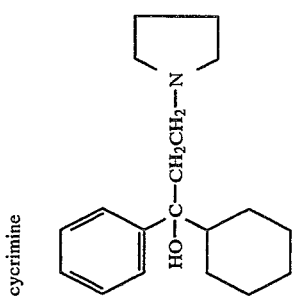 |
| trihexyphenidyl | | 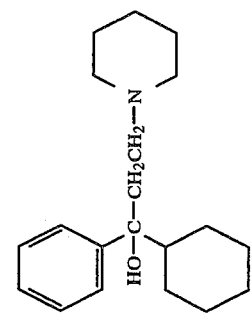 |

Method O

The procedure of Method K, second paragraph, is followed, except that removal of the N- protecting group is followed by reaction with 3-quinolinecarboxylic acid or its acid chloride or anhydride instead of nicotinic acid or its acid chloride or anhydride.

The representative drugs depicted below may be derivatized in this manner to the corresponding compounds of formulas (II) and (I), as may the remaining drugs listed with Method K.

The procedure of the first paragraph of Method K may be similarly adapted to the production of the 3-quinolinecarboxylic acid derivatives. Moreover, Method O may be combined with Method L or M to afford the corresponding derivatives, e.g. of the drugs listed with those methods.

The procedure of Method O may be repeated using 4-isoquinolinecarboxylic acid or its acid chloride or anhydride in place of 3-quinolinecarboxylic acid or its acid chloride or anhydride, to afford the corresponding derivatives of drugs such as those indicated with Methods K, L and M.

3-Quinolinecarboxylic acid or its acid chloride or anhydride or 4-isoquinolinecarboxylic acid or its acid chloride or anhydride can also be substituted for nicotinic acid or its acid chloride in Method E, fourth paragraph, to afford the corresponding derivatives, e.g. of the drugs listed with that method.

The general procedures described above may be utilized to provide the 1,2-dihydro derivatives as well as the depicted 1,4-dihydros.

| STARTING MATERIAL | QUATERNARY INTERMEDIATE (CATION) | DIHYDRO DERIVATIVE |
|---|---|---|

-continued
| STARTING MATERIAL | QUATERNARY INTERMEDIATE (CATION) | DIHYDRO DERIVATIVE |
|---|---|---|
| 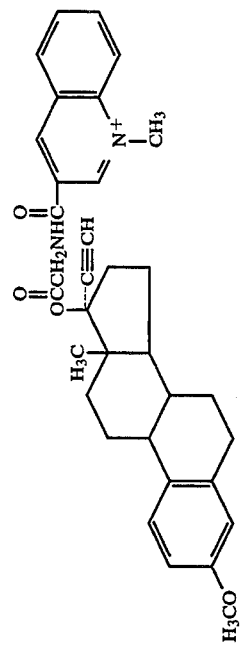<br>norethindrone | 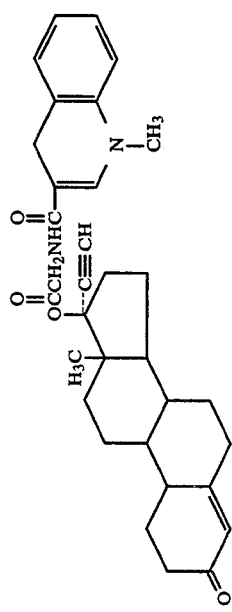 | 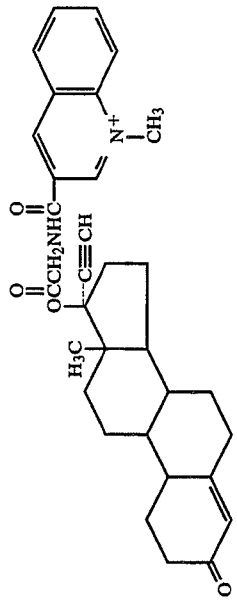 |
| 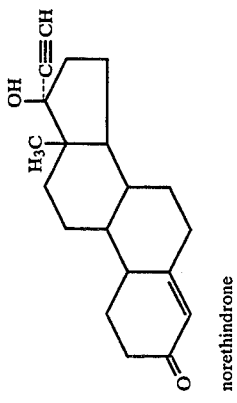<br>acyclovir | 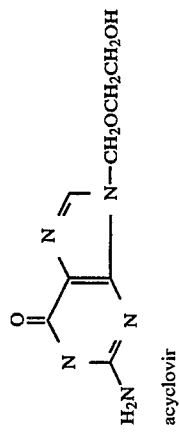 | 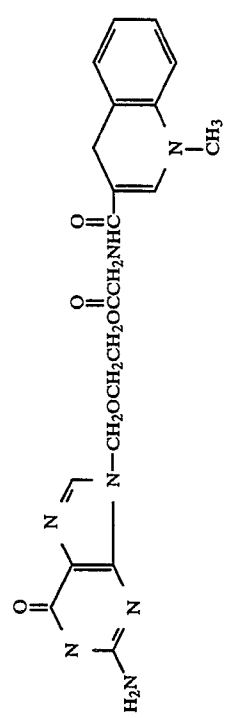 |

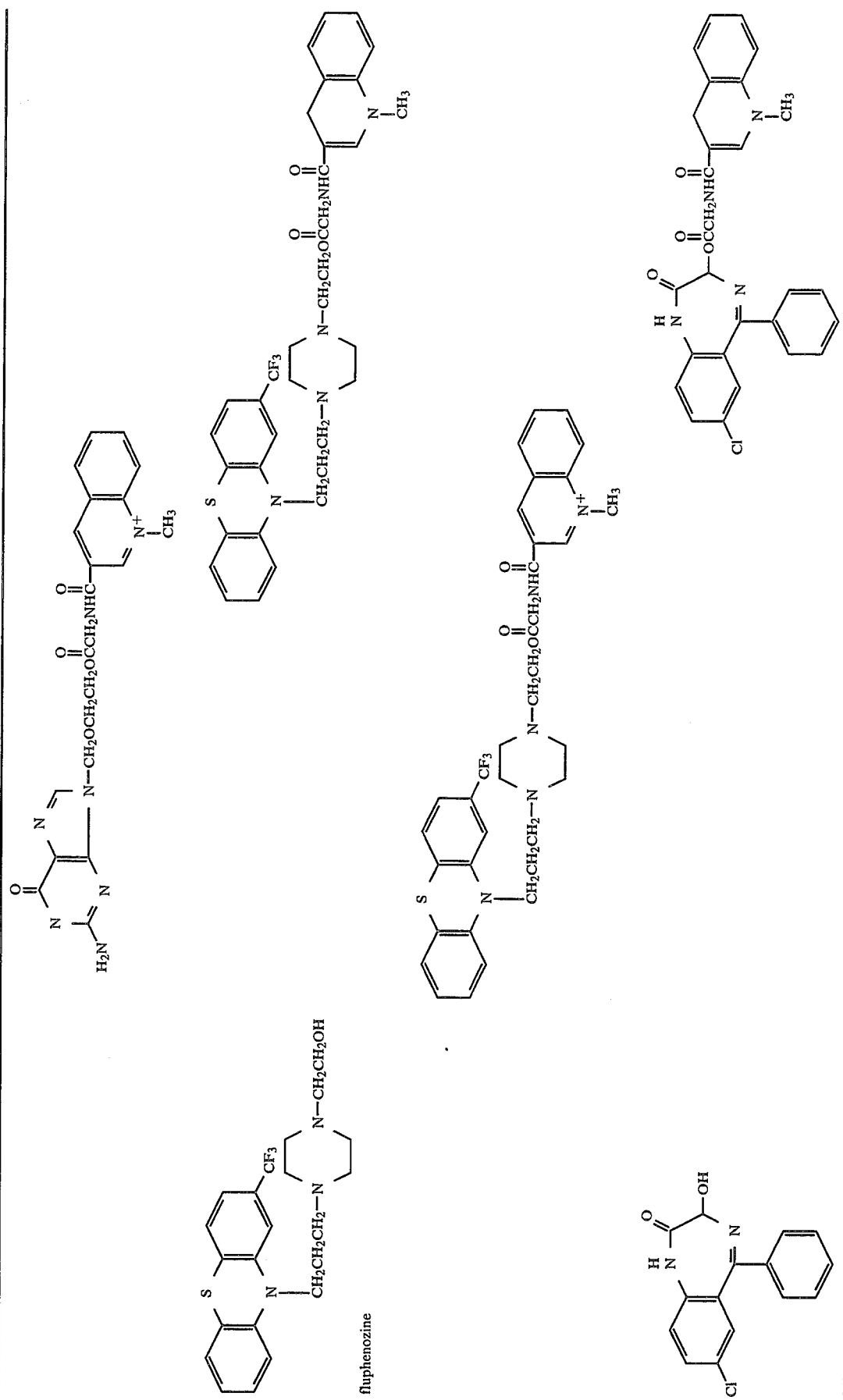

| STARTING MATERIAL | QUATERNARY INTERMEDIATE (CATION) | DIHYDRO DERIVATIVE |
|---|---|---|
| testosterone | 361 | |
| estradiol | 362 | |

| STARTING MATERIAL | QUATERNARY INTERMEDIATE (CATION) | DIHYDRO DERIVATIVE |
|---|---|---|
| 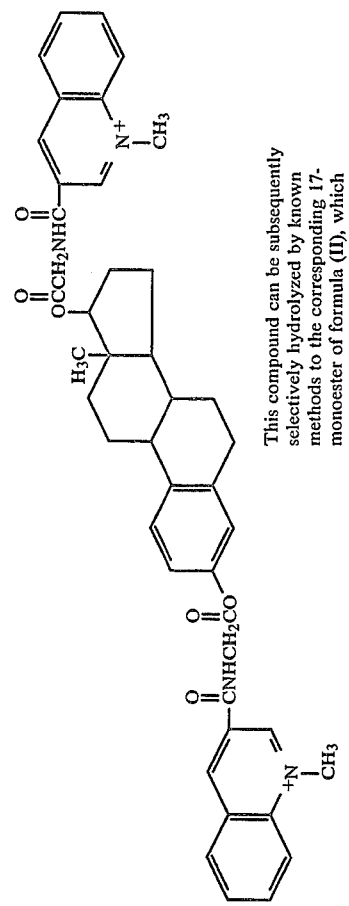 nalbuphine | 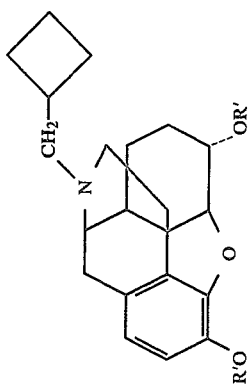 This compound can be subsequently selectively hydrolyzed by known methods to the corresponding 17-monoester of formula (II), which can be reduced to the corresponding preferred 17-monoester of formula (I). | 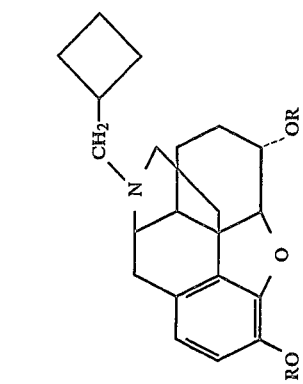 |

| STARTING MATERIAL | QUATERNARY INTERMEDIATE (CATION) | DIHYDRO DERIVATIVE |
|---|---|---|
| | 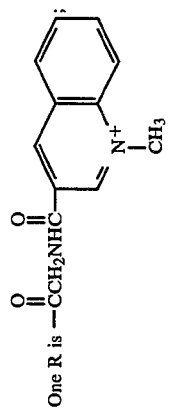
One R is —CCH₂NHC | 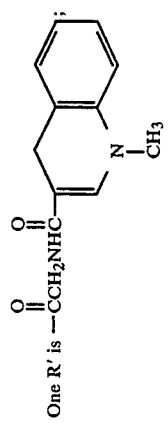
One R' is —CCH₂NHC |
| | 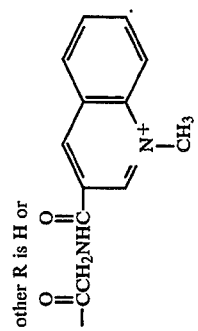
other R is H or
—CCH₂NHC | 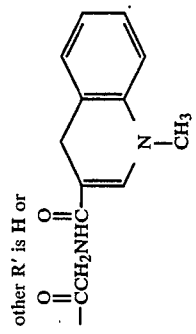
other R' is H or
—CCH₂NHC |

| STARTING MATERIAL | -continued<br>QUATERNARY INTERMEDIATE (CATION) | DIHYDRO DERIVATIVE |
|---|---|---|
| 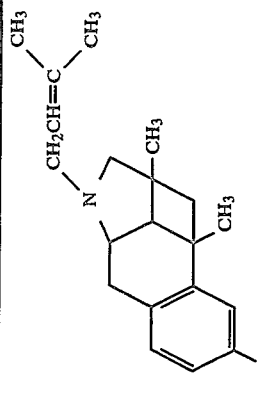<br>pentazocine | 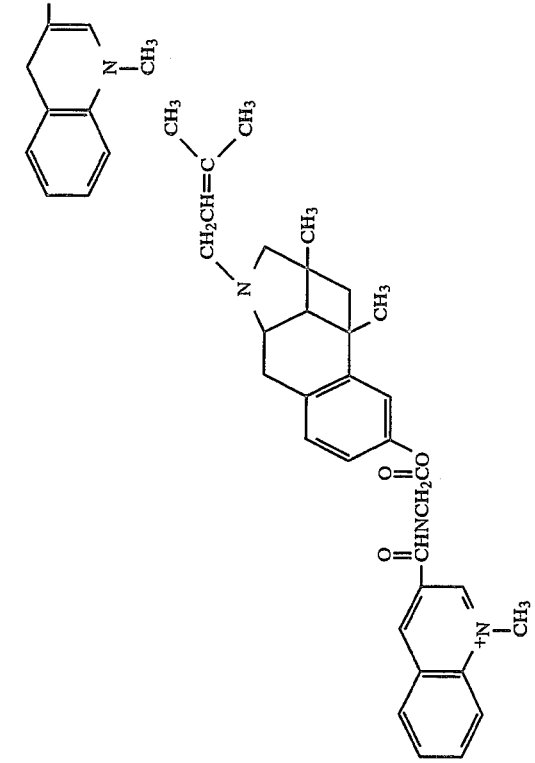 | |

Method P

The procedure of the second paragraph of Method K is followed, except that a reactant of the formula

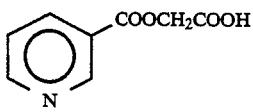

is used in place of nicotinic acid.

The representative drugs depicted below may be derivatized in this manner to the corresponding compounds of formulas (II) and (I), as may the remaining drugs listed with Method K.

Similarly, Method P may be combined with Methods L and M to afford the corresponding derivatives, e.g. of the drugs listed with those methods.

A starting material of the formula set forth immediately above can also be substituted for nicotinic acid in Method E, paragraph 4, to afford the corresponding derivatives, e.g. of the drugs listed with that method.

Alternatively, Method P may follow Method K, second paragraph, except that it employs a reactant of the formula

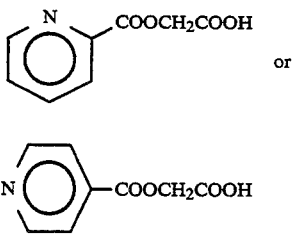

(prepared as described in Method I), to afford derivatives of the drugs indicated with Method K. This alternative form of Method P may also be combined with Method L or M, to afford the corresponding derivatives of the drugs listed with Method L or M. Also, these alternative Method P starting materials may be substituted for nicotinic acid in Method E, fourth paragraph, to give the corresponding derivatives of the drugs listed with that method.

The procedure of the first or fifth paragraph of this method may be repeated, substituting a different amino acid, e.g. alanine, valine, leucine, phenylalanine, isoleucine, methionine, asparagine or glutamine, for the glycine used in the first step. (See Method A, second paragraph).

| STARTING MATERIAL | QUATERNARY INTERMEDIATE (CATION) | DIHYDRO DERIVATIVE |
|---|---|---|
| 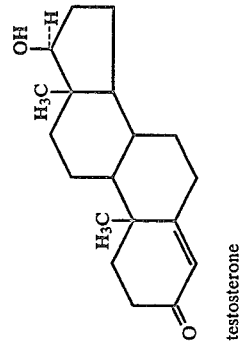<br>testosterone | 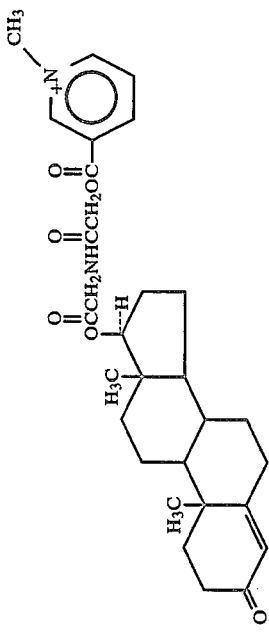 | 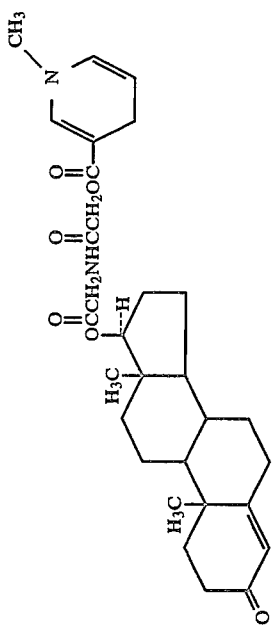 |
| 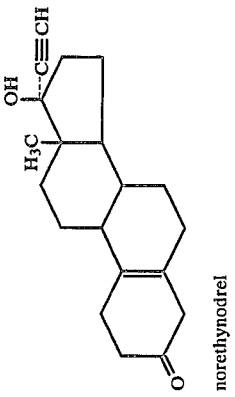<br>norethynodrel | | 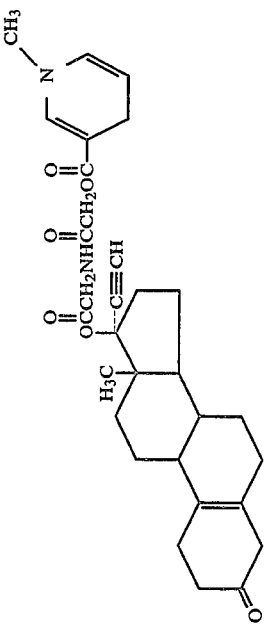 |

| STARTING MATERIAL | QUATERNARY INTERMEDIATE (CATION) | DIHYDRO DERIVATIVE |
|---|---|---|
| | -continued | |
| 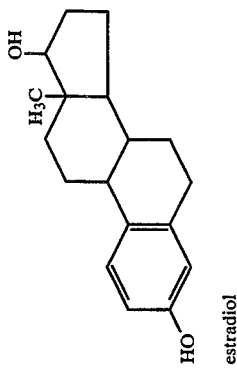 estradiol | 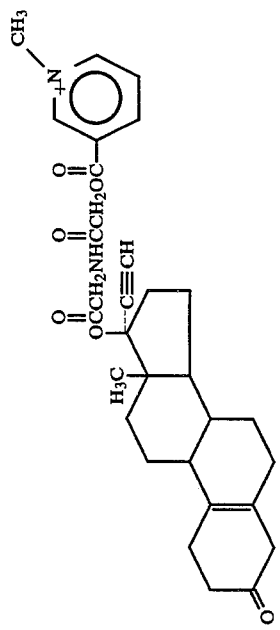 | 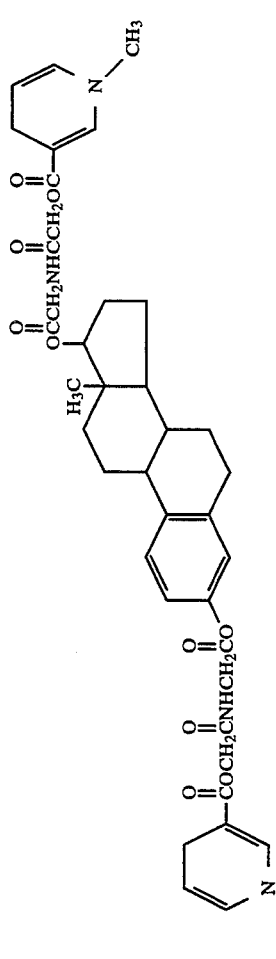 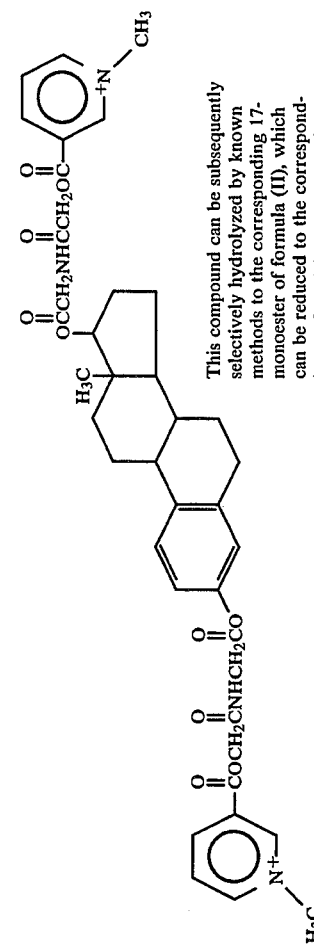 This compound can be subsequently selectively hydrolyzed by known methods to the corresponding 17-monoester of formula (II), which can be reduced to the corresponding preferred 17-monoester of formula (I). |

| STARTING MATERIAL | QUATERNARY INTERMEDIATE (CATION) | DIHYDRO DERIVATIVE |
|---|---|---|
| 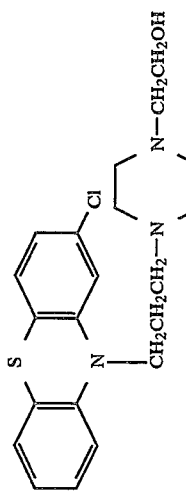 perphenazine | 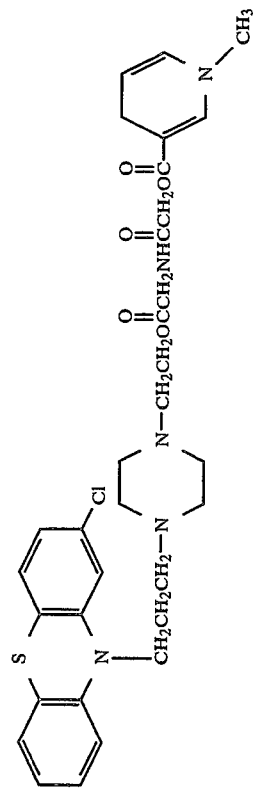 | 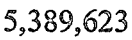 |
| 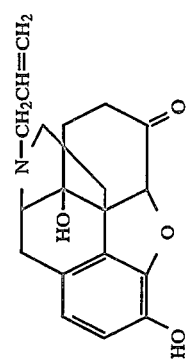 naloxone | 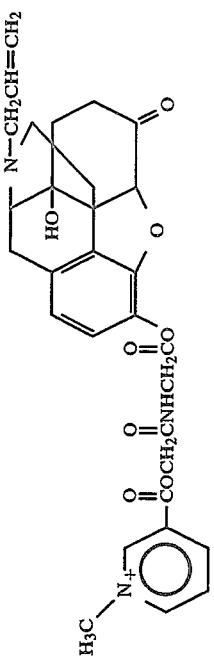 | 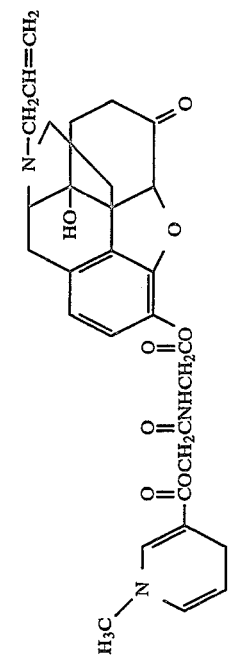 |

| STARTING MATERIAL | QUATERNARY INTERMEDIATE (CATION) | DIHYDRO DERIVATIVE |
|---|---|---|
| 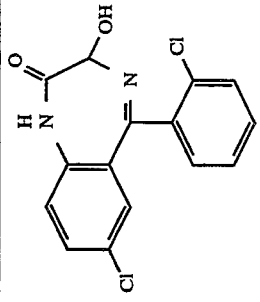 lorazepam | 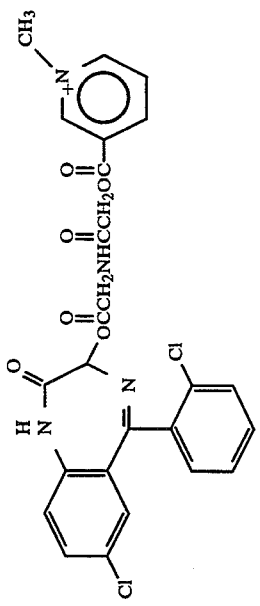 | 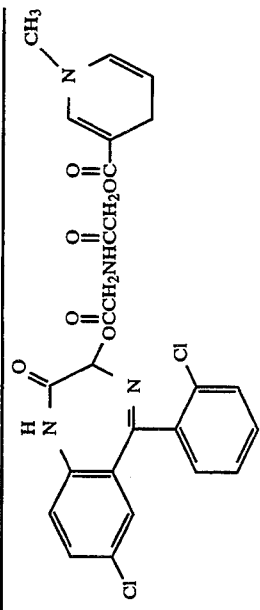 |

III. Methods for Derivatizing —COOH Functions in Drugs

Method Q

Nicotinuric acid (N-nicotinoylglycine) or an activated ester thereof is reacted with an aminoalkanol $$H_2N-Z'-OH$$

wherein $Z'$ is $C_1-C_8$ straight or branched alkylene, e.g. 2-aminoethanol, to afford the corresponding intermediate alcohol, e.g. in the case of 2-aminoethanol, intermediate of the formula

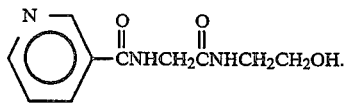

That alcohol is then reacted with a drug containing one or more —COOH functions, in the presence of a suitable coupling agent such as dicyclohexylcarbodiimide.

The compound thus obtained is then quaternized and subsequently reduced as described above in Method A.

Nicotinuric acid is commercially available. However, it and analogous starting materials can be readily prepared by reacting the selected amino acid with the acid chloride of nicotinic acid, of picolinic acid, of isonicotinic acid, of 3-quinolinecarboxylic acid, of 4-isoquinolinecarboxylic acid or the like to afford the desired N-substituted amino acid, which can then be reacted with an aminoalkanol as described above.

The representative drugs depicted below may be derivatized in this manner to the corresponding compounds of formulas (II) and (I). Drugs such as methicillin, ticarcillin, oxacillin, dicloxacillin, glyoxylic acid sulfonyl hydrazone, 5-methyltetrahydrohomofolic acid, phenoxymethylpenicillin, fenbufen, fenoprofen, indoprofen, ketoprofen, fluprofen, bucloxic acid, tolmetin, alclofenac, fenclozic acid, ibufenac, meclofenamic acid, flufenamic acid, flufenisal, clonixin, carprofen, etodolac, flutiazin, pirprofen, furosemide, cefoxitin and clorazepate may be similarly derivatized.

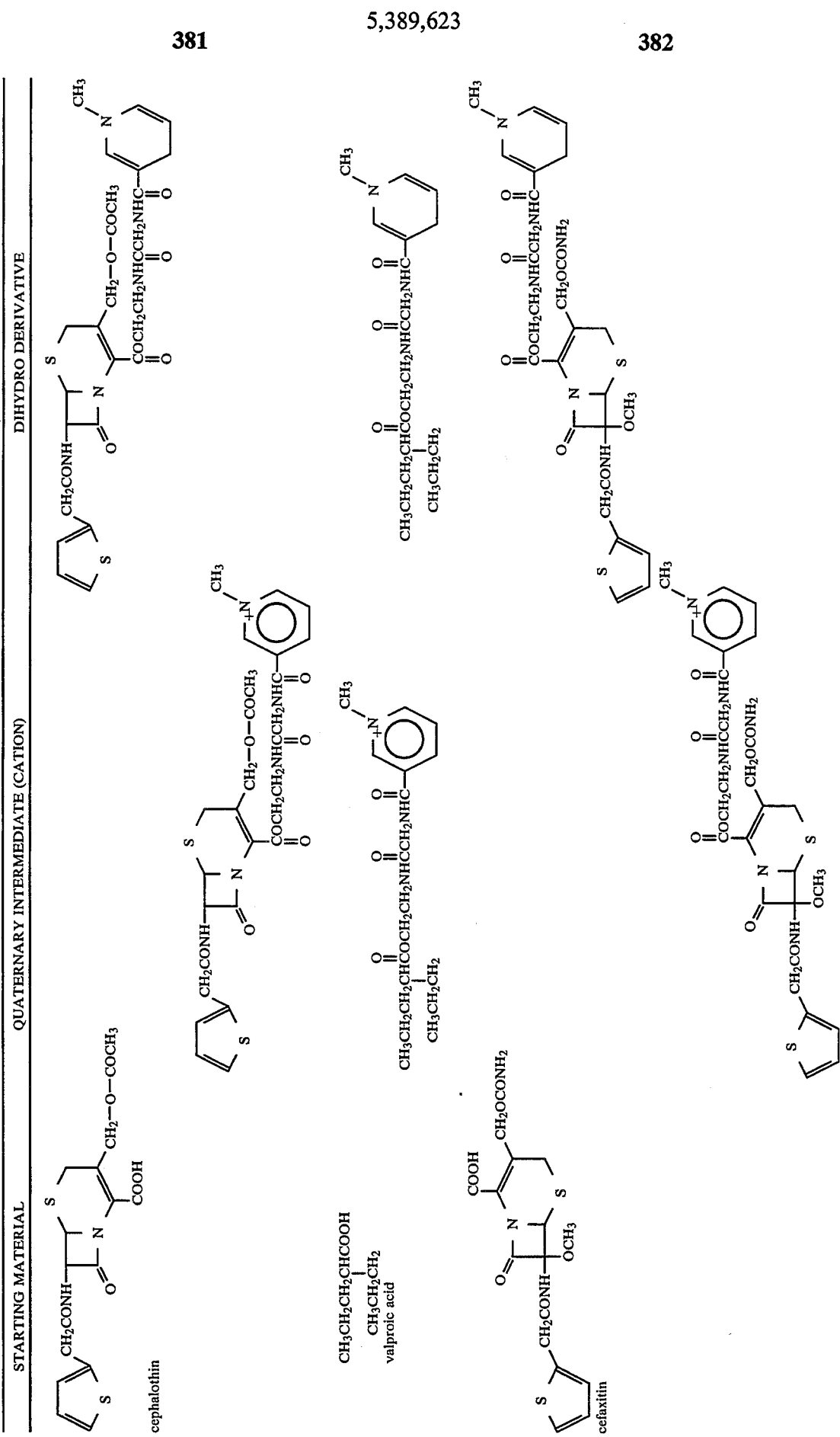

-continued
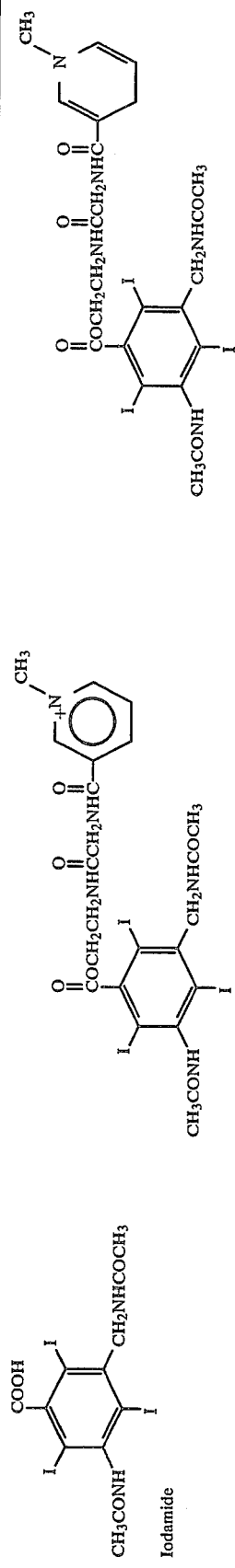
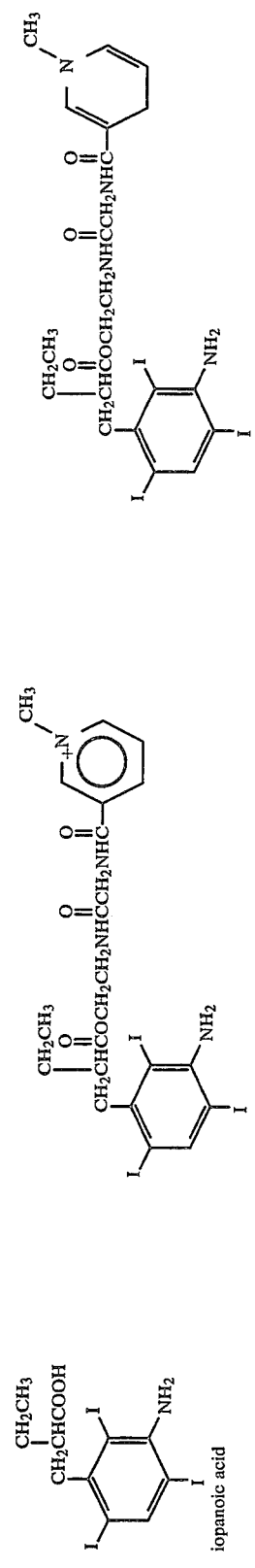
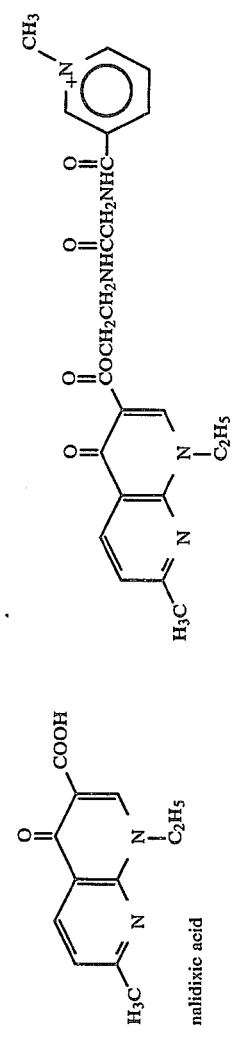
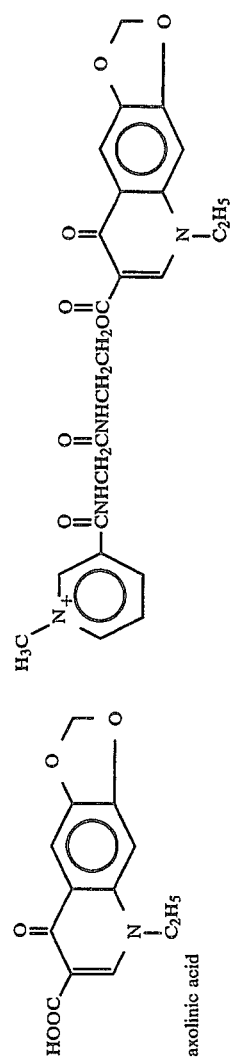

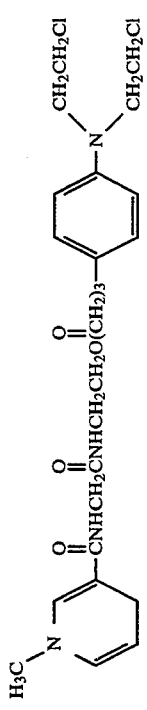
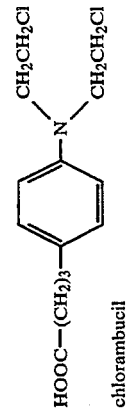
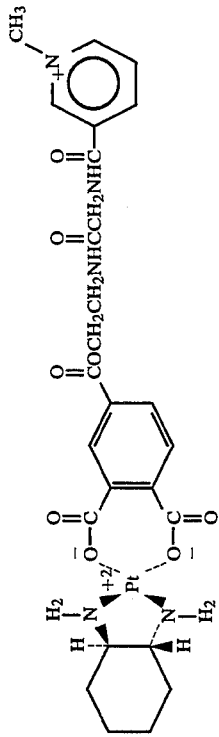
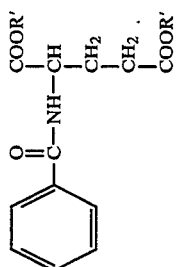
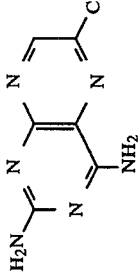
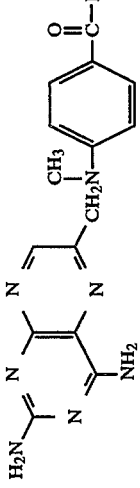

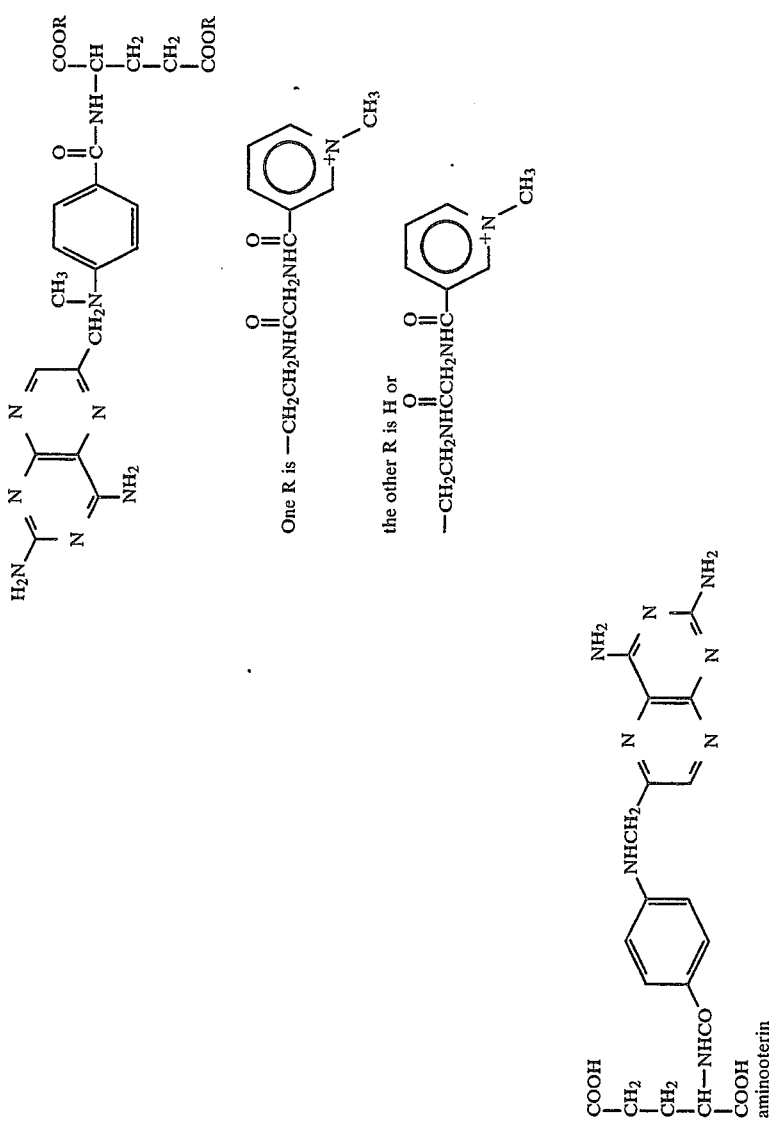
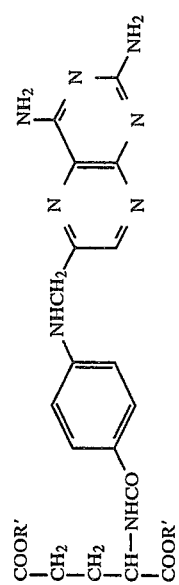
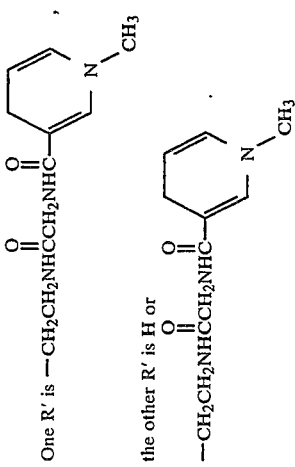

-continued
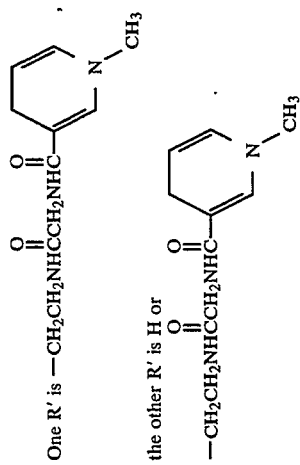
One R' is —CH$_2$CH$_2$NHCCH$_2$NHC—
the other R' is H or
—CH$_2$CH$_2$NHCCH$_2$NHC—
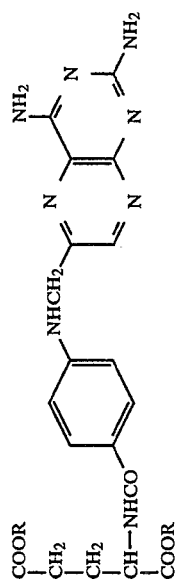
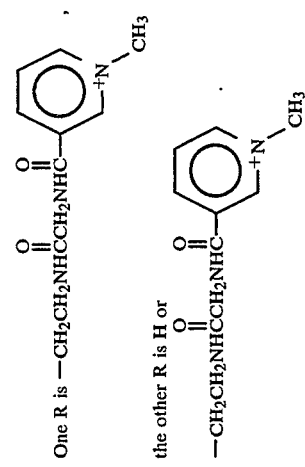
One R is —CH$_2$CH$_2$NHCCH$_2$NHC—
the other R is H or
—CH$_2$CH$_2$NHCCH$_2$NHC—
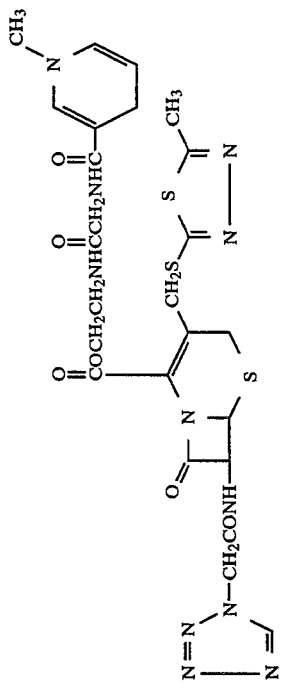
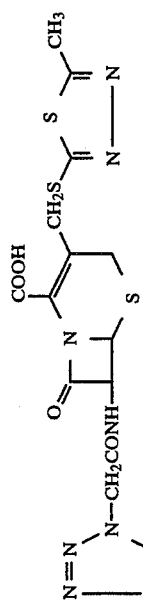
cefazolin

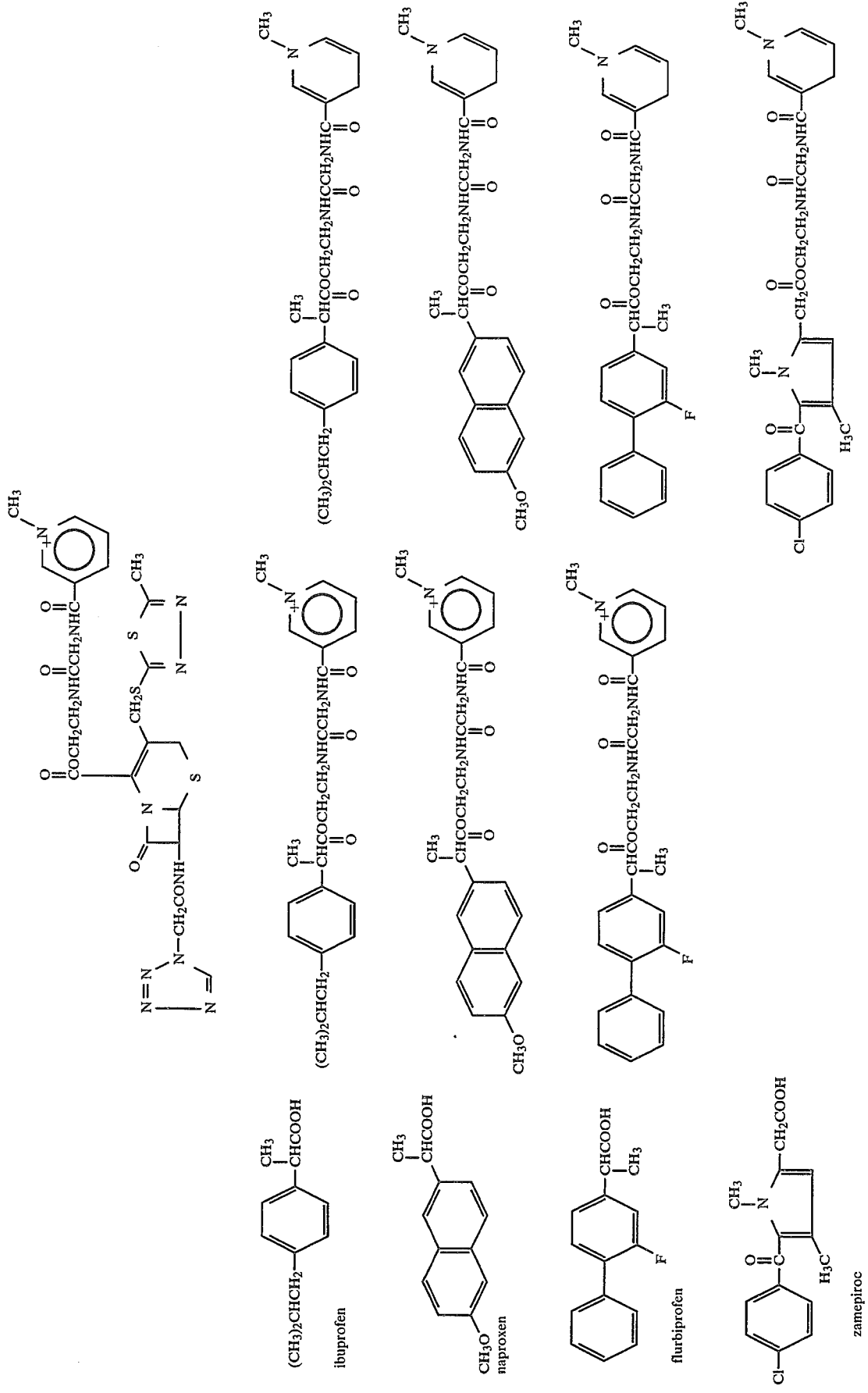

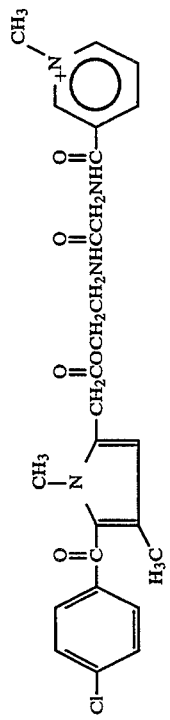
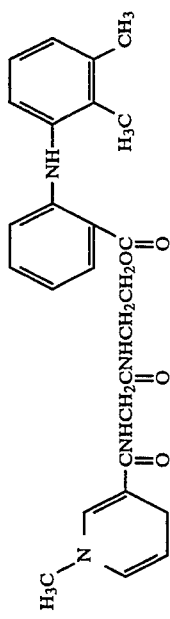
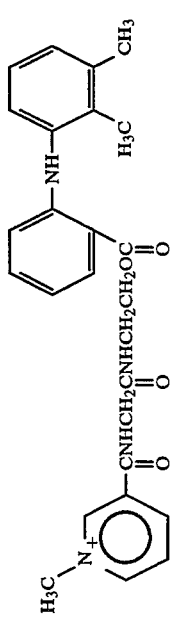
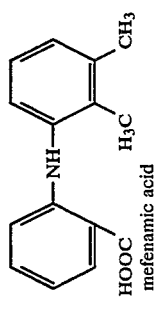
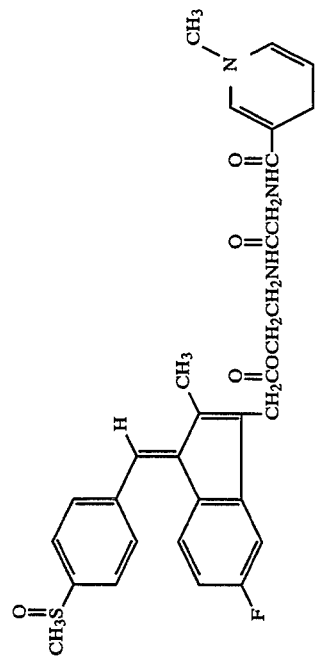
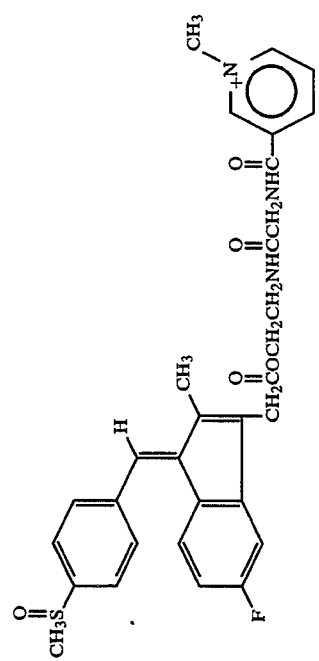
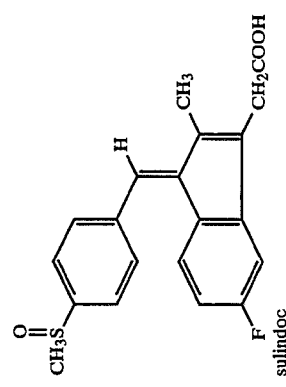
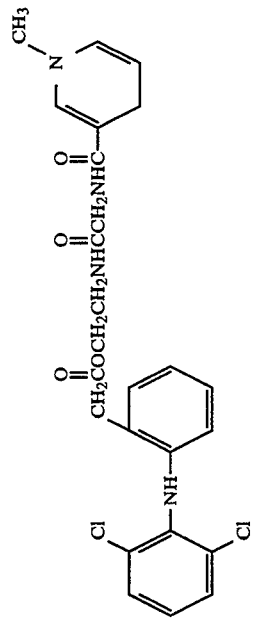
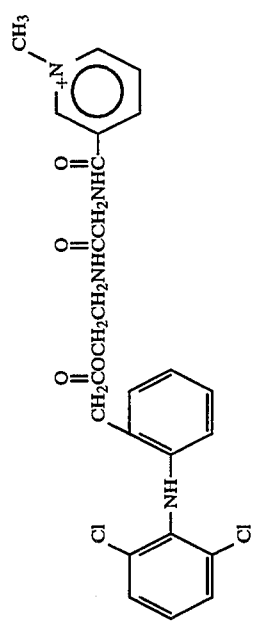
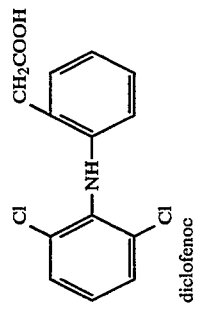

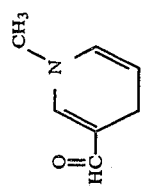
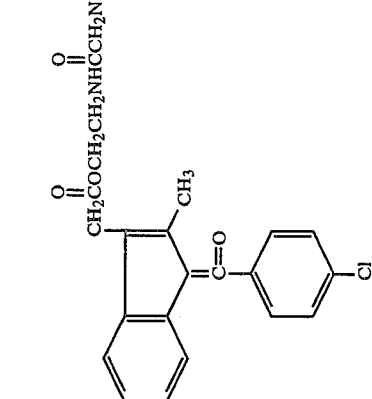
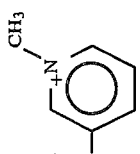
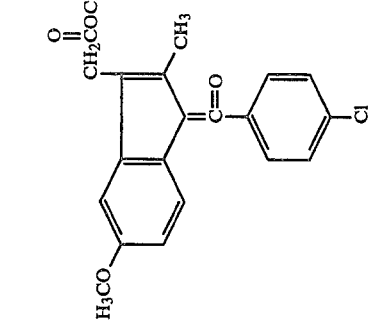
indomethocin
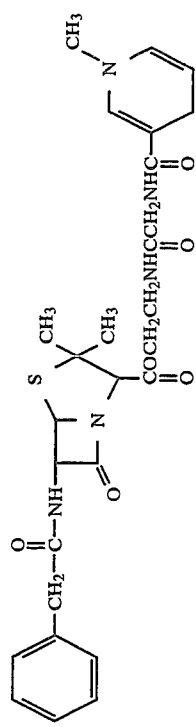
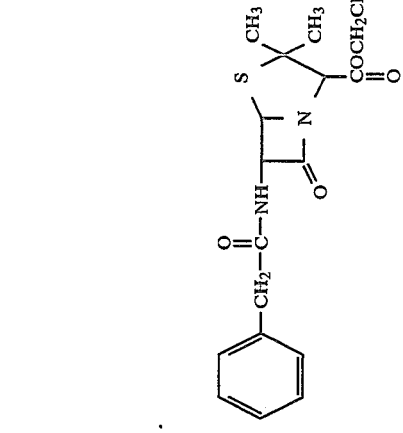
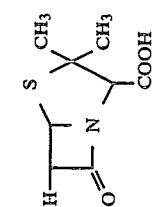
benzylpenicillin
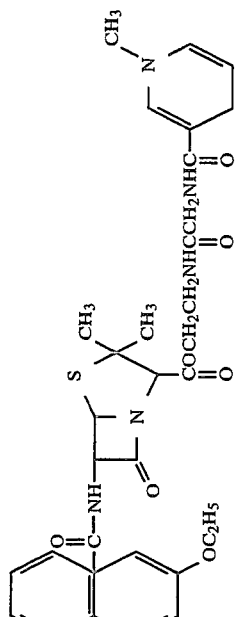
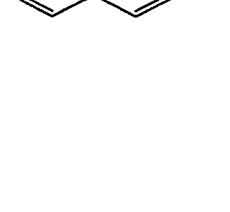
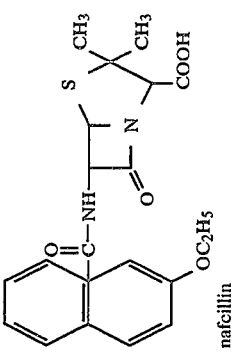
nafcillin -continued
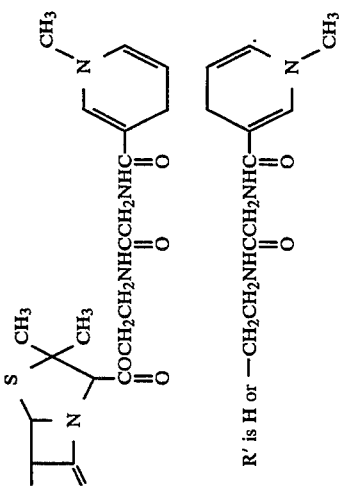
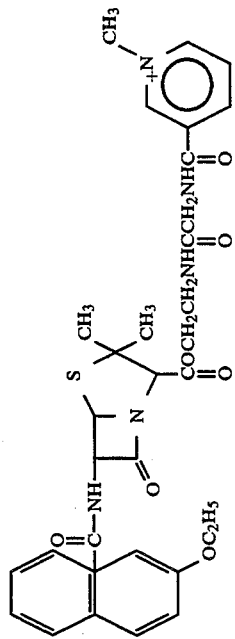
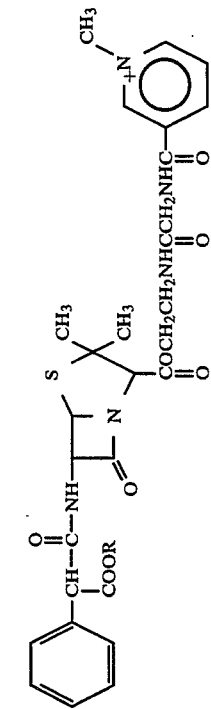
R' is H or —CH$_2$CH$_2$NHCCH$_2$NHC
R is H or —CH$_2$CH$_2$NHCCH$_2$NHC
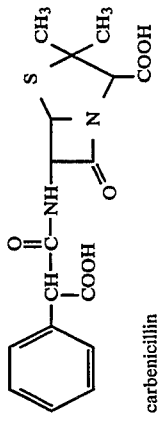
carbenicillin -continued
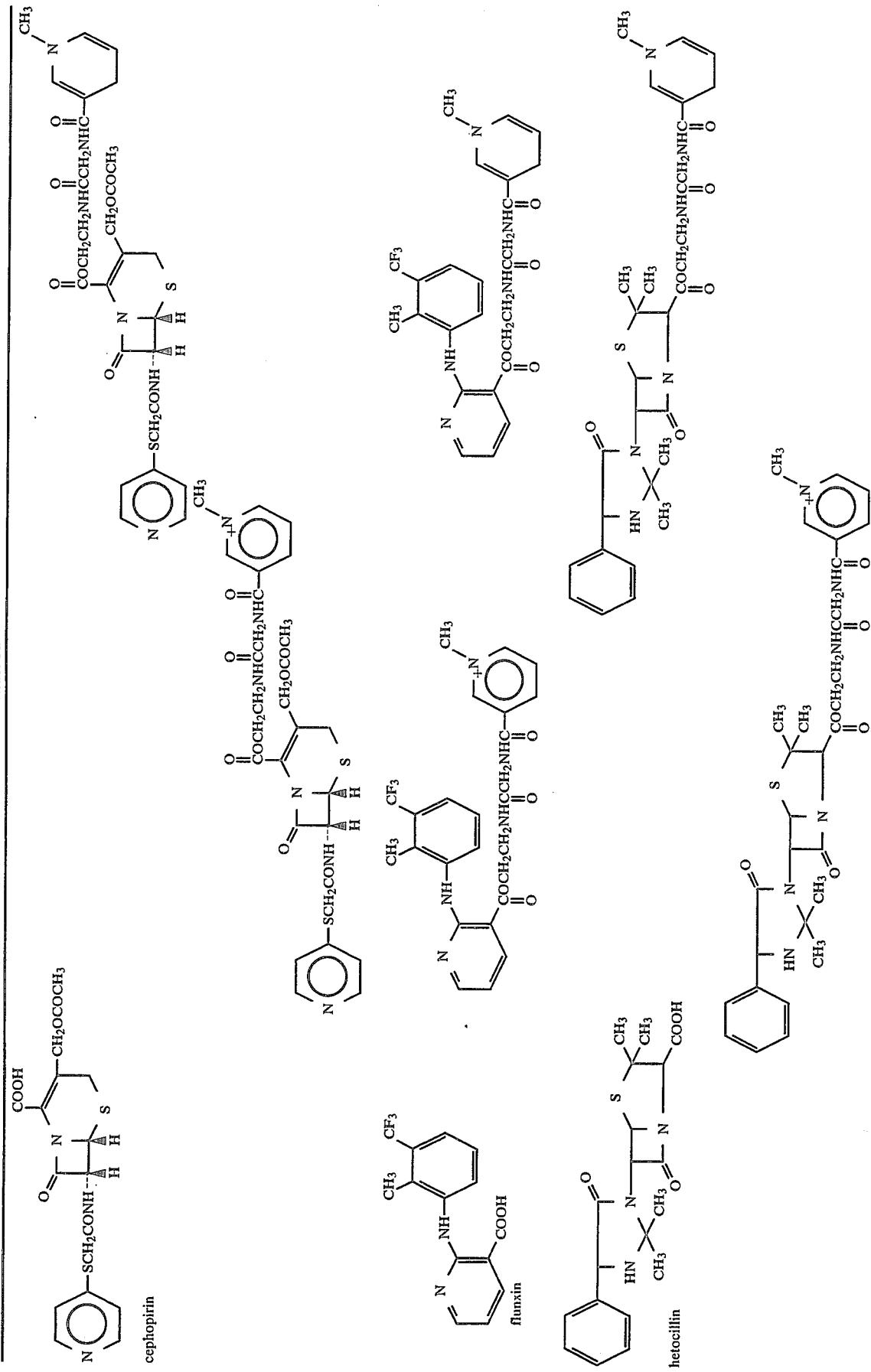

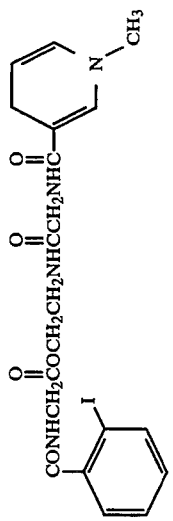
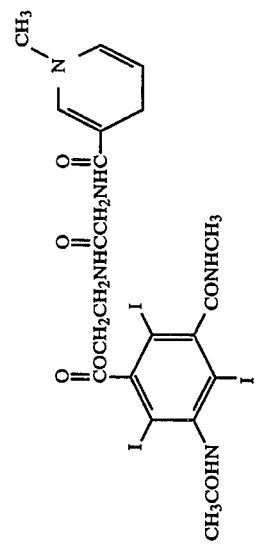
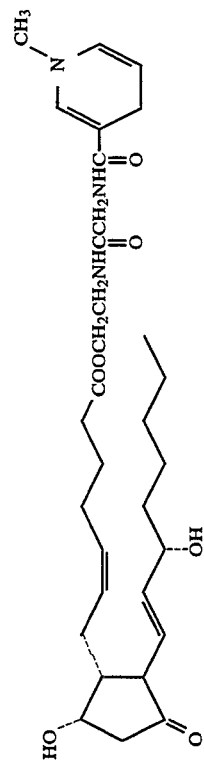
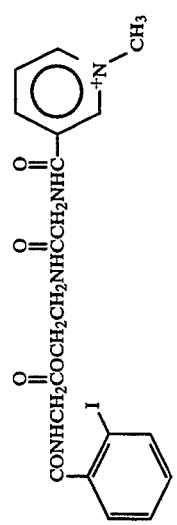
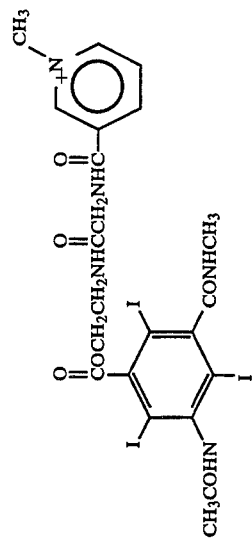
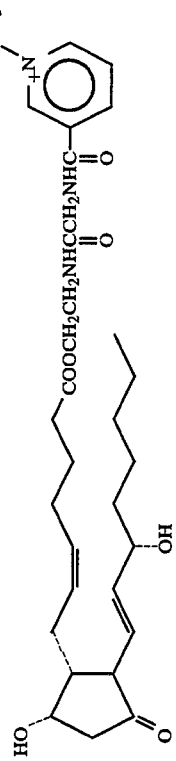
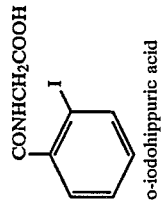
o-iodohippuric acid
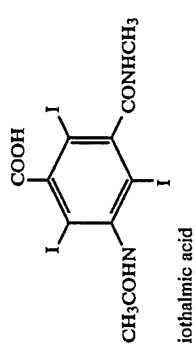
iothalmic acid
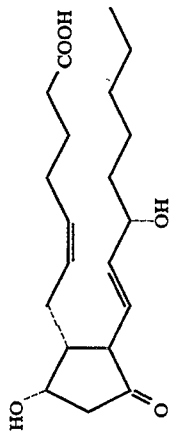
PGD$_2$ -continued
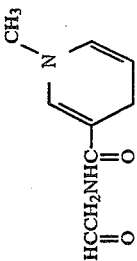
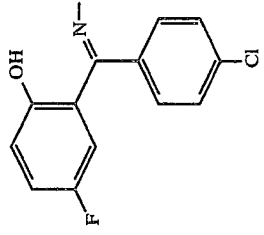
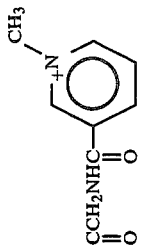
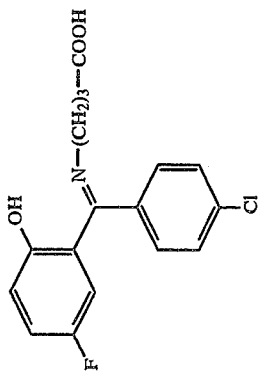
SL 75102

Method R

This is a variation of Method Q used when the drug contains one or more —OH or —SH functions which are to be protected.

The drug is first reacted with excess trimethylacetyl chloride to convert the hydroxy group(s) to pivalyloxy group(s). (Various other hydroxyl protecting groups may be introduced in similar fashion.) The protected drug is then reacted with the intermediate alcohol

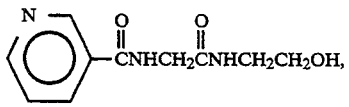

in the presence of dicyclohexylcarbodiimide or other appropriate agent for coupling the —COOH function of the drug to the hydroxy function of the depicted intermediate. (Other intermediate alcohols can be employed, e.g. as described in Method Q.) The resultant compound is then quaternized and the quaternary subsequently reduced as in Method A.

The representative drugs depicted below may be derivatized in this manner to the corresponding compounds of formulas (II) and (I). Drugs such as clorazepate, 4-hydroxy-2-n-propylpentanoic acid, 3-hydroxy-2-n-propylpentanoic acid and captopril may be similarly derivatized.

| STARTING MATERIAL | QUATERNARY INTERMEDIATE (CATION) | DIHYDRO DERIVATIVE |
|---|---|---|
| fendosol | | |
| sermetacin | | |

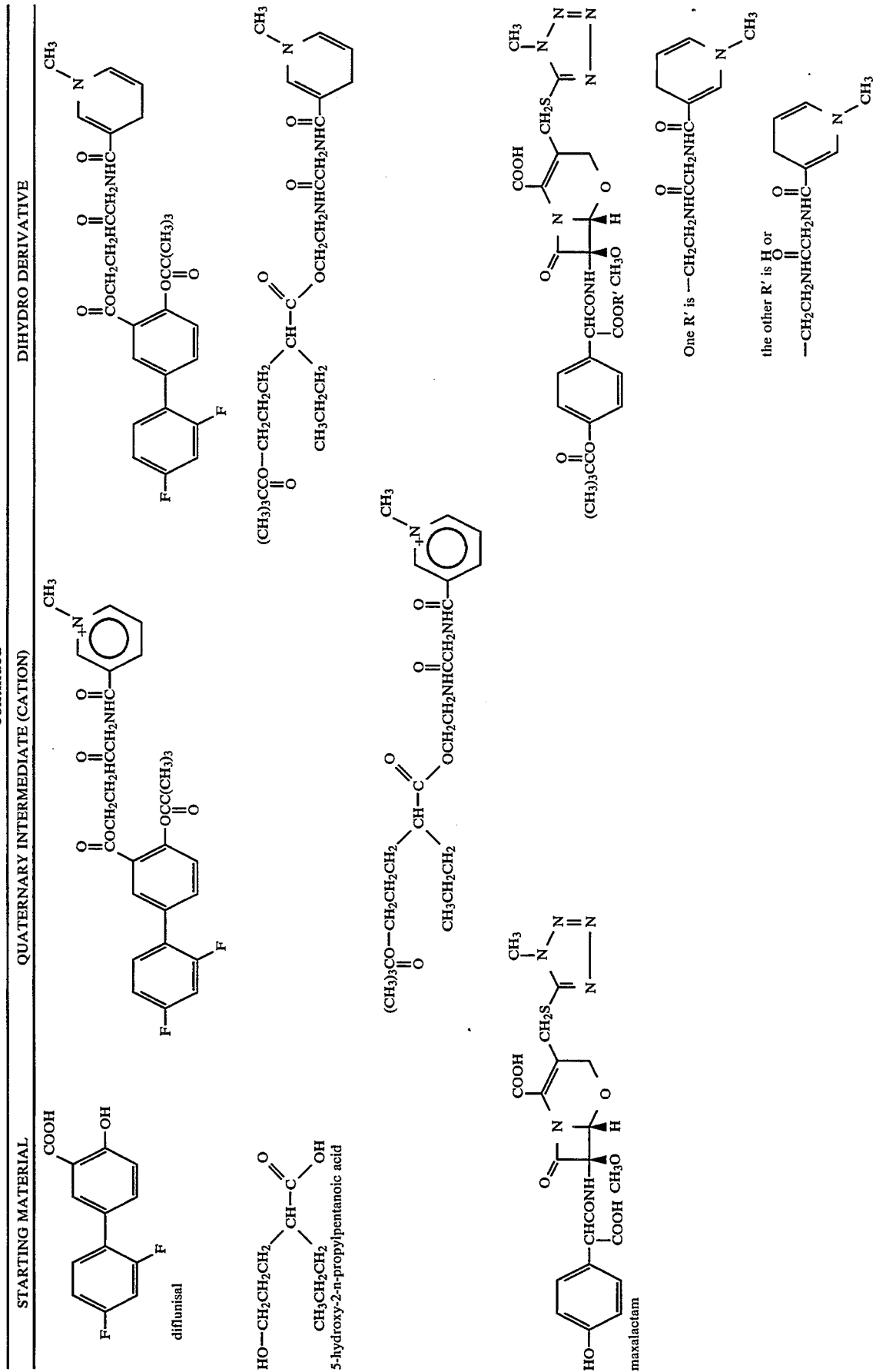

| STARTING MATERIAL | QUATERNARY INTERMEDIATE (CATION) | DIHYDRO DERIVATIVE |
|---|---|---|
| | 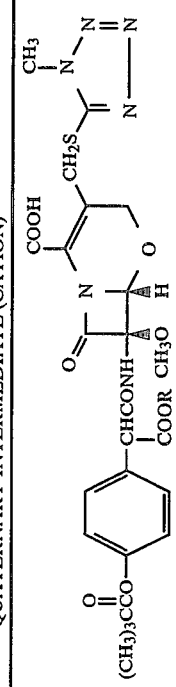 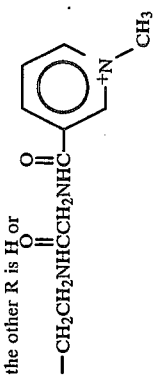 One R is —CH$_2$CH$_2$NHCCH$_2$NHC=O<br>the other R is H or<br>—CH$_2$CH$_2$NHCCH$_2$NHC=O | 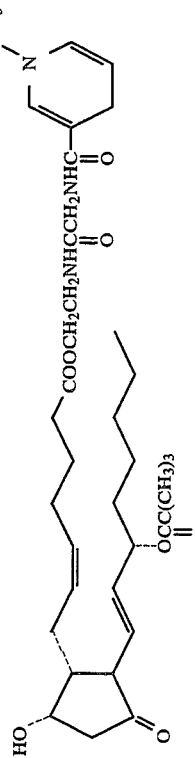 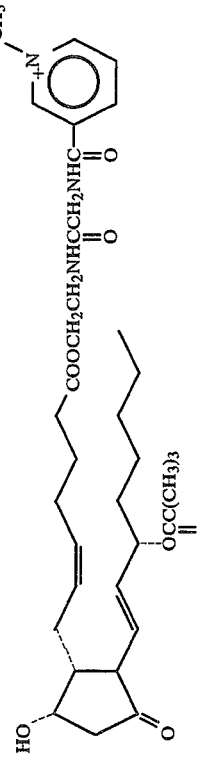 |
| 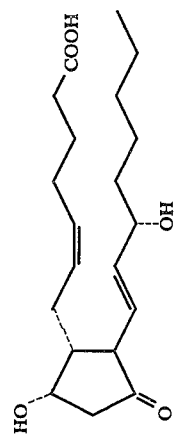 PGD$_2$ | | |

Method S

This is a variation of Method Q used when the drug contains one or more amino functions which are to be protected. Generally, the amino group is protected prior to any reaction of the carboxyl function; typically, a benzyloxycarbonyl group is introduced in conventional manner to protect the amino function and then the N-protected drug is reacted with the intermediate alcohol as is Methods Q and R. Removal of the protecting group, in conventional fashion, takes place when protection is no longer needed, generally before formation of the formula (II) quaternary and subsequent reduction to the compound of formula (I).

The representative drugs depicted below may be derivatized in this manner to the corresponding compounds of formulas (II) and (I).

| STARTING MATERIAL | QUATERNARY INTERMEDIATE (CATION) | DIHYDRO DERIVATIVE |
|---|---|---|
| 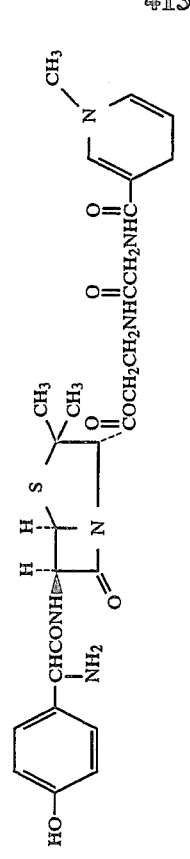 amoxicillin | 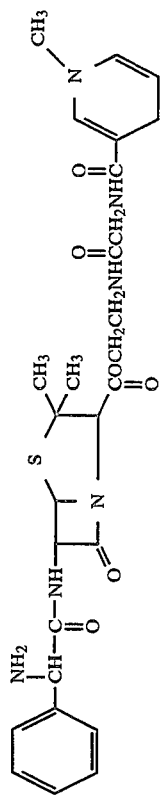 | 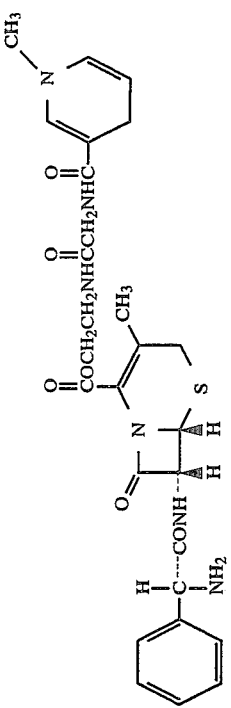 |
| 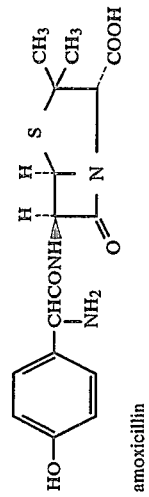 ampicillin | 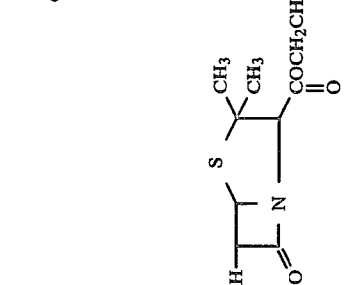 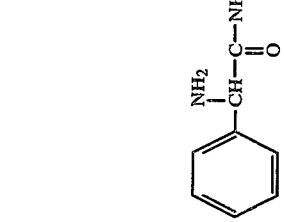 | |
| 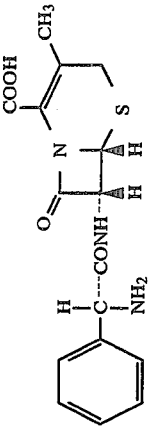 cephalexin | | |

| STARTING MATERIAL | QUATERNARY INTERMEDIATE (CATION) | DIHYDRO DERIVATIVE |
|---|---|---|
| 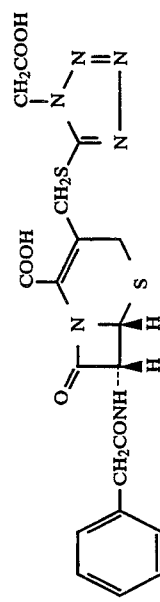 ceforanide | 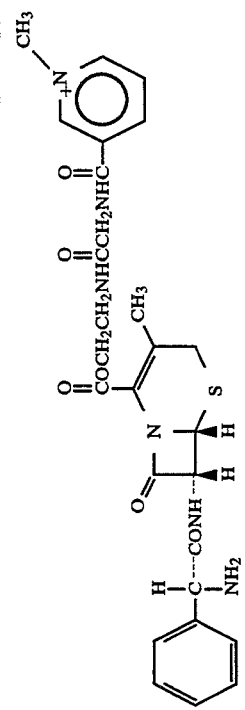 | 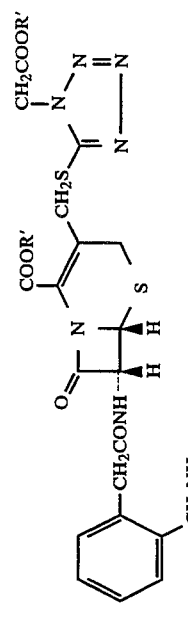 |
| | 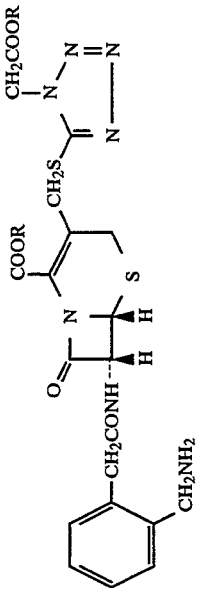 | 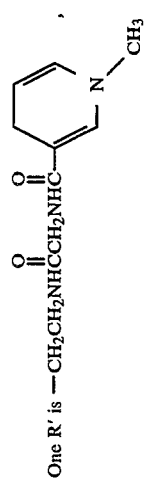 |
| | One R is —CH$_2$CH$_2$NHCCH$_2$NHC | One R' is —CH$_2$CH$_2$NHCCH$_2$NHC |

-continued
| STARTING MATERIAL | QUATERNARY INTERMEDIATE (CATION) | DIHYDRO DERIVATIVE |
|---|---|---|
| 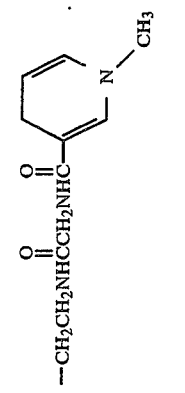 cefroxadine | 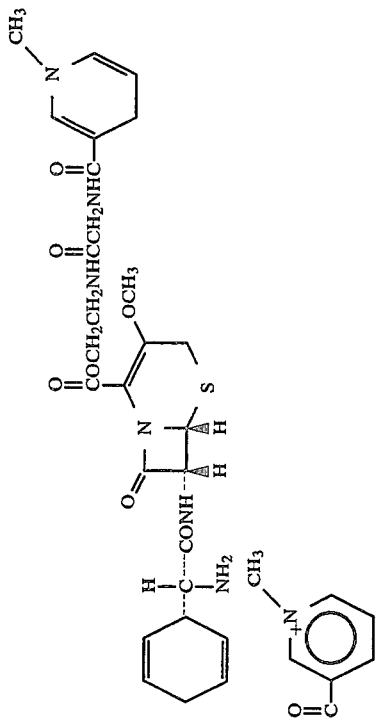 the other R is H or —CH$_2$CH$_2$NHCCH$_2$NHC— | the other R' is H or —CH$_2$CH$_2$NHCCH$_2$NHC— |
| 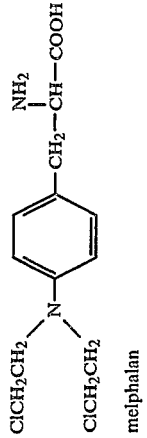 melphalan | 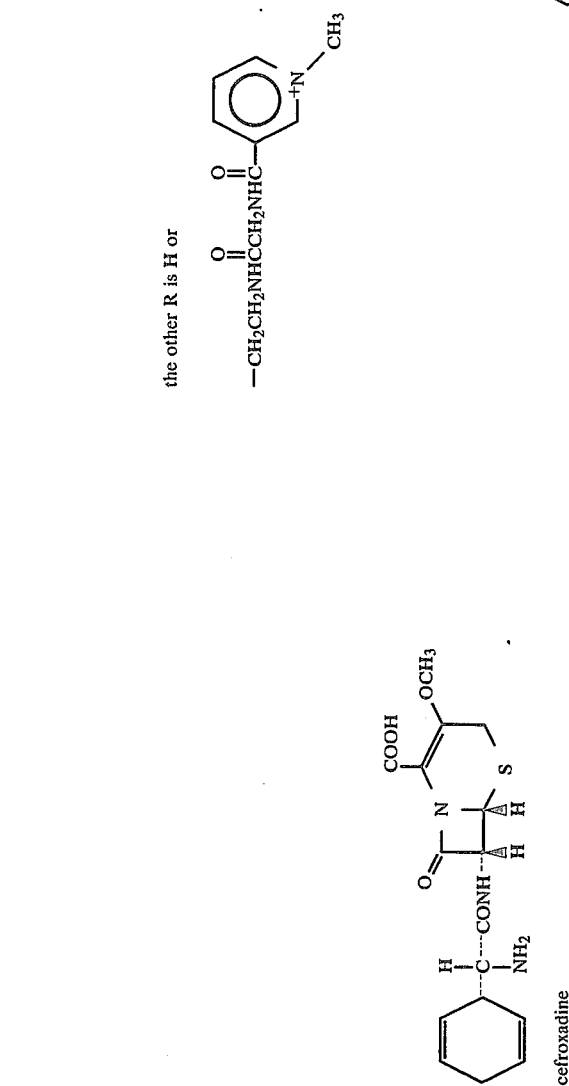 | 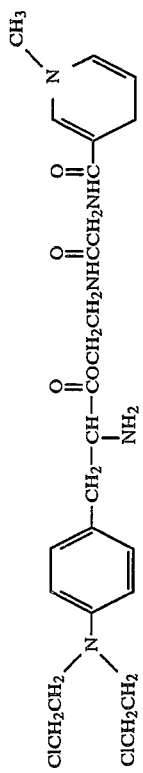 |

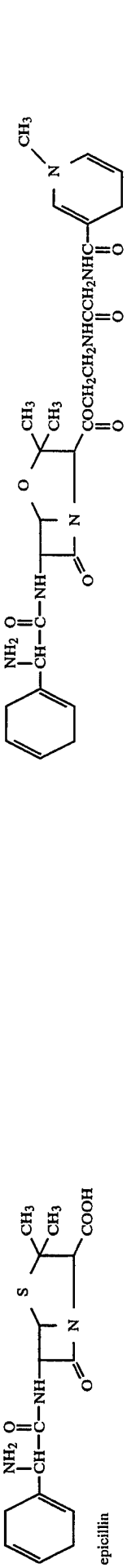

| STARTING MATERIAL | QUATERNARY INTERMEDIATE (CATION) | DIHYDRO DERIVATIVE |
|---|---|---|
| | 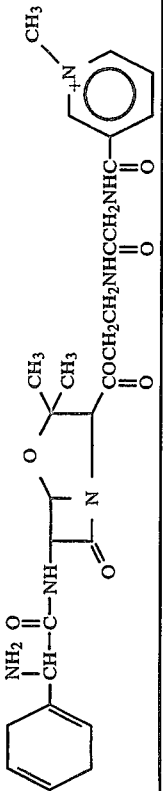 | |

Method T

This variation of Method Q can be used when the drug contains one or more NH$_2$ and OH functions which are to be protected. The protecting groups, for example, benzyloxycarbonyl for amino functions and pivalyloxy for hydroxyl functions, are introduced as described in Methods R and S, in the sequence considered most convenient. (Obviously, other protecting groups can be introduced instead.) The carboxyl function(s) are then derivatized according to Method Q. Typically, the hydroxy protecting group(s) are introduced first and are retained throughout the process, while the amino protecting group(s) are generally removed earlier, frequently prior to formation of the quaternary derivative of formula (II).

The representative drugs depicted below may be derivatized in this manner to the corresponding compounds of formulas (II) and (I).

| STARTING MATERIAL | QUATERNARY INTERMEDIATE (CATION) | DIHYDRO DERIVATIVE |
|---|---|---|
| 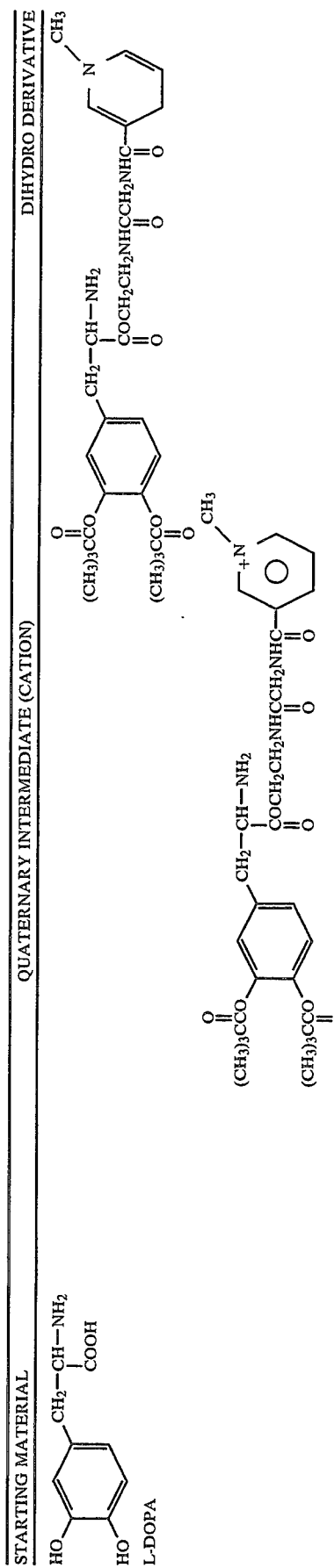 | 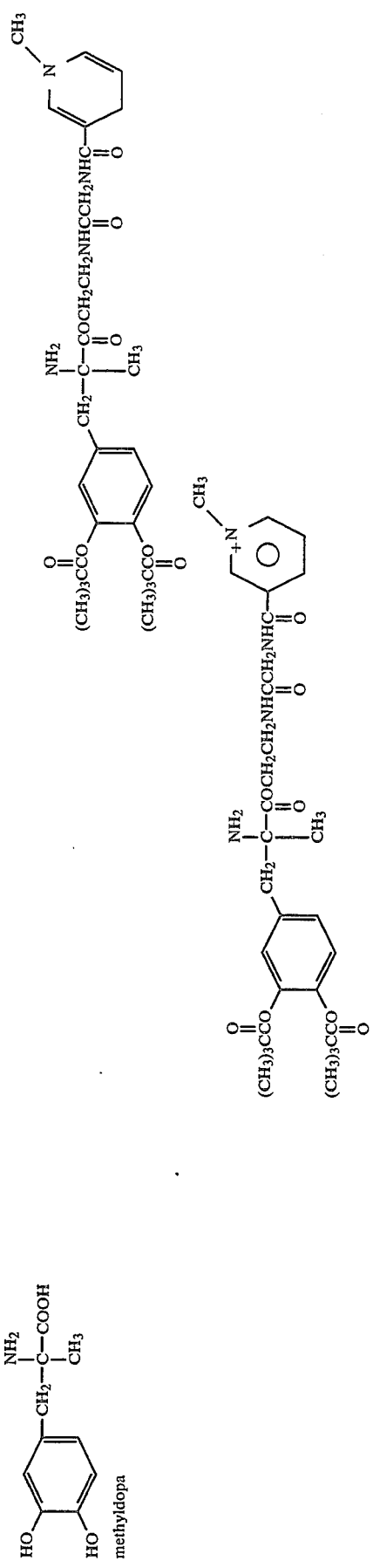 | 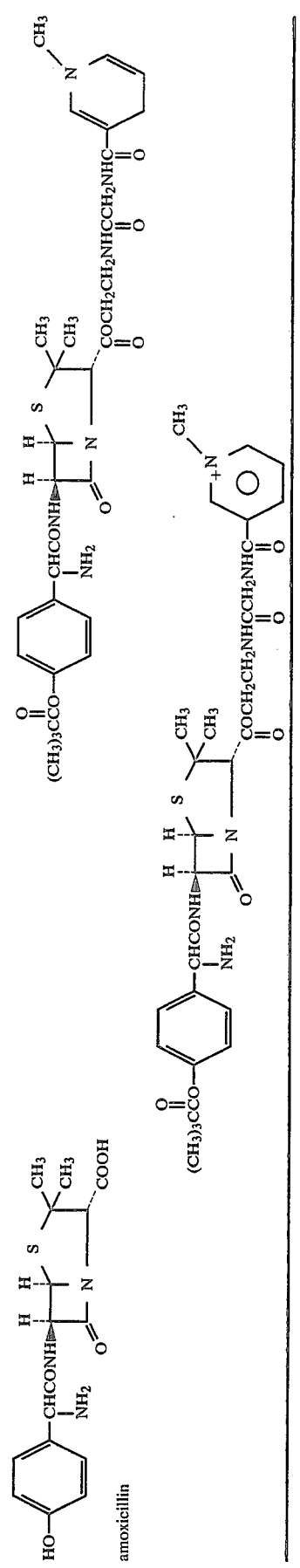 |

Method U

The drug is first reacted with ethylene glycol (or other dihydroxyalkanol having up to 8 carbon atoms), in the presence of a suitable coupling agent such as dicyclohexylcarbodiimide, to convert the —COOH function(s) to the corresponding

—COOCH$_2$CH$_2$OH (or

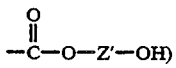
—C—O—Z'—OH)

group(s). Then, a N-protected amino acid, such as N-benzyloxycarbonylglycine, which has been prepared as described in Method A, is reacted therewith in the presence of dicyclohexylcarbodiimide or other appropriate coupling agent. Removal of the protecting group, e.g. by catalytic hydrogenation, affords a derivative of the drug in which the original —COOH group(s) has/have, in the case of utilizing ethylene glycol and glycine, been converted to the structure

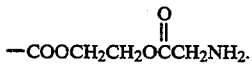
—COOCH$_2$CH$_2$OCCH$_2$NH$_2$.

That intermediate is then reacted with a compound of the formula

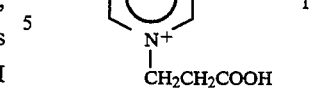

or the like, prepared as described in Method J, in the presence of a coupling agent such as dicyclohexylcarbodiimide, to give the desired quaternary derivative of formula (II). Subsequent reduction to the corresponding dihydro derivative of formula (I) proceeds as described in Method A.

The drugs depicted below may be derivatized in this manner to the corresponding compounds of formulas (II) and (I), as may the remaining drugs mentioned with Method Q.

The procedure described above may be repeated utilizing a reactant of the formula

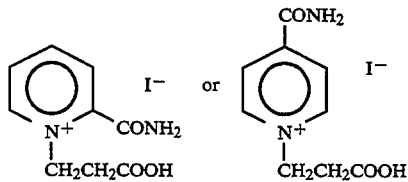

or the like, prepared as described in Method J, in place of the intermediate of the formula

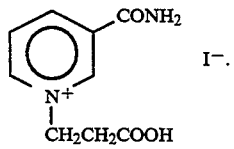

| STARTING MATERIAL | QUATERNARY INTERMEDIATE (CATION) | DIHYDRO DERIVATIVE |
|---|---|---|
| CH₂CH₂CH₂CHCOOH<br>    \|<br>    CH₃CH₂CH₂<br>valproic acid | [structure: valproic acid ester linked via -COOCH₂OCCH₂NHCCH₂- to pyridinium ring with CONH₂] | [structure: corresponding 1,4-dihydropyridine with CONH₂] |
| [structure: iodamide – triiodobenzene with COOH, CH₂NHCOCH₃, CH₃CONH substituents] | [structure: iodamide ester linked via -COOCH₂OCCH₂NHCCH₂- to pyridinium with CONH₂] | [structure: corresponding 1,4-dihydropyridine with CONH₂] |
| [structure: ibuprofen – (CH₃)₂CHCH₂-C₆H₄-CH(CH₃)COOH] | [structure: ibuprofen ester linked via -COOCH₂OCCH₂NHCCH₂- to pyridinium with CONH₂] | [structure: corresponding 1,4-dihydropyridine with CONH₂] |

| STARTING MATERIAL | QUATERNARY INTERMEDIATE (CATION) | DIHYDRO DERIVATIVE |
|---|---|---|
| chlorambucil | | |
| benzylpenicillin | | |
| cefoxitin | | |

| STARTING MATERIAL | QUATERNARY INTERMEDIATE (CATION) | DIHYDRO DERIVATIVE |
|---|---|---|
| 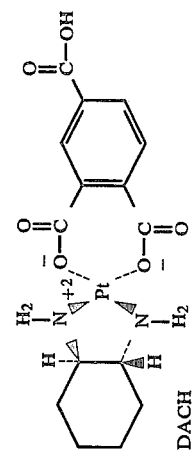 DACH | 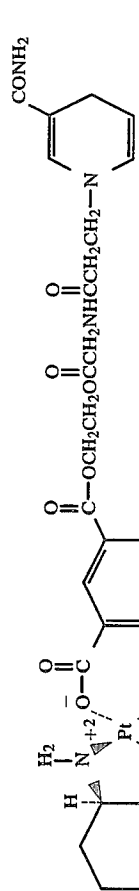  | 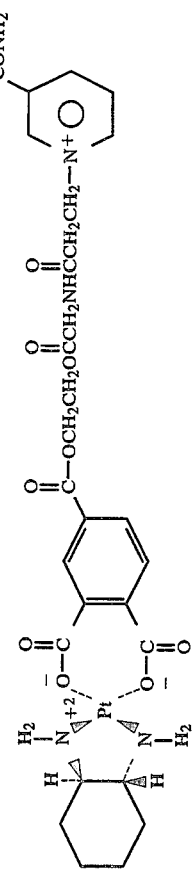 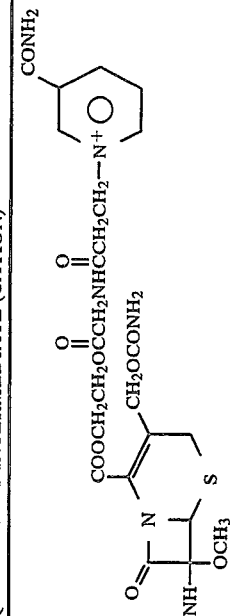 |

Method V

A drug containing one —COOH function is reacted with an equivalent amount of inositol, in the presence of dicyclohexylcarbodiimide or other suitable coupling agent, to convert the —COOH function to a group of the structure

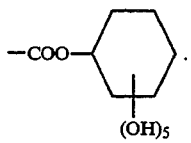

Reaction of that intermediate with nicotinuric acid, in the presence of a suitable coupling agent, or with an activated ester of nicotinuric acid, affords an intermediate in which the original —COOH has been converted to

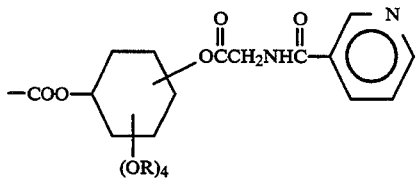

wherein each R is H or

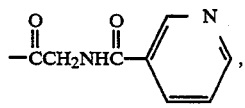

the number of original hydroxy groups esterified varying with the amount of nicotinuric acid employed. Subsequent quaternization and reduction are carried out as in Method A.

The drugs depicted below may be derivatized in this manner to the corresponding compounds of formulas (II) and (I), as may the remaining drugs mentioned with Method Q which contain a single —COOH function.

Alternatively, the above procedure may be repeated, replacing nicotinuric acid with an analogous starting material, prepared by reacting the selected amino acid with the acid chloride of nicotinic acid, of picolinic acid, or isonicotinic acid, of 3-quinolinecarboxylic acid, of 4-isoquinolinecarboxylic acid or the like.

Repetition of the procedure of the first paragraph of this method utilizing a greater amount of the drug (e.g. 2 to 5 or more moles per mole of inositol) provides an intermediate containing from 2 to 5 acid residues and from 4 to 1 hydroxyl groups. That intermediate is then reacted with nicotinuric acid to convert at least one hydroxyl group to the corresponding

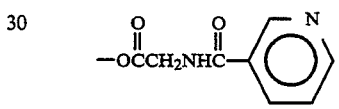

group. Subsequent formation of the quaternary and reduction proceed as in Method A.

| STARTING MATERIAL | QUATERNARY INTERMEDIATE (CATION) | DIHYDRO DERIVATIVE |
|---|---|---|
| CH₃CH₂CH₂CH₂CHCOOH<br>       \|<br>      CH₃CH₂CH₂<br>valproic acid | 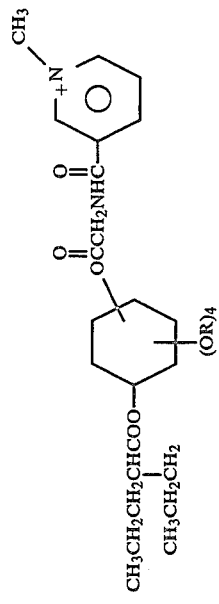 | 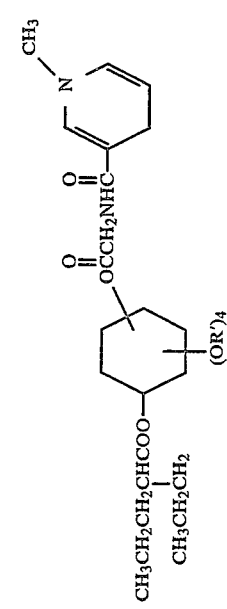 |
| | 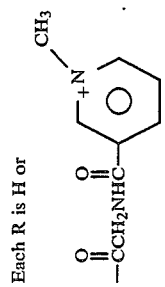  Each R is H or 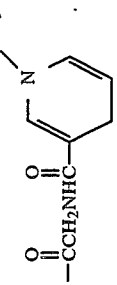 | Each R' is H or 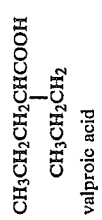 |
| 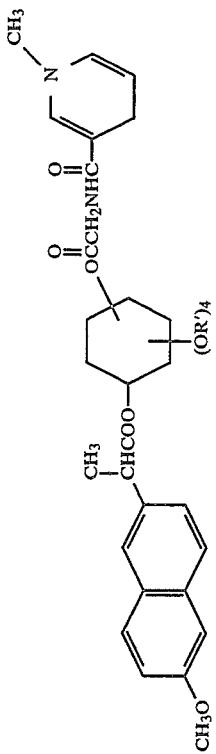 naproxen | | |

-continued
| STARTING MATERIAL | QUATERNARY INTERMEDIATE (CATION) | DIHYDRO DERIVATIVE |
|---|---|---|
| | 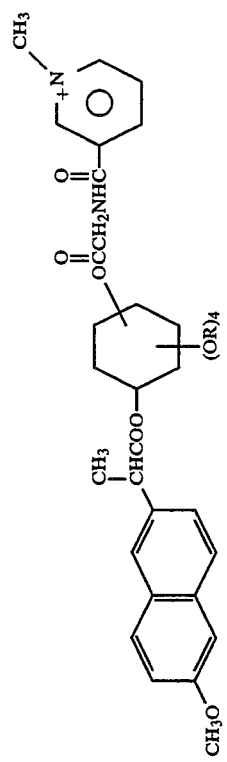 | 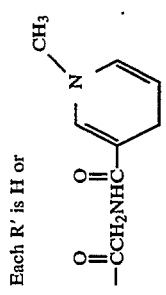
Each R' is H or
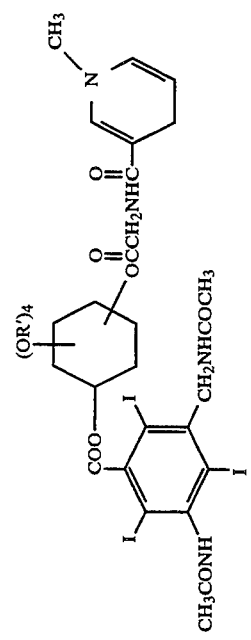 |
| | 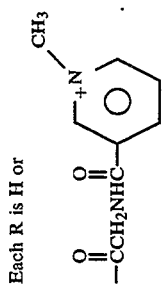
Each R is H or
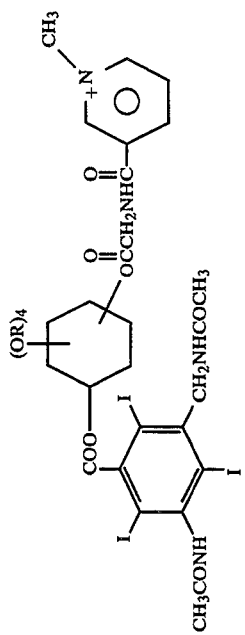 |
| 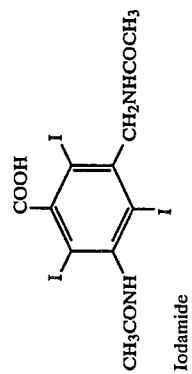
Iodamide | | |

-continued
| STARTING MATERIAL | QUATERNARY INTERMEDIATE (CATION) | DIHYDRO DERIVATIVE |
|---|---|---|
| 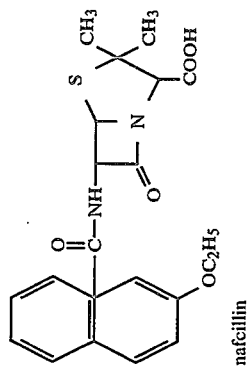<br>nafcillin | <br>Each R is H or<br>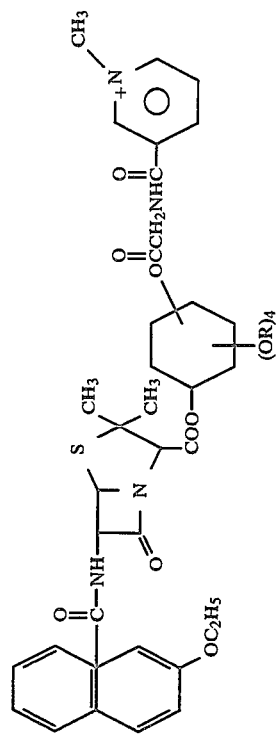 | 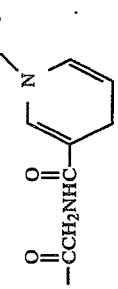<br>Each R' is H or<br>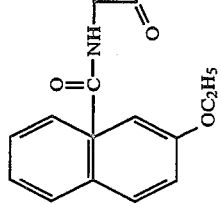<br>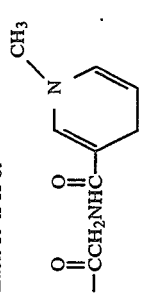<br>Each R' is H or |

| STARTING MATERIAL | QUATERNARY INTERMEDIATE (CATION) | DIHYDRO DERIVATIVE |
|---|---|---|
| | 445 | |
| | Each R is H or 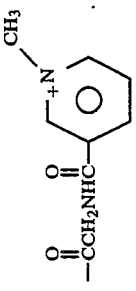 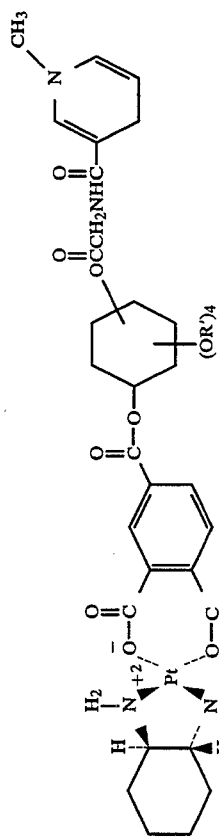 | Each R' is H or  |
| | 446 | |
| 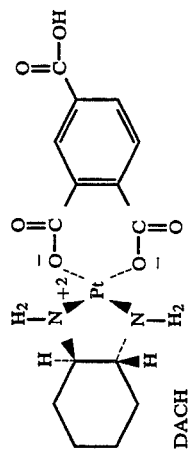 DACH | 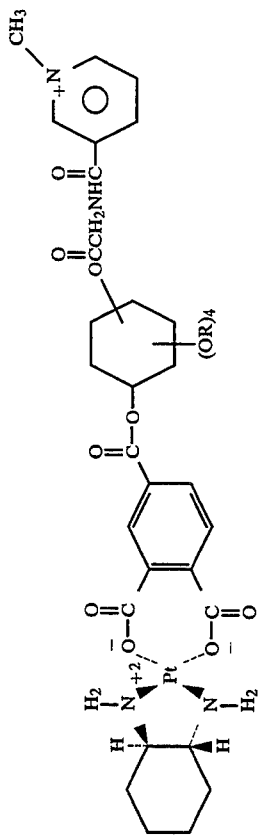 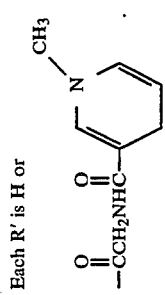 Each R is H or 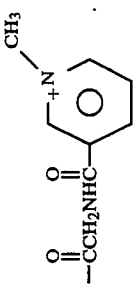 | |

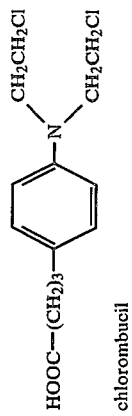
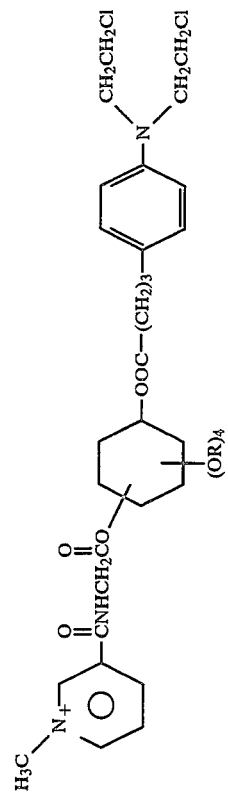
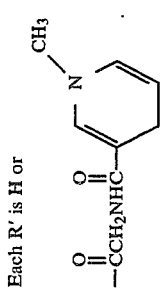
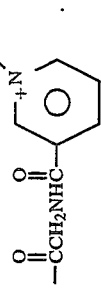

Method W

The drug is first reacted with 1,2-propylene glycol (or other dihydroxyalkanol having up to 8 carbon atoms), in the presence of a suitable coupling agent such as dicyclohexylcarbodiimide, to convert the —COOH function(s) to the corresponding

(or other

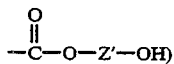

group(s). The resultant intermediate is then reacted with nicotinuric acid, in the presence of an appropriate coupling agent, or with an activated ester of nicotinuric acid, to give an intermediate of the partial formula

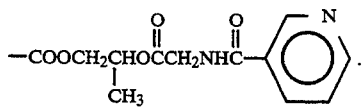

Subsequent quaternization and reduction are carried out as in Method A.

The drugs depicted below may be derivatized in this manner to the corresponding compounds of formulas (II) and (I), as may the remaining drugs mentioned with Method Q.

Alternatively, the above procedure may be repeated, replacing nicotinuric acid with an analogous starting material, prepared by reacting the selected amino acid with the acid chloride of nicotinic acid, of picolinic acid, of isonicotinic acid, of 3-quinolinecarboxylic acid, of 4-isoquinolinecarboxlic acid or the like.

| STARTING MATERIAL | QUATERNARY INTERMEDIATE (CATION) | DIHYDRO DERIVATIVE |
|---|---|---|
| chlorombucil | | |
| valproic acid | | |
| cefoxitin | | |

453 454
| STARTING MATERIAL | QUATERNARY INTERMEDIATE (CATION) | DIHYDRO DERIVATIVE |
|---|---|---|
| 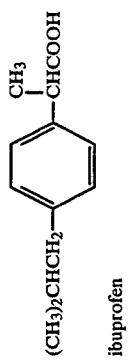 ibuprofen | 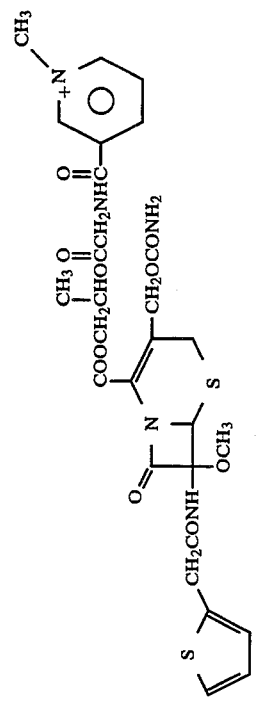 | 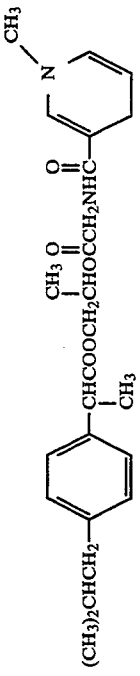 |
| 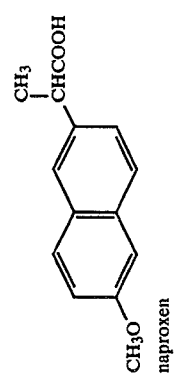 naproxen | 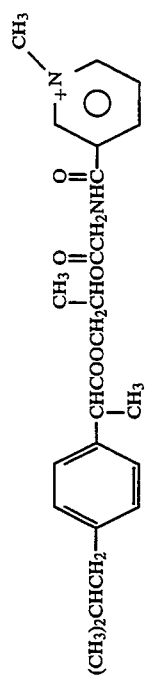 | |

| STARTING MATERIAL | QUATERNARY INTERMEDIATE (CATION) | DIHYDRO DERIVATIVE |
|---|---|---|
| iothalamic acid | | |

Method X

Glucosamine, of the structural formula

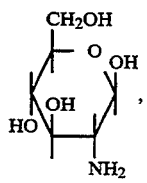, is reacted with nicotinuric acid, using equimolar amounts of the reactants, in the presence of a suitable coupling agent such as dicyclohexylcarbodiimide, or with an activated ester of nicotinuric acid. The resultant intermediate of the formula

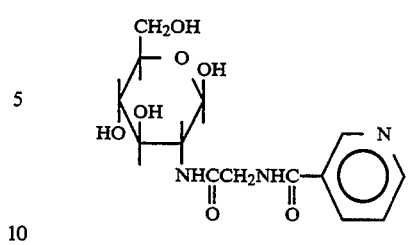

is then reacted with a drug containing one reactive —COOH function, in the presence of dicyclohexylcarbodiimide or other appropriate coupling agent, replacing one or more of the hydroxy groups with acid residue(s), the number of groups replaced varying with the relative amounts of reactants used.

The drugs depicted below may be derivatized in this manner to the corresponding compounds of formulas (II) and (I), as may the remaining drugs mentioned with Method Q which contain a single —COOH group.

Alternatively, the above procedure may be repeated, replacing nicotinuric acid with an analogous starting material, prepared by reacting the selected amino acid with the acid chloride of nicotinic acid, of picolinic acid, of isonicotinic acid, of 3-quinolinecarboxylic acid, of 4-isoquinolinecarboxylic acid or the like.

| STARTING MATERIAL | QUARTERNARY INTERMEDIATE (CATION) | DIHYDRO DERIVATIVE |
|---|---|---|
| $CH_3CH_2CH_2CHCOOH$<br>     \|<br>     $CH_3CH_2CH_2$<br><br>valproic acid | Each A is —OH or the valproic acid residue, $CH_3CH_2CH_2CHCOO—$,<br>                                                                \|<br>                                                                $CH_3CH_2CH_2$<br>provided that at least one A is the valproic acid residue. | |
| nafcillin | Each A is —OH or the nafcillin residue, provided that at least one A is the nafcillin residue. | |
| chlorombucil | Each A is —OH or chlorombucil residue, provided that at least one A is the chlorombucil residue. | |

-continued

| STARTING MATERIAL | QUARTERNARY INTERMEDIATE (CATION) | DIHYDRO DERIVATIVE |
|---|---|---|
| naproxen | Each A is —OH or the naproxen residue provided that at least one A is the naproxen residue. | |
| DACH | Each A is —OH or the DACH residue, provided that at least one A is the DACH residue. | |
| Iodomide | Each A is —OH or the Iodomide residue, provided that at least one A is the Iodomide residue. | |

Method Y

The procedure of Method W is repeated, using ethylene glycol in place of 1,2-propylene glycol.

The drugs depicted below may be derivatized in this manner to the corresponding compounds of formulas (II) and (I), as may the remaining drugs mentioned with Method Q.

Alternatively, nicotinuric acid may be replaced in this process with an analogous starting material, as described in the last paragraph of Method W.

| STARTING MATERIAL | QUARTERNARY INTERMEDIATE (CATION) | DIHYDRO DERIVATIVE |
|---|---|---|

(Page consists of chemical structure diagrams for cephalothin, valproic acid, and cefoxitin and their quaternary intermediate and dihydro derivative forms.)

| STARTING MATERIAL | QUARTERNARY INTERMEDIATE (CATION) | DIHYDRO DERIVATIVE |
|---|---|---|
| 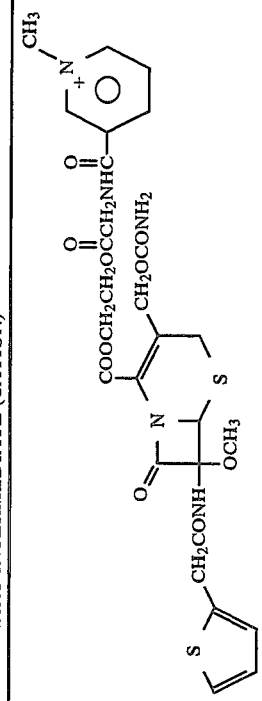 oxolinic acid | 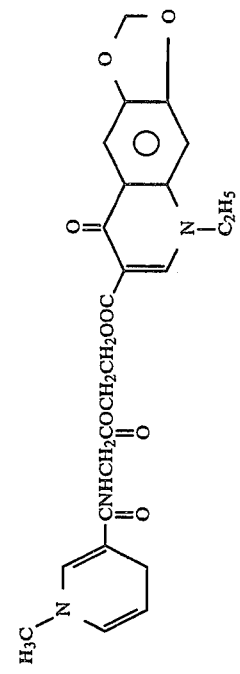 |  |
| 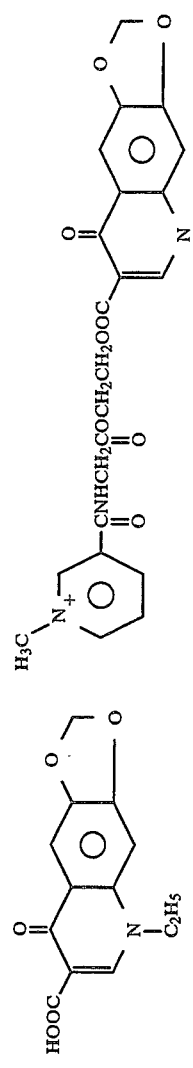 chlorombucil |  | 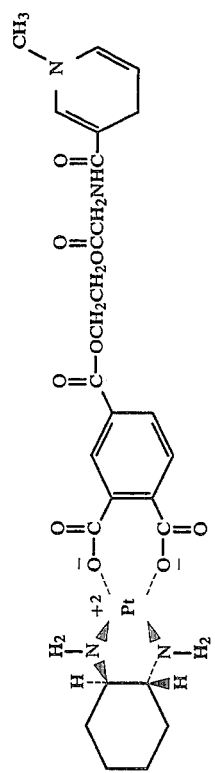 |
| DACH | | |

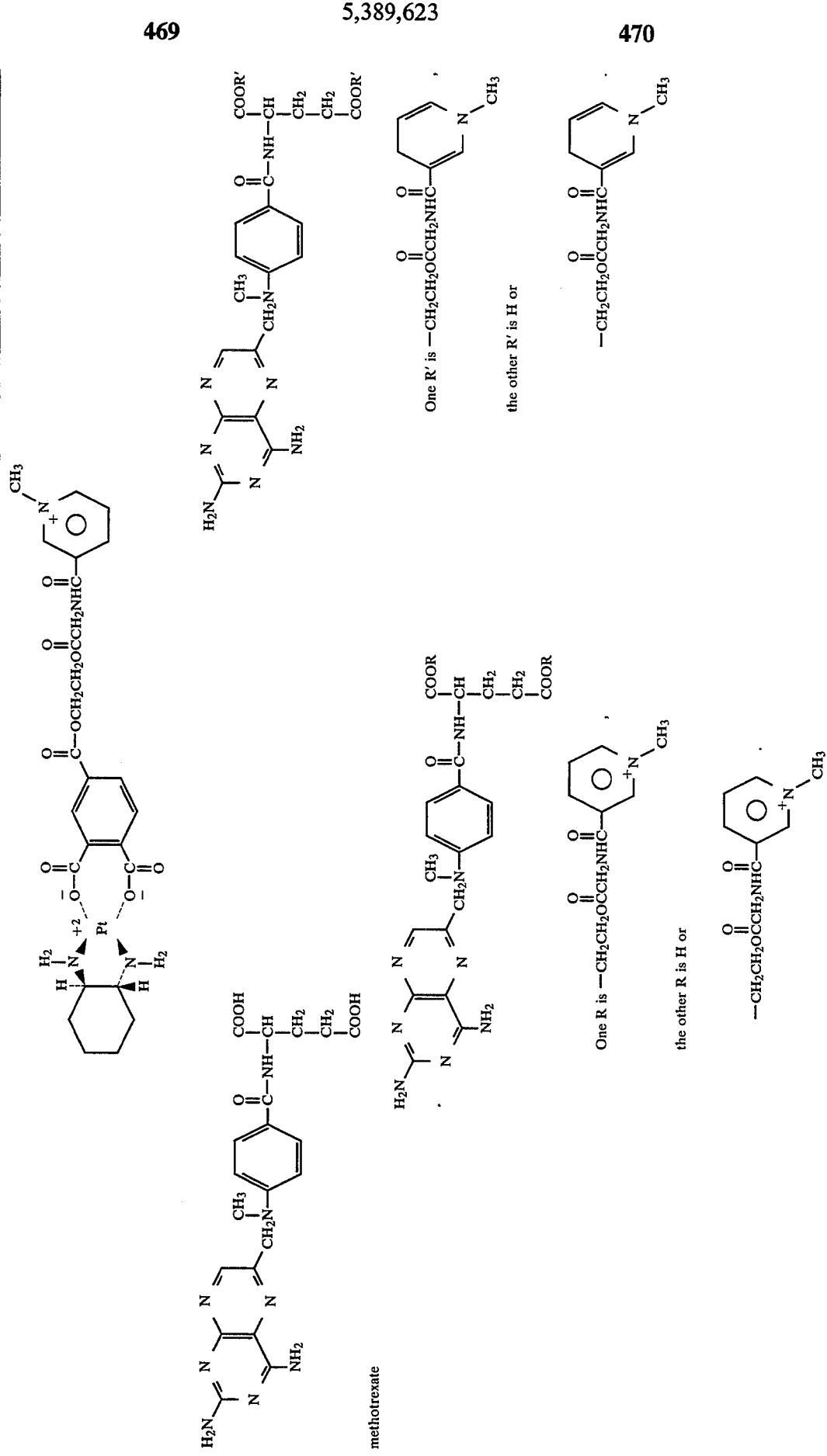

| STARTING MATERIAL | QUARTERNARY INTERMEDIATE (CATION) | DIHYDRO DERIVATIVE |
|---|---|---|
| 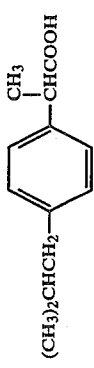 ibuprofen | 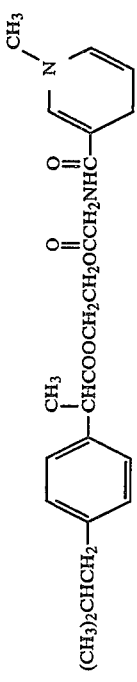 | 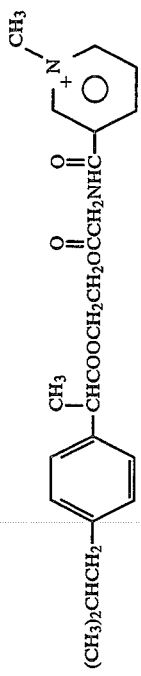 |
| 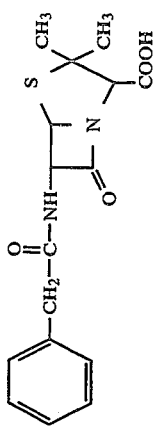 benzylpenicillin | 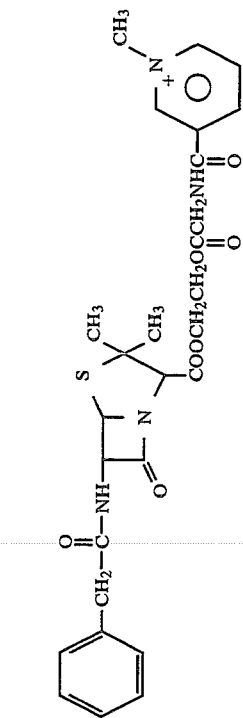 | |
| 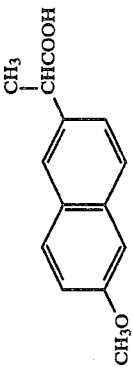 naproxen | | 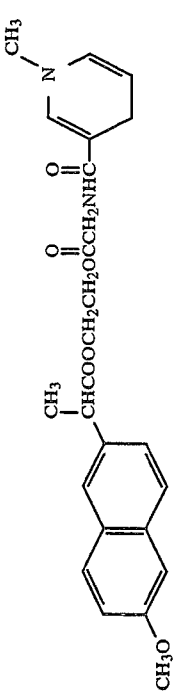 |

| STARTING MATERIAL | QUARTERNARY INTERMEDIATE (CATION) | DIHYDRO DERIVATIVE |
|---|---|---|
| 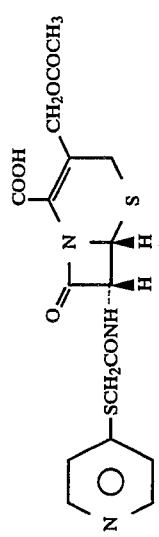
cephapirin | 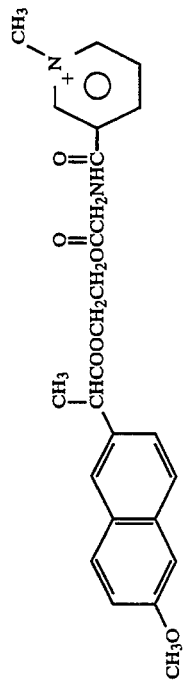 | 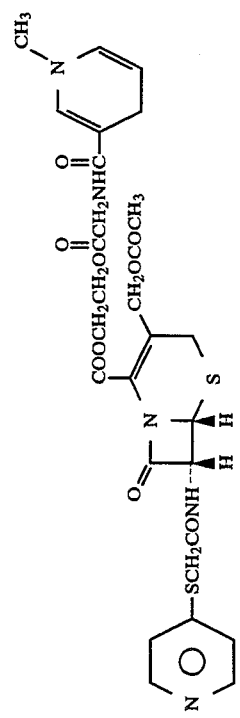 |
| 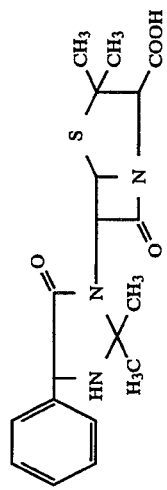
hetacillin | 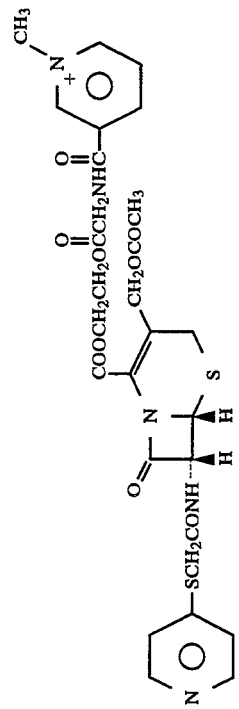 | 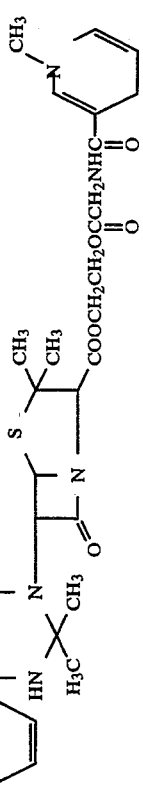 |

-continued
| STARTING MATERIAL | QUARTERNARY INTERMEDIATE (CATION) | DIHYDRO DERIVATIVE |
|---|---|---|
| 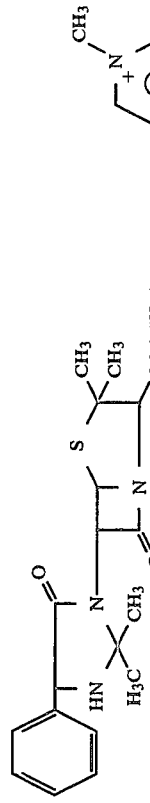 o-iodohippuric acid | 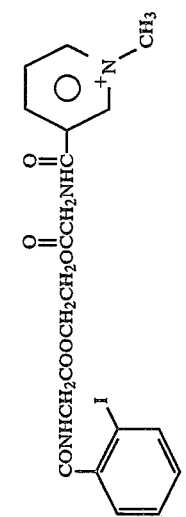 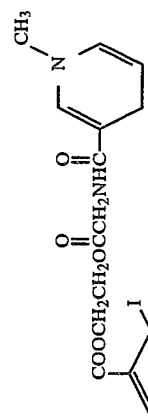 | 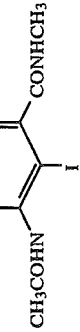 |
| 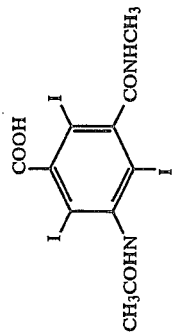 iothalamic acid | 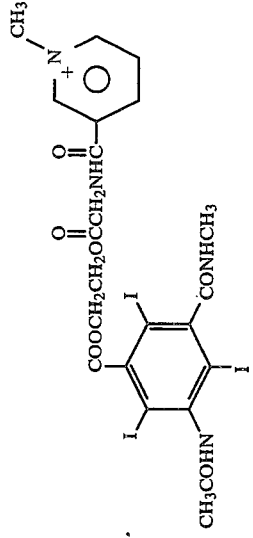 | |

Method Z

The process of the first paragraph of Method Q is repeated, using an aminoalkanol of the formula

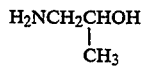

in place of 2-aminoethanol.

The drugs depicted below may be derivatized in this manner to the corresponding compounds of formulas (II) and (I), as may the remaining drugs mentioned with Method Q.

The process variation described in the second paragraph of Method Q may also be applied to Method Z.

| STARTING MATERIAL | QUARTERNARY INTERMEDIATE (CATION) | DIHYDRO DERIVATIVE |
|---|---|---|
| chlorambucil | | |
| valproic acid | | |
| cefoxitin | | |

| STARTING MATERIAL | QUARTERNARY INTERMEDIATE (CATION) | DIHYDRO DERIVATIVE |
|---|---|---|
| ibuprofen | | |
| naproxen | | |
| iothalamic acid | | |

IV. Methods for Salt Formation

An ether solution of a compound of formula (I) is treated with an equivalent amount of anhydrous p-toluenesulfonic acid dissolved in dry ether. Mixing at room temperature is continued until the imminium salt precipitates out of solution. The salt is then removed by filtration.

Imminium salts which may be prepared in this manner include those derived from the following representative compounds of formula (I):

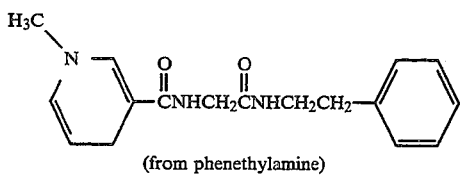
(from phenethylamine)

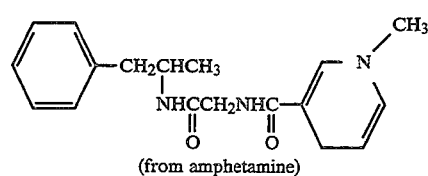
(from amphetamine)

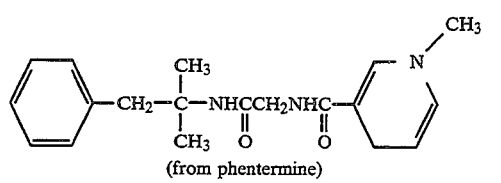
(from phentermine)

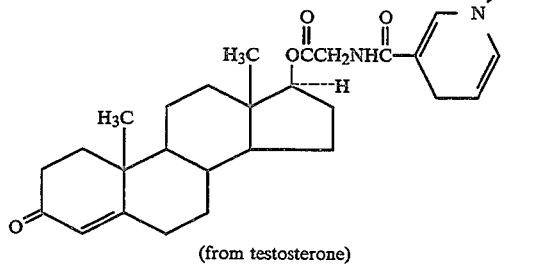
(from testosterone)

In order to further illustrate the present invention and the advantages thereof, the following specific examples are given, it being understood that same are intended only as illustrative and in nowise limitative.

In the examples immediately to follow, NMR spectra were determined by means of a Varian EM360A spectrometer. All chemical shifts reported are in δ units (parts per million) relative to tetramethylsilane.

EXAMPLE 1

Nicotinuric acid (413 mg, 2.29 mmol), having the structural formula

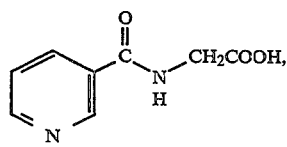

was combined with dicyclohexylcarbodiimide (519 mg, 10% excess) in dry pyridine (70 ml) and to that mixture was added a solution of L-DOPA 0-methyl ester hydrochloride (567 mg, 2.29 mmol), having the structural formula

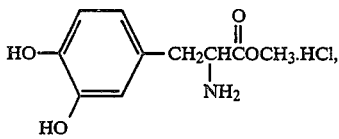

in dry pyridine (10 ml) at room temperature. The resultant reaction mixture was stirred at room temperature for 24 hours, then was cooled to 0° C. The dicyclohexylurea which precipitated was removed by filtration and washed with acetonitrile. The filtrate was evaporated to dryness in vacuo to leave a yellow oil, which was taken up in a minimum of acetonitrile. Undissolved dicyclohexylurea was removed by filtration. In this manner, 97% of the theoretical yield of dicyclohexylurea was removed. The product was dried by means of an oil pump for several hours to afford a pale orange hygroscopic foam. There was thus obtained, in nearly quantitative yield, N-(N'-nicotinoyl)glycyl L-DOPA 0-methyl ester, having the structural formula

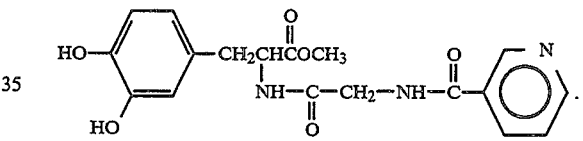

NMR(dmso d$_6$) 9.2(bs, 1H, pyridine H-2); 8.8(m, 1H, pyridine H-6); 8.4(m, 1H, pyridine H-4); 8.1(m, 1H, pyridine H-5); 7.5–7.8(m); 6.4–6.8(m, 3H, Ar); 5.2–6.8(-broad, NH, exchangeable); 4.5(m, 1H, ArCH$_2$CH); 3.9(d, 2H, CONHCH$_2$); 3.7(s, 3H, OCH$_3$); 2.7–2.9(m, ARCH$_2$). The product may also be named 3-(3,4-dihydroxy)phenyl-2-[N-(nicotinoyl)glycyl]aminopropanoic acid methyl ester.

EXAMPLE 2

The product of Example 1 (373 mg, 1 mmol) was suspended in chloroform (15 ml) and triethylamine (0.30 ml, 2.1 mmol) was added. Pivaloyl chloride (264 ml, 2.2 mmol) was added and the mixture was stirred at reflux overnight. Volatile substances were removed in vacuo, leaving a pale orange solid. The solid residue was taken up in chloroform (30 ml) and washed, first with aqueous sodium bicarbonate solution (15 ml, 0.5% NaHCO$_3$) and then with water (10 ml). The aqueous phase was twice re-extracted with chloroform, using 20 ml portions of solvent, and the combined organic layers were dried over anhydrous sodium sulfate. Evaporation to dryness left a dark orange oil which foamed on prolonged vacuum treatment. There were thus obtained 380 mg of 3-(3,4-dipivaloyloxy)phenyl-2-[N-(nicotinoyl)glycyl]aminopropanoic acid methyl ester, having the structural formula

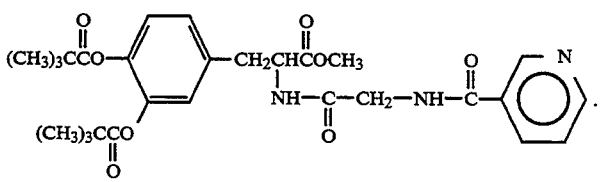

NMR(CDCl₃) 9.1(bs, 1H, pyridine H-2); 8.8(d, 1H, pyridine H-6); 8.0–8.3(dt, 1H, pyridine 4-H); 7.8(t, 2H, NH-exchangeable); 7.3(m, pyridine H-5); 6.95(bs, 3H, OCH₃); 3.2(m, 2H, ArCH₂); 1.3(s, ~18H); +impurity, extra t-butyl peaks.

EXAMPLE 3

The product of Example 2 (300 mg, ~0.55 mmol) in dry acetonitrile (10 ml) was treated with methyl iodide (180 ml, ~5-fold excess) at room temperature for 10 minutes. The mixture was then brought to the reflux temperature and maintained at that temperature for one hour, then allowed to stand at room temperature for two days. Evaporation to dryness gave an orange, hygroscopic solid/foam. The resultant quaternary salt has the formula

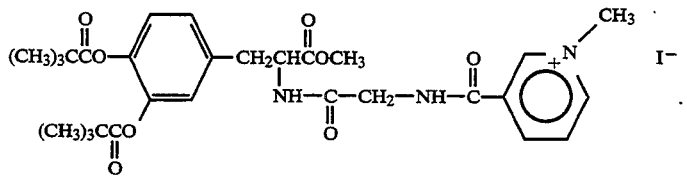

NMR(CD₃CN) 9.6(bs, 1H, pyridinium H-2); 8.7–9.1(m, 2H, pyridinium H-4, H-6); 8.2–8.6(m, ~1H, NH-exchangeable), 7.1–7.3(bs, 3H, Ar); 4.6–4.9(m, 1H, ArCH₂CH); 4.5(s, 3H, +NCH₃); 4.1(d, 2H, NCH₂CO.NH); 3.1–3.3(d, distorted, 2H, ArCH₂); 1.35(s, 18H) +impurity, t-butyl.

EXAMPLE 4

The product of Example 3 (250 mg, 0.365 mmol) in cold deareated (N₂) water (50 ml) was treated with sodium bicarbonate (123 mg, 4 equivalents) and sodium dithionite (196 mg, 3 equivalents). Ether (50 ml) was added and the reaction mixture was stirred under nitrogen at 0° C. for 45 minutes. A portion of the ether layer was removed after 2 minutes and the ultraviolent absorption spectra was examined. Absorption due to the dihydropyridine moiety was visible at 356 nm. Further aliquots were removed every 10 minutes and similarly examined. When there was no longer any change in the ratio of quaternary to dihydro absorption, the reaction mixture was separated into aqueous and organic layers. The aqueous layer was extracted three times with 20 ml portions of ethyl ether and the combined organic layers were washed with cold water (20 ml), dried over anhydrous sodium sulfate and evaporated to dryness. The residual yellow-orange oil was taken up in chloroform (15 ml) and filtered through a plug of neutral alumina. Evaporation to dryness gave a yellow-orange oil/foam which was slowly oxidized by methanolic silver nitrate solution. The product has the formula

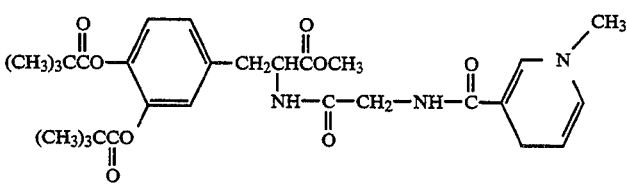

NMR(CDCl₃) 6.8–7.1(m, 4H, Ar and pyridine H-2); 5.9–6.2(m, pyridine H-6); 5.6(d, 1H, pyridine H-5); 4.5–4.9(m, 2H, ArCH₂CH and NH); 3.95(t, 2H, glycine CH₂); 3.7(s, 3H, OCH₃); 3.0–3.3(m, 4H, ArCH₂ and pyridine C-4 H₂); 2.9(s, 3H, NCH₃); 1.3(s, 18H)+ᵗBu impurity.

The present invention can thus be seen to provide two major classes of novel chemical compounds, i.e. the compounds of general formula (I) above, including their salts, and the compounds of general formula (II) above, wherein D is the residue of a centrally acting drug containing at least one reactive functional group selected from the group consisting of amino, hydroxyl, mercapto, carboxyl, amide and imide and the other structural variables are as defined broadly above. Within each of these major classes, the following subclasses are particularly noteworthy:

(A) Compounds of formulas (I) and (II) wherein the D portion of the compound of formula (I) or (II) is identical to the corresponding portion of the centrally acting drug from which D can be considered to be derived, and the carrier is attached through an amino functional group in the drug. Preferred groups of compounds in this subclass include the following:

(1) Cerebral stimulants, including sympathomimetic amine-type cerebral stimulants, such as amphetamine, dextroamphetaine, levamphetamine, aletamine, cypenamine, tyramine, phentermine, methamphetamine, fencamfamin, zylofuramine, phenethylamine, etryptamine and tranylcypromine; tricyclic antidepressant-type cerebral stimulants, expecially dibenzazepines and their analogues, e.g. desipramine, nortriptyline, protriptyline, maprotiline, octriptyline, and many other cerebral stimulants, alerting agents and antidepressants of various types, as exemplified by amiphenazole, amedalin, cartazolate, daledalin, fluoxetine, nisoxetine, bupropion, difluamine and methylphenidate.

(2) Neurotransmitters, such as dopamine, histamine, tryptamine and serotonin.

(3) Narcotic analgesics, such as anileridine, noracymethadol and piminodine.

(4) Hypotensives, such as clonidine, hydralazine, bethanidine, guanethidine, debrisoquin, propranolol and prizidilol.

(5) Sympathomimetic amines, such as ephedrine, oxymetazoline and pseudoephedrine.

(6) Anticancer and antitumor agents, such as doxorubicin and daunomycin.

(7) Antiviral agents, such as amantadine, 2-guanidino-4,5-di-n-propyloxazole, 2-guanidino-4,5-diphenyloxazole, glucosamine and 6-amino-6-deoxy-D-glucose (8) Antibiotic and antibacterial agents, such as phenazopyridine, bacampicillin and pivampicillin.

(9) Sedatives, muscle relaxants, anticonvulsants, tranquilizers (including benzodiazepine tranquilizers) e.g. benzoctamine, tracazolate, chlordiazepoxide, tiletamine and aminoglutethimide.

(10) Diagnostics, including radiolabeled diagnostics, e.g. iodometaraminol.

(B) Compounds of formulas (I) and (II) wherein the drug from which D can be considered to be derived contains an amino function through which the carrier is attached and also contains at least one —OH functional group, and D in formula (I) or (II) contains, in place of the hydrogen atom of at least one of the —OH groups in the drug, at least one hydrolytically or metabolically cleavable hydroxyl protective group. Within subclass (B), preferred compounds are those in which D is a protected residue of a neurotransmitter, such as dopamine or serotonin; a cerebral stimulant, such as tyramine; a sympathomimetic amine, such as ephedrine, phenylephrine or pseudoephedrine; a CNS prostaglandin, such as PGD$_2$; an adrenergic agent, such as norepinephrine or epinephrine; an anticancer or antitumor agent, such as pentostatin; an antiviral such as glucosamine or 6-amino-6-deoxy-D-glucose; or a hypotensive, such as atenolol or metoprolol.

(C) Compounds of formulas (I) and ( II) wherein the drug from which D can be considered to be derived contains an amino function through which the carrier is attached and also contains at least one —COOH functional group, and D in formula (I) or (II) contains, in place of the hydrogen atom of at least one of the —COOH groups, at least one hydrolytically or metabolically cleavable carboxyl protective group. Preferred compounds within this subclass are those in which D is a protected residue of anticancer and antitumor agents, e.g. melphalan, DON, L-alanosine and acivicin; antibiotics, especially penicillins such as amoxacillin and ampicillin and cephalosporins such as cephalexin, cefroxadine and ceforanide; hypotensives such as methyldopa and furosemide; and dopaminergic agents such as L-DOPA.

(D) Compounds of formulas (I) and (II) wherein the drug from which D can be considered to be derived contains an amino function through which the carrier is attached and also contains at least one —OH functional group and at least one —COOH functional group, and D in formula (I) or (II) contains, in place of the hydrogen atom of at least one of the —OH functional groups and at least one of the —COOH functional groups in said drug, respectively, at least one hydrolytically or metabolically cleavable hydroxyl protective group and at least one hydrolytically or metabolically cleavable carboxyl protective group. Of particular interest are the compounds in which D is a protected residue of a hypotensive, e.g. methyldopa; or a sympathetic stimulant-/dopaminergic agent e.g. levodopa.

(E) Compounds of formulas (I) and (II) wherein the D portion of the compound of formula (I) or (II) is identical to the corresponding portion of the drug from which D can be considered to be derived and the carrier is attached through a hydroxyl or mercapto functional group in the drug. Preferred groups of compounds in this subclass include the following:

(1) Tranquilizers, including benzodiazepines, such as oxazepam, temazeam and lorazepam; phenothiazines, such as carphenazine, fluphenazine, acetophenazine and the like; and other tranquilizers such as halopertdol, clopenthixol and hydroxyzine.

(2) Steroids, including androgens, e.g. testosterone; progestins, e.g. norgestrel and norethynodrel; estrogens, e.g. natural estrogens such as estradiol and semi-synthetic estrogens such as mestranol; and antiinflammatory steroids such as cortisone, hydrocortisone, triamcinolone and the like.

(3) Narcotic analgesics, such as codeine, pentazocine and morphine.

(4) Narcotic antagonists and mixed agonists/antagonists, e.g. nalorphine, naloxone, buprenorphine, nalbuphine and butorphanol.

(5) Cerebral stimulants, including tricyclic anti depressants such as opipramol and centrally active hydroxylated metabolites of tricyclic antidepressants, e.g. 2-hydroxyimipramine.

(6) Anticancer and antitumor agents, e.g. mitoxantrone, etoposide, hydroxyurea and Ara-AC.

(7) Antivitals, e.g. ribavarin and acyclovir.

(8) Non-steroidal antiinflammatory agents, e.g. clonixeril and naproxol.

(9) Hypotensives, e.g. prizidilol and nadolol.

(10) Diagnostics, e.g. iopydol.

(F) Compounds of formulas (I) and (II) wherein the drug from which D can be considered to be derived contains a hydroxyl or mercapto function through which the carrier is attached and also contains at least one amino functional group, and D in formula (I) or (II) contains, in place of a hydrogen atom of at least one of the amino groups in the drug, at least one amino protective group. Of particular interest are derivatives of neurotransmitters, stimulants, sympathetic amines, anticancer or antitumor agents, adrenergic agents and antiviral agents. The stimulants include centrally active metabolites of tricyclic antidepressants (e.g. 2-hydroxydesipramine).

(G) Compounds of formulas (I) and (II) wherein the drug from which D can be considered to be derived contains a hydroxyl or mercapto function through which the carrier is attached and also contains at least one carboxyl group, and D in formula (I) or (II) contains, in place of the hydrogen atom of at least one of the carboxyl groups in the drug, at least one hydrolytically or metabolically cleavable carboxyl protective group. Of particular interest here are the derivatives of valproic acid metabolite anticonvulsants and CNS prostaglandins.

(H) Compounds of formulas (I) and (II) wherein the drug from which D can be considered to be derived contains an amide or imide or low pKa primary or secondary amine function through which the carrier is attached and the D portion of the compound of formula (I) or (II) is identical to the corresponding portion of the drug from which D can be considered to be derived. Especially significant members of this group are the hydantoin anticonvulsants, e.g. phenytoin, ethotoin and mephenytoin, as well as other anticonvulsants, e.g. phenobarbital, aminoglutethimide, progabide and valpromide; tranquilizers, e.g. benzodiazepine-type tranquilizers such as bromazepam and oxazepam, and centrally active N-desmethyl metabolites of N-methylated benzodiazepine tranquilizers; hypnotics; nonsteroidal antiinflammatory agents; anticancer agents such as cyclophosphamide; antidepressants, such as sulpiride; antibiotics, especially tetracyc-lines; and antivirals, such as trifluridine.

(I) Compounds of formulas (I) and (II) wherein the drug from which D can be considered to be derived contains an amide or imide or low pKa primary or secondary amine function through which the carrier is attached and the drug also contains at least one hydroxyl group, D in formula (I) or (II) containing, in place of the hydrogen atom of at least one hydroxyl group in the drug, at least one hydrolytically or metabolically cleavable hydroxyl protective group. Significant members of this group include antivitals such as trifluridine and benzodiazepine tranquilizers such as oxazepam.

(J) Compounds of formulas (I) and (II) wherein the drug from which D can be considered to be derived contains an amide or imide or low pKa primary or secondary amine function through which the carrier is attached and the drug also contains at least one carboxyl functional group, D in formula (I) or (II) containing, in place of the hydrogen atom of at least one —COOH in the drug, at least one hydrolytically or metabolically cleavable carboxyl protective group. Especially significant members of this group include anticancer and antitumor agents, antibiotics (particularly penicillins and cephalosporins) and CNS anticholinergics.

(K) Compounds of formulas (I) and (II) wherein the drug from which D can be considered to be derived contains a —COOH function through which the carrier is attached, and the D portion of the compound of formula (I) or (II) is identical to the corresponding portion of the drug from which D can be considered to be derived. Especially significant members of this group include nonsteroidal antiinflammatory agents such as naproxen, ibuprofen and the like; diagnostics, including radiolabeled ones such as o-iodohippuric acid and iothalamic acid, as well as the corresponding "cold" compounds; CNS prostaglandins, such as $PGD_2$; antibiotics, especially cephalosporins and penicillins; anticonvulsants,. e.g. valproic acid and SL 75102; anticancer and antitumor agents, e.g. chlorambucil, DACH, and methotrexate.

(L) Compounds of formulas (I) and (II) wherein the drug from which D can be considered to be derived contains a —COOH function through which the carrier is attached and the drug also contains at least one hydroxyl function, D in formula (I) or (II) containing, in place of the hydrogen atom of at least one —OH in the drug, at least one hydrolytically or metabolically cleavable hydroxyl protective group. Within this class, derivatives of valproic acid metabolite-type anticonvulsants and NSAID's are especially noteworthy.

(M) Compounds of formulas (I) and (II) wherein the drug from which D can be considered to be derived contains a —COOH function through which the carrier is attached and the drug also contains at least one amino function, D in formula (I) or (II) containing, in place of a hydrogen atom of at least one of the amino functions in the drug, at least one amino protective group. Significant members of this group include penicillins antibiotics, cephalosporin antibiotics and anticancer and antitumor agents.

(N) Compounds of formulas (I) and (II) wherein the drug from which D can be considered to be derived contains a —COOH function through which the carrier is attached and the drug also contains at least one amino function and at least one hydroxyl function, D in formula (I) or (II) containing, in place of a hydrogen atom of at least one amino function and in place of the hydrogen atom of at least one hydroxyl function, respectively, at least one amino protective group and at least one hydrolytically or metabollically cleavable hydroxyl protective group. Particularly significant members of this class include dopaminergic agents, hypotensive agents and antibiotics.

While the invention has been described in terms of various preferred embodiments, the skilled artisan will appreciate that various modifications, substitutions, omissions and changes may be made without departing from the spirit thereof. Accordingly, it is intended that the scope of the present invention be limited solely by the scope of the following claims.

What is claimed is:

1. A compound of the formula $$D+DHC)_n \qquad (I)$$

or a nontoxic pharmaceutically acceptable salt thereof, wherein D is the residue of a centrally acting drug having at least one reactive hydroxyl functional group, said drug being a steroid sex hormone or antiinflammatory steroid, said residue being characterized by the absence of a hydrogen atom from at least one reactive hydroxyl functional group in said drug; n is a positive integer equal to the number of said functional groups from which a hydrogen atom is absent; and (DHC) is a radical of the formula

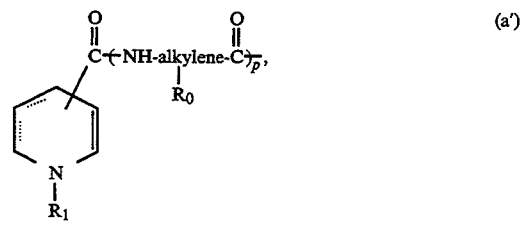

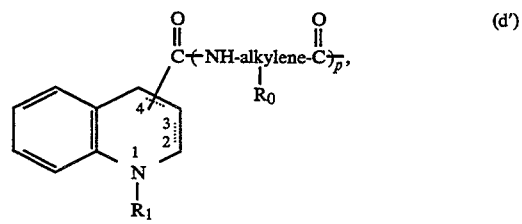

or

-continued

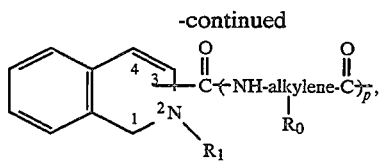 (g')

wherein the alkylene group can be straight or branched and can contain 1 to 3 carbon atoms; $R_0$ is hydrogen, methyl,

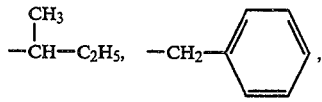

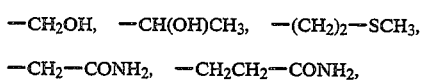

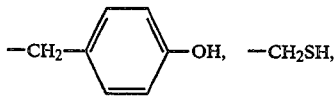

—CH$_2$COOH or —CH$_2$CH$_2$COOH; p is 1 or 2, provided that, when p is 2, then the alkylene groups can be the same or different and the $R_0$ radicals can be the same or different; the dotted line in formula (a') indicates the presence of a double bond in either the 4 or 5 position of the dihydropyridine ring; the dotted line in formula (d') indicates the presence of a double bond in either the 2 or 3 position of the dihydroquinoline ring; $R_1$ is $C_1$–$C_7$ alkyl, $C_1$–$C_7$ haloalkyl or $C_7$–$C_{10}$ aralkyl; the carbonyl-containing grouping in formula (a') can be attached at the 2, 3 or 4 position of the dihydropyridine ring; the carbonyl-containing grouping in formula (d') can be attached at the 2, 3 or 4 position of the dihydroquinoline ring; and the carbonyl-containing grouping in formula (g') can be attached at the 1, 3 or 4 position of the dihydroisoquinoline ring.

2. A compound according to claim 1, wherein (DHC) comprises the reduced form of an N-substituted nicotinic acid derivative.

3. A compound according to claim 1, wherein (DHC) comprises the reduced form of a trigonelline.

4. A compound according to claim 1, wherein n is 1.

5. A compound according to claim 1, wherein $R_o$ is hydrogen.

6. A compound according to claim 1, wherein p is 1.

7. A compound according to claim 1, wherein the steroid is hydrocortisone, betamethasone, dexamethasone, cortisone, flumethasone, fluprednisolone, meprednisone, methylprednisolone, prednisolone, prednisone, triamcinolone, cortodoxone, fludrocortisone, flurandrenolide, paramethasone, testosterone, methyltestosterone, ethinyl estradiol, norgestrel, mestranol, norethindrone, ethisterone, estradiol, estriol, estrone, dimethisterone, allylestrenol, cingestol, ethynerone, lynestrenol, norethynodrel, norgesterone, norvinisterone, ethynodiol, oxogestone, tigestol or quinestrol.

8. A compound according to claim 7, wherein the steroid is dexamethasone.

9. A compound according to claim 1, wherein the alkylene group has 1 carbon atom.

10. A compound according to claim 1, wherein $R_0$ is hydrogen, methyl,

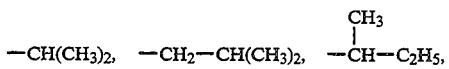

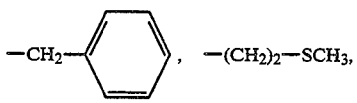

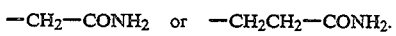

11. The compound according to claim 1, which has the formula:

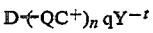

12. A compound according to claim 1, wherein $R_1$ is $CH_3$.

13. A compound according to claim 1, wherein (DHC) has formula (a') wherein the carbonyl-containing grouping is attached at the 3-position of the dihydropyridine ring, or wherein (DHC) has formula (d') wherein the carbonyl-containing grouping is attached at the 3-position of the dihydroquinoline ring, or wherein (DHC) has formula (g') wherein the carbonyl-containing grouping is attached at the 4-position of the dihydroisoquinoline ring.

14. A pharmaceutical composition, in unit dosage form, said composition comprising:
(i) an amount of a compound as claimed in claim 1, or a nontoxic pharmaceutically acceptable salt thereof, sufficient to release a pharmacologically effective amount of a steroid sex hormone or antiinflammatory steroid to the brain; and
(ii) a nontoxic pharmaceutically acceptable carrier therefor.

15. A pharmaceutical composition as claimed in claim 14, said composition being a pharmaceutically acceptable sustained release composition.

16. A quaternary salt of the formula $$D\text{-}(QC^+)_n \, qY^{-\prime} \qquad (II)$$

wherein D is the residue of a centrally acting drug having at least one reactive hydroxyl functional group, said drug being a steroid sex hormone or antiinflammatory steroid, said residue being characterized by the absence of a hydrogen atom from at least one reactive hydroxyl functional group in said drug; n is a positive integer equal to the number of said functional groups from which a hydrogen atom is absent; and $(QC^+)$ is a radical of the formula

493

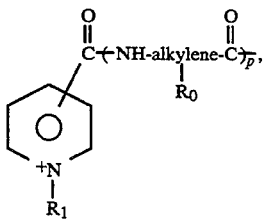 (a)

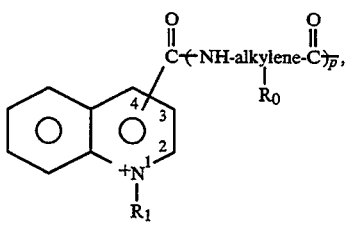 (d)

or

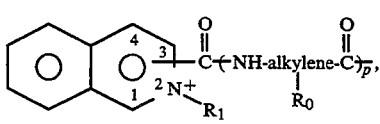 (g)

wherein the alkylene group can be straight or branched and can contain 1 to 3 carbon atoms; R₀ is hydrogen, methyl,

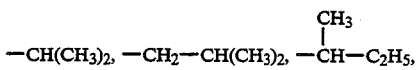

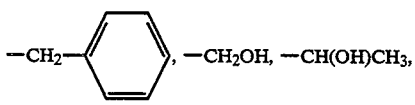

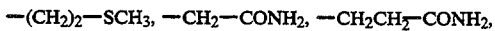

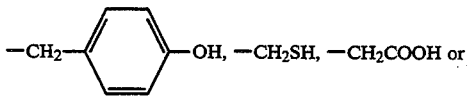

—CH₂CH₂COOH;

p is 1 or 2, provided that, when p is 2, then the alkylene groups can be the same or different and the R₀ radicals can be the same or different; R₁ is C₁-C₇ alkyl, C₁-C₇ haloalkyl or C₇-C₁₀ aralkyl; the carbonyl-containing grouping in formula (a) can be attached at the 2, 3 or 4 position of the pyridinium ring; the carbonyl-containing grouping in formula (d) can be attached at the 2, 3 or 4 position of the quinolinium ring; and the carbonyl-containing grouping in formula (g) can be attached at the 1, 3 or 4 position of the isoquinolinium ring; Y⁻ is the anion of a pharmaceutically acceptable organic or inorganic acid; t is the valence of the acid anion; and q is the number which when multiplied by t is equal to n.

17. A quaternary salt according to claim 16, wherein the steroid is hydrocortisone, betamethasone, dexamethasone, cortisone, flumethasone, fluprednisolone, meprednisone, methylprednisolone, prednisolone, prednisone, triamcinolone, cortodoxone, fludrocortisone, flurandrenolide, paramethasone, testosterone, methyltestosterone, ethinyl estradiol, norgestrel, mestranol, norethindrone, ethisterone, estradiol, estriol, estrone, dimethisterone, allylestrenol, cingestol, ethynerone, lynestrenol, norethynodrel, norgesterone, norvinisterone, ethynodiol, oxogestone, tigestol or quinestrol.

18. A quaternary salt according to claim 17, wherein the steroid is dexamethasone.

19. A quaternary salt according to claim 16, wherein the alkylene group has 1 carbon atom.

20. A quaternary salt according to claim 16, wherein R₀ is hydrogen, methyl,

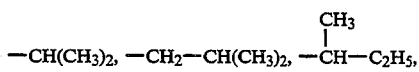

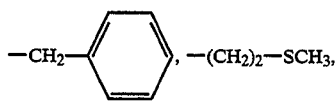

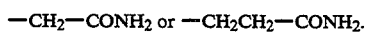

21. A quaternary salt according to claim 16, wherein (QC⁺) comprises the oxidized form of an N-substituted nicotinic acid derivative.

22. A quaternary salt according to claim 16, wherein (QC⁺) comprises the oxidized form of a trigonelline.

23. A quaternary salt according to claim 16, wherein n is 1.

24. A quaternary salt according to claim 16, wherein R₀ is hydrogen.

25. A quaternary salt according to claim 16, wherein p is 1.

26. A quaternary salt according to claim 16, wherein R₁ is CH₃.

27. A quaternary salt according to claim 16, wherein (QC⁺) has formula (a) wherein the carbonyl-containing grouping is attached at the 3-position of the pyridinium ring, or wherein (QC⁺) has formula (d) wherein the carbonyl-containing grouping is attached at the 3-position of the quinolinium ring, or wherein (QC⁺) has formula (g) wherein the carbonyl-containing grouping is attached at the 4-position of the isoquinolinium ring.

28. The quaternary salt according to claim 16, the cation of which has the formula:

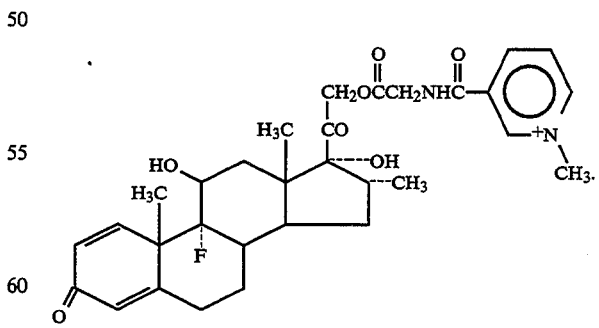

* * * * *